(12) United States Patent
Lu et al.

(10) Patent No.: US 7,312,041 B2
(45) Date of Patent: Dec. 25, 2007

(54) METHODS OF DIAGNOSING CERVICAL CANCER

(75) Inventors: Peter S. Lu, Mountain View, CA (US); Johannes Schweizer, Mountain View, CA (US); Chamorro Somoza Diaz-Sarmiento, Palo Alto, CA (US); Michael P. Belmares, San Jose, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 0 days.

(21) Appl. No.: 10/630,590

(22) Filed: Jul. 29, 2003

(65) Prior Publication Data

US 2004/0018487 A1 Jan. 29, 2004

Related U.S. Application Data

(63) Continuation-in-part of application No. PCT/US02/24655, filed on Aug. 2, 2002, and a continuation-in-part of application No. 10/080,273, filed on Feb. 19, 2002, now abandoned.

(60) Provisional application No. 60/450,464, filed on Feb. 27, 2003, provisional application No. 60/409,298, filed on Sep. 9, 2002, provisional application No. 60/360,061, filed on Feb. 25, 2002, provisional application No. 60/309,841, filed on Aug. 3, 2001, provisional application No. 60/269,523, filed on Feb. 16, 2001.

(51) Int. Cl.
   *C12Q 1/00* (2006.01)
   *C12Q 1/70* (2006.01)
   *G01N 33/53* (2006.01)

(52) U.S. Cl. ............... 435/7.1; 435/4; 435/5; 435/7.9; 435/7.92; 435/7.94; 424/204.1

(58) Field of Classification Search ............. 424/130.1, 424/138.1, 139.1, 147.1, 159.1, 174.1, 178.1, 424/184.1, 185.1, 186.1, 192.1, 195.1, 204.1, 424/277.1; 435/4.5, 7.1, 7.6, 7.7, 7.9, 7.92, 435/7.93, 7.94; 436/64; 530/300, 350, 387.1, 530/388.3, 388.8, 389.4, 389.7, 391.1, 391.3

See application file for complete search history.

(56) References Cited

U.S. PATENT DOCUMENTS

| | | |
|---|---|---|
| 4,777,239 A | 10/1988 | Schoolnik et al. |
| 5,204,061 A | 4/1993 | Covington et al. |
| 5,415,995 A | 5/1995 | Schoolnik et al. |
| 5,610,077 A | 3/1997 | Davis et al. |
| 5,648,459 A | 7/1997 | Cole et al. |
| 5,665,535 A | 9/1997 | Orth et al. |
| 5,747,274 A | 5/1998 | Jackowski |
| 5,753,233 A | 5/1998 | Bleul et al. |
| 5,876,723 A | 3/1999 | Cole et al. |
| 6,322,794 B1 | 11/2001 | Bleul et al. |
| 6,344,314 B2 | 2/2002 | Cole et al. |
| 6,391,539 B1 | 5/2002 | Orth et al. |
| 6,440,696 B1 * | 8/2002 | Band et al. ............... 435/69.1 |

FOREIGN PATENT DOCUMENTS

EP 0523391 1/1993

OTHER PUBLICATIONS

Kehmeier et al., Virology, vol. 299 No. 1, pp. 72-87 (Jul. 2002).*
Thomas et al., Oncogene, vol. 20 No. 39, pp. 5431-5439 (Sep. 2001).*
NCBI Printout, GenPept AAB91995, putative membrane-associated guanylate kinase 1 [*Mus musculus*] (Dec. 1997).*
Gardiol et al., Mutational Analysis of the Discs Large Tumour Suppressor Identifies Domains Responsible for Human Papillomavirus Type 18 E6-Mediated Degradation, Journal of General Virology, 2002, 83: 283-289.
Guiot et al., Immunological Detection of E6 Region Protein from Human Papillomavirus Types 16 and 18 in Premalignant Cervical Lesions, Cancer Cells, 1989, 7: 193-196.
Mathur et al., Human Papillomavirus (HPV)-E6/E7 and Epidermal Growth Factor Receptor (EGF-R) Protein Levels in Cervical Cancer and Cervical Intraepithelial Neoplasia (CIN), American Journal of Re. Immun., 2001, 46(4): 280-287.
Park, et al. HPV-16-related proteins as the serologic markers in cervical neoplasia. Gynecol Oncol. 1998; 69(1):47-55.
Rosales, et al. Antibodies against human papillomavirus (HPV) type 16 and 18 E2, E6 and E7 proteins in sera: Correlation with presence of papillomavirus DNA. J. Medical Virology. 2001; 65:736-744.
Gardiol et al., Oncogenic Human Papillomavirus E6 Proteins Target the Discs Large Tumour Suppressor fro Proteasome-Mediated Degradation, Oncogene, (1999), 18:5487-96.
Glaunsinger et al., Interactions of the PDZ-Protein MAGI-1 with Adenovirus E4-ORF1 and High-Risk Papillomavirus E6 Oncoproteins, Oncogene, (2000), 19:5270-80.
Kiyono et al., Binding of High-Risk Human Papillomavirus E6 Oncoproteins to the Human Homologue of the Drosophila Discs Large Tumor Suppressor Protein, Proc. Natl. Acad. Sci., (1997), 94:11612-6.
Lee et al., Binding of Human Virus Oncoproteins to HDLG/SAP97, A Mammalian Homolog of the Drosophila Discs Large Tumor Suppressor Protein, Proc. Natl. Acad. Sci., (1997), 94:6670-5.
Meschede et al., Antibodies Against Early Proteins of Human Papillomaviruses as Diagnostic Markers for Invasive Cervical Cancer, J. Clin. Microbiol., (1998), 36:475-80.
Munger et al., The Role of Human Papillomaviruses in Human Cancers, Front. Biosci., (2002), 7:d641-9.
Pim et al., HPV-18 E6*I Protein Modulates the E6-Directed Degradation of P53 by Binding to Full-Length HPV-18 E6, Oncogene, (1999), 18:7403-8.

* cited by examiner

*Primary Examiner*—Zachariah Lucas
(74) *Attorney, Agent, or Firm*—Wilson Sonsini Goodrich & Rosati

(57) ABSTRACT

The invention provides reagents and methods for detecting pathogen infections in human samples. This detection utilizes specific proteins to detect the presence of pathogen proteins or abnormal expression of human proteins resulting from pathogen infections. Specific methods, compositions and kits are disclosed herein for the detection of oncogenic Human *papillomavirus* E6 proteins in clinical samples.

15 Claims, 10 Drawing Sheets

◇ MBP-E6-16 in lysates
□ MBP-E6-16 in PBS

A GST-Magi1

B GST-Syn2bp

C GST-Tip1

D GST-Sast1

METHODS OF DIAGNOSING CERVICAL CANCER

CROSS-REFERENCE

This application: a) claims the benefit of U.S. Provisional Application No. 60/409,298, filed Sep. 9, 2002, and U.S. Provisional Application No. 60/450,464, filed Feb. 27, 2003 b) is a CIP of of PCT Application No. US02/24655, filed Aug. 2, 2002, which application clalms the benefit of U.S. Provisional Application No. 60/309841, filed Aug. 3, 2001, and U.S. Provisional Application No. 60/360061, filed Feb. 25, 2002, and c) is a CIP of U.S. Non-Provisional Application No. 10/080,273, filed Feb. 19, 2002, now abandoned, which application clalms the benefit of U.S. Provisional Application No. 60/269,523, filed Feb. 16, 2001 all of which applications are incorporated herein by reference in their entirety.

ACKNOWLEDGMENT OF GOVERNMENT SUPPORT

This invention was made with Government support under Small Business Innovation Research Grant No. IR43CA103383-01, awarded by the National Cancer Institute. The Government may have certain rights in this invention.

FIELD OF THE INVENTION

The present invention relates to detection of biological markers from pathogenic organisms, such as observed in certain human Papillomavirus (HPV) infections, and methods for using such diagnostics to identify samples that are infected and may lead to cancerous growth or other disorders. The present invention also discloses composition, methods and kits for the detection of oncogenic HPV E6 proteins in clinical samples as a cancer diagnostic.

BACKGROUND OF THE INVENTION

Cervical cancer is the second most common cancer diagnosis in women and is linked to high-risk human *papillomavirus* infection 99.7% of the time. Currently, 12,000 new cases of invasive cervical cancer are diagnosed in US women annually, resulting in 5,000 deaths each year. Furthermore, there are approximately 400,000 cases of cervical cancer and close to 200,000 deaths annually worldwide. Human papillomaviruses (HPVs) are one of the most common causes of sexually transmitted disease in the world. Overall, 50-75% of sexually active men and women acquire genital HPV infections at some point in their lives. An estimated 5.5 million people become infected with HPV each year in the US alone, and at least 20 million are currently infected. The more than 100 different isolates of HPV have been broadly subdivided into high-risk and low-risk subtypes based on their association with cervical carcinomas or with benign cervical lesions or dysplasias.

A number of lines of evidence point to HPV infections as the etiological agents of cervical cancers. Multiple studies in the 1980's reported the presence of HPV variants in cervical dysplasias, cancer, and in cell lines derived from cervical cancer. Further research demonstrated that the E6-E7 region of the genome from oncogenic HPV 18 is selectively retained in cervical cancer cells, suggesting that HPV infection could be causative and that continued expression of the E6-E7 region is required for maintenance of the immortalized or cancerous state. The following year, Sedman et al demonstrated that the E6-E7 genes from HPV 16 were sufficient to immortalize human keratinocytes in culture. Barbosa et al demonstrated that although E6-E7 genes from high risk HPVs could transform cell lines, the E6-E7 regions from low risk, or non-oncogenic variants such as HPV 6 and HPV 11 were unable to transform human keratinocytes. More recently, Pillai et al examined HPV 16 and 18 infection by in situ hybridization and E6 protein expression by immunocytochemistry in 623 cervical tissue samples at various stages of tumor progression and found a significant correlation between histological abnormality and HPV infection.

Current treatment paradigms are focused on the actual cervical dysplasia rather than the underlying infection with HPV. Women are screened by physicians annually for cervical dysplasia and are treated with superficial ablative techniques, including cryosurgery, laser ablation and excision. As the disease progresses, treatment options become more aggressive, including partial or radical hysterectomy, radiation or chemotherapy. A significant unmet need exists for early and accurate diagnosis of oncogenic HPV infection as well as for treatments directed at the causative HPV infection, preventing the development of cervical cancer by intervening earlier in disease progression. Human papillomaviruses characterized to date are associated with lesions confined to the epithelial layers of skin, or oral, pharyngeal, respiratory, and, most importantly, anogenital mucosae. Specific human *papillomavirus* types, including HPV 6 and 11, frequently cause benign mucosal lesions, whereas other types such as HPV 16, 18, and a host of other strains, are predominantly found in high-grade lesions and cancer. Individual types of human papillomaviruses (HPV) which infect mucosal surfaces have been implicated as the causative agents for carcinomas of the cervix, anus, penis, larynx and the buccal cavity, occasional periungal carcinomas, as well as benign anogenital warts. The identification of particular HPV types is used for identifying patients with premalignant lesions who are at risk of progression to malignancy. Although visible anogenital lesions are present in some persons infected with human papillomavirus, the majority of individuals with HPV genital tract infection do not have clinically apparent disease, but analysis of cytomorphological traits present in cervical smears can be used to detect HPV infection. Papanicolaou tests are a valuable screening tool, but they miss a large proportion of HPV-infected persons due to the unfortunate false positive and false negative test results. In addition, they are not amenable to worldwide testing because interpretation of results requires trained pathologists.

Conventional viral detection assays, including serologic assays, sandwich ELISA assays and growth in cell culture, are not commercially available and/or are not suitable for the diagnosis and tracking of HPV infection. Recently, several PCR (polymerase chain reaction)-based tests for HPV infections have become available. Though the tests provide the benefit of differentiating oncogenic from non-oncogenic infections, they are fairly expensive to administer and require highly trained technicians to perform PCR and/or luminometer assays. In addition, PCR has a natural false positive rate that may invoke further testing or procedures that are not required. Since the oncogenicity of HPV has been shown to be protein based, early detection of HPV DNA or RNA may lead to unnecessary medical procedures that the body's immune system may solve naturally.

The detection and diagnosis of disease is a prerequisite for the treatment of disease. Numerous markers and characteristics of diseases have been identified and many are used for the diagnosis of disease. Many diseases are preceded by, and are characterized by, changes in the state of the affected cells. Changes can include the expression of pathogen genes or proteins in infected cells, changes in the expression patterns of genes or proteins in affected cells, and changes in cell morphology. The detection, diagnosis, and monitoring of diseases can be aided by the accurate assessment of these changes. Inexpensive, rapid, early and accurate detection of pathogens can allow treatment and prevention of diseases that range in effect from discomfort to death.

The following publications are of interest: Munger (2002) Front. Biosci. 7:d641-9; Glaunsinger (2000) Oncogene 19:5270-80; Gardiol (1999) Oncogene 18:5487-96; Pim (1999) Oncogene 18:7403-8; Meschede (1998) J. Clin. Microbiol. 36:475-80; Kiyono (1997) Proc. Natl. Acad. Sci. 94:11612-6; and Lee (1997) Proc. Natl. Acad. Sci. 94:6670-5. In addition, the following patents and patent applications are of interest: Bleul, 6,322,794; Cole, 6,344,314; Schoolnik, 5,415,995; Bleul, 5753233; Cole, 5,876,723; Cole, 5,648,459; Orth, 6,391,539; Orth, 5,665,535; Schoolnik, 4,777,239.

SUMMARY

Methods and compositions for detection of proteins from pathogens that may result in oncogenic cellular transformation or biological abnormalities in a variety of cell types (e.g., cervical, anal, penile, throat) are provided herein. These methods and compositions can be utilized to detect the presence of pathogens including, but not limited to, those that result in diseases such as cervical cancer, penile cancer, anal cancer and throat cancer, for example. More specifically, methods, compositions and kits are described for the detection of oncogenic HPV E6 proteins in clinical samples

DETAILED DESCRIPTION

I. Definitions

Figure 1:
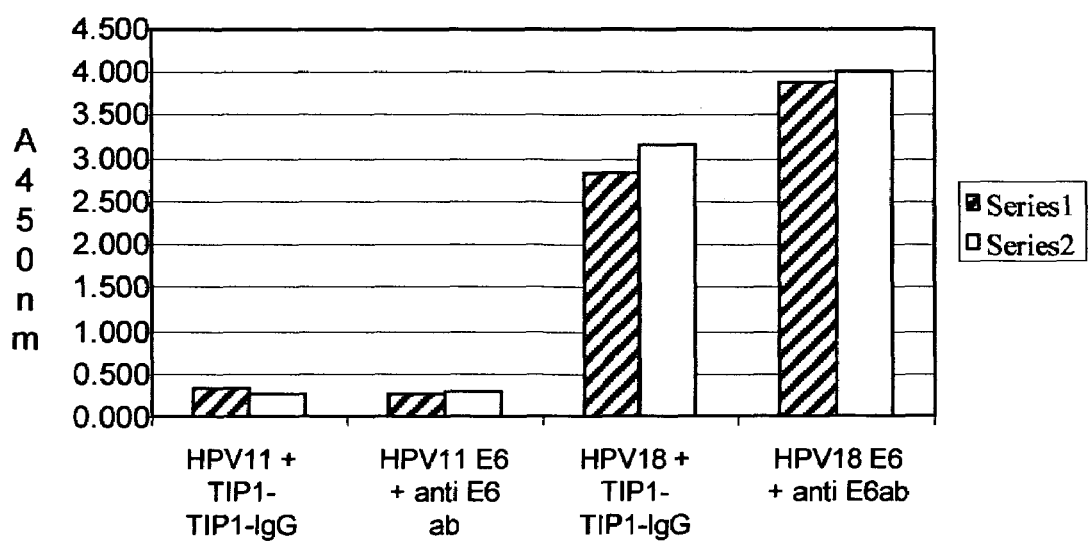
FIG. 1 is a bar graph showing that PDZ proteins can specifically recognize oncogenic E6 proteins from human papillomavirus. An ELISA assay was used to demonstrate that a PDZ protein (TIP-1) could specifically recognize full length E6 protein from an oncogenic strain (HPV18) but did not show any reactivity with a non-oncogenic strain (HPV11). Series 1 and Series 2 represent independent trials. E6 ab indicates that an antibody against E6 from HPV 18 was used for detection instead of the PDZ protein.

A "marker" or "biological marker" as used herein refers to a measurable or detectable entity in a biological sample. Examples or markers include nucleic acids, proteins, or chemicals that are present in biological samples. One example of a marker is the presence of viral or pathogen proteins or nucleic acids in a biological sample from a human source.

As used herein the term "isolated" refers to a polynucleotide, a polypeptide, an antibody, or a host cell that is in an environment different from that in which the polynucleotide, the polypeptide, the antibody, or the host cell naturally occurs. A polynucleotide, a polypeptide, an antibody, or a host cell which is isolated is generally substantially purified. As used herein, the term "substantially purified" refers to a compound (e.g., either a polynucleotide or a polypeptide or an antibody) that is removed from its natural environment and is at least 60% free, preferably 75% free, and most preferably 90% free from other components with which it is naturally associated. Thus, for example, a composition containing A is "substantially free of" B when at least 85% by weight of the total A+B in the composition is A. Preferably, A comprises at least about 90% by weight of the total of A+B in the composition, more preferably at least about 95% or even 99% by weight.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples. The term "biological sample" is meant to distinguish between a sample in a clinical setting from a sample that may be a recombinant sample or derived from a recombinant sample.

A "fusion protein" or "fusion polypeptide" as used herein refers to a composite protein, i.e., a single contiguous amino acid sequence, made up of two (or more) distinct, heterologous polypeptides that are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous protein, or by chemical synthesis methods well known in the art.

A "fusion protein construct" as used herein is a polynucleotide encoding a fusion protein.

An "oncogenic HPV strain" is an HPV strain that is known to cause cervical cancer as determined by the National Cancer Institute (NCI, 2001). "Oncogenic E6 proteins" are E6 proteins encoded by the above oncogenic HPV strains. Exemplary oncogenic strains are shown in Table 3.

An "oncogenic E6 protein binding partner" can be any molecule that specifically binds to an oncogenic E6 protein. Suitable oncogenic E6 protein binding partners include a PDZ domain (as described below), an antibody against an oncogenic E6 protein; other proteins that recognize oncogenic E6 protein (e.g., p53, E6-AP or E6-BP); DNA (i.e., cruciform DNA); and other partners such as aptamers or single chain antibodies from phage display). In some embodiments, detection of more than 1 oncogenic E6 protein (e.g., all oncogenic E6 proteins, E6 proteins from HPV strains 16, 18 and 33 or E6 proteins from HPV strains 16, 18 and 45) is desirable, and, as such, an oncogenic E6 protein binding partner may be antibody that binds to these proteins, a mixture of antibodies that each bind to a different proteins. As is known in the art, such binding partners may be labeled to facilitate their detection. In general, binding partner bind E6 with an binding affinity of $10^{-5}$ M or more, e.g., $10^{-6}$ or more, $10^{-7}$ or more, $10^{-8}$ M or more (e.g., $10^{-9}$ M, $10^{-10}$, $10^{-11}$, etc.).

As used herein, the term "PDZ domain" refers to protein sequence (i.e., modular protein domain) of less than approximately 90 amino acids, (i.e., about 80-90, about 70-80, about 60-70 or about 50-60 amino acids), characterized by homology to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, *Cell* 85: 1067-76).

PDZ domains are found in diverse membrane-associated proteins including members of the MAGUK family of guanylate kinase homologs, several protein phosphatases and kinases, neuronal nitric oxide synthase, tumor suppressor proteins, and several dystrophin-associated proteins, collectively known as syntrophins.

Exemplary PDZ domain-containing proteins and PDZ domain sequences are shown in TABLE 2 and EXAMPLE 4. The term "PDZ domain" also encompasses variants (e.g., naturally occurring variants) of the sequences (e.g., polymorphic variants, variants with conservative substitutions, and the like) and domains from alternative species (e.g. mouse, rat). Typically, PDZ domains are substantially identical to those shown in U.S. patent application Ser. No. 09/724553, e.g., at least about 70%, at least about 80%, or at least about 90% amino acid residue identity when compared and aligned for maximum correspondence. It is appreciated in the art that PDZ domains can be mutated to give amino acid changes that can strengthen or weaken binding and to alter specificity, yet they remain PDZ domains (Schneider et al., 1998, *Nat. Biotech.* 17:170-5). Unless otherwise indicated, a reference to a particular PDZ domain (e.g. a MAGI-1 domain 2) is intended to encompass the particular PDZ domain and HPV E6-binding variants thereof. In other words, if a reference is made to a particular PDZ domain, a reference is also made to variants of that PDZ domain that bind oncogenic E6 protein of HPV, as described below. In this respect it is noted that the numbering of PDZ domains in a protein may change. For example, the MAGI-1 domain 2, as referenced herein, may be referenced as MAGI-1 domain 1 in other literature. As such, when a particular PDZ domain of a protein is referenced in this application, this reference should be understood in view of the sequence of that domain, as described herein, particularly in the sequence listing. Table 9, inserted before the claims, shows the relationship between the sequences of the sequence listing and the names and Genbank accession numbers for various domains, where appropriate.

As used herein, the term "PDZ protein" refers to a naturally occurring protein containing a PDZ domain. Exemplary PDZ proteins include CASK, MPP1, DLG1, DLG2, PSD95, NeDLG, TIP-33, SYN1a, TIP-43, LDP, LIM, LIMK1, LIMK2, MPP2, NOS1, AF6, PTN-4, prIL16, 41.8kD, KIAA0559, RGS12, KIAA0316, DVL1, TIP-40, TIAM1, MINT1, MAGI-1, MAGI-2, MAGI-3, KIAA0303, CBP, MINT3, TIP-2, KIAA0561, and TIP-1.

As used herein, the term "PDZ-domain polypeptide" refers to a polypeptide containing a PDZ domain, such as a fusion protein including a PDZ domain sequence, a naturally occurring PDZ protein, or an isolated PDZ domain peptide. A PDZ-domain polypeptide may therefore be about 60 amino acids or more in length, about 70 amino acids or more in length, about 80 amino acids or more in length, about 90 amino acids or more in length, about 100 amino acids or more in length, about 200 amino acids or more in length, about 300 amino acids or more in length, about 500 amino acids or more in length, about 800 amino acids or more in length, about 1000 amino acids or more in length, usually up to about 2000 amino acids or more in length. PDZ domain peptides are usually no more than about 100 amino acids (e.g. 50-60 amino acids, 60-70 amino acids, 80-90 amino acids, or 90-100 amino acids), and encode a PDZ domain.

As used herein, the term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 4-25 residues, e.g., 8, 10, 12, 14 or 16 residues), forms such a molecular complex. The molecular complex can be observed in vitro using the "A assay" or "G assay" described infra, or in vivo. Exemplary PL proteins listed in TABLES 3 and 4 are demonstrated to bind specific PDZ proteins. This definition is not intended to include anti-PDZ antibodies and the like.

As used herein, a "PL sequence" refers to the amino acid sequence of the C-terminus of a PL protein (e.g., the C-terminal 2, 3, 4, 5, 6, 7, 8, 9, 10, 12, 14, 16, 20 or 25 residues) ("C-terminal PL sequence") or to an internal sequence known to bind a PDZ domain ("internal PL sequence").

As used herein, a "PL peptide" is a peptide of having a sequence from, or based on, the sequence of the C-terminus of a PL protein. Exemplary PL peptides (biotinylated) are listed in TABLE 3.

As used herein, a "PL detector" is a protein that can specifically recognize and bind to a PL sequence.

As used herein, a "PL fusion protein" is a fusion protein that has a PL sequence as one domain, typically as the C-terminal domain of the fusion protein. An exemplary PL fusion protein is a tat-PL sequence fusion.

As used herein, the term "PL inhibitor peptide sequence" refers to PL peptide amino acid sequence that (in the form of a peptide or PL fusion protein) inhibits the interaction between a PDZ domain polypeptide and a PL peptide (e.g., in an A assay or a G assay).

As used herein, a "PDZ-domain encoding sequence" means a segment of a polynucleotide encoding a PDZ domain. In various embodiments, the polynucleotide is DNA, RNA, single stranded or double stranded.

As used herein, the terms "antagonist" and "inhibitor," when used in the context of modulating a binding interaction (such as the binding of a PDZ domain sequence to a PL sequence), are used interchangeably and refer to an agent that reduces the binding of the, e.g., PL sequence (e.g., PL peptide) and the, e.g., PDZ domain sequence (e.g., PDZ protein, PDZ domain peptide).

As used herein, the terms "agonist" and "enhancer," when used in the context of modulating a binding interaction (such as the binding of a PDZ domain sequence to a PL sequence), are used interchangeably and refer to an agent that increases the binding of the, e.g., PL sequence (e.g., PL peptide) and the, e.g., PDZ domain sequence (e.g., PDZ protein, PDZ domain peptide).

As used herein, the terms "peptide mimetic," "peptidomimetic," and "peptide analog" are used interchangeably and refer to a synthetic chemical compound that has substantially the same structural and/or functional characteristics of a PL inhibitory or PL binding peptide of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. As with polypeptides of the invention which are conservative variants, routine experimentation will determine whether a mimetic is within the scope of the invention, i.e., that its structure and/or function is not substantially altered. Thus, a mimetic composition is within the scope of the invention if it is capable of binding to a PDZ domain and/or inhibiting a PL-PDZ interaction.

Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N=-dicyclohexylcarbodiimide (DCC) or N,N=-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, A Peptide Backbone Modifications, Marcell Dekker, N.Y.).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R=—N—C—N—R=) such as, e.g., 1-cyclohexyl-3(2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids omithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines, to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxy-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4,pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a natural polypeptide (e.g., a PL polypeptide or PDZ polypeptide) can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R— or S— form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647-650; Feigl (1986) J. Amer. Chem. Soc. 108:181-182; Kahn (1988) J. Amer. Chem. Soc. 110: 1638-1639; Kemp (1988) Tet. Lett. 29:5057-5060; Kahn (1988) J. Molec. Recognition 1:75-79. Beta sheet mimetic structures have been described, e.g., by Smith (1992) J. Amer. Chem. Soc. 114:10672-10674. For example, a type VI beta turn induced by a cis amide surrogate, 1,5-disubstituted tetrazol, is described by Beusen (1995) Biopolymers 36:181-200. Incorporation of achiral omega-amino acid residues to generate polymethylene units as a substitution for amide bonds is described by Banerjee (1996) Biopolymers 39:769-777. Secondary structures of polypeptides can be analyzed by, e.g., high-field 1H NMR or 2D NMR spectroscopy, see, e.g., Higgins (1997) J. Pept. Res. 50:421-435. See also, Hruby (1997) Biopolymers 43:219-266, Balaji, et al., U.S. Pat. No. 5,612,895.

As used herein, "peptide variants" and "conservative amino acid substitutions" refer to peptides that differ from a reference peptide (e.g., a peptide having the sequence of the carboxy-terminus of a specified PL protein) by substitution of an amino acid residue having similar properties (based on size, polarity, hydrophobicity, and the like). Thus, insofar as the compounds that are encompassed within the scope of the invention are partially defined in terms of amino acid residues of designated classes, the amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with groups such as alkyl, alkenyl, alkynyl, hydroxyl, sulfanyl, nitro and amino groups, as well as others. Examples of genetically encoded aromatic amino acids include Phe, Tyr and Trp. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chloro-phenylalanine, 2-fluorophenyl-alanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include Gly, Pro and Met. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include Asp and Glu.

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include Arg, Lys and His. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include Asx and Glx. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in TABLE 1, below. It is to be understood that TABLE 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$BU |
| Polar | Q, N, S, T, Y | Cit, AcLys, MSO, hSer |
| Cysteine-Like | C | Pen, hCys, p-methyl Cys |

In the case of the PDZ domains described herein, a "HPV E6-binding variant" of a particular PDZ domain is a PDZ domain variant that retains HPV E6 PDZ ligand binding activity. Assays for determining whether a PDZ domain variant binds HPV E6 are described in great detail below, and guidance for identifying which amino acids to change in a specific PDZ domain to make it into a variant may be found in a variety of sources. In one example, a PDZ domain may be compared to other PDZ domains described herein and amino acids at corresponding positions may be substituted, for example. In another example, the sequence a PDZ domain of a particular PDZ protein may be compared to the sequence of an equivalent PDZ domain in an equivalent PDZ protein from another species. For example, the sequence a PDZ domain from a human PDZ protein may be compared to the sequence of other known and equivalent PDZ domains from other species (e.g., mouse, rat, etc.) and any amino acids that are variant between the two sequences may be substituted into the human PDZ domain to make a variant of the PDZ domain. For example, the sequence of the human MAGI-1 PDZ domain 2 may be compared to equivalent MAGI-1 PDZ domains from other species (e.g. mouse Genbank gi numbers 7513782 and 28526157 or other homologous sequences) to identify amino acids that may be substituted into the human MAGI-1-PDZ domain to make a variant thereof. Such method may be applied to any of the MAGI-1 PDZ domains described herein. Minimal MAGI-PDZ domain 2 sequence is provided as SEQ ID NOS: 293-301. Particular variants may have 1, up to 5, up to about 10, up to about 15, up to about 20 or up to about 30 or more, usually up to about 50 amino acid changes as compared to a sequence set forth in the sequence listing. Exemplary MAGI-1 PDZ variants include the sequences set forth in SEQ ID NOS: 302-330. In making a variant, if a GFG motif is present in a PDZ domain, in general, it should not be altered in sequence.

In general, variant PDZ domain polypeptides have a PDZ domain that has at least about 70 or 80%, usually at least about 90%, and more usually at least about 98% sequence identity with a variant PDZ domain polypeptide described herein, as measured by BLAST 2.0 using default parameters, over a region extending over the entire PDZ domain.

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horse radish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label. Thus, a label is any composition detectable by spectroscopic, photochemical, biochemical, immunochemical, electrical, optical or chemical means. The label may be coupled directly or indirectly to the desired component of the assay according to methods well known in the art. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal generating system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly to signal generating compounds, e.g., by conjugation with an enzyme or fluorophore. Means of detecting labels are well known to those of skill in the art. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the color associated with the label. It will be appreciated that when pairs of fluorophores are used in an assay, it is often preferred that they have distinct emission patterns (wavelengths) so that they can be easily distinguished.

As used herein, the term "substantially identical" in the context of comparing amino acid sequences, means that the sequences have at least about 70%, at least about 80%, or at least about 90% amino acid residue identity when compared and aligned for maximum correspondence. An algorithm that is suitable for determining percent sequence identity and sequence similarity is the FASTA algorithm, which is described in Pearson, W. R. & Lipman, D. J., 1988, *Proc. Natl. Acad. Sci. U.S.A.* 85: 2444. See also W. R. Pearson, 1996, *Methods Enzymol.* 266: 227-258. Preferred parameters used in a FASTA alignment of DNA sequences to calculate percent identity are optimized, BL50 Matrix 15: −5, k-tuple=2; joining penalty=40, optimization=28; gap penalty -12, gap length penalty=−2; and width=16.

As used herein, the terms "sandwich", "sandwich ELISA", "Sandwich diagnostic" and "capture ELISA" all refer to the concept of detecting a biological polypeptide with two different test agents. For example, a PDZ protein could be directly or indirectly attached to a solid support. Test sample could be passed over the surface and the PDZ protein could bind it's cognate PL protein(s). A labeled antibody or alternative detection reagent could then be used to determine whether a specific PL protein had bound the PDZ protein.

By "solid phase support" or "carrier" is intended any support capable of binding polypeptide, antigen or antibody. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to a PDZ domain polypeptide or an E6 antibody. Thus, the support configuration can be spherical, as in a bead, or cylindrical, as in the inside surface of a test tube, or the external surface of a rod. Alternatively, the surface can be flat, such as a sheet, culture dish, test strip, etc. Those skilled in the art will know many other suitable carriers for binding antibody, peptide or antigen, or can ascertain the same by routine experimentation.

As used herein, the terms "test compound" or "test agent" are used interchangeably and refer to a candidate agent that may have enhancer/agonist, or inhibitor/antagonist activity, e.g., inhibiting or enhancing an interaction such as PDZ-PL binding. The candidate agents or test compounds may be any of a large variety of compounds, both naturally occurring and synthetic, organic and inorganic, and including polymers (e.g., oligopeptides, polypeptides, oligonucleotides, and polynucleotides), small molecules, antibodies (as broadly defined herein), sugars, fatty acids, nucleotides and nucleotide analogs, analogs of naturally occurring structures (e.g., peptide mimetics, nucleic acid analogs, and the like), and numerous other compounds. In certain embodiment, test agents are prepared from diversity libraries, such as random or combinatorial peptide or non-peptide libraries. Many libraries are known in the art that can be used, e.g., chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994, *Proc. Natl. Acad. Sci. USA* 91:1614-1618; Salmon et al., 1993, *Proc. Natl. Acad. Sci. USA* 90:11708-11712; PCT Publication No. WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science,* 249:404-406; Christian, R. B., et al., 1992, *J. Mol. Biol.* 227:711-718); Lenstra, 1992, *J. Immunol. Meth.* 152: 149-157; Kay et al., 1993, *Gene* 128:59-65; and PCT Publication No. WO 94/18318 dated Aug. 18, 1994. In vitro translation-based libraries include but are not limited to those described in PCT Publication No. WO 91/05058 dated Apr. 18, 1991; and Mattheakis et al., 1994, *Proc. Natl. Acad. Sci. USA* 91:9022-9026. By way of examples of nonpeptide libraries, a benzodiazepine library (see e.g., Bunin et al., 1994, *Proc. Natl. Acad. Sci. USA* 91:4708-4712) can be adapted for use. Peptoid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

In some embodiments "proteasome inhibitors", i.e., inhibitors of the proteasome, may be used. These inhibitors, including carbobenzoxyl-leucinyl-leuciny-1 norvalinal II (MG 115) or CBZ-LLL can be purchased from chemical supply companies (e.g., Sigma). As a skilled person would understand, proteasonie inhibitors are not protease inhibitors.

As used herein, a "plurality" of PDZ proteins (or corresponding PDZ domains or PDZ fusion polypeptides) has its usual meaning. In some embodiments, the plurality is at least 5, and often at least 25, at least 40, or at least 60 different PDZ proteins. In some embodiments, the plurality is selected from the list of PDZ polypeptides listed in TABLE 2. In some embodiments, the plurality of different PDZ proteins are from (i.e., expressed in) a particular specified tissue or a particular class or type of cell. In some embodiments, the plurality of different PDZ proteins represents a substantial fraction (e.g., typically at least 50%, more often at least 80%) of all of the PDZ proteins known to be, or suspected of being, expressed in the tissue or cell(s), e.g., all of the PDZ proteins known to be present in lymphocytes or hematopoetic cells. In some embodiments, the plurality is at least 50%, usually at least 80%, at least 90% or all of the PDZ proteins disclosed herein as being expressed in a particular cell.

When referring to PL peptides (or the corresponding proteins, e.g., corresponding to those listed in TABLE 3, or elsewhere herein) a "plurality" may refer to at least 5, at least 10, and often at least 16 PLs such as those specifically listed herein, or to the classes and percentages set forth supra for PDZ domains.

II. Overview

The present inventors have identified a large number of interactions between PDZ proteins and PL proteins that can play a significant role in the biological function of a variety of physiological systems. As used herein, the term "biological function" in the context of a cell, refers to a detectable biological activity normally carried out by the cell, e.g., a phenotypic change such as cell proliferation (e.g., cancer), cell activation, cytokine release, degranulation, tyrosine phosphorylation, ion (e.g., calcium) flux, metabolic activity, apoptosis, changes in gene expression, maintenance of cell structure, cell migration, adherence to a substrate, signal transduction, cell-cell interactions, and others described herein or known in the art.

Because the interactions involve proteins that are involved in diverse physiological systems (see Background section supra), the methods provided herein can be utilized to broadly or selectively diagnose inappropriate cellular phenotypes or pathogenic infections. Methods are also disclosed herein for determining whether vertebrate biological samples contain pathogenic organisms using PDZ:PL protein interactions.

As will be discussed in great detail below, the use of PDZ-PL interactions for diagnostic purposes is amenable to a number of different test formats and is not intended to be limited by the discussion herein. Diagnostic tests could be formatted for ELISA assays, as a dipstick test such as is used for pregnancy tests, as a film test that can be incubated with test sample, as a slide test that sample could be placed upon, or other such mediums. Such formats are well known in the art, and are described in U.S. Pat. Nos. 6,180,417, 4,703,017 5,591,645

III. PDZ Protein and PL Protein Interactions

TABLE 4 lists PDZ proteins and PL proteins which the current inventors have identified as binding to one another. Each page of TABLE 4 includes four columns. The columns in each section are number from left to right such that the left-most column in each section is column 1 and the right-most column in each section is column 4. Thus, the first column in each section is labeled "HPV Strain" and lists the various E6 proteins that contain the PDZ-Ligand sequences (PLs) that were examined (shown in parenthesis). This column lists C-terminal four amino acids that correspond to the carboxyl-terminal end of a 20 amino acid peptide used in this binding study. All ligands are biotinylated at the amino-terminus and partial sequences are presented in TABLE 3.

The PDZ protein (or proteins) that interact(s) with HPV E6—PL peptides are listed in the second column labeled "PDZ binding partner". This column provides the gene name for the PDZ portion of the GST-PDZ fusion that interacts with the PDZ-ligand to the left. For PDZ domain-containing proteins with multiple domains the domain number is listed to the right of the PDZ (i.e., in column 4 labeled "PDZ Domain"), and indicates the PDZ domain number when numbered from the amino-terminus to the carboxy-terminus. This table only lists interactions of a stronger nature, e.g., those that give a '4' or '5' classification in the 'G assay'. "Classification" is a measure of the level of binding. In particular, it provides an absorbance value at 450 nm which indicates the amount of PL peptide bound to the PDZ protein. The following numerical values have the following meanings: '1'—$A_{450}$ nm 0-1; '2'—$A_{450}$nm 1-2; '3'—$A_{450}$nm 2-3; '4'—$A_{450}$ nm 3-4; '5'—$A_{450}$ nm of 4 more than 2× repeated; '0'—$A_{450}$ nm 0, i.e., not found to interact.

The third and fourth columns of TABLE 4 are merely a repetition of the columns 1 and 2 with different E6 PLs tested and the PDZs bound by them at higher affinity.

Further information regarding these PL proteins and PDZ proteins is provided in TABLES 2 and 3 and EXAMPLEs 4 and 5. In particular, TABLE 3 provides a listing of the partial amino acid sequences of peptides used in the assays. When numbered from left to right, the first column labeled "HPV strain" provides the HPV strain number used to refer to the E6 protein from that strain. The column labeled "E6 C-terminal sequence" provides the predicted sequence of the carboxy-terminal 10 amino acids of the E6 protein. The third column labeled "PL yes/no" designates whether the E6-PL sequence contains sequence elements predicted to bind to PDZ domains. The final column labeled "oncogenic" indicates that this HPV strain is known to cause cervical cancer as determined by the National Cancer Institute (NCI, 2001).

EXAMPLE 5 lists representative sequences of PDZ domains cloned into a vector (PGEX-3× vector) for production of GST-PDZ fusion proteins (Pharmacia). An extended list of PDZ domains cloned into pGEX vectors for production of GST-PDZ fusion proteins is listed in U.S. Pat. No. 09/724553.

As discussed in detail herein, the PDZ proteins listed in TABLE 2 are naturally occurring proteins containing a PDZ domain. Only significant interactions are presented in this table. Thus, the present invention is particularly directed to the detection and modulation of interactions between a PDZ protein and PL protein. In a similar manner, PDZ domains that bind other pathogens can be used to diagnose infection. Additional examples of PL proteins from pathogens suitable for diagnostic applications are included in TABLE 8, but are not intended to limit the scope of the invention.

In another embodiment of the invention, cellular abnormalities or diseases can be diagnosed through the detection of imbalances in the expression levels of cellular PDZ proteins or PL proteins. Using either the PL protein or the PDZ protein in an assay derived from the 'A assay' or 'G assay' one can determine the protein expression levels of binding partners in a normal or abnormal cell. Differences in protein expression levels have been correlated with a number of diseases.

In certain embodiments of the invention, a PDZ protein is used to diagnose the presence of a PL protein from a pathogenic organism. Examples of pathogenic organisms with PL sequences include, but are not limited to, viruses such as Human Papillomaviruses, Hepatitis B virus, Adenovirus, Human T Cell Leukemia Virus, bacteria and fungi.

IV. Assays for Detection of PDZ Proteins or PDZ-Ligand Proteins (PL Proteins)

Two complementary assays, termed "A" and "G", were developed to detect binding between a PDZ-domain polypeptide and candidate PDZ ligand. In each of the two different assays, binding is detected between a peptide having a sequence corresponding to the C-terminus of a protein anticipated to bind to one or more PDZ domains (i.e. a candidate PL peptide) and a PDZ-domain polypeptide (typically a fusion protein containing a PDZ domain). In the "A" assay, the candidate PL peptide is immobilized and binding of a soluble PDZ-domain polypeptide to the immobilized peptide is detected (the "A'" assay is named for the fact that in one embodiment an avidin surface is used to immobilize the peptide). In the "G" assay, the PDZ-domain polypeptide is immobilized and binding of a soluble PL peptide is detected (The "G" assay is named for the fact that in one embodiment a GST-binding surface is used to immobilize the PDZ-domain polypeptide). Preferred embodiments of these assays are described in detail infra. However, it will be appreciated by ordinarily skilled practitioners that these assays can be modified in numerous ways while remaining useful for the purposes of the present invention.

A. Production of Fusion Proteins Containing PDZ-Domains

GST-PDZ domain fusion proteins were prepared for use in the assays of the invention. PCR products containing PDZ encoding domains (as described supra) were subcloned into an expression vector to permit expression of fusion proteins containing a PDZ domain and a heterologous domain (i.e., a glutathione-S transferase sequence, "GST"). PCR products (i.e., DNA fragments) representing PDZ domain encoding DNA were extracted from agarose gels using the "Sephaglas" gel extraction system (Pharmacia) according to the manufacturer's recommendations.

As noted supra, PCR primers were designed to include endonuclease restriction sites to facilitate ligation of PCR fragments into a GST gene fusion vector (pGEX-3×; Pharmacia, GenBank accession no. XXU13852) in-frame with the glutathione-S transferase coding sequence. This vector contains an IPTG inducible lacZ promoter. The pGEX-3× vector was linearized using Bam HI and Eco RI or, in some cases, Eco RI or Sma I, and dephosphorylated. For most cloning approaches, double digestion with Bam HI and Eco RI was performed, so that the ends of the PCR fragments to clone were Bam HI and Eco RI. In some cases, restriction endonuclease combinations used were Bgl II and Eco RI, Bam HI and Mfe I, or Eco RI only, Sma I only, or BamHI only. When more than one PDZ domain was cloned, the DNA portion cloned represents the PDZ domains and the cDNA portion located between individual domains. Precise locations of cloned fragments used in the assays are indicated in U.S. patent application Ser. No. (60/360061). DNA linker sequences between the GST portion and the PDZ domain containing DNA portion vary slightly, dependent on which of the above described cloning sites and approaches were used. As a consequence, the amino acid sequence of the GST-PDZ fusion protein varies in the linker region between GST and PDZ domain. Protein linker sequences corresponding to different cloning sites/approaches are shown below. Linker sequences (vector DNA encoded) are bold, PDZ domain containing gene derived sequences are in italics.

1) GST—BamHI/BamHI—PDZ domain insert
   Gly—Ile—PDZ domain insert
2) GST—BamHI/BglII—PDZ domain insert
   Gly—Ile—PDZ domain insert
3) GST—EcoRI/EcoRI—PDZ domain insert
   Gly—Ile—Pro—Gly—Asn—PDZ domain insert
4) GST—SmaI/SmaI—PDZ domain insert
   Gly—Ile—Pro—PDZ domain insert The PDZ-encoding PCR fragment and linearized pGEX-3× vector were ethanol precipitated and resuspended in 10 ul standard ligation buffer. Ligation was performed for 4-10 hours at 7° C. using T4 DNA ligase. It will be understood that some of the resulting constructs include very short linker sequences and that, when multiple PDZ domains were cloned, the constructs included some DNA located between individual PDZ domains.

The ligation products were transformed in DH5alpha or BL-21 E. coli bacteria strains. Colonies were screened for presence and identity of the cloned PDZ domain containing DNA as well as for correct fusion with the glutathione S-transferase encoding DNA portion by PCR and by sequence analysis. Positive clones were tested in a small-scale assay for expression of the GST/PDZ domain fusion protein and, if expressing, these clones were subsequently grown up for large scale preparations of GST/PDZ fusion protein.

GST-PDZ domain fusion protein was overexpressed following addition of IPTG to the culture medium and purified.

Detailed procedure of small scale and large-scale fusion protein expression and purification are described in "GST Gene Fusion System" (second edition, revision 2; published by Pharmacia). In brief, a small culture (50 mls) containing a bacterial strain (DH5α, BL21 or JM109) with the fusion protein construct was grown overnight in 2×YT media at 37° C. with the appropriate antibiotic selection (100 ug/ml ampicillin; a.k.a. 2×YT-amp). The overnight culture was poured into a fresh preparation of 2×YT-amp (typically 1 liter) and grown until the optical density (OD) of the culture was between 0.5 and 0.9 (approximately 2.5 hours). IPTG (isopropyl β-D-thiogalactopyranoside) was added to a final concentration of 1.0 mM to induce production of GST fusion protein, and culture was grown an additional 1 hour. All following steps, including centrifugation, were performed on ice or at 4° C. Bacteria were collected by centrifugation (4500×g) and resuspended in Buffer A- (50 mM Tris, pH 8.0, 50 mM dextrose, 1 mM EDTA, 200 uM phenylmethylsulfonylfluoride). An equal volume of Buffer A+ (Buffer A-, 4 mg/ml lysozyme) was added and incubated on ice for 3 min to lyse bacteria, or until lysis had begun. An equal volume of Buffer B (10 mM Tris, pH 8.0, 50 mM KCl, 1 mM EDTA. 0.5% Tween-20, 0.5% NP40 (a.k.a. IGEPAL CA-630), 200 uM phenylmethylsulfonylfluoride) was added and incubated for an additional 20 min on ice. The bacterial cell lysate was centrifuged (×20,000 g), and supernatant was run over a column containing 20 ml Sepharose CL-4B (Pharmacia) "precolumn beads," i.e., sepharose beads without conjugated glutathione that had been previously washed with 3 bed volumes PBS. The flow-through was added to glutathione Sepharose 4B (Pharmacia, cat no. 17-0765-01) previously swelled (rehydrated) in 1× phosphate-buffered saline (PBS) and incubated while rotating for 30 min-1 hr. The supernatant-Sepharose slurry was poured into a column and washed with at least 20 bed volumes of 1×PBS. GST fusion protein was eluted off the glutathione sepharose by applying 0.5-1.0 ml aliquots of 5 mM glutathione and collected as separate fractions. Concentrations of fractions were determined by reading absorbance at 280 nm and calculating concentration using the absorbance and extinction coefficient. Those fractions containing the highest concentration of fusion protein were pooled and an equal volume of 70% glycerol was added to a final concentration of 35% glycerol. Fusion proteins were assayed for size and quality by SDS gel electrophoresis (PAGE) as described in "Sambrook." Fusion protein aliquots were stored at minus 80° C. and at minus 20° C.

TABLE 2

PDZ Domains Used in Assays of the Invention

| Gene Name | GI or Acc# | PDZ# | Sequence fused to GST Construct | Seq ID |
|---|---|---|---|---|
| 26s subunit p27 | 9184389 | 1 | RDMAEAHKEAMSRKLGQSESQGPPRAFAKVNSISPGSPSIAGLQVDDEIVEFGSVN TQNFQSLHNIGSVVQHSEGALAPTILLSVSM | 1 |
| AF6 | 430993 | 1 | LRKEPEIITVTLKKQNGMGLSIVAAKGAGQDKLGIYVKSVVKGGAADVDGRLAAGDQ LLSVDGRSLVGLSQERAAELMTRTSSVVTLEVAKQG | 2 |
| AIPC | 12751451 | 1 | LIRPSVISIIGLYKEKGKGLGFSIAGGRDCIRGQMGIFVKTIFPNGSAAEDGRLKEGDEI LDVNGIPIKGLTFQEAIHTFKQIRSGLPVLTVRTKLVSPSLTNSS | 3 |
| AIPC | 12751451 | 2 | GISSLGRKTPGPKDRIVMEVTLNKEPRVGLGIGACCLALENSPPGIYIHSLAPGSVAK MESNLSRGDQILEVNSVNVRHAALSKVHAILSKCPPGPVRLVIGRHPNPKVSEQEMD EVIARSTYQESKEANSS | 4 |
| AIPC | 12751451 | 3 | QSENEEDVCFIVLNRKEGSGLGFSVAGGTDVEPKSITVHRVFSQGAASQEGTMNRG DFLLSVNGASLAGLAHGNVLKVLHQAQLHKDALVVIKKGMDQPRPSNSS | 5 |
| AIPC | 12751451 | 4 | LGRSVAVHDALCVEVLKTSAGLGLSLDGGKSSVTGDGPLVIKRVYKGGAAEQAGIIE AGDEILAINGKPLVGLMHFDAWNIMKSVPEGPVQLLIRKHRNSS | 6 |
| alpha actinin-2 associated LIM protein | 2773059 | 1 | QTVILPGPAAWGFRLSGGIDFNQPLVITRITPGSKAAAANLCPGDVILAIDGFGTESMT HADGQDRIKAAEFIV | 7 |
| APXL-1 | 13651263 | 1 | ILVEVQLSGGAPWGFTLKGGREHGEPLVITKIEEGSKAAAVDKLLAGDEIVGINDIGLS GFRQEAICLVKGSHKTLKLVVKRNSS | 8 |
| Atrophin-1 Interacting Protein | 2947231 | 1 | REKPLFTRDASQLKGTFLSTTLKKSNMGFGFTIIGGDEPDEFLQVKSVIPDGPAAQD GKMETGDVIVYINEVCVLGHTHADVVKLFQSVPIGQSVNLVLCRGYP | 9 |
| Atrophin-1 Interacting Protein | 2947231 | 2 | LSGATQAELMTLTIVKGAQGFGFTIADSPTGQRVKQILDIQGCPGLCEGDLIVEINQQ NVQNLSHTEVVDILKDCPIGSETSLIIHRGGFF | 10 |
| Atrophin-1 Interacting Protein | 2947231 | 3 | HYKELDVHLRRMESGFGFRILGGDEPGQPILIGAVIAMGSADRDGRLHPGDELVYVD GIPVAGKTHRYVIDLMHHAARNGQVNLTVRRKVLCG | 11 |
| Atrophin-1 Interacting Protein | 2947231 | 4 | EGRGISSHSLQTSDAVIHRKENEGFGFVIISSLNRPESGSTITVPHKIGRIIDGSPADR CAKLKVGDRILAVNGQSIINMPHADIVKLIKDAGLSVTLRIIPQEEL | 12 |

TABLE 2-continued

PDZ Domains Used in Assays of the Invention

| Gene Name | GI or Acc# | PDZ# | Sequence fused to GST Construct | Seq ID |
|---|---|---|---|---|
| Atrophin-1 Interacting Protein | 2947231 | 5 | LSDYRQPQDFDYFTVDMEKGAKGFGFSIRGGREYKMDLYVLRLAEDGPAIRNGRM RVGDQIIEINGESTRDMTHARAIELIKSGGRRVRLLLKRGTGQ | 13 |
| Atrophin-1 Interacting Protein | 2947231 | 6 | HESVIGRNPEGQLGFELKGGAENGQFPYLGEVKPGKVAYESGSKLVSEELLLEVNE TPVAGLTIRDVLAVIKHCKDPLRLKCVKQGGIHR | 14 |
| CARD11 | 12382772 | 1 | NLMFRKFSLERPFRPSVTSVGHVRGPGPSVQHTTLNGDSLTSQLTLLGGNARGSFV HSVKPGSLAEKAGLREGHQLLLLEGCIRGERQSVPLDTCTKEEAHWTIQRCSGPVTL HYKVNHEGYRKLV | 15 |
| CARD14 | 13129123 | 1 | ILSQVTMLAFQGDALLEQISVIGGNLTGIFIHRVTPGSAADQMALRPGTQIVMVDYEA SEPLFKAVLEDTTLEEAVGLLRRVDGFCCLSVKVNTDGYKRL | 16 |
| CASK | 3087815 | 1 | TRVRLVQFQKNTDEPMGITLKMNELNHCIVARIMHGGMIHRQGTLHVGDEIREINGIS VANQTVEQLQKMLREMRGSITFKIVPSYRTQS | 17 |
| Connector Enhancer | 3930780 | 1 | LEQKAVLEQVQLDSPLGLEIHTTSNCQHFVSQVDTQVPTDSRLQIQPGDEVVQINEQ VVVGWPRKNMVRELLREPAGLSLVLKKIPIP | 18 |
| Cytohesin Binding Protein | 3192908 | 1 | QRKLVTVEKQDNETFGFEIQSYRPQNQNACSSEMFTLICKIQEDSPAHCAGLQAGD VLANINGVSTEGFTYKQVVDLIRSSGNLLTIETLNG | 19 |
| Densin 180 | 16755892 | 1 | RCLIQTKGQRSMDGYPEQFCVRIEKNPGLGFSISGGISGQGNPFKPSDKGIFVTRVQ PDGPASNLLQPGDKILQANGHSFVHMEHEKAVLLLKSFQNTVDLVIQRELTV | 20 |
| DLG1 | 475816 | 1 | IQVNGTDADYEYEEITLERGNSGLGFSIAGGTDNPHIGDDSSIFITKIITGGAAAQDGR LRVNDCILQVNEVDVRDVTHSKAVEALKEAGSIVRLYVKRRN | 21 |
| DLG1 | 475816 | 2 | IQLIKGPKGLGFSIAGGVGNQHIPGDNSIYVTKIIEGGAAHKDGKLQIGDKLLAVNNVC LEEVTHEEAVTALKNTSDFVYLKVAKPTSMYMNDGN | 22 |
| DLG1 | 475816 | 3 | ILHRGSTGLGFNIVGGEDGEGIFISFILAGGPADLSGELRKGDRIISVNSVDLRAASHE QAAAALKNAGQAVTIVAQYRPEEYSR | 23 |
| DLG2 | 12736552 | 1 | ISYVNGTEIEYEFEEITLERGNSGLGFSIAGGTDNPHIGDDPGIFITKIIPGGAAAEDGR LRVNDCILRVNEVDVSEVSHSKAVEALKEAGSIVRLYVRRR | 24 |
| DLG2 | 12736552 | 2 | ISVVEIKLFKGPKGLGFSIAGGVGNQHIPGDNSIYVTKIIDGGAAQKDGRLQVGDRLL MVNNYSLEEVTHEEAVAILKNTSEVVYLKVGNPTTI | 25 |
| DLG2 | 12736552 | 3 | IVVAVSLEGEPRKVVLHKGSTGLGFNIVGGEDGEGIFVSFILAGGPADLSGELQRGDQ ILSVNGIDLRGASHEQAAAALKGAGQTVTIIAQYQPED | 26 |
| DLG5 | 3650451 | 1 | GIPYVEEPRHVKVQKGSEPLGISIVSGEKGGIVSKVTVGSIAHQAGLEYGDQLLEFN GINLRSATEQQARLIIGQQCDTITILAQYNPHVHQLRNSSZLTD | 27 |
| DLG5 | 3650451 | 2 | GILAGDANKKTLEPRVVFIKKSQLELGVHLCGGNLHGVFVAEVEDDSPAKGPDGLVP GDLILEYGSLDVRNKTVEEVYVEMLKPRDGVRLKVQYRPEEFIVTD | 28 |
| DLG6, splice variant 1 | 14647140 | 1 | PTSPEIQELRQMLQAPHFKALLSAHDTIAQKDFEPLLPPLPDNIPESEEAMRIVCLVKN QQPLGATIKRHEMTGDILVARIIHGGLAERSGLLYAGDKLVEVNGVSVEGLDPEQVIH ILAMSRGTIMFKVVPVSDPPVNSS | 29 |
| DLG6, splice variant 2 | AB053303 | 1 | PTSPEIQELRQMLQAPHFKGATIKRHEMTGDILVARIIHGGLAERSGLLYAGDKLVEV NGVSVEGLDPEQVIHILAMSRGTIMFKVVPVSDPPVNSS | 30 |
| DVL1 | 2291005 | 1 | LNIVTVTLNMERHHFLGISIVGQSNDRGDGGIYIGSIMKGGAVAADGRIEPGDMLLQV NDVNFENMSNDDAVRVLREIVSQTGPISLTVAKCW | 31 |
| DVL2 | 2291007 | 1 | LNIITVTLNMEKYNFLGISIVGQSNERGDGGIYIGSIMKGGAVAADGRIEPGDMLLQVN DMNFENMSNDDAVRVLRDIVHKPGPIVLTVAKCVVDPSPQNS | 32 |
| DVL3 | 6806886 | 1 | IITVTLNMEKYNFLGISIVGQSNERGDGGIYIGSIMKGGAVAADGRIEPGDMLLQVNEI NFENMSNDDAVRVLREIVHKPGPITLTVAKCWDPSP | 33 |
| ELFIN 1 | 2957144 | 1 | TTQQIDLQGPGPWGFRLVGRKDFEQPLAISRVTPGSKAALANLCIGDVITAIDGENTS NMTHLEAQNRIKGCTDNLTLTVARSEHKVWSPLV | 34 |
| ENIGMA | 561636 | 1 | IFMDSFKVVLEGPAPWGFRLQGGKDFNVPLSISRLTPGGKAAQAGVAVGDWVLSID GENAGSLTHIEAQNKIRACGERLSLGLSRAQPV | 35 |

TABLE 2-continued

PDZ Domains Used in Assays of the Invention

| Gene Name | GI or Acc# | PDZ# | Sequence fused to GST Construct | Seq ID |
|---|---|---|---|---|
| ERBIN | 8923908 | 1 | QGHELAKQEIRVRVEKDPELGFSISGGVGGRGNPFRPDDDGIFVTRVQPEGPASKL LQPGDKIIQANGYSFINIEHGQAVSLLKTFQNTVELIIVREVSS | 36 |
| EZRIN Binding Protein 50 | 3220018 | 1 | ILCCLEKGPNGYGFHLHGEKGKLGQYIRLVEPGSPAEKAGLLAGDRLVEVNGENVE EGKETHQQVVSRIRAALNAVRLLVVDPEFIVTD | 37 |
| EZRIN Binding Protein 50 | 3220018 | 2 | IRLCTMKKGPSGYGFNLHSDKSKPGQFIRSVDPDSPAEASGLRAQDRIVEVNGVCM EGKQHGDVVSAIRAGGDETKLLVVDRETDEFFMNSS | 38 |
| FLJ00011 | 10440352 | 1 | KNPSGELKTVTLSKMKQSLGISISGGIESKVQPMVKIEKIFPGGAAFLSGALQAGFEL VAVDGENLEQVTHQRAVDTIRRAYRNKAREPMELVVRVPGPSPRPSPSD | 39 |
| FLJ11215 | 11436365 | 1 | EGHSHPRVVELPKTEEGLGFNIMGGKEQNSPIYISRIIPGGIADRHGGLKRGDQLLSV NGVSVEGEHHEKAVELLKAAQGKVKLVVRYTPKVLEEME | 40 |
| FLJ12428 | BC012040 | 1 | PGAPYARKTFTIVGDAVGWGFVVRGSKPCHIQAVDPSGPAAAAGMKVCQFVVSVN GLNVLHVDYRTVSNLILTGPRTIVMEVMEELEC | 41 |
| FLJ12615 | 10434209 | 1 | GQYGGETVKIVRIEKARDIPLGATVRNEMDSVIISRIVKGGAAEKSGLLHEGDEVLEIN GIEIRGKDVNEVFDLLSDMHGTLTFVLIPSQQIKPPPA | 42 |
| FLJ20075 | 7019938 | 1 | ILAHVKGIEKEVNVYKSEDSLGLTITDNGVGYAFIKRIKDGGVIDSVKTICVGDHIESIN GENIVGWRHYDVAKKLKELKKEELFTMKLIEPKKAFEI | 43 |
| FLJ21687 | 10437836 | 1 | KPSQASGHFSVELVRGYAGFGLTLGGGRDVAGDTPLAVRGLLKDGPAQRCGRLEV GDLVLHINGESTQGLTHAQAVERIRAGGPQLHLVIRRPLETHPGKPRGV | 44 |
| FLJ31349 | AK055911 | 1 | PVMSQCACLEEVHLPNIKPGEGLGMYIKSTYDGLHVITGTTENSPADRSQKIHAGDE VIQVNQQTVVGVVQLKNLVKKLRENPTGVVLLLKKRPTGSFNFTPEFIVTD | 45 |
| FLJ32798 | AK057360 | 1 | LDDEEDSVKIIRLVKNREPLGATIKKDEQTGAIIVARIMRGGAADRSGLIHVGDELREV NGIPVEDKRPEEIIQILAQSQGAITFKIIPGSKEETPSNSS | 46 |
| GRIP 1 | 4539083 | 1 | VVELMKKEGTTLGLTVSGGIDKDGKPRVSNLRQGGIAARSDQLDVGDYIKAVNGINL AKFRHDEIISLLKNVGERVVLEVEYE | 47 |
| GRIP 1 | 4539083 | 2 | RSSVIFRTVEVTLHKEGNTFGFVIRGGAHDDRNKSRPVVITCVRPGGPADREGTIKP GDRLLSVDGIRLLGTRHAEAMSILKQCGQEAALLIEYDVSVMDSVATASGNSS | 48 |
| GRIP 1 | 4539083 | 3 | HVATASGPLLVEVAKTPGASLGVALTTSMCCNKQVIVIDKIKSASIADRCGALHVGDH ILSIDGTSMEYCTLAEATQFLANTTDQVKLEILPHHQTRLALKGPNSS | 49 |
| GRIP 1 | 4539083 | 4 | TETTEVVLTADPVTGFGIQLQGSVFATETLSSPPLISYIEADSPAERCGVLQIGDRVM AINGIPTEDSTFEEASQLLRDSSITSKVTLEIEFDVAES | 50 |
| GRIP 1 | 4539083 | 5 | AESVIPSSGTFHVKLPKKHNVELGITISSPSSRKPGDPLVISDIKKGSVAHRTGTLELG DKLLAIDNIRLDNCSMEDAVQILQQCEDLVKLKIRKDEDNSD | 51 |
| GRIP 1 | 4539083 | 6 | IYTVELKRYGGPLGITISGTEEPFDPIIISSLTKGGLAERTGAIHIGDRILAINSSSLKGKP LSEAIHLLQMAGETVTLKIKKQTDAQSA | 52 |
| GRIP 1 | 4539083 | 7 | IMSPTPVELHKVTLYKDSDMEDFGFSVADGLLEKGVYVKNIRPAGPGDLGGLKPYDR LLQVNHVRTRDFDCCLVVPLIAESGNKLDLVISRNPLA | 53 |
| GTPase Activating Enzyme | 2389008 | 1 | SRGCETRELALPRDGQGRLGFEVDAEGFVTHVERFTFAETAGLRPGARLLRVCGQT LPSLRPEAAAQLLRSAPKVCVTVLPPDESGRP | 54 |
| Guanine Exchange Factor | 6650765 | 1 | AKAKVVRQVVLQKASRESPLQFSLNGGSEKGFGIFVEGVEPGSKAADSGLKRGDQI MEVNGQNFENITFMKAVEILRNNTHLALTVKTNIFVFKEL | 55 |
| HEMBA 1000505 | 10436367 | 1 | LENVIAKSLLIKSNEGSYGFGLEDKNKVPIIKLVEKGSNAEMAGMEVGKKIFAINGDLV FMRPFNEVDCFLKSCLNSRKPLRVLVSTKP | 56 |
| HEMBA 1000505 | 10436367 | 2 | PRETVKIPDSADGLGFQIRGFGPSVVHAVGRGTVAAAAGLHPGQCIIKVNGINVSKET HASVIAHVTACRKYRRPTKQDSIQ | 57 |
| HEMBA 1003117 | 7022001 | 1 | EDFCYVFTVELERGPSGLGMGLIDGMHTHLGAPGLYIQTLLPGSPAAADGRLSLGD RILEVNGSSLLGLGYLRAVDLIRHGGKKMRFLVAKSDVETAKKI | 58 |
| HTRA3 | AY040094 | 1 | LTEFQDKQIKDVVKKRFIGRMRTITPSLVDELKASNPDFPEVSSGIYVQEVAPNSPSQ RGGIQDGDIIVKVNGRPLVDSSELQEAVLTESPLLLEVRRGNDDLLFSNSS | 59 |

TABLE 2-continued

PDZ Domains Used in Assays of the Invention

| Gene Name | GI or Acc# | PDZ# | Sequence fused to GST Construct | Seq ID |
|---|---|---|---|---|
| HTRA4 | AL576444 | 1 | HKKYLGLQMLSLTVPLSEELKMHYPDFPDVSSGVYVCKVVEGTAAQSSGLRDHDVI VNINGKPITTTTDVVKALDSDSLSMAVLRGKDNLLLTVNSS | 60 |
| INADL | 2370148 | 1 | IWQIEYIDIERPSTGGLGFSVVALRSQNLGKVDIFVKDVQPGSVADRDQRLKENDQIL AINHTPLDQNISHQQAIALLQQTTGSLRLIVAREPVHTKSSTSSSE | 61 |
| INADL | 2370148 | 2 | PGHVEEVELINDGSGLGFGIVGGKTSGVVVRTIVPGGLADRDGRLQTGDHILKIGGT NVQGMTSEQVAQVLRNCGNSS | 62 |
| INADL | 2370148 | 3 | PGSDSSLFETYNVELVRKDGQSLGIRIVGYVGTSHTGEASGIYVKSIIPGSAAYHNGH IQVNDKIVAVDGVNIQGFANHDVVEVLRNAGQVVHLTLVRRKTSSTSRIHRD | 63 |
| INADL | 2370148 | 4 | NSDDAELQKYSKLLPIHTLRLGVEVDSFDGHHYISSIVSGGPVDTLGLLQPEDELLEV NGMQLYGKSRREAVSFLKEVPPPFTLVCCRRLFDDEAS | 64 |
| INADL | 2370148 | 5 | LSSPEVKIVELVKDCKGLGFSILDYQDPLDPTRSVIVIRSLVADGVAERSGGLLPGDR LVSVNEYCLDNTSLAEAVEILKAVPPGLVHLGICKPLVEFIVTD | 65 |
| INADL | 2370148 | 6 | PNFSHVVGPPRIVEIFREPNVSLGISIVVGQTVIKRLKNGEELKGIFIKQVLEDSPAGKT NALKTGDKILEVSGVDLQNASHSEAVEAIKNAGNPVVFIVQSLSSTPRVIPNVHNKAN SS | 66 |
| INADL | 2370148 | 7 | PGELHIIELEKDKNGLGLSLAGNKDRSRMSIFVVGINPEGPAAADGRMRIGDELLEIN NQILYGRSHQNASAIIKTAPSKVKLVFIRNEDAVNQMANSS | 67 |
| INADL | 2370148 | 8 | PATCPIVPGQEMIIEISKGRSGLGLSIVGGKDTPLNAIVIHEVYEEGAAARDGRLVVAG DQILEVNGVDLRNSSHEEAITALRQTPQKVRLVVY | 68 |
| KIAA0147 | 1469875 | 1 | ILTLTILRQTGGLGISIAGGKGSTPYKGDDEGIFISRVSEEGPAARAGVRVGDKLLEVN GVALQGAEHHEAVEALRGAGTAVQMRVWRERMVEPENAEFIVTD | 69 |
| KIAA0147 | 1469875 | 2 | PLRQRHVACLARSERGLGFSIAGGKGSTPYRAGDAGIFVSRIAEGGAAHRAGTLQV GDRVLSINGVDVTEARHDHAVSLLTAASPTIALLLEREAGG | 70 |
| KIAA0147 | 1469875 | 3 | ILEGPYPVEEIRLPRAGGPLGLSIVGGSDHSSHPFGVQEPGVFISKVLPRGLAARSGL RVGDRILAVNGQDVRDATHQEAVSALLRPCLELSLLVRRDPAEFIVTD | 71 |
| KIAA0147 | 1469875 | 4 | RELCIQKAPGERLGISIRGGARGHAGNPRDPTDEGIFISKVSPTGAAGRDGRLRVGL RLLEVNQQSLLGLTHGEAVQLLRSVGDTLTVLVCDGFEASTDAALEVS | 72 |
| KIAA0303 | 2224546 | 1 | PHQPIVIHSSGKNYGFTIRAIRVYVGDSDIYTVHHIVWNNVEEGSPACQAGLKAGDLIT HINGEPVHGLVHTEVIELLLKSGNKVSITTTPF | 73 |
| KIAA0313 | 7657260 | 1 | ILACAAKAKRRLMTLTKPSREAPLPFILLGGSEKGFGIFVDSVDSGSKATEAGLKRGD QILEVNGQNFENIQLSKAMEILRNNTHLSITVKTNLFVFKELLTNSS | 74 |
| KIAA0316 | 6683123 | 1 | IPPAPRKVEMRRDPVLGFGFVAGSEKPVVVRSVTPGGPSEGKLIPGDQIVMINDEPV SAAPRERVIDLVRSCKESILLTVIQPYPSPK | 75 |
| KIAA0340 | 2224620 | 1 | LNKRTTMPKDSGALLGLKVVGGKMTDLGRLGAFITKVKKGSLADVVGHLRAGDEVL EVVNGKPLPGATNEEVYNIILESKSEPQVEIIVSRPIGDIPRIHRD | 76 |
| KIAA0380 | 2224700 | 1 | QRCVIIQKDQHGFGFRVSGDRIVLVQSVRPGGAAMKAGVKEGDRIIKVNGTMVTNSS HLEVVKLIKSGAYVALTLLGSS | 77 |
| KIAA0382 | 7662087 | 1 | ILVQRCVIIQKDDNGFGLTVSGDNPVFVQSVKEDGAAMRAGVQTGDRIIKVNGTLVT HSNHLEVVKLIKSGSYVALTVQGRPPGNSS | 78 |
| KIAA0440 | 2662160 | 1 | SVEMTLRRNGLGQLGFHVNYEGIVADVEPYGYAVVQAGLRQGSRLVEICKVAVATLS HEQMIDLLRTSVTVKVVIIPPHD | 79 |
| KIAA0545 | 14762850 | 1 | LKVMTSGWETVDMTLRRNGLGQLGFHVKYDGTVAEVEDYGFAWQAGLRQGSRLV EICKVAVVTLTHDQMIDLLRTSVTVKVVIIPPFEDGTPRRGVV | 80 |
| KIAA0559 | 3043641 | 1 | HYIFPHARIKITRDSKDHTVSGNGLGIRIVGGKEIPGHSGEIGAYIAKILPGGSAEQTGK LMEGMQVLEWNGIPLTSKTYEEVQSIISQQSGEAEICVRLDLNML | 81 |
| KIAA0561 | 3043645 | 1 | LCGSLRPPIVIHSSGKKYGFSLRAIRVYMGDSDVYTVHHVVWSVEDGSPAQEAGLR AGDLITHINGESVLGLVHMDVVELLLKSGNKISLRTTALENTSIKVG | 82 |
| KIAA0613 | 3327039 | 1 | SYSVTLTGPGPWGFRLQGGKDFNMPLTISRITPGSKAAQSQLSQGDLVVAIDGVNT DTMTHLEAQNKIKSASYNLSLTLQKSKNSS | 83 |
| KIAA0751 | 12734165 | 1 | ISRDSGAMLGLKVVGGKMTESGRLCAFITKVKKGSLADTVGHLRPGDEVLEVVNGRL LQGATFEEVYNIILESKPEPQVELVVSRPIAIHRD | 84 |

TABLE 2-continued

PDZ Domains Used in Assays of the Invention

| Gene Name | GI or Acc# | PDZ# | Sequence fused to GST Construct | Seq ID |
|---|---|---|---|---|
| KIAA0807 | 3882334 | 1 | ISALGSMRPPIIIHRAGKKYGFTLRAIRVYMGDSDVYTVHHMVWHVEDGGPASEAGL RQGDLITHVNGEPVHGLVHTEVVELILKSGNKVAISTTPLENSS | 85 |
| KIAA0858 | 4240204 | 1 | FSDMRISINQTPGKSLDFGFTIKWDIPGIFVASVEAGSPAEFSQLQVDDEIIAINNTKFS YNDSKEVVEEAMAKAQETGHLVMDVRRYGKAGSPE | 86 |
| KIAA0902 | 4240292 | 1 | QSAHLEVIQLANIKPSEGLGMYIKSTYDGLHVITGTTENSPADRCKKIHAGDEVIQVN HQTVVGWQLKNLVNALREDPSGVILTLKKRPQSMLTSAPA | 87 |
| KIAA0967 | 4589577 | 1 | ILTQTLIPVRHTVKIDKDTLLQDYGFHISESLPLTVVAVTAGGSAHGKLFPGDQILQMN NEPAEDLSVVERAVDILREAEDSLSITVVRCTSGVPKSSNSS | 88 |
| KIAA0973 | 4589589 | 1 | GLRSPITIQRSGKKYGFTLRAIRVYMGDTDVYSVHHIVWHVEEGGPAQEAGLCAGDL ITHVNGEPVHGMVHPEVVELILKSGNKVAVTTTPFE | 89 |
| KIAA1095 | 5889526 | 1 | QGEETKSLTLVLHRDSGSLGFNIIGGRPSVDNHDGSSSEGIFVSKIVDSGPAAKEGG LQIHDRIIEVNGRDLSRATHDQAVEAFKTAKEPIVVQVLRRTPRTKMFTP | 90 |
| KIAA1095 | 5889526 | 2 | QEMDREELELEEVDLYRMNSQDKLGLTVCYRTDDEDDIGIYISEIDPNSIAAKDGRIR EGDRIIQINGIEVQNREEAVALLTSEENKNFSLLIARPELQLD | 91 |
| KIAA1202 | 6330421 | 1 | RSFQYVPVQLQGGAPWGFTLKGGLEHCEPLTVSKIEDGGKAALSQKMRTGDELVNI NGTPLYGSRQEALILIKGSFRILKLIVRRRNAPVS | 92 |
| KIAA1222 | 6330610 | 1 | ILEKLELFPVELEKDEDGLGISIIGMGVGADAGLEKLGIFVKTVTEGGAAQRDGRIQVN DQIVEVDGISLVGVTQNFAATVLRNTKGNVRFVIGREKPGQVS | 93 |
| KIAA1284 | 6331369 | 1 | KDVNVYVNPKKLTVIKAKEQLKLLEVLVGIIHQTKWSWRRTGKQGDGERLVVHGLLP GGSAMKSGQVLIGDVLVAVNDVDVTTENIERVLSCIPGPMQVKLTFENAYDVKRET | 94 |
| KIAA1389 | 7243158 | 1 | TRGCETVEMTLRRNGLGQLGFHVNFEGIVADVEPFGFAWKAGLRQGSRLVEICKVA VATLTHEQMIDLLRTSVTVKVVIIQPHDDGSPRR | 95 |
| KIAA1415 | 7243210 | 1 | VENILAKRLLILPQEEDYGFDIEEKNKAVVVKSVQRGSLAEVAGLQVGRKIYSINEDLV FLRPFSEVESILNQSFCSRRPLRLLVATKAKEIIKIP | 96 |
| KIAA1526 | 5817166 | 1 | PDSAGPGEVRLVSLRRAKAHEGLGFSIRGGSEHGVGIYVSLVEPGSLAEKEGLRVG DQILRVNDKSLARVTHAEAVKALKGSKKLVLSVYSAGRIPGGYVTNH | 97 |
| KIAA1526 | 5817166 | 2 | LQGGDEKKVNLVLGDGRSLGLTIRGGAEYGLGIYITGVDPGSEAEGSGLKVGDQILE VNWRSFLNILHDEAVRLLKSSRHLILTVKDVGRLPHARTTVDE | 98 |
| KIAA1526 | 5817166 | 3 | WTSGAHVHSGPCEEKCGHPGHRQPLPRIVTIQRGGSAHNCGQLKVGHVILEVNGLT LRGKEHREAARIIAEAFKTKDRDYIDFLDSL | 99 |
| KIAA1620 | 10047316 | 1 | ELRRAELVEIIVETEAQTGVSGINVAGGGKEGIFVRELREDSPAARSLSLQEGDQLLS ARVFFENFKYEDALRLLQCAEPYKVSFCLKRTVPTGDLALRP | 100 |
| KIAA1634 | 10047344 | 1 | PSQLKGVLVRASLKKSTMGFGFTIIGGDRPDEFLQVKNVLKQGPAAQDGKIAPGDVI VDINGNCVLGHTHADVVQMFQLVPVNQYVNLTLCRGYPLPDDSED | 101 |
| KIAA1634 | 10047344 | 2 | ASSGSSQPELVTIPLIKGPKGFGFAIADSPTGQKVKMILDSQVVCQGLQKGDIIKEIYH QNVQNLTHLQVVEVLKQFPVGADVPLLILRGGPPSPTKTAKM | 102 |
| KIAA1634 | 10047344 | 3 | LYEDKPPLTNTFLISNPRTTADPRILYEDKPPNTKDLDVFLRKQESGFGFRVLGGDGP DQSIYIGAIIPLGAAEKDGRLRAADELMCIDGIPVKGKSHKQVLDLMTRAARNGHVLLT VRRKIFYGEKQPEDDSGSPGIHRELT | 103 |
| KIAA1634 | 10047344 | 4 | PAPQEPYDVVLQRKENEGFGFVILTSKNKPPPGVIPHKIGRVIEGSPADRCGKLKVG DHISAVNGQSIVELSHDNIVQLIKDAGVTVTLTVIAEEEHHGPPS | 104 |
| KIAA1634 | 10047344 | 5 | QNLGCYPVELERGPRGFGFSLRGGKEYNMGLFILRLAEDGPAIKDGRIHVGDQIVEI NGEPTQGITHTRAIELIQAGGNKVLLLLRPGTGLIPDHGLA | 105 |
| KIAA1719 | 1267982 | 0 | ITVVELIKKEGSTLGLTISGGTDKDGKPRVSNLRPGGLAARSDLLNIGDYIRSVNGIHL TRLRHDEIITLLKNVGERVVLEVEY | 106 |
| KIAA1719 | 1267982 | 1 | ILDVSLYKEGNSFGFVLRGGAHEDGHKSRPLVLTYVRPGGPADREGSLKVGDRLLS VDGIPLHGASHATALATLRQCSHEALFQVEYDVATP | 107 |
| KIAA1719 | 1267982 | 2 | IHTVANASGPLMVEIVKTPGSALGISLTTTSLRNKSVITIDRIKPASVVDRSGALHPGD HILSIDGTSMEHCSLLEATKLLASISEKVRLEILPVPQSQRPL | 108 |
| KIAA1719 | 1267982 | 3 | IQIVHTETTEVVLCGDPLSGFGLQLQGGIFATETLSSPPLVCFIEPDSPAERCGLLQV GDRVLSINGIATEDGTMEEANQLLRDAALAHKVVLEVEFDVAESV | 109 |

TABLE 2-continued

PDZ Domains Used in Assays of the Invention

| Gene Name | GI or Acc# | PDZ# | Sequence fused to GST Construct | Seq ID |
|---|---|---|---|---|
| KIAA1719 | 1267982 | 4 | IQFDVAESVIPSSGTFHVKLPKKRSVELGITISSASRKRGEPLIISDIKKGSVAHRTGTL EPGDKLLAIDNIRLDNCPMEDAVQILRQCEDLVKLKIRKDEDN | 110 |
| KIAA1719 | 1267982 | 5 | IQTTGAVSYTVELKRYGGPLGITISGTEEPFDPIVISGLTKRGLAERTGAIHVGDRILAI NNVSLKGRPLSEAIHLLQVAGETVTLKIKKQLDR | 111 |
| KIAA1719 | 1267982 | 6 | ILEMEELLLPTPLEMHKVTLHKDPMRHDFGFSVSDGLLEKGVYVHTVRPDGPAHRG GLQPFDRVLQVNHVRTRDFDCCLAVPLLAEAGDVLELIISRKPHTAHSS | 112 |
| LIM Mystique | 12734250 | 1 | MALTVDVAGPAPWGFRITGGRDFHTPIMVTKVAERGKAKDADLRPGDIIVAINGESA EGMLHAEAQSKIRQSPSPLRLQLDRSQATSPGQT | 113 |
| LIM Protein | 3108092 | 1 | SNYSVSLVGPAPWGFRLQGGKDFNMPLTISSLKDGGKAAQANVRIGDVVLSIDGINA QGMTHLEAQNKIKGCTGSLNMTLQRAS | 114 |
| LIMK1 | 4587498 | 1 | TLVEHSKLYCGHCYYQTVVTPVIEQILPDSPGSHLPHTVTLVSIPASSHGKRGLSVSI DPPHGPPGCGTEHSHTVRVQGVDPGCMSPDVKNSIHVGDRILEINGTPIRNVPLDEI DLLIQETSRLLQLTLEHD | 115 |
| LIMK2 | 1805593 | 1 | PYSVTLISMPATTEGRRGFSVSVESACSNYATTVQVKEVNRMHISPNNRNAIHPGDR ILEINGTPVRTLRVEEVEDAISQTSQTLQLLIEHD | 116 |
| LIM-RIL | 1085021 | 1 | IHSVTLRGPSPWGFRLVGRDFSAPLTISRVHAGSKASLAALCPGDLIQAINGESTELM THLEAQNRIKGCHDHLTLSVSRPE | 117 |
| LU-1 | U52111 | 1 | VCYRTDDEEDLGIYVGEVNPNSIAAKDGRIREGDRIIQINGVDVQNREEAVAILSQEE NTNISLLVARPESQLA | 118 |
| MAGI1 | 3370997 | 1 | IQKKNHVVTSRVHECTVKRGPQGELGVTVLGGAEHGEFPYVGAVAAVEAAGLPGGG EGPRLGEGELLLEVQGVRVSGLPRYDVLGVIDSCKEAVTFKAVRQGGR | 119 |
| MAGI1 | 3370997 | 2 | PSELKGKFIHTKLRKSSRGFGFTVVGGDEPDEFLQIKSLVLDGPAALDGKMETGDVI VSVNDTCVLGHTHAQVVKIFQSIPIGASVDLELCRGYPLPFDPDDPN | 120 |
| MAGI1 | 3370997 | 3 | PATQPELITVHIVKGPMGFGFTIADSPGGGQRVKQIVDSPRCRGLKEGDLIVEVNK KNVQALTHNQVVDMLVECPKGSEVTLLVQRGGNLS | 121 |
| MAGI1 | 3370997 | 4 | PDYQEQDIFLWRKETGFGFRILGGNEPGEPIYIGHIVPLGAADTDGRLRSGDELICVD GTPVIGKSHQLVVQLMQQAAKQGHVNLTVRRKVVFAVPKTENSS | 122 |
| MAGI1 | 3370997 | 5 | GVVSTVVQPYDVEIRRGENEGFGFVIVSSVSRPEAGTTFAGNACVAMPHKIGRIIEG SPADRCGKLKVGDRILAVNGCSITNKSHSDIVNLIKEAGNTVRLRIIPGDESSNA | 123 |
| MAGI1 | 3370997 | 6 | QATQEQDFYTVELERGAKGFGFSLRGGREYNMDLYVLRLAEQGPAERCGKMRIGD EILEINGETTKNMKHSRAIELIKNGGRRVRLFLKRG | 124 |
| MGC5395 | BC012477 | 1 | PAKMEKEETTRELLLPNWQGSGSHGLTIAQRDDGVFVQEVTQNSPAARTGVVKEG DQIVGATIYFDNLQSGEVTQLLNTMGHHTVGLKLHRKGDRSPNSS | 125 |
| MINT1 | 2625024 | 1 | SENCKdVFIEKQKGEILGVVIVESGWGSILPTVIIANMMHGGPAEKSGKLNIGDQIMSI NGTSLVGLPLSTCQSIIKGLKNQSRVKLNIVRCPPVNSS | 126 |
| MINT1 | 2625024 | 2 | LRCPPV1TVLIRRPDLRYQLGFSVQNGIICSLMRGGIAERGGVRVGHRIIEINGQSVV ATPHEKIVHILSNAVGEIHMKTMPAAMYRLLNSS | 127 |
| MINT3 | 3169808 | 1 | LSNSDNCREVHLEKRRGEGLGVALVESGWGSLLPTAVIANLLHGGPAERSGALSIG DRLTAINGTSLVGLPLAACQAAVRETKSQTSVTLSIVHCPPVTTAIM | 128 |
| MINT3 | 3169808 | 2 | LVHCPPVTTAIIHRPHAREQLGFCVEDGIICSLLRGGIAERGGIRVGHRIIEINGQSVVA TPHARIIELLTEAYGEVHIKTMPAATYRLLTG | 129 |
| MPP1 | 189785 | 1 | RKVRLIQFEKVTEEPMGITLKLNEKQSCTVARILHGGMIHRQGSLHVGDEILEINGTN VTNHSVDQLQKAMKETKGMISLKVIPNQ | 130 |
| MPP2 | 939884 | 1 | PVPPDAVRMVGIRKTAGEHLGVTFRVEGGELVIARILHGGMVAQQGLLHVGDIIKEV NGQPVGSDPRALQELLRNASGSVILKILPNYQ | 131 |
| MUPP1 | 2104784 | 1 | QGRHVEVFELLKPPSGGLGFSVVGLRSENRGELGIFVQEIQEGSVAHRDGRLKETD QILAINGQALDQTITHQQAISILQKAKDTVQLVIARGSLPQLV | 132 |
| MUPP1 | 2104784 | 2 | PVHVVQHMETIELVNDGSGLGFGIIGGKATGVIVKTILPGGVADQHGRLCSGDHILKIG DTDLAGMSSEQVAQVLRQCGNRVKLMIARGAIEERTAPT | 133 |
| MUPP1 | 2104784 | 3 | QESETFDVELTKNVQGLGITIAGYIGDKKLEPSGIFVKSITKSSAVEHDGRIQIGDQIIA VDGTNLQGFTNQQAVEVLRHTGQTVLLTLMRRGMKQEA | 134 |

TABLE 2-continued

PDZ Domains Used in Assays of the Invention

| Gene Name | GI or Acc# | PDZ# | Sequence fused to GST Construct | Seq ID |
|---|---|---|---|---|
| MUPP1 | 2104784 | 4 | LNYEIVVAHVSKFSENSGLGISLEATVGHHFIRSVLPEGPVGHSGKLFSGDELLEVNG ITLLGENHQDVVNILKELPIEVTMVCCRRTVPPT | 135 |
| MUPP1 | 2104784 | 5 | WEAGIQHIELEKGSKGLGFSILDYQDPIDPASTVIIRSLVPGGIAEKDGRLLPGDRLMF VNDVNLENSSLEEAVEALKGAPSGTVRIGVAKPLPLSPEE | 136 |
| MUPP1 | 2104784 | 6 | RNVSKESFERTINIAKGNSSLGMTVSANKDGLGMIVRSIIHGGAISRDGRIAIGDCILSI NEESTISVTNAQARAMLRRHSLIGPDIKITYVPAEHLEE | 137 |
| MUPP1 | 2104784 | 7 | LNWNQPRRVELWREPSKSLGISIVGGRGMGSRLSNGEVMRGIFIKHVLEDSPAGKN GTLKPGDRIVEVDGMDLRDASHEQAVEAIRKAGNPVVFMVQSIINRPRKSPLPSLL | 138 |
| MUPP1 | 2104784 | 8 | LTGELHMIELEKGHSGLGLSLAGNKDRSRMSVFIVGIDPNGAAGKDGRLQIADELLEI NGQILYGRSHQNASSIIKCAPSKVKIIFIRNKDAVNQ | 139 |
| MUPP1 | 2104784 | 9 | LSSFKNVQHLELPKDQGGLGIAISEEDTLSGVIIKSLTEHGVAATDGRLKVGDQILAVD DEIVVGYPIEKFISLLKTAKMTVKLTIHAENPDSQ | 140 |
| MUPP1 | 2104784 | 10 | LPGCETTIEISKGRTGLGLSIVGGSDTLLGAIIIHEVYEEGAACKDGRLWAGDQILEVN GIDLRKATHDEAINVLRQTPQRVRLTLYRDEAPYKE | 141 |
| MUPP1 | 2104784 | 11 | KEEEVCDTLTIELQKKPGKGLGLSIVGKRNDTGVFVSDIVKGGIADADGRLMQGDQIL MVNGEDVRNATQEAVAALLKCSLGTVTLEVGRIKAGPFHS | 142 |
| MUPP1 | 2104784 | 12 | LQGLRTVEMKKGPTDSLGISIAGGVGSPLGDVPIFIAMMHPTGVAAQTQKLRVGDRI VTICGTSTEGMTHTQAVNLLKNASGSIEMQVVAGGDVSV | 143 |
| MUPP1 | 2104784 | 13 | LGPPQCKSITLERGPDGLGFSIVGGYGSPHGDLPIYVKTVFAKGMSEDGRLKRGDQ IIAAVNGQSLEGVTHEEAVAILKRTKGTVTLMVLS | 144 |
| NeDLG | 10863920 | 1 | IQYEEIVLERGNSGLGFSIAGGIDNPHVPDDPGIFITKIIPGGAAAMDGRLGVNDCVLR VNEVEVSEVVHSRAVEALKEAGPVVRLVVRRRQN | 145 |
| NeDLG | 10863920 | 2 | ITLLKGPKGLGFSIAGGIGNQHIPGDNSIYITKIIEGGAAQKDGRLQIGDRLLAVNNTNL QDVRHEEAVASLKNTSDMVYLKVAKPGSLE | 146 |
| NeDLG | 10863920 | 3 | ILLHKGSTGLGFNIVGGEDGEGIFVSFILAGGPADLSGELRRGDRILSVNGVNLRNAT HEQAAAALKRAGQSVTIVAQYRPEEYSRFESKIHDLREQMMNSSMSSGSGSLRTSE KRSLE | 147 |
| Neurabin II | AJ401189 | 1 | CVERLELFPVELEKDSEGLGISIIGMGAGADMGLEKLGIFVKTVTEGGAAHRDGRIQV NDLLVEVDGTSLVGVTQSFAASVLRNTKGRVRFMIGRERPGEQSEVAQRIHRD | 148 |
| NOS1 | 642525 | 1 | IQPNVISVRLFKRKVGGLGFLVKERVSKPPVIISDLIRGGAAEQSGLIQAGDIILAVNGR PLVDLSYDSALEVLRGIASETHVVLILRGP | 149 |
| novel PDZ gene | 7228177 | 1 | QANSDESDIIHSVRVEKSPAGRLGFSVRGGSEHGLGIFVSKVEEGSSAERAGLCVG DKITEVNGLSLESTTMGSAVKVLTSSSRLHMMVRRMGRVPGIKFSKEKNSS | 150 |
| novel PDZ gene | 7228177 | 2 | PSDTSSEDGVRRIVHLY1TSDDFCLGFNIRGGKEFGLGIYVSKVDHGGLAEENGIKV GDQVLAANGVRFDDISHSQAVEVLKGQTHIMLTIKETGRYPAYKEMNSS | 151 |
| Novel Serine Protease | 1621243 | 1 | KIKKFLTESHDRQAKGKAITKKKYIGIRMMSLTSSKAKELKDRHRDFPDVISGAYIIEVI PDTPAEAGGLKENDVIISINGQSVSANDVSDVIKRESTLNMVVRRGNEDIMITV | 152 |
| Numb Binding Protein | AK056823 | 1 | PDGEITSIKINRVDPSESLSIRLVGGSETPLVHIIIQHIYRDGVIARDGRLLPGDIILKVNG MDISNVPHNYAVRLLRQPCQVLWLTVMREQKFRSRNSS | 153 |
| Numb Binding Protein | AK056823 | 2 | HRPRDDSFHVILNKSSPEEQLGIKLVRKVDEPGVFIFNVLDGGVAYRHGQLEENDRV LAINGHDLRYGSPESAAHLIQASERRVHLVVSRQVRQRSPENSS | 154 |
| Numb Binding Protein | AK056823 | 3 | PTITCHEKVVNIQKDPGESLGMTVAGGASHREWDLPIYVISVEPGGVISRDGRIKTGD ILLNVDGVELTEVSRSEAVALLKRTSSSIVLKALEVKEYEPQEFIV | 155 |
| Numb Binding Protein | AK056823 | 4 | PRCLYNCKDIVLRRNTAGSLGFCIVGGYEEYNGNKPFFIKSIVEGTPAYNDGRIRCGD ILLAVNGRSTSGMIHACLARLLKELKGRITLTIVSWPGTFL | 156 |
| Outer Membrane | 7023825 | 1 | LLTEEEINLTRGPSGLGFNIVGGTDQQYVSNDSGIYVSRIKENGAAALDGRLQEGDKI LSVNGQDLKNLLHQDAVDLFRNAGYAVSLRVQHRLQVQNGIHS | 157 |
| p55T | 12733367 | 1 | PVDAIRILGIHKRAGEPLGVTFRVENNDLVIARILHGGMIDRQGLLHVGDIIKEVNGHE VGNNPKELQELLKNISGSVTLKILPSYRDTITPQQ | 158 |
| PAR3 | 8037914 | 1 | DDMVKLVEVPNDGGPLGIHVVPFSARGGRTLGLLVKRLEKGGKAEHENLFRENDCI VRINDGDLRNRRFEQAHMFRQAMRTPIIWFHVVPAA | 159 |

TABLE 2-continued

PDZ Domains Used in Assays of the Invention

| Gene Name | GI or Acc# | PDZ# | Sequence fused to GST Construct | Seq ID |
|---|---|---|---|---|
| PAR3 | 8037914 | 2 | GKRLNIQLKKGTEGLGFSITSRDVTIGGSAPIYVKNILPRGAAIQDGRLKAGDRLIEVN GVDLVGKSQEEVVSLLRSTKMEGTVSLLVFRQEDA | 160 |
| PAR3 | 8037914 | 3 | TPDGTREFLTFEVPLNDSGSAGLGVSVKGNRSKENHADLGIFVKSIINGGAASKDGR LRVNDQLIAVNGESLLGKTNQDAMETLRRSMSTEGNKRGMIQLIVA | 161 |
| PAR6 | 2613011 | 1 | LPETHRRVRLHKHGSDRPLGFYIRDGMSVRVAPQGLERVPGIFISRLVRGGLAESTG LLAVSDEILEVNGIEVAGKTLDQVTDMMVANSHNLIVTVKPANQR | 162 |
| PAR6 GAMMA | 13537118 | 1 | IDVDLVPETHRRVRLHRHGCEKPLGFYIRDGASVRVTPHGLEKVPGIFISRMVPGGL AESTGLLAVNDEVLEVNGIEVAGKTLDQVTDMMIANSHNLIVTVKPANQRNNVV | 163 |
| PDZ-73 | 5031978 | 1 | RSRKLKEVRLDRLHPEGLGLSVRGGLEFGCGLFISHLIKGGQADSVGLQVGDEIVRI NGYSISSCTHEEVINLIRTKKTVSIKVRHIGLIPVKSSPDEFH | 164 |
| PDZ-73 | 5031978 | 2 | IPGNRENKEKKVFISLVGSRGLGCSISSGPIQKPGIFISHVKPGSLSAEVGLEIGDQIVE VNGVDFSNLDHKEAVNLKSSRSLTISIVAAAGRELFMTDEF | 165 |
| PDZ-73 | 5031978 | 3 | PEQIMGKDVRLLRIKKEGSLDLALEGGVDSPIGKVVVSAVYERGAAERHGGIVKGDEI MAINGKIVTDYTLAEADAALQKAWNQGGDWIDLVVAVCPPKEYDD | 166 |
| PDZK1 | 2944188 | 1 | LTSTFNPRECKLSKQEGQNYGFFLRIEKDTEGHLVRVVEKCSPAEKAGLQDGDRVL RINGVFVDKEEHMQVVDLVRKSGNSVTLLVLDGDSYEKAGSPGIHRD | 167 |
| PDZK1 | 2944188 | 2 | RLCYLVKEGGSYGFSLKTVQGKKGVYMTDITPQGVAMRAGVLADDHLIEVNGENVE DASHEEVVEKVKKSGSRVMFLLVDKETDKREFIVTD | 168 |
| PDZK1 | 2944188 | 3 | QFKRETASLKLLPHQPRIVEMKKGSNGYGFYLRAGSEQKGQIIKDIDSGSPAEEAGL KNNDLVVAVNGESVETLDHDSVVEMIRKGGDQTSLLVVDKETDNMYRLAEFIVTD | 169 |
| PDZK1 | 2944188 | 4 | PDTTEEVDHKPKLCRLAKGENGYGFHLNAIRGLPGSFIKEVQKGGPADLAGLEDEDV IIEVNGVNVLDEPYEKVVDRIQSSGKNVTLLVZGKNSS | 170 |
| PICK1 | 4678411 | 1 | PTVPGKVTLQKDAQNLIGISIGGGAQYCPCLYIVQVFDNTPAALDGTVAAGDEITGVN GRSIKGKTKVEVAKMIQEVKGEVTIHYNKLQ | 171 |
| PIST | 98374330 | 1 | SQGVGPIRKVLLLKEDHEGLGISITGGKEHGVPILISEIHPGQPADRCGGLHVGDAILA VNGVNLRDTKHKEAVTILSQQRGEIEFEVVYVAPEVDSD | 172 |
| prIL16 | 1478492 | 1 | IHVTILHKEEGAGLGFSLAGGADLENKVIVVHRVFPNGLASQEGTIQKGNEVLSINGK SLKGTTHHDALAILRQAREPRQAVIVTRKLTPEEFIVTD | 173 |
| prIL16 | 1478492 | 2 | TAEATVCTVTLEKMSAGLGFSLEGGKGSLHGDKPLTINRIFKGAASEQSEEVQPGDE ILQLGGTAMQGLTRFEAWNIIKALPDGPVTIVIRRKSLQSK | 174 |
| PSD95S | 3318652 | 1 | LEYEeITLERGNSGLGFSIAGGTDNPHIGDDPSIITKIIPGGAAAQDGRLRVNDSILFV NEVDVREVTHSAAVEALKEAGSIVRLYVMRRKPPAENSS | 175 |
| P5D95 | 3318652 | 2 | HVMRRKPPAEKVMEIKLIKGPKGLGFSIAGGVGNQHIPGDNSIYVTKIIEGGAAHKDG RLQIGDKILAVNSVGLEDVMHEDAVAALKNTYDVVYLKVAKPSNAYL | 176 |
| P5D95 | 3318652 | 3 | REDIPREPRRIVIHRGSTGLGFNIVGGEDGEGIFISFILAGGPADLSGELRKGDQILSV nGVDLRNASHEQAAIALKNAGQTVTIIAQYKPEFIVTD | 177 |
| PTN-3 | 179912 | 1 | LIRITPDEDGKFGFNLKGGVDQKMPLVVSRINPESPADTCIPKLNEGDQIVLINGRDIS EHTHDQVVMFIKASRESH5RELALVIRRR | 178 |
| PTN-4 | 190747 | 1 | IRMKPDENGRFGFNVKGGYDQKMPVIVSRVAPGTPADLCVPRLNEGDQVVLINGRD IAEHTHDQVVLFIKASCERHSGELMLLVRPNA | 179 |
| PTPL1 | 515030 | 1 | PEREITLVNLKKDAKYGLGFQIIGGEKMGRLDLGIFISSVAPGGPADFHGCLKPGDRLI SVNSVSLEGVSHHAAIEILQNAPEDVTLVISQPKEKISKVPSTPVHL | 180 |
| PTPL1 | 515030 | 2 | GDIFEVELAKNDNSLGISVTGGVNTSVRHGGIYVKAVIPQGAAESDGRIHKGDRVLAV NGVSLEGATHKQAVETLRNTGQVVHLLLEKGQSPTSK | 181 |
| PTPL1 | 515030 | 3 | TEENTFEVKLFKNSSGLGFSFSREDNLIPEQINASIVRVKKLFAGQPAAESGKIDVGD VILKVNGASLKGLSQQEVISALRGTAPEVFLLLCRPPPGVLPEIDT | 182 |
| PTPL1 | 515030 | 4 | ELEVELLITLIKSEKASLGFTVTKGNQRIGCYVHDVIQDPAKSDGRLKPGDRLIKVNDT DVTNMTHTDAVNLLRAASK1VRLVIGRVLELPRIPMLPH | 183 |
| PTPL1 | 515030 | 5 | MLPHLLPDITLTCNKEELGFSLCGGHDSLYQVVYISDINPRSVAAIEGNLQLLDVIHYV NGVSTQGMTLEEVNRALDMSLPSLVLKATRNDLPV | 184 |

TABLE 2-continued

PDZ Domains Used in Assays of the Invention

| Gene Name | GI or Acc# | PDZ# | Sequence fused to GST Construct | Seq ID |
|---|---|---|---|---|
| RGS12 | 3290015 | 1 | RPSPPRVRSVEVARGRAGYGFTLSGQAPCVLSCVMRGSPADFVGLRAGDQILAVN EINVKKASHEDVVKLIGKCSGVLHMVIAEGVGRFESCS | 185 |
| RGS3 | 18644735 | 1 | LCSERRYRQITIPRGKDGFGFTICCDSPVRVQAVDSGGPAERAGLQQLDTVLQLNE RPVEHVVKCVELAHEIRSCPSEIILLVWRMVPQVKPGIHRD | 186 |
| Rhophilin-like | 14279408 | 1 | ISFSANKRWTPPRSIRFTAEEGDLGFTLRGNAPVQVHFLDPYCSASVAGAREGDYIV SIQLVDCKWLTLSEVMKLLKSFGEDEIEMKVVSLLDSTSSMHNKSAT | 187 |
| Serine Protease | 2738914 | 1 | RGEKKNSSSGISGSQRRYIGVMMLTLSPSILAELQLREPSFPDVQHGVLIHKVILGSP AHRAGLRPGDVILAIGEQMVQNAEDVYEAVRTQSQLAVQIRRGRETLTLYV | 188 |
| Shank 1 | 6049185 | 1 | EEKTVVLQKKDNEGFGFVLRGAKADTPIEEFTPTPAFPALQYLESVDEGGVAWQAG LRTGDFLIEVNNENVVKVGHRQVVNMIRQGGNHLVLKVV1VTRNLDPDDTARKKA | 189 |
| Shank 3 | | 1 | SDYVIDDKVAVLQKRDHEGFGFVLRGAKAETPIEEFTPTPAFPALQYLESVDVEGVA WRAGLRTGDFLIEVNGVNVVKVGHKQVVALIRQGGNRLVMKVVSVTRKPEEDG | 190 |
| Shroom | 18652858 | 1 | IYLEAFLEGGAPWGFTLKGGLEHGEPLIISKVEEGGKADTLSSKLQAGDEVVHINEVT LSSSRKEAVSLVKGSYKTLRLVVRRDVCTDPGH | 191 |
| SIP1 | 2047327 | 1 | IRLCRLVRGEQYGFHLHGEKGRRGQFIRRVEPGSPAEAAALRAGDRLVEVNGVNV EGETHHQVVQRIKAVEGQTRLLVVDQN | 192 |
| SIP1 | 2047327 | 2 | IRHLRKGPQGYGFNLHSDKSRPGQYIRSVDPGSPAARSGLRAQDRLIEVNGQNVEG LRHAEVVASIKAREDEARLLVVDPETDE | 193 |
| SITAC-18 | 8886071 | 1 | PGVREIHLCKDERGKTGLRLRKVDQGLFVQLVQANTPASLVGLRFGDQLLQIDGRD CAGWSSHKAHQVVKKASGDKIVVVVRDRPFQRTVTM | 194 |
| SITAG-18 | 8886071 | 2 | PFQRTVTMHKDSMGHVGFIKKGKIVSLVKGSSAARNGLLTNHYVCEVDGQNVIGL KDKKIMEILATAGNVVTLTIIPSVIYEHIVEFIV | 195 |
| SSTRIP | 7025450 | 1 | LKEKVVLLQKKDSEGFGFVLRGAKAQTPIEEFTPTPAFPALQYLESVDEGGVAWRAG LRMGDFLIEVNGQNVVKVGHRQVVNMIRQGGNTLMVKVVMVTRHPDMDEAVQ | 196 |
| SYNTENIN | 2795862 | 1 | LEIKQGIREVILCKDQDGKIGLRLKSIDNGIFVQLVQANSPASLVGLRFGDQVLQINGE NCAGWSSDKAHKVLKQAFGEKITMRIHRD | 197 |
| SYNTENIN | 2795862 | 2 | RDRPFERTITMHKDSTGHVGFIFKNGKITSIVKDSSAARNGLLTEHNICEINGQNVIGL KDSQIADILSTSGNSS | 198 |
| Syntrophin 1 alpha | 1145727 | 1 | QRRRVTVRKADAGGLGISIKGGRENKMPILISKIFKGLAADQTEALFVGDAILSVNGE DLSSATHDEAVQVLKKTGKEVVLEVKYMKDVSPYFK | 199 |
| Syntrophin beta 2 | 476700 | 1 | IRVVKQEAGGLGISIKGGRENRMPILISKIFPGLAADQSRALRLGDAILSVNGTDLRQA THDQAVQALKRAGKEVLLEVKFIREFIVTD | 200 |
| Syntrophin gamma 1 | 9507164 | 1 | EPFYSGERTVTIRRQTVGGFGLSIKGGAEHNIPVVVSKISKEQRAELSGLLFIGDAILQI NGINVRKCRHEEVVQVLRNAGEEVTLTVSFLKRAPAFLKLP | 201 |
| Syntrophin gamma 2 | 9507164 | 1 | SHQGRNRRTVTLRRQPVGGLGLSIKGGSEHNVPVVISKIFEDQAADQTGMLFVGDA VLQVNGIHVENATHEEVVHLLRNAGDEVTITVEYLREAPAFLK | 202 |
| TAX2-like protein | 3253116 | 1 | RGETKEVEVTKTEDALGLTITDNGAGYAFIKRIKEGSIINRIEAVCVGDSIEAINDHSIV GCRHYEVAKMLRELPKSQPFTLRLVQPKRAF | 203 |
| TIAM 1 | 4507500 | 1 | HSIHIEKSDTAADTYGFSLSSVEEDGIRRLYVNSVKETGLASKKGLKAGDEILEINNRA ADALNSSMLKDPLSQPSLGLLVRTYPELE | 204 |
| TIAM 2 | 6912703 | 1 | PLNVYDVQLTKTGSVCDFGFAVTAQVDERQHLSRIFISDVLPDGLAYEGGLRKGNEI MTLNGEAVSDLDLKQMEALFSEKSVGLTLIARPPDTKATL | 205 |
| TIP1 | 2613001 | 1 | QRVEIHKLRQGENLILGFSIGGGIDQDPSQNPFSEDKTDKGIYVTRVSEGGPAEIAGL QIGDKIMQVNGWDMTMVTHDQARKRLTKRSEEVVRLLVTRQSLQK | 206 |
| TIP2 | 2613003 | 1 | RKEVEVFKSEDALGLTITDNGAGYAFIKRIKEGSVIDHIHLISVGDMIEAINGQSLLGCR HYEVARLLKELPRGRTFTLKLTEPRK | 207 |
| TIP33 | 2613007 | 1 | HSHPRVVELPKTDEGLGFNVMGGKEQNSPIYISRIIPGGVAERHGGLKRGDQLLSVN GVSVEGEHHEKAVELLKAAKDSVKLVVRYTPKVL | 208 |
| TIP43 | 2613011 | 1 | ISNQKRGVKVLKQELGGLGISIKGGKENKMPILISKIFKGLAADQTQALYVGDAILSVN GADLRDATHDEAVQALKRAGKEVLLEVKYMREATPYV | 209 |

TABLE 2-continued

PDZ Domains Used in Assays of the Invention

| Gene Name | Gl or Acc# | PDZ# | Sequence fused to GST Construct | Seq ID |
|---|---|---|---|---|
| X-11 beta | 3005559 | 1 | IHFSNSENCKELQLEKHKGEILGVVVVESGWGSILPTVILANMMNGGPAARSGKLSIG DQIMSINGTSLVGLPLATCQGIIKGLKNQTQVKLNIVSCPPVTTVLIKRNSS | 210 |
| X-11 beta | 3005559 | 2 | IPPVTTVLIKRPDLKYQLGFSVQNGIICSLMRGGIAERGGVRVGHRIIEINGQSVVATA HEKIVQALSNSVGEIHMKTMPAAMFRLLTGQENSS | 211 |
| ZO-1 | 292937 | 1 | IWEQHTVTLHRAPGFGFGIAISGGRDNPHFQSGETSIVISDVLKGGPAEGQLQENDR VAMVNGVSMDNVEHAFAVQQLRKSGKNAKITIRRKKKVQIPNSS | 212 |
| ZO-1 | 292937 | 2 | ISSQPAKPTKVTLVKSRKNEEYGLRLASHIFVKEISQDSLAARDGNIQEGDVVLKINGT VTENMSLTDAKTLIERSKGKLKMVVQRDRATLLNSS | 213 |
| ZO-1 | 292937 | 3 | IRMKLVKFRKGDSVGLRLAGGNDVGIFVAGVLEDSPAAKEGLEEGD0ILRVNNVDFT NIIREEAVLFLLDLPKGEEVTILAQKKKDVFSN | 214 |
| ZO-2 | 12734763 | 1 | LIWEQYTVTLQKDSKRGFGIAVSGGRDNPHFENGETSIVISDVLPGGPADGLLQEND RVVMVNGTPMEDVLHSFAVQQLRKSGKVAAIVVKRPRKV | 215 |
| ZO-2 | 12734763 | 2 | RVLLMKSRANEEYGLRLGSQIFVKEMTRTGLATKDGNLHEGDIILKINGTVTENMSLT DARKLIEKSRGKLQLVVLRDS | 216 |
| ZO-2 | 12734763 | 3 | HAPNTKMVRFKKGDSVGLRLAGGNDVGIFVAGIQEGTSAEQEGLQEGDQILKVNTQ DFRGLVREDAVLYLLEIPKGEMVTILAQSRADVY | 217 |
| ZO-3 | 10092690 | 1 | IPGNSTIWEQHTATLSKDPRRGFGIAISGGRDRPGGSMVVSDVVPGGPAEGRLQTG DHIVMVNGVSMENATSAFAIQILKTCTKMANITVKRPRRIHLPAEFIVTD | 218 |
| ZO-3 | 10092690 | 2 | QDVQMKPVKSVLVKRRDSEEFGVKLGSQIFIKHITDSGLAARHRGLQEGDLILQINGV SSQNLSLNDTRRLIEKSEGKLSLLVLRDRGQFLVNIPNSS | 219 |
| ZO-3 | 10092690 | 3 | RGYSPDTRVVRFLKGKSIGLRLAGGNDVGIFVSGVQAGSPADGQGIQEGDQILQVN DVPFQNLTREEAVQFLLGLPPGEEMELVTQRKQDIFVVKMVQSEFIVTD | 220 |

The amino acid sequences provided in Table 2 above may contain amino acids derived from a fusion protein, e.g., GST. PDZ domain sequence of particular interest may be up to 20 amino acids shorter (e.g., 5, 8, 10, 12 or 15 amino acids shorter) than the sequence provided in Table 2. For example, a sequence may be shortened by up to 3, 6, 9, or 12 amino acids from the C-terminus, the N-terminus, or both termini.

B. Identification of Candidate PL Proteins and Synthesis of Peptides

Certain PDZ domains are bound by the C-terminal residues of PDZ-binding proteins. To identify PL proteins the C-terminal residues of sequences were visually inspected for sequences that one might predict would bind to PDZ-domain containing proteins (see, e.g., Doyle et al., 1996, *Cell* 85, 1067; Songyang et al., 1997, *Science* 275, 73), including the additional consensus for PLs identified at Arbor Vita Corporation (U.S. patent application Ser. No. 60/360061). TABLE 3 lists some of these proteins, and provides corresponding C-terminal sequences.

Synthetic peptides of defined sequence (e.g., corresponding to the carboxyl-termini of the indicated proteins) can be synthesized by any standard resin-based method (see, e.g., U.S. Pat. No. 4,108,846; see also, Caruthers et al., 1980, *Nucleic Acids Res. Symp. Ser.,* 215-223; Horn et al., 1980, *Nucleic Acids Res. Symp. Ser.,* 225-232; Roberge, et al., 1995, *Science* 269:202). The peptides used in the assays described herein were prepared by the FMOC (see, e.g., Guy and Fields, 1997, *Meth. Enz.* 289:67-83; Wellings and Atherton, 1997, *Meth. Enz.* 289:44-67). In some cases (e.g., for use in the A and G assays of the invention), peptides were labeled with biotin at the amino-terminus by reaction with a four-fold excess of biotin methyl ester in dimethylsulfoxide with a catalytic amount of base. The peptides were cleaved from the resin using a halide containing acid (e.g. trifluoroacetic acid) in the presence of appropriate antioxidants (e.g. ethanedithiol) and excess solvent lyophilized.

Following lyophilization, peptides can be redissolved and purified by reverse phase high performance liquid chromatography (HPLC). One appropriate HPLC solvent system involves a Vydac C-18 semi-preparative column running at 5 mL per minute with increasing quantities of acetonitrile plus 0.1% trifluoroacetic acid in a base solvent of water plus 0.1% trifluoroacetic acid. After HPLC purification, the identities of the peptides are confirmed by MALDI cation-mode mass spectrometry.

C. Detecting PDZ-PL Interactions

The present inventors were able in part to identify the interactions summarized in TABLE 4 by developing new high throughput screening assays which are described in greater detail infra. Various other assay formats known in the art can be used to select ligands that are specifically reactive with a particular protein. For example, solid-phase ELISA immunoassays, immunoprecipitation, Biacore, and Western blot assays can be used to identify peptides that specifically bind PDZ-domain polypeptides. As discussed supra, two different, complementary assays were developed to detect PDZ-PL interactions. In each, one binding partner of a PDZ-PL pair is immobilized, and the ability of the second binding partner to bind is determined. These assays, which are described infra, can be readily used to screen for hundreds to thousands of potential PDZ-ligand interactions in a few hours. Thus these assays can be used to identify yet more novel PDZ-PL interactions in cells. In addition, they can be used to identify antagonists of PDZ-PL interactions (see infra).

In various embodiments, fusion proteins are used in the assays and devices of the invention. Methods for constructing and expressing fusion proteins are well known. Fusion proteins generally are described in Ausubel et al., supra, Kroll et al., 1993, DNA Cell. Biol. 12:441, and Imai et al., 1997, Cell 91:521-30. Usually, the fusion protein includes a domain to facilitate immobilization of the protein to a solid substrate ("an immobilization domain"). Often, the immobilization domain includes an epitope tag (i.e., a sequence recognized by an antibody, typically a monoclonal antibody) such as polyhistidine (Bush et al, 1991, *J. Biol Chem* 266:13811-14), SEAP (Berger et al, 1988, *Gene* 66: 1-10), or M1 and M2 flag (see, e.g, U.S. Pat. Nos. 5,011,912; 4,851,341; 4,703,004; 4,782,137). In an embodiment, the immobilization domain is a GST coding region. It will be recognized that, in addition to the PDZ-domain and the particular residues bound by an immobilized antibody, protein A, or otherwise contacted with the surface, the protein (e.g., fusion protein), will contain additional residues. In some embodiments these are residues naturally associated with the PDZ-domain (i.e., in a particular PDZ-protein) but they may include residues of synthetic (e.g., poly(alanine)) or heterologous origin (e.g., spacers of, e.g., between 10 and 300 residues).

PDZ domain-containing polypeptide used in the methods of the invention (e.g., PDZ fusion proteins) of the invention are typically made by (1) constructing a vector (e.g., plasmid, phage or phagemid) comprising a polynucleotide sequence encoding the desired polypeptide, (2) introducing the vector into an suitable expression system (e.g., a prokaryotic, insect, mammalian, or cell free expression system), (3) expressing the fusion protein and (4) optionally purifying the fusion protein.

(1) In one embodiment, expression of the protein comprises inserting the coding sequence into an appropriate expression vector (i.e., a vector that contains the necessary elements for the transcription and translation of the inserted coding sequence required for the expression system employed, e.g., control elements including enhancers, promoters, transcription terminators, origins of replication, a suitable initiation codon (e.g., methionine), open reading frame, and translational regulatory signals (e.g., a ribosome binding site, a termination codon and a polyadenylation sequence. Depending on the vector system and host utilized, any number of suitable transcription and translation elements, including constitutive and inducible promoters, can be used.

The coding sequence of the fusion protein includes a PDZ domain and an immobilization domain as described elsewhere herein. Polynucleotides encoding the amino acid sequence for each domain can be obtained in a variety of ways known in the art; typically the polynucleotides are obtained by PCR amplification of cloned plasmids, cDNA libraries, and cDNA generated by reverse transcription of RNA, using primers designed based on sequences determined by the practitioner or, more often, publicly available (e.g., through GenBank). The primers include linker regions (e.g., sequences including restriction sites) to facilitate cloning and manipulation in production of the fusion construct. The polynucleotides corresponding to the PDZ and immobilization regions are joined in-frame to produce the fusion protein-encoding sequence.

The fusion proteins of the invention may be expressed as secreted proteins (e.g., by including the signal sequence encoding DNA in the fusion gene; see, e.g., Lui et al, 1993, *PNAS USA*, 90:8957-61) or as nonsecreted proteins.

In some embodiments, the PDZ-containing proteins or PL polypeptides are immobilized on a solid surface. The substrate to which the polypeptide is bound may in any of a variety of forms, e.g., a microtiter dish, a test tube, a dipstick, a microcentrifuge tube, a bead, a spinnable disk, a permeable or semi-permeable membrane, and the like. Suitable materials include glass, plastic (e.g., polyethylene, PVC, polypropylene, polystyrene, and the like), protein, paper, carbohydrate, lipid monolayer or supported lipid bilayer, films and other solid supports. Other materials that may be employed include ceramics, metals, metalloids, semiconductive materials, cements and the like.

In some embodiments, the PDZ and/or PL fusion proteins are organized as an array. The term "array," as used herein, refers to an ordered arrangement of immobilized fusion proteins, in which particular different fusion proteins (i.e., having different PDZ domains) are located at different predetermined sites on the substrate. Because the location of particular fusion proteins on the array is known, binding at that location can be correlated with binding to the PDZ domain situated at that location. Immobilization of fusion proteins on beads (individually or in groups) is another particularly useful approach. In one embodiment, individual fusion proteins are immobilized on beads. In one embodiment, mixtures of distinguishable beads are used. Distinguishable beads are beads that can be separated from each other on the basis of a property such as size, magnetic property, color (e.g., using FACS) or affinity tag (e.g., a bead coated with protein A can be separated from a bead not coated with protein A by using IgG affinity methods). Binding to particular PDZ domain may be determined.

Methods for immobilizing proteins are known, and include covalent and non-covalent methods. One suitable immobilization method is antibody-mediated immobilization. According to this method, an antibody specific for the sequence of an "immobilization domain" of the PDZ-domain containing protein is itself immobilized on the substrate (e.g., by adsorption). One advantage of this approach is that a single antibody may be adhered to the substrate and used for immobilization of a number of polypeptides (sharing the same immobilization domain). For example, an immobilization domain consisting of poly-histidine (Bush et al, 1991, *J. Biol Chem* 266:13811-14) can be bound by an anti-histidine monoclonal antibody (R&D Systems, Minneapolis, Minn.); an immobilization domain consisting of secreted alkaline phosphatase ("SEAP") (Berger et al, 1988, *Gene* 66:1-10) can be bound by anti-SEAP (Sigma Chemical Company, St. Louis, Mo.); an immobilization domain consisting of a FLAG epitope can be bound by anti-FLAG. Other ligand-antiligand immobilization methods are also suitable (e.g., an immobilization domain consisting of protein A sequences (Harlow and Lane, 1988, Antibodies A Laboratory Manual, Cold Spring Harbor Laboratory; Sigma Chemical Co., St. Louis, Mo.) can be bound by IgG; and an immobilization domain consisting of streptavidin can be bound by biotin (Harlow & Lane, supra; Sigma Chemical Co., St. Louis, Mo.). In a preferred embodiment, the immobilization domain is a GST moiety, as described herein.

When antibody-mediated immobilization methods are used, glass and plastic are especially useful substrates. The substrates may be printed with a hydrophobic (e.g., Teflon) mask to form wells. Preprinted glass slides with 3, 10 and 21 wells per 14.5 cm$^2$ slide "working area" are available from, e.g., SPI Supplies, West Chester, Pa.; also see U.S. Pat. No. 4,011,350). In certain applications, a large format (12.4 cm×8.3 cm) glass slide is printed in a 96 well format is used; this format facilitates the use of automated liquid handling equipment and utilization of 96 well format plate readers of various types (fluorescent, colorimetric, scintillation). However, higher densities may be used (e.g., more than 10 or 100 polypeptides per cm$^2$). See, e.g., MacBeath et al, 2000, *Science* 289:1760-63.

Typically, antibodies are bound to substrates (e.g., glass substrates) by adsorption. Suitable adsorption conditions are well known in the art and include incubation of 0.5-50 ug/ml (e.g., 10 ug/ml) mAb in buffer (e.g., PBS, or 50 to 300 mM Tris, MOPS, HEPES, PIPES, acetate buffers, pHs 6.5 to 8, at 4° C.) to 37° C. and from 1hr to more than 24 hours.

Proteins may be covalently bound or noncovalently attached through nonspecific bonding. If covalent bonding between the fusion protein and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

Exemplary assays are provided below.

"A Assay" Detection of PDZ-Ligand Binding Using Immobilized PL Peptide.

In one aspect, the invention provides an assay in which biotinylated candidate PL peptides are immobilized on an avidin-coated surface. The binding of PDZ-domain fusion protein to this surface is then measured. In a preferred embodiment, the PDZ-domain fusion protein is a GST/PDZ fusion protein and the assay is carried out as follows:

(1) Avidin is bound to a surface, e.g. a protein binding surface. In one embodiment, avidin is bound to a polystyrene 96 well plate (e.g., Nunc Polysorb (cat #475094) by addition of 100 uL per well of 20 ug/mL of avidin (Pierce) in phosphate buffered saline without calcium and magnesium, pH 7.4 ("PBS", GibcoBRL) at 4° C. for 12 hours. The plate is then treated to block nonspecific interactions by addition of 200 uL per well of PBS containing 2 g per 100 mL protease-free bovine serum albumin ("PBS/BSA") for 2 hours at 4° C. The plate is then washed 3 times with PBS by repeatedly adding 200 uL per well of PBS to each well of the, plate and then dumping the contents of the plate into a waste container and tapping the plate gently on a dry surface.

(2) Biotinylated PL peptides (or candidate PL peptides, e.g. see TABLE 3) are immobilized on the surface of wells of the plate by addition of 50 uL per well of 0.4 uM peptide in PBS/BSA for 30 minutes at 4° C. Usually, each different peptide is added to at least eight different wells so that multiple measurements (e.g. duplicates and also measurements using different (GST/PDZ-domain fusion proteins and a GST alone negative control) can be made, and also additional negative control wells are prepared in which no peptide is immobilized. Following immobilization of the PL peptide on the surface, the plate is washed 3 times with PBS.

(3) GST/PDZ-domain fusion protein (prepared as described stpra) is allowed to react with the surface by addition of 50 uL per well of a solution containing 5 ug/mL GST/PDZ-domain fusion protein in PBS/BSA for 2 hours at 4° C. As a negative control, GST alone (i.e. not a fusion protein) is added to specified wells, generally at least 2 wells (i.e. duplicate measurements) for each immobilized peptide. After the 2 hour reaction, the plate is washed 3 times with PBS to remove unbound fusion protein.

(4) The binding of the GST/PDZ-domain fusion protein to the avidin-biotinylated peptide surface can be detected using a variety of methods, and detectors known in the art. In one embodiment, 50 uL per well of an anti-GST antibody in PBS/BSA (e.g. 2.5 ug/mL of polyclonal goat-anti-GST antibody, Pierce) is added to the plate and allowed to react for 20 minutes at 4° C. The plate is washed 3 times with PBS and a second, detectably labeled antibody is added. In one embodiment, 50 uL per well of 2.5 ug/mL of horseradish peroxidase (HRP)-conjugated polyclonal rabbit anti-goat immunoglobulin antibody is added to the plate and allowed to react for 20 minutes at 4° C. The plate is washed 5 times with 50 mM Tris pH 8.0 containing 0.2% Tween 20, and developed by addition of 100 uL per well of HRP-substrate solution (TMB, Dako) for 20 minutes at room temperature (RT). The reaction of the HRP and its substrate is terminated by the addition of 100 uL per well of IM sulfuric acid and the absorbance (A) of each well of the plate is read at 450 nm.

(5) Specific binding of a PL peptide and a PDZ-domain polypeptide is detected by comparing the signal from the well(s) in which the PL peptide and PDZ domain polypeptide are combined with the background signal(s). The background signal is the signal found in the negative controls. Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value <0.05, more typically a p-value <0.01, and most typically a p-value <0.001 or less.

As noted, in an embodiment of the "A" assay, the signal from binding of a GST/PDZ-domain fusion protein to an avidin surface not exposed to (i.e. not covered with) the PL peptide is one suitable negative control (sometimes referred to as "B"). The signal from binding of GST polypeptide alone (i.e. not a fusion protein) to an avidin-coated surface that has been exposed to (i.e. covered with) the PL peptide is a second suitable negative control (sometimes referred to as "B2"). Because all measurements are done in multiples (i.e. at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the plate-bound PL peptide is determined by comparing the mean signal ("mean S") and standard error of the signal ("SE") for a particular PL-PDZ combination with the mean B1 and/or mean B2.

"G Assay"—Detection of PDZ-Ligand Binding Using Immobilized PDZ-Domain Fusion Polypeptide In one aspect, the invention provides an assay in which a GST/PDZ fusion protein is immobilized on a surface ("G" assay). The binding of labeled PL peptide (e.g., as listed in TABLE 3) to this surface is then measured. In a preferred embodiment, the assay is carried out as follows:

(1) A PDZ-domain polypeptide is bound to a surface, e.g. a protein binding surface. In a preferred embodiment, a GST/PDZ fusion protein containing one or more PDZ domains is bound to a polystyrene 96-well plate. The GST/PDZ fusion protein can be bound to the plate by any of a variety of standard methods known to one of skill in the art, although some care must be taken that the process of binding the fusion protein to the plate does not alter the ligand-binding properties of the PDZ domain. In one embodiment, the GST/PDZ fusion protein is bound via an anti-GST antibody that is coated onto the 96-well plate. Adequate binding to the plate can be achieved when:

a. 100 uL per well of 5 ug/mL goat anti-GST polyclonal antibody (Pierce) in PBS is added to a polystyrene 96-well plate (e.g., Nunc Polysorb) at 4° C. for 12 hours.

b. The plate is blocked by addition of 200 uL per well of PBS/BSA for 2 hours at 4° C.

c. The plate is washed 3 times with PBS.

d. 50 uL per well of 5 ug/mL GST/PDZ fusion protein) or, as a negative control, GST polypeptide alone (i.e. not a fusion protein) in PBS/BSA is added to the plate for 2 hours at 4° C.

e. The plate is again washed 3 times with PBS.

(2) Biotinylated PL peptides are allowed to react with the surface by addition of 50 uL per well of 20 uM solution of the biotinylated peptide in PBS/BSA for 10 minutes at 4° C., followed by an additional 20 minute incubation at 25° C. The plate is washed 3 times with ice cold PBS.

(3) The binding of the biotinylated peptide to the GST/PDZ fusion protein surface can be detected using a variety of methods and detectors known to one of skill in the art. In one embodiment, 100 uL per well of 0.5 ug/mL streptavidin-horse radish peroxidase (HRP) conjugate dissolved in BSA/PBS is added and allowed to react for 20 minutes at 4° C. The plate is then washed 5 times with 50 mM Tris pH 8.0 containing 0.2% Tween 20, and developed by addition of 100 uL per well of HRP-substrate solution (TMB, Dako) for 20 minutes at room temperature (RT). The reaction of the HRP and its substrate is terminated by addition of 100 uL per well of 1M sulfuric acid, and the absorbance of each well of the plate is read at 450 nm.

(4) Specific binding of a PL peptide and a PDZ domain polypeptide is determined by comparing the signal from the well(s) in which the PL peptide and PDZ domain polypeptide are combined, with the background signal(s). The background signal is the signal found in the negative control(s). Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with —repeated measurements of the background will result in a p-value <0.05, more typically a p-value <0.01, and most typically a p-value <0.001 or less. As noted, in an embodiment of the "G" assay, the signal from binding of a given PL peptide to immobilized (surface bound) GST polypeptide alone is one suitable negative control (sometimes referred to as "B 1"). Because all measurement are done in multiples (i.e. at least duplicate) the arithmetic mean (or, equivalently, average.) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the platebound peptide is determined by comparing the mean signal ("mean S") and standard error of the signal ("SE") for a particular PL-PDZ combination with the mean B1.

"G' assay" and "G" assay"

Two specific modifications of the specific conditions described supra for the "G assay" are particularly useful. The modified assays use lesser quantities of labeled PL peptide and have slightly different biochemical requirements for detection of PDZ-ligand binding compared to the specific assay conditions described supra.

For convenience, the assay conditions described in this section are referred to as the "G' assay" and the "G" assay," with the specific conditions described in the preceding section on G assays being referred to as the "$G^0$ assay." The "G' assay" is identical to the "$G^0$ assay" except at step (2) the peptide concentration is 10 uM instead of 20 uM. This results in slightly lower sensitivity for detection of interactions with low affinity and/or rapid dissociation rate. Correspondingly, it slightly increases the certainty that detected interactions are of sufficient affinity and half-life to be of biological importance and useful therapeutic targets.

The "G" assay" is identical to the "$G^0$ assay" except that at step (2) the peptide concentration is 1 uM instead of 20 uM and the incubation is performed for 60 minutes at 25° C. (rather than, e.g., 10 minutes at 4° C. followed by 20 minutes at 25° C.). This results in lower sensitivity for interactions of low affinity, rapid dissociation rate, and/or affinity that is less at 25° C. than at 4° C. Interactions will have lower affinity at 25° C. than at 4° C. if (as we have found to be generally true for PDZ-ligand binding) the reaction entropy is negative (i.e. the entropy of the products is less than the entropy of the reactants). In contrast, the PDZ-PL binding signal may be similar in the "G" assay" and the "$G^0$ assay" for interactions of slow association and dissociation rate, as the PDZ-PL complex will accumulate during the longer incubation of the "G" assay." Thus comparison of results of the "G" assay" and the "$G^0$ assay" can be used to estimate the relative entropies, enthalpies, and kinetics of different PDZ-PL interactions. (Entropies and enthalpies are related to binding affinity by the equations delta G=RT 1 n (Kd)=delta H—T delta S where delta G, H, and S are the reaction free energy, enthalpy, and entropy respectively, T is the temperature in degrees Kelvin, R is the gas constant, and Kd is the equilibrium dissociation constant). In particular, interactions that are detected only or much more strongly in the "$G^0$ assay" generally have a rapid dissociation rate at 25° C. (t½<10 minutes) and a negative reaction entropy, while interactions that are detected similarly strongly in the "G" assay" generally have a slower dissociation rate at 25° C. (t½>10 minutes). Rough estimation of the thermodynamics and kinetics of PDZ-PL interactions (as can be achieved via comparison of results of the "$G^0$ assay" versus the "G" assay" as outlined supra) can be used in the design of efficient inhibitors of the interactions. For example, a small molecule inhibitor based on the chemical structure of a PL that dissociates slowly from a given PDZ domain (as evidenced by similar binding in the "G" assay" as in the "$G^0$ assay") may itself dissociate slowly and thus be of high affinity.

In this manner, variation of the temperature and duration of step (2) of the "G assay" can be used to provide insight into the kinetics and thermodynamics of the PDZ-ligand binding reaction and into design of inhibitors of the reaction.

Assay Variations

As discussed supra, it will be appreciated that many of the steps in the above-described assays can be varied, for example, various substrates can be used for binding the PL and PDZ-containing proteins; different types of PDZ containing fusion proteins can be used; different labels for detecting PDZ/PL interactions can be employed; and different ways of detection can be used.

The PDZ-PL detection assays can employ a variety of surfaces to bind the PL and/or PDZ-contaning proteins. For example, a surface can be an "assay plate" which is formed from a material (e.g. polystyrene) which optimizes adherence of either the PL protein or PDZ-containing protein thereto. Generally, the individual wells of the assay plate will have a high surface area to volume ratio and therefore a suitable shape is a flat bottom well (where the proteins of the assays are adherent). Other surfaces include, but are not limited to, polystyrene or glass beads, polystyrene or glass slides, papers, dipsticks, plastics, films and the like.

For example, the assay plate can be a "microtiter" plate. The term "microtiter" plate when used herein refers to a multiwell assay plate, e.g., having between about 30 to 200 individual wells, usually 96 wells. Alternatively, high-density arrays can be used. Often, the individual wells of the microtiter plate will hold a maximum volume of about 250 ul. Conveniently, the assay plate is a 96 well polystyrene plate (such as that sold by Becton Dickinson Labware, Lincoln Park, N.J.), which allows for automation and high throughput screening. Other surfaces include polystyrene microtiter ELISA plates such as that sold by Nunc Maxisorp, Inter Med, Denmark. Often, about 50 ul to 300 ul, more preferably 100 ul to 200 ul, of an aqueous sample comprising buffers suspended therein will be added to each well of the assay plate.

The detectable labels of the invention can be any detectable compound or composition which is conjugated directly or indirectly with a molecule (such as described above). The label can be detectable by itself (e.g., radioisotope labels or fluorescent labels) or, in the case of an enzymatic label, can catalyze a chemical alteration of a substrate compound or composition which is detectable. The preferred label is an enzymatic one which catalyzes a color change of a non-radioactive color reagent.

Sometimes, the label is indirectly conjugated with the antibody. One of skill is aware of various techniques for direct and indirect conjugation. For example, the antibody can be conjugated with biotin and any of the categories of labels mentioned above can be conjugated with avidin, or vice versa (see also "A" and "G" assay above). Biotin binds selectively to avidin and thus, the label can be conjugated with the antibody in this indirect manner. See, Au subel, supra, for a review of techniques involving biotin-avidin conjugation and similar assays. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

Assay variations can include different washing steps. By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or HRP antibody) is removed therefrom. To reduce background noise, it is convenient to include a detergent (e.g., Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) can be required.

Various buffers can also be used in PDZ-PL detection assays. For example, various blocking buffers can be used to reduce assay background. The term "blocking buffer" refers to an aqueous, pH buffered solution containing at least one blocking compound which is able to bind to exposed surfaces of the substrate which are not coated with a PL or PDZ-containing protein. The blocking compound is normally a protein such as bovine serum albumin (BSA), gelatin, casein or milk powder and does not cross-react with any of the reagents in the assay. The block buffer is generally provided at a pH between about 7 to 7.5 and suitable buffering agents include phosphate and TRIS.

Various enzyme-substrate combinations can also be utilized in detecting PDZ-PL interactions. Examples of enzyme-substrate combinations include, for example:

(i) Horseradish peroxidase (HRP or HRPO) with hydrogen peroxidase as a substrate, wherein the hydrogen peroxidase oxidizes a dye precursor (e.g. orthophenylene diamine [OPD] or 3,3',5,5'-tetramethyl benzidine hydrochloride [TMB]) (as described above).

(ii) alkaline phosphatase (AP) with para-Nitrophenyl phosphate as chromogenic substrate.

(iii) Beta-D-galactosidase (Beta D-Gal) with a chromogenic substrate (e.g. p-nitrophenyl-Beta-D-galactosidase) or fluorogenic substrate 4-methylumbelliferyl-Beta-D-galactosidase.

Numerous other enzyme-substrate combinations are available to those skilled in the art. For a general review of these, see U.S. Pat. Nos. 4,275,149 and 4,318,980, both of which are herein incorporated by reference.

Further, it will be appreciated that, although, for convenience, the present discussion primarily refers to detection of PDZ-PL interactions, agonists or antagonists of PDZ-PL interactions can be used to diagnose cellular abnormalities.

V. Collection of Tissue Samples Such as Cervical Tissues

Diagnosing the presence of pathogens requires collection of samples appropriate to the organism. For detection of oncogenic HPV E6 proteins, one would collect tissue for testing from the cervix, penis, anus, or throat using a scrape, swab or biopsy technique. For diagnosis of bloodborne pathogens such as HIV, collection of blood through standard means would be most appropriate. Diagnosis of fungal or viral infections that may have caused skin lesions would require the collection of a sample from the affected area.

This invention is not intended to cover sampling devices. However, it should be noted that since the invention is predicated on the detection of PDZ or PL proteins, appropriate care must be taken to collect a sufficient amount of sample to detect pathogen proteins and to maintain the integrity of proteins in the sample. The amount of sample to collect should be determined empirically for each diagnostic test. Factors in the decision may include, but not be limited to, the stage at which detection is desired, the amount of pathogen per unit sample, the amount of diagnostic protein per unit per unit sample, availability of diagnostic epitopes and the stability of diagnostic epitopes.

Exemplary collection devices for cervical tissue include, but are not limited to, those described in U.S. Pat. Nos. 6,241,687, 6,352,513, 6,336,905, 6,115,990 and 6,346,086. These collection devices would facilitate the collection of cervical tissue for the diagnosis of oncogenic human *papillomavirus* infection. These devices are predominantly collection of cervical cells or tissues through scraping; alternatively, one could use standard biopsy methods to collect samples from any tissues to be examined.

Although the diagnostic method disclosed in this application is directed at the detection of PL proteins, sample collection need not be limited to collection of proteins. One could alternatively collect RNA from tissue samples, use an in vitro translation kit to produce protein from collected templates, and then assay using methods disclosed herein. In a similar manner, DNA could be collected from test samples, specific primers for oncogenic E6 proteins could be used to either amplify the DNA content (using a DNA polymerase) or transcribe and translate the sample into proteins that could be tested with methods disclosed herein.

VI. Assays for Detecting Oncogenic E6 Proteins

Oncogenic E6 proteins can be detected by their ability to bind to PDZ domains. This could be a developed into a single detection stage approach or more favorably as a two-stage or 'sandwich' approach for increased sensitivity and specificity.

For single stage approaches, a 'tagged' version of a PDZ domain that specifically recognizes oncogenic E6 proteins, such as those disclosed in TABLES 3 and 4, can be used to directly probe for the presence of oncogenic E6 protein in a sample. As noted supra, an example of this would be to attach the test sample to a solid support (for example, cervical cells or tissue could be coated on a slide and 'fixed' to permeablize the cell membranes), incubate the sample with a tagged 'PL detector' protein (a PDZ domain fusion) under appropriate conditions, wash away unbound PL detector, and assay for the presence of the 'tag' in the sample. In addition, even without a tag, one could measure the physical properties of the PDZ protein and the PDZ protein bound to and E6 protein. Techniques such as surface plasmon resonance, circular dichoism, and other techniques that directly assess binding could be used to detect the presence of oncogenic E6 proteins. One should note, however, that PDZ domains may also bind endogenous cellular proteins. Thus, frequency of binding must be compared to control cells that do not contain E6 oncoproteins or the 'PL detector' should be modified such that it is significantly more specific for the oncogenic E6 proteins (see section X).

For two-stage or sandwich approaches, use of the PL detector is coupled with a second method of either capturing or detecting captured proteins. The second method could be using an antibody that binds to the E6 oncoprotein or a second compound or protein that can bind to E6 oncorproteins at a location on the E6 protein that does not reduce the availability of the E6 PL. Such proteins may include, but not be limited to, p53, E6-AP, E6-BP or engineered compounds that bind E6 oncoproteins. Alternatively, one could also use DNA binding or Zn2+ binding to assay for the presence of captured E6 protein, since oncogenic E6 proteins are known to bind certain DNA structures through the use of divalent cations. Additionally, one could use the PDZ-captured E6 protein in an activity assay, since E6 is known to degrade DNA and certain proteins including p53 in the presence of a reticulocyte lysate.

Antibodies

Many biological assays are designed as a 'sandwich', where an antibody constitutes one side of the sandwich. This method can improve the signal to noise ratio for a diagnostic by reducing background signal and amplifying appropriate signals. Antibodies can be generated that specifically recognize the diagnostic protein. Since this invention discloses the method of using PDZ or PL proteins to diagnose pathogen infections, antibodies should be generated that do not conflict with the PDZ:PL interaction.

For the production of antibodies, various host animals, including but not limited to rabbits, mice, rats, etc., may be immunized by injection with a peptide. The peptide may be attached to a suitable carrier, such as BSA or KLH, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, Nature 256:495-497, the human B-cell hybridoma technique, Kosbor et al., 1983, Immunology Today 4:72; Cote et al., 1983, Proc. Natl. Acad. Sci. U.S.A. 80:2026-2030 and the EBV-hybridoma technique (Cole et al., 1985, Monoclonal Antibodies and Cancer Therapy, Alan R. Liss, Inc., pp. 77-96 (1985)). In addition, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce peptide-specific single chain antibodies.

Antibody fragments which contain deletions of specific binding sites may be generated by known techniques. For example, such fragments include but are not limited to $F(ab')_2$ fragments, which can be produced by pepsin digestion of the antibody molecule and Fab fragments, which can be generated by reducing the disulfide bridges of the $F(ab')_2$ fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, Protein Purification: Principles and Practice, Springer-Verlag New York, Inc., N.Y., Livingstone, 1974, Methods Enzymology: Immunoaffmity Chromatography of Proteins 34:723-731. Antibodies can also be linked to other solid supports for diagnostic applications, or alternatively labeled with a means of detection such an enzyme that can cleave a colorimetric substrate, a fluorophore, a magnetic particle, or other measurable compositions of matter.

Specific antibodies against E6 proteins have historically been difficult to produce. In conjunction with the methods describe supra, one could employ a number of techniques to increase the likelihood of producing or selecting high affinity antibodies. An example is to prepare the E6 antigen (to raise antibodies against) in the same manner that one would prepare tissue or cell samples for testing. Alternatively, one could immunize with E6 fusion protein prepared in one manner, and screen for specific E6 antibodies using a second E6 protein prepared in a different manner. This should select for antibodies that recognize E6 epitopes that are conserved under different sample collection and preparation procedures. In another example, one could immunize animals with E6 antigen that has been rapidly denatured and renatured, such that epitopes that are insensitive to preparation conditions are selected for. Another method that could be employed is to use peptides corresponding to antigenic regions of the E6 proteins as predicted by Major Histocompatibility Complex (MHC) and T Cell Receptor (TCR) consensus binding.

2. Alternative Detection Methods for Captured E6 Protein

E6 proteins that have been captured by PDZ domains could be detected by several alternative methods. Several proteins are known to associate with E6 proteins. Any of them that had a reasonable affinity for E6 could be used to detect the presence of captured and concentrated E6 protein in a sample by one skilled in the art. In addition, new binding proteins or aptamers could be identified that bound to E6 proteins. Third, activity assays specific for E6 could be employed.

The detection assay itself could also be carried out using a variety of methods. A standard ELISA using a PDZ to capture could be set up as a competition, where the PDZ domain is pre-loaded with a labeled PL that has lower affinity than the E6 proteins. Thus, in the presence of E6, the label is displaced and one sees a reduction of signal that corresponds to E6 presence. Other variants that use aspects of competition and inhibition of binding are intended to be included as well. One variant could even have the PL covalently attached to the PDZ domain through a linker such that the PL could bind it's own PDZ domain. Using donor quenching dyes, one would only see an increase in signal when the PL of an oncogenic E6 protein was able to displace the labeled PL. All such competition methods must be measured against controls that assess the amount of endogenous PL proteins that can bind the PDZ domain used to assess the presence of oncogenic E6 proteins.

VIII. Measurements of Assay Sensitivity

The "A" and "G" assays of the invention can be used to determine the "apparent affinity" of binding of a PDZ ligand peptide to a PDZ-domain polypeptide. Apparent affinity is determined based on the concentration of one molecule required to saturate the binding of a second molecule (e.g., the binding of a ligand to a receptor). Two particularly useful approaches for quantitation of apparent affinity of PDZ-ligand binding are provided infra. These methods can be used to compare the sensitivity and affinity of differing PL detector constructs. Understanding the sensitivity of the PDZ for pathogen PLs is essential because it helps to define the amount of tissue or cell sample that must be tested to obtain a definitive result.

(1) A GST/PDZ fusion protein, as well as GST alone as a negative control, are bound to a surface (e.g., a 96-well plate) and the surface blocked and washed as described supra for the "G" assay.

(2) 50 uL per well of a solution of biotinylated PL peptide (e.g. as shown in TABLE 3) is added to the surface in increasing concentrations in PBS/BSA (e.g. at 0.1 uM, 0.33 uM, 1 uM, 3.3 uM, 10 uM, 33 uM, and 100 uM). In one embodiment, the PL peptide is allowed to react with the bound GST/PDZ fusion protein (as well as the GST alone negative control) for 10 minutes at 4° C. followed by 20 minutes at 25° C. The plate is washed 3 times with ice cold PBS to remove unbound labeled peptide.

(3) The binding of the PL peptide to the immobilized PDZ-domain polypeptide is detected as described supra for the "G" assay.

(4) For each concentration of peptide, the net binding signal is determined by subtracting the binding of the peptide to GST alone from the binding of the peptide to the GST/PDZ fusion protein. The net binding signal is then plotted as a function of ligand concentration and the plot is fit (e.g. by using the Kaleidagraph software package curve fitting algorithm; Synergy Software) to the following equation, where "Signal$_{[ligand]}$" is the net binding signal at PL peptide concentration "[ligand]," "Kd" is the apparent affinity of the binding event, and "Saturation Binding" is a constant determined by the curve fitting algorithm to optimize the fit to the experimental data:

Signal$_{[ligand]}$=Saturation Binding×([ligand]/([ligand]+ Kd))

For reliable application of the above equation it is necessary that the highest peptide ligand concentration successfully tested experimentally be greater than, or at least similar to, the calculated Kd (equivalently, the maximum observed binding should be similar to the calculated saturation binding). In cases where satisfying the above criteria proves difficult, an alternative approach (infra) can be used.

Approach 2:

(1) A fixed concentration of a PDZ-domain polypeptide and increasing concentrations of a labeled PL peptide (labeled with, for example, biotin or fluorescein, see TABLE 3 for representative peptide amino acid sequences) are mixed together in solution and allowed to react. In one embodiment, preferred peptide concentrations are 0.1 uM, 1 uM, 10 uM, 100 uM, 1 mM. In various embodiments, appropriate reaction times can range from 10 minutes to 2 days at temperatures ranging from 4° C. to 37° C. In some embodiments, the identical reaction can also be carried out using a non-PDZ domain-containing protein as a control (e.g., if the PDZ-domain polypeptide is fusion protein, the fusion partner can be used).

(2) PDZ-ligand complexes can be separated from unbound labeled peptide using a variety of methods known in the art. For example, the complexes can be separated using high performance size-exclusion chromatography (HPSEC, gel filtration) (Rabinowitz et al., 1998, Immunity 9:699), affinity chromatography(e.g. using glutathione Sepharose beads), and affinity absorption (e.g., by binding to an anti-GST-coated plate as described supra).

(3) The PDZ-ligand complex is detected based on presence of the label on the peptide ligand using a variety of methods and detectors known to one of skill in the art. For example, if the label is fluorescein and the separation is achieved using HPSEC, an in-line fluorescence detector can be used. The binding can also be detected as described supra for the G assay.

(4) The PDZ-ligand binding signal is plotted as a function of ligand concentration and the plot is fit. (e.g., by using the Kaleidagraph software package curve fitting algorithm) to the following equation, where "Signal$_{[ligand]}$" is the binding signal at PL peptide concentration "[ligand]," "Kd" is the apparent affinity of the binding event, and "Saturation Binding" is a constant determined by the curve fitting algorithm to optimize the fit to the experimental data:

$$\text{Signal}_{[Ligand]} = \text{Saturation Binding} \times ([ligand]/([ligand]+Kd]))$$

Measurement of the affinity of a labeled peptide ligand binding to a PDZ-domain polypeptide is useful because knowledge of the affinity (or apparent affinity) of this interaction allows rational design of inhibitors of the interaction with known potency. The potency of inhibitors in inhibition would be similar to (i.e. within one-order of magnitude of) the apparent affinity of the labeled peptide ligand binding to the PDZ-domain.

Thus, in one aspect, the invention provides a method of determining the apparent affinity of binding between a PDZ domain and a ligand by immobilizing a polypeptide comprising the PDZ domain and a non-PDZ domain on a surface, contacting the immobilized polypeptide with a plurality of different concentrations of the ligand, determining the amount of binding of the ligand to the immobilized polypeptide at each of the concentrations of ligand, and calculating the apparent affinity of the binding based on that data. Typically, the polypeptide comprising the PDZ domain and a non-PDZ domain is a fusion protein. In one embodiment, the e.g., fusion protein is GST-PDZ fusion protein, but other polypeptides can also be used (e.g., a fusion protein including a PDZ domain and any of a variety of epitope tags, biotinylation signals and the like) so long as the polypeptide can be immobilized In an orientation that does not abolish the ligand binding properties of the PDZ domain, e.g, by tethering the polypeptide to the surface via the non-PDZ domain via an anti-domain antibody and leaving the PDZ domain as the free end. It was discovered, for example, reacting a PDZ-GST fusion polypeptide directly to a plastic plate provided suboptimal results. The calculation of binding affinity itself can be determined using any suitable equation (e.g., as shown supra; also see Cantor and Schimmel (1980) BIOPHYSICAL CHEMISTRY W H Freeman & Co., San Francisco) or software.

Thus, in a preferred embodiment, the polypeptide is immobilized by binding the polypeptide to an immobilized immunoglobulin that binds the non-PDZ domain (e.g., an anti-GST antibody when a GST-PDZ fusion polypeptide is used). In a preferred embodiment, the step of contacting the ligand and PDZ-domain polypeptide is carried out under the conditions provided supra in the description of the "G" assay. It will be appreciated that binding assays are conveniently carried out in multiwell plates (e.g., 24-well, 96-well plates, or 384 well plates).

The present method has considerable advantages over other methods for measuring binding affinities PDZ-PL affinities, which typically involve contacting varying concentrations of a GST-PDZ fusion protein to a ligand-coated surface. For example, some previously described methods for determining affinity (e.g., using immobilized ligand and GST-PDZ protein in solution) did not account for oligomerization state of the fusion proteins used, resulting in potential errors of more than an order of magnitude.

Although not sufficient for quantitative measurement of PDZ-PL binding affinity, an estimate of the relative strength of binding of different PDZ-PL pairs can be made based on the absolute magnitude of the signals observed in the "G assay." This estimate will reflect several factors, including biologically relevant aspects of the interaction, including the affinity and the dissociation rate. For comparisons of different ligands binding to a given PDZ domain-containing protein, differences in absolute binding signal likely relate primarily to the affinity and/or dissociation rate of the interactions of interest.

IX. Measurements of Assay Specificity

As described supra, the present invention provides powerful methods for analysis of PDZ-ligand interactions, including high-throughput methods such as the "G" assay and affinity assays described supra. In one embodiment of the invention, the affinity is determined for a particular ligand and a plurality of PDZ proteins. Typically the plurality is at least 5, and often at least 25, or at least 40 different PDZ proteins. In a preferred embodiment, the plurality of different PDZ proteins are from a particular tissue (e.g., central nervous system, spleen, cardiac muscle, kidney) or a particular class or type of cell, (e.g., a hematopoietic cell, a lymphocyte, a neuron) and the like. In a most preferred embodiment, the plurality of different PDZ proteins represents a substantial fraction (e.g., typically a majority, more often at least 80%) of all of the PDZ proteins known to be, or suspected of being, expressed in the tissue or cell(s), e.g., all of the PDZ proteins known to be present in lymphocytes. In an embodiment, the plurality is at least 50%, usually at least 80%, at least 90% or all of the PDZ proteins disclosed herein as being expressed in hematopoietic cells.

In one embodiment of the invention, the binding of a ligand to the plurality of PDZ proteins is determined. Using this method, it is possible to identify a particular PDZ domain bound with particular specificity by the ligand. The binding may be designated as "specific" if the affinity of the ligand to the particular PDZ domain is at least 2-fold that of the binding to other PDZ domains in the plurality (e.g., present in that cell type). The binding is deemed "very specific" if the affinity is at least 10-fold higher than to any other PDZ in the plurality or, alternatively, at least 10-fold higher than to at least 90%, more often 95% of the other PDZs in a defined plurality. Similarly, the binding is deemed "exceedingly specific" if it is at least 100-fold higher. For example, a ligand could bind to 2 different PDZs with an affinity of 1 uM and to no other PDZs out of a set 40 with an affinity of less than 100 uM. This would constitute specific binding to those 2 PDZs. Similar measures of specificity are used to describe binding of a PDZ to a plurality of PLs.

It will be recognized that high specificity PDZ-PL interactions represent potentially more valuable targets for achieving a desired biological effect. The ability of an inhibitor or enhancer to act with high specificity is often desirable. In particular, the most specific PDZ-ligand interactions are also the diagnostic targets, allowing specific detection of the interaction or disruption of an interaction.

Thus, in one embodiment, the invention provides a method of identifying a high specificity interaction between a particular PDZ domain and a ligand known or suspected of binding at least one PDZ domain, by providing a plurality of different immobilized polypeptides, each of said polypeptides comprising a PDZ domain and a non-PDZ domain; determining the affinity of the ligand for each of said polypeptides, and comparing the affinity of binding of the ligand to each of said polypeptides, wherein an interaction between the ligand and a particular PDZ domain is deemed to have high specificity when the ligand binds an immobilized polypeptide comprising the particular PDZ domain with at least 2-fold higher affinity than to immobilized polypeptides not comprising the particular PDZ domain.

In a related aspect, the affinity of binding of a specific PDZ domain to a plurality of ligands (or suspected ligands)

is determined. For example, in one embodiment, the invention provides a method of identifying a high specificity interaction between a PDZ domain and a particular ligand known or suspected of binding at least one PDZ domain, by providing an immobilized polypeptide comprising the PDZ domain and a non-PDZ domain; determining the affinity of each of a plurality of ligands for the polypeptide, and comparing the affinity of binding of each of the ligands to the polypeptide, wherein an interaction between a particular ligand and the PDZ domain is deemed to have high specificity when the ligand binds an immobilized polypeptide comprising the PDZ domain with at least 2-fold higher affinity than other ligands tested. Thus, the binding may be designated as "specific" if the affinity of the PDZ to the particular PL is at least 2-fold that of the binding to other PLs in the plurality (e.g., present in that cell type). The binding is deemed "very specific" if the affinity is at least 10-fold higher than to any other PL in the plurality or, alternatively, at least 10-fold higher than to at least 90%, more often 95% of the other PLs in a defined plurality. Similarly, the binding is deemed "exceedingly specific" if it is at least 100-fold higher. Typically the plurality is at least 5 different ligands, more often at least 10.

A. Use of Array for Global Predictions

One discovery of the present inventors relates to the important and extensive roles played by interactions between PDZ proteins and PL proteins, particularly in the biological function of hematopoietic cells and other cells involved in the immune response. Further, it has been discovered that valuable information can be ascertained by analysis (e.g., simultaneous analysis) of a large number of PDZ-PL interactions. In a preferred embodiment, the analysis encompasses all of the PDZ proteins expressed in a particular tissue (e.g., spleen) or type or class of cell (e.g., hematopoietic cell, neuron, lymphocyte, B cell, T cell and the like). Alternatively, the analysis encompasses at least about 5, or at least about 10, or at least about 12, or at least about 15 and often at least 50 different polypeptides, up to about 60, about 80, about 100, about 150, about 200, or even more different polypeptides; or a substantial fraction (e.g., typically a majority, more often at least 80%) of all of the PDZ proteins known to be, or suspected of being, expressed in the tissue or cell(s), e.g., all of the PDZ proteins known to be present in lymphocytes.

It will be recognized that the arrays and methods of the invention are directed to the analysis of PDZ and PL interactions, and involve selection of such proteins for analysis. While the devices and methods of the invention may include or involve a small number of control polypeptides, they typically do not include significant numbers of proteins or fusion proteins that do not include either PDZ or PL domains (e.g., typically, at least about 90% of the arrayed or immobilized polypeptides in a method or device of the invention is a PDZ or PL sequence protein, more often at least about 95%, or at least about 99%).

It will be apparent from this disclosure that analysis of the relatively large number of different interactions preferably takes place simultaneously. In this context, "simultaneously" means that the analysis of several different PDZ-PL interactions (or the effect of a test agent on such interactions) is assessed at the same time. Typically the analysis is carried out in a high throughput (e.g., robotic) fashion. One advantage of this method of simultaneous analysis is that it permits rigorous comparison of multiple different PDZ-PL interactions. For example, as explained in detail elsewhere herein, simultaneous analysis (and use of the arrays described infra) facilitates, for example, the direct comparison of the effect of an agent (e.g., an potential interaction inhibitor) on the interactions between a substantial portion of PDZs and/or PLs in a tissue or cell.

Accordingly, in one aspect, the invention provides an array of immobilized polypeptide comprising the PDZ domain and a non-PDZ domain on a surface. Typically, the array comprises at least about 5, or at least about 10, or at least about 12, or at least about 15 and often at least 50 different polypeptides. In one preferred embodiment, the different PDZ proteins are from a particular tissue (e.g., central nervous system, spleen, cardiac muscle, kidney) or a particular class or type of cell, (e.g., a hematopoietic cell, a lymphocyte, a neuron) and the like. In a most preferred embodiment, the plurality of different PDZ proteins represents a substantial fraction (e.g., typically a majority, more often at least 60%, 70% or 80%) of all of the PDZ proteins known to be, or suspected of being, expressed in the tissue or cell(s), e.g., all of the PDZ proteins known to be present in lymphocytes.

Certain embodiments are arrays which include a plurality, usually at least 5, 10, 25, 50 PDZ proteins present in a particular cell of interest. In this context, "array" refers to an ordered series of immobilized polypeptides in which the identity of each polypeptide is associated with its location. In some embodiments the plurality of polypeptides are arrayed in a "common" area such that they can be simultaneously exposed to a solution (e.g., containing a ligand or test agent). For example, the plurality of polypeptides can be on a slide, plate or similar surface, which may be plastic, glass, metal, silica, beads or other surface to which proteins can be immobilized. In a different embodiment, the different immobilized polypeptides are situated in separate areas, such as different wells of multi-well plate (e.g., a 24-well plate, a 96-well plate, a 384 well plate, and the like). It will be recognized that a similar advantage can be obtained by using multiple arrays in tandem.

B. Analysis of PDZ-PL Inhibition Profile

In one aspect, the invention provides a method for determining if a test compound inhibits any PDZ-ligand interaction in large set of PDZ-ligand interactions (e.g., a plurality of the PDZ-ligands interactions described in U.S. patent application Ser. No. 09/724553; a majority of the PDZ-ligands identified in a particular cell or tissue as described supra (e.g., cervical tissue) and the like. In one embodiment, the PDZ domains of interest are expressed as GST-PDZ fusion proteins and immobilized as described herein. For each PDZ domain, a labeled ligand that binds to the domain with a known affinity is identified as described herein.

For any known or suspected modulator (e.g., inhibitor) of a PDZ-PL interaction(s), it is useful to know which interactions are inhibited (or augmented). This information could be used as a diagnostic marker for the presence of a pathogen (e.g., oncogenic HPV strains). The profile of PDZ interactions inhibited by a particular agent is referred to as the "inhibition profile" for the agent, and is described in detail below. The profile of PDZ interactions enhanced by a particular agent is referred to as the "enhancement profile" for the agent. It will be readily apparent to one of skill guided by the description of the inhibition profile how to determine the enhancement profile for an agent. The present invention provides methods for determining the PDZ interaction (inhibition/enhancement) profile of an agent in a single assay.

In one aspect, the invention provides a method for determining the PDZ-PL inhibition profile of a compound by providing (i) a plurality of different immobilized polypeptides, each of said polypeptides comprising a PDZ domain and a non-PDZ domain and (ii) a plurality of corresponding ligands, wherein each ligand binds at least one PDZ domain in (i), then contacting each of said immobilized polypeptides in (i) with a corresponding ligand in (ii) in the presence and absence of a test compound, and determining for each polypeptide-ligand pair whether the test compound inhibits binding between the immobilized polypeptide and the corresponding ligand.

Typically the plurality is at least 5, and often at least 25, or at least 40 different PDZ proteins. In a preferred embodiment, the plurality of different ligands and the plurality of different PDZ proteins are from the same tissue or a particular class or type of cell, e.g., a cervical cell, a penile cell, an anal cell and the like. In a most preferred embodiment, the plurality of different PDZs represents a substantial fraction (e.g., at least 80%) of all of the PDZs known to be, or suspected of being, expressed in the tissue or cell(s), e.g., all of the PDZs known to be present in lymphocytes (for example, at least 80%, at least 90% or all of the PDZs disclosed herein as being expressed in hematopoietic cells).

In one embodiment, the inhibition profile is determined as follows: A plurality (e.g., all known) PDZ domains expressed in a cell (e.g., cervical cells) are expressed as GST-fusion proteins and immobilized without altering their ligand binding properties as described supra. For each PDZ domain, a labeled ligand that binds to this domain with a known affinity is identified. If the set of PDZ domains expressed in lymphocytes is denoted by {P1 . . . Pn}, any given PDZ domain Pi binds a (labeled) ligand Li with affinity $K_di$. To determine the inhibition profile for a test agent "compound X" the "G" assay (supra) can be performed as follows in 96-well plates with rows A-H and columns 1-12. Column 1 is coated with P1 and washed. The corresponding ligand L1 is added to each washed coated well of column 1 at a concentration 0.5 $K_d1$ with (rows B, D, F, H) or without (rows A, C, E, F) between about 1 and about 1000 uM) of test compound X. Column 2 is coated with P2, and L2 (at a concentration 0.5 $K_d2$) is added with or without inhibitor X. Additional PDZ domains and ligands are similarly tested.

Compound X is considered to inhibit the binding of Li to Pi if the average signal in the wells of column i containing X is less than half the signal in the equivalent wells of the column lacking X. Thus, in this single assay one determines the full set of lymphocyte PDZs that are inhibited by compound X.

In some embodiments, the test compound X is a mixture of compounds, such as the product of a combinatorial chemistry synthesis as described supra. In some embodiments, the test compound is known to have a desired biological effect, and the assay is used to determine the mechanism of action (i.e., if the biological effect is due to modulating a PDZ-PL interaction).

It will be apparent that an agent that modulates only one, or a few PDZ-PL interactions, in a panel (e.g., a panel of all known PDZs lymphocytes, a panel of at least 10, at least 20 or at least 50 PDZ domains) is a more specific modulator than an agent that modulate many or most interactions. Typically, an agent that modulates less than 20% of PDZ domains in a panel (e.g., Table 2) is deemed a "specific" inhibitor, less than 6% a "very specific" inhibitor, and a single PDZ domain a "maximally specific" inhibitor.

It will also be appreciated that "compound X" may be a composition containing mixture of compounds (e.g., generated using combinatorial chemistry methods) rather than a single compound.

Several variations of this assay are contemplated:

In some alternative embodiments, the assay above is performed using varying concentrations of the test compound X, rather than fixed concentration. This allows determination of the Ki of the X for each PDZ as described above.

In an alternative embodiment, instead of pairing each PDZ-PL with a specific labeled ligand Li, a mixture of different labeled ligands is created that such that for every PDZ at least one of the ligands in the mixture binds to this PDZ sufficiently to detect the binding in the "G" assay. This mixture is then used for every PDZ domain.

In one embodiment, compound X is known to have a desired biological effect, but the chemical mechanism by which it has that effect is unknown. The assays of the invention can then be used to determine if compound X has its effect by binding to a PDZ domain.

In one embodiment, PDZ-domain containing proteins are classified in to groups based on their biological function, e.g. into those that regulate chemotaxis versus those that regulate transcription. An optimal inhibitor of a particular function (e.g., including but not limited to an anti-chemotactic agent, an anti-T cell activation agent, cell-cycle control, vesicle transport, apoptosis, etc.) will inhibit multiple PDZ-ligand interactions involved in the function (e.g., chemotaxis, activation) but few other interactions. Thus, the assay is used in one embodiment in screening and design of a drug that specifically blocks a particular function. For example, an agent designed to block chemotaxis might be identified because, at a given concentration, the agent inhibits 2 or more PDZs involved in chemotaxis but fewer than 3 other PDZs, or that inhibits PDZs involved in chemotaxis with a Ki>10-fold better than for other PDZs. Thus, the invention provides a method for identifying an agent that inhibits a first selected PDZ-PL interaction or plurality of interactions but does not inhibit a second selected PDZ-PL interaction or plurality of interactions. The two (or more) sets of interactions can be selected on the basis of the known biological function of the PDZ proteins, the tissue specificity of the PDZ proteins, or any other criteria. Moreover, the assay can be used to determine effective doses (i.e., drug concentrations) that result in desired biological effects while avoiding undesirable effects.

C. Agonists and Antagonists of PDZ-PL Interactions

As described herein, interactions between PDZ proteins and PL proteins in cells (e.g., cervical cells) may be disrupted or inhibited by the presence of pathogens. Pathogens can be identified using screening assays described herein. Agonists and antagonists of PDZ-Pathogen PL interactions or PDZ-Cellular PL interactions can be useful in discerning or confirming specific interactions. In some embodiments, an agonist will increase the sensitivity of a PDZ-pathogen PL interaction. In other embodiments, an antagonist of a PDZ-pathogen PL interaction can be used to verify the specificity of an interaction. In one embodiment, the motifs disclosed herein are used to design inhibitors. In some embodiments, the antagonists of the invention have a structure (e.g., peptide sequence) based on the C-terminal residues of PL-domain proteins listed in TABLE 3. In some embodiments, the antagonists of the invention have a structure (e.g., peptide sequence) based on a PL motif disclosed herein or in U.S. patent application Ser. No. 09/724553.

The PDZ/PL antagonists and antagonists of the invention may be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Although, for convenience, the present discussion primarily refers antagonists of PDZ-PL interactions, it will be recognized that PDZ-PL interaction agonists can also be use in the methods disclosed herein.

In one aspect, the peptides and peptide mimetics or analogues of the invention contain an amino acid sequence that binds a PDZ domain in a cell of interest. In one embodiment, the antagonists comprise a peptide that has a sequence corresponding to the carboxy-terminal sequence of a PL protein listed in TABLE 3 or in U.S. patent application Ser. No. 09/724553, e.g., a peptide listed TABLE 3. Typically, the peptide comprises at least the C-terminal two (3), three (3) or four (4) residues of the PL protein, and often the inhibitory peptide comprises more than four residues (e.g., at least five, six, seven, eight, nine, ten, twelve or fifteen residues) from the PL protein C-terminus.

In some embodiments, the inhibitor is a peptide, e.g., having a sequence of a PL C-terminal protein sequence.

In some embodiments, the antagonist is a fusion protein comprising such a sequence. Fusion proteins containing a transmembrane transporter amino acid sequence are particularly useful.

In some embodiments, the inhibitor is conserved variant of the PL C-terminal protein sequence having inhibitory activity.

In some embodiments, the antagonist is a peptide mimetic of a PL C-terminal sequence.

In some embodiments, the inhibitor is a small molecule (i.e., having a molecular weight less than 1 kD).

D. Peptide Antagonists

In one embodiment, the antagonists comprise a peptide that has a sequence of a PL protein carboxy-terminus listed in TABLE 3. The peptide comprises at least the C-terminal two (2) residues of the PL protein, and typically, the inhibitory peptide comprises more than two residues (e.g, at least three, four, five, six, seven, eight, nine, ten, twelve or fifteen residues) from the PL protein C-terminus. The peptide may be any of a variety of lengths (e.g., at least 2, at least 3, at least 4, at least 5, at least 6, at least 8, at least 10, or at least 20 residues) and may contain additional residues not from the PL protein. It will be recognized that short PL peptides are sometime used in the rational design of other small molecules with similar properties.

Although most often, the residues shared by the inhibitory peptide with the PL protein are found at the C-terminus of the peptide. However, in some embodiments, the sequence is internal. Similarly, in some cases, the inhibitory peptide comprises residues from a PL sequence that is near, but not at the c-terminus of a PL protein (see, Gee et al., 1998, *J Biological Chem.* 273:21980-87).

Sometime the PL protein carboxy-terminus sequence is referred to as the "core PDZ motif sequence" referring to the ability of the short sequence to interact with the PDZ domain. For example, in an embodiment, the "core PDZ motif sequence" contains the last four C-terminus amino acids. As described above, the four amino acid core of a PDZ motif sequence may contain additional amino acids at its amino terminus to further increase its binding affinity and/or stability. Thus, in one embodiment, the PDZ motif sequence peptide can be from four amino acids up to 15 amino acids. It is preferred that the length of the sequence to be 6-10 amino acids. More preferably, the PDZ motif sequence contains 8 amino acids. Additional amino acids at the amino terminal end of the core sequence may be derived from the natural sequence in each hematopoietic cell surface receptor or a synthetic linker. The additional amino acids may also be conservatively substituted. When the third residue from the C-terminus is S, T or Y, this residue may be phosphorylated prior to the use of the peptide.

In some embodiments, the peptide and nonpeptide inhibitors of the are small, e.g., fewer than ten amino acid residues in length if a peptide. Further, it is reported that a limited number of ligand amino acids directly contact the PDZ domain (generally less than eight) (Kozlov et al., 2000, Biochemistry 39, 2572; Doyle et al., 1996, Cell 85, 1067) and that peptides as short as the C-terminal three amino acids often retain similar binding properties to longer (>15) amino acids peptides (Yanagisawa et al., 1997, J. Biol. Chem. 272, 8539).

E. Peptide Variants

Having identified PDZ binding peptides and PDZ-PL interaction inhibitory sequences, variations of these sequences can be made and the resulting peptide variants can be tested for PDZ domain binding or PDZ-PL inhibitory activity. In embodiments, the variants have the same or a different ability to bind a PDZ domain as the parent peptide. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class.

F. Peptide Mimetics

Having identified PDZ binding peptides and PDZ-PL interaction inhibitory sequences, peptide mimetics can be prepared using routine methods, and the inhibitory activity of the mimetics can be confirmed using the assays of the invention. Thus, in some embodiments, the agonist or antagonist is a peptide mimetic of a PL C-terminal sequence. The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

G. Small Molecules

In some embodiments, the agonist or antagonist is a small molecule (i.e., having a molecular weight less than 1 kD). Methods for screening small molecules are well known in the art and include those described supra.

X. Methods of Optimizing a PL Detector

Although described supra primarily in terms of identifying interactions between PDZ-domain polypeptides and PL proteins, the assays described supra and other assays can also be used to identify the binding of other molecules (e.g., peptide mimetics, small molecules, and the like) to PDZ domain sequences. For example, using the assays disclosed herein, combinatorial and other libraries of compounds can be screened, e.g., for molecules that specifically bind to PDZ domains. Screening of libraries can be accomplished by any of a variety of commonly known methods. See, e.g., the following references, which disclose screening of peptide libraries: Parmley and Smith, 1989, *Adv. Exp. Med. Biol.* 251:215-218; Scott and Smith, 1990, *Science* 249:386-390; Fowlkes et al., 1992; *BioTechniques* 13:422-427; Oldenburg et al., 1992, *Proc. Natl. Acad. Sci. USA* 89:5393-5397; Yu et al., 1994, *Cell* 76:933-945; Staudt et al., 1988, *Science* 241:577-580; Bock et al., 1992, *Nature* 355:564-566; Tuerk et al., 1992, *Proc. Natl. Acad. Sci. USA* 89:6988-6992; Ellington et al., 1992, *Nature* 355:850-852; U.S. Pat. No. 5,096,815, U.S. Pat. No. 5,223,409, and U.S. Pat. No. 5,198,346, all to Ladner et al.; Rebar and Pabo, 1993, *Science* 263:671-673; and PCT Publication No. WO 94/18318.

In a specific embodiment, screening can be carried out by contacting the library members with a PDZ-domain polypeptide immobilized on a solid support (e.g. as described supra in the "G" assay) and harvesting those library members that bind to the protein. Examples of such screening methods, termed "panning" techniques are described by way of example in Parmley and Smith, 1988, *Gene* 73:305-318; Fowlkes et al., 1992, *BioTechniques* 13:422-427; PCT Publication No. WO 94/18318; and in references cited hereinabove.

In another embodiment, the two-hybrid system for selecting interacting proteins in yeast (Fields and Song, 1989, *Nature* 340:245-246; Chien et al., 1991, *Proc. Natl. Acad. Sci. USA* 88:9578-9582) can be used to identify molecules that specifically bind to a PDZ domain-containing protein. Furthermore, the identified molecules are further tested for their ability to inhibit transmembrane receptor interactions with a PDZ domain.

In one aspect of the invention, antagonists of an interaction between a PDZ protein and a PL protein are identified. In one embodiment, a modification of the "A" assay described supra is used to identify antagonists. In one embodiment, a modification of the "G" assay described supra is used to identify antagonists.

In one embodiment, screening assays are used to detect molecules that specifically bind to PDZ domains. Such molecules are useful as agonists or antagonists of PDZ-protein-mediated cell function (e.g., cell activation, e.g., T cell activation, vesicle transport, cytokine release, growth factors, transcriptional changes, cytoskeleton rearrangement, cell movement, chemotaxis, and the like). In one embodiment, such assays are performed to screen for leukocyte activation inhibitors for drug development. The invention thus provides assays to detect molecules that specifically bind to PDZ domain-containing proteins. For example, recombinant cells expressing PDZ domain-encoding nucleic acids can be used to produce PDZ domains in these assays and to screen for molecules that bind to the domains. Molecules are contacted with the PDZ domain (or fragment thereof) under conditions conducive to binding, and then molecules that specifically bind to such domains are identified. Methods that can be used to carry out the foregoing are commonly known in the art.

It will be appreciated by the ordinarily skilled practitioner that, in one embodiment, antagonists are identified by conducting the A or G assays in the presence and absence of a known or candidate antagonist. When decreased binding is observed in the presence of a compound, that compound is identified as an antagonist. Increased binding in the presence of a compound signifies that the compound is an agonist.

For example, in one assay, a test compound can be identified as an inhibitor (antagonist) of binding between a PDZ protein and a PL protein by contacting a PDZ domain polypeptide and a PL peptide in the presence and absence of the test compound, under conditions in which they would (but for the presence of the test compound) form a complex, and detecting the formation of the complex in the presence and absence of the test compound. It will be appreciated that less complex formation in the presence of the test compound than in the absence of the compound indicates that the test compound is an inhibitor of a PDZ protein -PL protein binding.

In one embodiment, the "G" assay is used in the presence or absence of a candidate inhibitor. In one embodiment, the "A" assay is used in the presence or absence of a candidate inhibitor.

In one embodiment (in which a G assay is used), one or more PDZ domain-containing GST-fusion proteins are bound to the surface of wells of a 96-well plate as described supra (with appropriate controls including nonfusion GST protein). All fusion proteins are bound in multiple wells so that appropriate controls and statistical analysis can be done. A test compound in BSA/PBS (typically at multiple different concentrations) is added to wells. Immediately thereafter, 30 uL of a detectably labeled (e.g., biotinylated) peptide known to bind to the relevant PDZ domain (see, e.g., TABLE 4) is added in each of the wells at a final concentration of, e.g., between about 2 uM and about 40 uM, typically 5 uM, 15 uM, or 25 uM. This mixture is then allowed to react with the PDZ fusion protein bound to the surface for 10 minutes at 4° C. followed by 20 minutes at 25° C. The surface is washed free of unbound peptide three times with ice cold PBS and the amount of binding of the peptide in the presence and absence of the test compound is determined. Usually, the level of binding is measured for each set of replica wells (e.g. duplicates) by subtracting the mean GST alone background from the mean of the raw measurement of peptide binding in these wells.

In an alternative embodiment, the A assay is carried out in the presence or absence of a test candidate to identify inhibitors of PL-PDZ interactions.

In one embodiment, a test compound is determined to be a specific inhibitor of the binding of the PDZ domain (P) and a PL (L) sequence when, at a test compound concentration of less than or equal to 1 mM (e.g., less than or equal to: 500 uM, 100 uM, 10 uM, 1 uM, 100 nM or 1 nM) the binding of P to L in the presence of the test compound less than about 50% of the binding in the absence of the test compound. (in various embodiments, less than about 25%, less than about 10%, or less than about 1%). Preferably, the net signal of binding of P to L in the presence of the test compound plus six (6) times the standard error of the signal in the presence of the test compound is less than the binding signal in the absence of the test compound.

In one embodiment, assays for an inhibitor are carried out using a single PDZ protein-PL protein pair (e.g., a PDZ domain fusion protein and a PL peptide). In a related embodiment, the assays are carried out using a plurality of pairs, such as a plurality of different pairs listed in TABLE 4.

In some embodiments, it is desirable to identify compounds that, at a given concentration, inhibit the binding of one PL-PDZ pair, but do not inhibit (or inhibit to a lesser degree) the binding of a specified second PL-PDZ pair. These antagonists can be identified by carrying out a series of assays using a candidate inhibitor and different PL-PDZ pairs (e.g., as shown in the matrix of TABLE 4) and comparing the results of the assays. All such pairwise combinations are contemplated by the invention (e.g., test compound inhibits binding of $PL_1$ to $PDZ_1$ to a greater degree than it inhibits binding of $PL_1$ to $PDZ_2$ or $PL_2$ to $PDZ_2$). Importantly, it will be appreciated that, based on the data provided in TABLE 4 and disclosed herein (and additional data that can be generated using the methods described herein) inhibitors with different specificities can readily be designed.

For example, according to the invention, the Ki ("potency") of an inhibitor of a PDZ-PL interaction can be determined. Ki is a measure of the concentration of an inhibitor required to have a biological effect. For example, administration of an inhibitor of a PDZ-PL interaction in an amount sufficient to result in an intracellular inhibitor concentration of at least between about 1 and about 100 Ki is expected to inhibit the biological response mediated by the target PDZ-PL interaction. In one aspect of the invention, the Kd measurement of PDZ-PL binding as determined using the methods supra is used in determining Ki.

Thus, in one aspect, the invention provides a method of determining the potency (Ki) of an inhibitor or suspected inhibitor of binding between a PDZ domain and a ligand by immobilizing a polypeptide comprising the PDZ domain and a non-PDZ domain on a surface, contacting the immobilized polypeptide with a plurality of different mixtures of the ligand and inhibitor, wherein the different mixtures comprise a fixed amount of ligand and different concentrations of the inhibitor, determining the amount of ligand bound at the different concentrations of inhibitor, and calculating the Ki of the binding based on the amount of ligand bound in the presence of different concentrations of the inhibitor. In an embodiment, the polypeptide is immobilized by binding the polypeptide to an immobilized immunoglobulin that binds the non-PDZ domain. This method, which is based on the "G" assay described supra, is particularly suited for high-throughput analysis of the Ki for inhibitors of PDZ-ligand interactions. Further, using this method, the inhibition of the PDZ-ligand interaction itself is measured, without distortion of measurements by avidity effects.

Typically, at least a portion of the ligand is detectably labeled to permit easy quantitation of ligand binding.

It will be appreciated that the concentration of ligand and concentrations of inhibitor are selected to allow meaningful detection of inhibition. Thus, the concentration of the ligand whose binding is to be blocked is close to or less than its binding affinity (e.g., preferably less than the 5× Kd of the interaction, more preferably less than 2× Kd, most preferably less than 1× Kd). Thus, the ligand is typically present at a concentration of less than 2 Kd (e.g., between about 0.01 Kd and about 2 Kd) and the concentrations of the test inhibitor typically range from 1 nM to 100 uM (e.g. a 4-fold dilution series with highest concentration 10 uM or 1 mM). In a preferred embodiment, the Kd is determined using the assay disclosed supra.

The Ki of the binding can be calculated by any of a variety of methods routinely used in the art, based on the amount of ligand bound in the presence of different concentrations of the inhibitor. In an illustrative embodiment, for example, a plot of labeled ligand binding versus inhibitor concentration is fit to the equation:

$$S_{inhibitor} = S_0 * Ki/([I]+Ki)$$

where $S_{inhibitor}$ is the signal of labeled ligand binding to immobilized PDZ domain in the presence of inhibitor at concentration [I] and $S_0$ is the signal in the absence of inhibitor (i.e., [I]=0). Typically [I] is expressed as a molar concentration.

In another aspect of the invention, an enhancer (sometimes referred to as, augmentor or agonist) of binding between a PDZ domain and a ligand is identified by immobilizing a polypeptide comprising the PDZ domain and a non-PDZ domain on a surface, contacting the immobilized polypeptide with the ligand in the presence of a test agent and determining the amount of ligand bound, and comparing the amount of ligand bound in the presence of the test agent with the amount of ligand bound by the polypeptide in the absence of the test agent. At least two-fold (often at least 5-fold) greater binding in the presence of the test agent compared to the absence of the test agent indicates that the test agent is an agent that enhances the binding of the PDZ domain to the ligand. As noted supra, agents that enhance PDZ-ligand interactions are useful for disruption (dysregulation) of biological events requiring normal PDZ-ligand function (e.g., cancer cell division and metastasis, and activation and migration of immune cells).

The invention also provides methods for determining the "potency" or "$K_{enhancer}$" of an enhancer of a PDZ-ligand interaction. For example, according to the invention, the $K_{enhancer}$ of an enhancer of a PDZ-PL interaction can be determined, e.g., using the Kd of PDZ-PL binding as determined using the methods described supra. $K_{enhancer}$ is a measure of the concentration of an enhancer expected to have a biological effect. For example, administration of an enhancer of a PDZ-PL interaction in an amount sufficient to result in an intracellular inhibitor concentration of at least between about 0.1 and about 100 $K_{enhancer}$ (e.g., between about 0.5 and about 50 $K_{enhancer}$) is expected to disrupt the biological response mediated by the target PDZ-PL interaction.

Thus, in one aspect the invention provides a method of determining the potency ($K_{enhancer}$) of an enhancer or suspected enhancer of binding between a PDZ domain and a ligand by immobilizing a polypeptide comprising the PDZ domain and a non-PDZ domain on a surface, contacting the immobilized polypeptide with a plurality of different mixtures of the ligand and enhancer, wherein the different mixtures comprise a fixed amount of ligand, at least a portion of which is detectably labeled, and different concentrations of the enhancer, determining the amount of ligand bound at the different concentrations of enhancer, and calculating the potency ($K_{enhancer}$) of the enhancer from the binding based on the amount of ligand bound in the presence of different concentrations of the enhancer. Typically, at least a portion of the ligand is detectably labeled to permit easy quantitation of ligand binding. This method, which is based on the "G" assay described supra, is particularly suited for high-throughput analysis of the $K_{enhancer}$ for enhancers of PDZ-ligand interactions.

It will be appreciated that the concentration of ligand and concentrations of enhancer are selected to allow meaningful detection of enhanced binding. Thus, the ligand is typically present at a concentration of between about 0.01 Kd and about 0.5 Kd and the concentrations of the test agent/enhancer typically range from 1 nM to 1 mM (e.g. a 4-fold dilution series with highest concentration 10 uM or 1 mM). In a preferred embodiment, the Kd is determined using the assay disclosed supra.

The potency of the binding can be determined by a variety of standard methods based on the amount of ligand bound in the presence of different concentrations of the enhancer or augmentor. For example, a plot of labeled ligand binding versus enhancer concentration can be fit to the equation:

$$S([E]) = S(0) + (S(0) * (D_{enhancer} - 1) * [E] / ([E] + K_{enhancer})$$

where "$K_{enhancer}$" is the potency of the augmenting compound, and "$D_{enhancer}$" is the fold-increase in binding of the labeled ligand obtained with addition of saturating amounts of the enhancing compound, [E] is the concentration of the enhancer. It will be understood that saturating amounts are the amount of enhancer such that further addition does not significantly increase the binding signal. Knowledge of "$K_{enhancer}$" is useful because it describes a concentration of the augmenting compound in a target cell that will result in a biological effect due to dysregulation of the PDZ-PL interaction. Typical therapeutic concentrations are between about 0.1 and about 100 $K_{enhancer}$.

For certain of the PDZ proteins and PL proteins shown to bind together and for which Kd values had been obtained, additional testing was conducted to determine whether certain pharmaceutical compounds would act to antagonize or agonize the interactions. Assays were conducted as for the G' assay described supra both in the presence and absence of test compound, except that 50 ul of a 10 uM solution of the biotinylated PL peptide is allowed to react with the surface bearing the PDZ-domain polypeptide instead of a 20 uM solution as specified in step (2) of the assay.

Another method of increasing the specificity or sensitivity of a PDZ-PL interaction is through mutagenesis and selection of high affinity or high specificity variants. Methods such as V, chemical (e.g., EMS) or biological mutagenesis (e.g. Molecular shuffling or DNA polymerase mutagenesis) can be applied to create mutations in DNA encoding PDZ domains or PL domains. Proteins can then be made from variants and tested using a number of methods described herein (e.g., 'A' assay, 'G' assay or yeast two hybrid). In general, one would assay mutants for high affinity binding between the mutated PDZ domain and a test sample (such as an oncogenic E6 PL) that have reduced afinity for other cellular PLs (as described in section IX). These methods are known to those skilled in the art and examples herein are not intended to be limiting.

XI. Recombinant Detector Synthesis

As indicated in the Background section, PDZ domain-containing proteins are involved in a number of biological functions, including, but not limited to, vesicular trafficking, tumor suppression, protein sorting, establishment of membrane polarity, apoptosis, regulation of immune response and organization of synapse formation. In general, this family of proteins has a common function of facilitating the assembly of multi-protein complexes, often serving as a bridge between several proteins, or regulating the function of other proteins. Additionally, as also noted supra, these proteins are found in essentially all cell types. Consequently, detection of inappropriate PDZ:PL interactions or abnormal interactions can be utilized to diagnose a wide variety of biological and physiological conditions. In particular, detection of PL proteins from pathogenic organisms can be diagnosed using PDZ domains. Most, but not all, embodiments of this invention, require the addition of a detectable marker to the PDZ or PL protein used for detection. Examples are given below.

A. Chemical Synthesis

The peptides of the invention or analogues thereof, may be prepared using virtually any art-known technique for the preparation of peptides and peptide analogues. For example, the peptides may be prepared in linear form using conventional solution or solid phase peptide syntheses and cleaved from the resin followed by purification procedures (Creighton, 1983, Protein Structures And Molecular Principles, W. H. Freeman and Co., N.Y.). Suitable procedures for synthesizing the peptides described herein are well known in the art. The composition of the synthetic peptides may be confirmed by amino acid analysis or sequencing (e.g., the Edman degradation procedure and mass spectroscopy).

In addition, analogues and derivatives of the peptides can be chemically synthesized. The linkage between each amino acid of the peptides of the invention may be an amide, a substituted amide or an isostere of amide. Nonclassical amino acids or chemical amino acid analogues can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

B. Recombinant Synthesis

If the peptide is composed entirely of gene-encoded amino acids, or a portion of it is so composed, the peptide or the relevant portion may also be synthesized using conventional recombinant genetic engineering techniques. For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

In some embodiments, increasing the number of copies of a PL detector may be used to increase the specificity or sensitivity of detection. An example of this is presented in EXAMPLE 4. The TIP-TIP-IgG vector produces a fusion protein that has duplicated copies of the PDZ domain from TIP-1 and the protein itself should dimerize on the basis of the IgG constant region backbone. Hence, a single protein contains 2-4 copies of the TIP-1 PDZ domain. In a similar manner, addition tandem repeats of PL detectors could be fashioned. In some embodiments, different PDZ domains from different proteins could be engineered to express as a single protein (e.g., the PDZ domains of TIP-1 and MAGI-1 could be engineered to detect oncogenic HPV E6 proteins). In a similar manner, a different Ig backbone could be used to increase the avidity of a construct. For example, the IgG constant regions will dimerize with itself, but the IgM constant regions will form a complex of ten monomers.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:559-565) may be used. These constructs can be introduced into planleukocytes using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA 79:7415-7419; Mackett et al., 1984, J. Virol. 49:857-864; Panicali et al., 1982, Proc. Natl. Acad. Sci. USA 79:4927-4931).

Other expression systems for producing linear peptides of the invention will be apparent to those having skill in the art.

C. Tags or Markers

Tags and markers are frequently used to aid in purification of components or detection of biological molecules. Examples of biological tags include, but are not limited to, glutathione-S-transferase, maltose binding protein, Immunoglobulin domains, Intein, Hemagglutinin epitopes, myc epitopes, etc. Examples of chemical tags include, but are not limited to, biotin, gold, paramagnetic particles or fluorophores. These examples can be used to identify the presence of proteins or compounds they are attached to or can be used by those skilled in the art to purify proteins or compounds from complex mixtures.

D. Purification of the Peptides and Peptide Analogues

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art. The purified peptides can be identified by assays based on their physical or functional properties, including radioactive labeling followed by gel electrophoresis, radioimmuno-assays, ELISA, bioassays, and the like.

XII. Kits

The present invention also includes kits for carrying out the methods of the invention. A subject kit usually contains a first and a second oncogenic HPV E6 binding partner. In most embodiments, the first binding partner is a PDZ domain polypeptide, and, the second binding partner is at least one antibody for E6. In some embodiments, the second binding partner is labeled with a detectable label. In other embodiments, a secondary labeling component, such as a detectably labeled secondary antibody, is included. In some embodiments, a subject kit further comprises a means, such as a device or a system, for isolating oncogenic HPV E6 from the sample. The kit may optionally contain proteasome inhibitor.

A subject kit can further include, if desired, one or more of various conventional components, such as, for example, containers with one or more buffers, detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized. Exemplary embodiments of the diagnostic methods of the invention are described above in detail.

In a subject kit, the oncogenic E6 detection reaction may be performed using an aqueous or solid substrate, where the kit may comprise reagents for use with several separation and detection platforms such as test strips, sandwich assays, etc. In many embodiments of the test strip kit, the test strip has bound thereto a PDZ domain polypeptide that specifically binds the PL domain of an oncogenic E6 protein and captures oncogenic E6 protein on the solid support. In some embodiments, the kit further comprises a detection antibody or antibodies, which is either directly or indirectly detectable, and which binds to the oncogenic E6 protein to allow its detection. Kits may also include components for conducting western blots (e.g., pre-made gels, membranes, transfer systems, etc.); components for carrying out ELISAs (e.g., 96-well plates); components for carrying out immunoprecipitation (e.g. protein A); columns, especially spin columns, for affinity or size separation of oncogenic E6 protein from a sample (e.g. gel filtration columns, PDZ domain polypeptide columns, size exclusion columns, membrane cut-off spin columns etc.).

Subject kits may also contain control samples containing oncogenic or non-oncogenic E6, and/or a dilution series of oncogenic E6, where the dilution series represents a range of appropriate standards with which a user of the kit can compare their results and estimate the level of oncogenic E6 in their sample. Such a dilution series may provide an estimation of the progression of any cancer in a patient. Fluorescence, color, or autoradiological film development results may also be compared to a standard curves of fluorescence, color or film density provided by the kit.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention is are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing rabbit antibodies that are less immunogenic in a non-rabbit host than a parent antibody, or nucleotide sequences them.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

Methods of Determining if a Subject is Infected with an Oncogenic Strain of HPV

The present invention provides methods of detecting oncogenic HPV E6 protein in a sample and finds utility in diagnosing HPV infection in a subject. In many embodiments, a biological sample is obtained from a subject, and, the presence of oncogenic HPV E6 protein in the sample is determined. The presence of a detectable amount of oncogenic HPV E6 protein in a sample indicates indicates that the individual is infected with a oncogenic strain of HPV. In other embodiments, the level of oncogenic HPV E6 protein in a biological sample is determined, and compared to the amount of a control in the sample. The relative amount of oncogenic HPV E6 protein in a sample indicates the severity of the infection by HPV.

The methods generally involve two binding partners of oncogenic HPV E6 protein, one of which is a PDZ domain polypeptide, as described above. In general, the methods involve a) isolating the oncogenic HPV E6 protein from a sample using one of the binding partners, and b) detecting the oncogenic HPV E6 protein with the other binding partner.

Isolating Oncogenic HPV E6 Protein

In general, methods of the invention involve at least partially separating (i.e., isolating) native oncogenic HPV E6 protein from other proteins in a sample. This separation is usually achieved using a first binding partner for the oncogenic HPV E6. In many embodiments, the first binding partner is a PDZ domain polypeptide, or, in other embodiments an anti-HPV E6 antibody or mixture of antibodies.

In certain embodiments, one of the oncogenic HPV E6 binding partners is bound, directly or via a linker, to an insoluble support. Insoluble supports are known in the art and include, but are not limited to, a bead (e.g, magnetic beads, polystyrene beads, and the like); a membrane; and the like. In one non-limiting example, a PDZ domain polypeptide is bound to a magnetic bead. The PDZ domain polypeptide bound to the magnetic bead is contacted with the sample, and, after a complex is formed between the antibody and any E6 protein in the sample, a magnetic field is applied, such that the complex is removed from the sample. Where the PDZ domain polypeptide is bound to an insoluble support, such as a membrane, E6 protein bound to the PDZ domain polypeptide is removed from the sample by removing the membrane, or by transferring the sample to a separate container. Where the PDZ domain polypeptide is bound to a bead, the E6 protein bound to the bead is removed from the sample by centrifugation or filtration. Such embodiments are envisioned using a different E6 binding partner, e.g., an anti-E6 antibody.

In general, a suitable separation means is used with a suitable platform for performing the separation. For example, where oncogenic HPV E6 is separated by binding to PDZ domain polypeptides, the separation is performed using any of a variety of platforms, including, but not limited to, affinity column chromatography, capillary action or lateral flow test strips, immunoprecipitation, etc.

In many embodiments, oncogenic HPV E6 is separated from other proteins in the sample by applying the sample to one end of a test strip, and allowing the proteins to migrate by capillary action or lateral flow. Methods and devices for lateral flow separation, detection, and quantitation are known in the art. See, e.g., U.S. Pat. Nos. 5,569,608; 6,297,020; and 6,403,383. In these embodiments, a test strip comprises, in order from proximal end to distal end, a region for loading the sample (the sample-loading region) and a test region containing an oncogenic E6 protein binding partner, e.g., a region containing an PDZ domain polypeptide or, in other embodiments, a region containing an anti-E6 antibody. The sample is loaded on to the sample-loading region, and the proximal end of the test strip is placed in a buffer. oncogenic E6 protein is captured by the bound antibody in the first test region. Detection of the captured oncogenic E6 protein is carried out as described below. For example, detection of captured E6 proteins is carried out using detectably labeled antibody specific for an epitope of E6 proteins that is common to all oncogenic E6 proteins, or a mixture of antibodies that can, together, bind to all oncogenic E6 proteins. In alternative embodiments, an E6 antibody may be present in the test region and detection of oncogenic E6 bound to the E6 antibody uses a labeled PDZ domain polypeptide.

Detecting and Quantitating Oncogenic E6 Protein

Once oncogenic E6 protein is separated from other proteins in the sample, oncogenic E6 protein is detected and/or the level or amount of oncogenic E6 protein is determined (e.g., measured). As discussed above, oncogenic E6 protein is generally detected using a binding partner, e.g. an antibody or antibodies specific to E6, or a PDZ domain polypeptide.

Detection with a specific antibody is carried out using well-known methods. In general, the binding partner is detectably labeled, either directly or indirectly. Direct labels include radioisotopes (e.g., $^{125}$I; $^{35}$S, and the like); enzymes whose products are detectable (e.g., luciferase, β-galactosidase, horse radish peroxidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin; fluorescent proteins; and the like. Fluorescent proteins include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973; and the like.

Indirect labels include second antibodies specific for E6-specific antibodies, wherein the second antibody is labeled as described above; and members of specific binding pairs, e.g., biotin-avidin, and the like.

In some embodiments, a level of oncogenic E6 is quantitated. Quantitation can be carried out using any known method, including, but not limited to, enzyme-linked immunosorbent assay (ELISA); radioimmunoassay (RIA); and the like. In general, quantitation is accomplished by comparing the level of expression product detected in the sample with a standard curve.

In some embodiments, oncogenic HPV E6 is separated on a test strip, as described above. In these embodiments, oncogenic HPV E6 is detected using a detectably labeled binding partner that binds oncogenic HPV E6. Oncogenic HPV E6 may be quantitated using a reflectance spectrophotometer, or by eye, for example.

Biological Samples

Biological samples to be analyzed using the methods of the invention are obtained from any mammal, e.g., a human or a non-human animal model of HPV. In many embodiments, the biological sample is obtained from a living subject.

In some embodiments, the subject from whom the sample is obtained is apparently healthy, where the analysis is performed as a part of routine screening. In other embodiments, the subject is one who is susceptible to HPV, (e.g., as determined by family history; exposure to certain environmental factors; etc.). In other embodiments, the subject has symptoms of HPV (e.g., cervical warts, or the like). In other embodiments, the subject has been provisionally diagnosed as having HPV (e.g. as determined by other tests based on e.g., PCR).

The biological sample may be derived from any tissue, organ or group of cells of the subject. In some embodiments a cervical scrape, biopsy, or lavage is obtained from a subject.

In some embodiments, the biological sample is processed, e.g., to remove certain components that may interfere with an assay method of the invention, using methods that are standard in the art. In some embodiments, the biological sample is processed to enrich for proteins, e.g., by salt precipitation, and the like. In certain embodiments, the sample is processed in the presence proteasome inhibitor to inhibit degradation of the E6 protein.

In the assay methods of the invention, in some embodiments, the level of E6 protein in a sample may be quantified and/or compared to controls. Suitable control samples are from individuals known to be healthy, e.g., individuals known not to have HPV. Control samples can be from individuals genetically related to the subject being tested, but can also be from genetically unrelated individuals. A suitable control sample also includes a sample from an individual taken at a time point earlier than the time point at which the test sample is taken, e.g., a biological sample taken from the individual prior to exhibiting possible symptoms of HPV.

Utility

The methods of the instant invention are useful for a variety of diagnostic analyses. The instant methods are useful for diagnosing infection by an oncogenic strain of HPV in an individual; for determining the likelihood of having cancer; for determining a patient's response to treatment for HPV; for determining the severity of HPV infection in an individual; and for monitoring the progression of HPV in an individual.

The subject methods may generally be performed on biological samples from living subjects. A particularly advantageous feature of the invention is that the methods can simultaneously detect, in one reaction, all known oncogenic strains of HPV.

EXAMPLE 1

Sequence Analysis of HPV E6 Proteins to Determine Oncogenic Potential

PDZ proteins are known to bind certain carboxyl-terminal sequences of proteins (PLs). PL sequences that bind PDZ domains are predictable, and have been described in greater detail in U.S. patent applications Ser. Nos. 09/710059, 09/724553 and 09/688017. One of the major classes of PL motifs is the set of proteins terminating in the sequences —X—(S/T)-X—(V/I/L). We have examined the C-terminal sequences of E6 proteins from a number of HPV strains. All of the strains determined to be oncogenic by the National Cancer Institute exhibit a consensus PDZ binding sequence. Those E6 proteins from *papillomavirus* strains that are not cancerous lack a sequence that would be predicted to bind to PDZ domains, thus suggesting that interaction with PDZ proteins is a prerequisite for causing cancer in humans. This correlation between presence of a PL and ability to cause cancer is 100% in the sequences examined (Table 3A). In theory, with the disclosed PL consensus sequences from the patents listed supra, new variants of HPVs can be assessed for their ability to bind PDZ proteins and oncogenicity can be predicted on the basis of whether a PL is present. Earlier this year, five new oncogenic strains of Human *papillomavirus* were identified and their E6 proteins sequenced. As predicted, these proteins all contain a PL consensus sequence (Table 3B).

TABLE 3A

Correlation of E6 PDZ-ligands and oncogenicity

| HPV strain | E6 C-terminal sequence | PL yes/no | oncogenic | Seq ID No |
|---|---|---|---|---|
| HPV 4 | GYCRNCIRKQ | No | No | 221 |
| HPV 11 | WTTCMEDLLP | No | No | 222 |
| HPV 20 | GICRLCKHFQ | No | No | 223 |
| HPV 24 | KGLCRQCKQI | No | No | 224 |
| HPV 28 | WLRCTVRIPQ | No | No | 225 |
| HPV 36 | RQCKHFYNDW | No | No | 226 |
| HPV 48 | CRNCISHEGR | No | No | 227 |
| HPV 50 | CCRNCYEHEG | No | No | 228 |
| HPV 16 | SSRTRRETQL | Yes | Yes | 229 |
| HPV 18 | RLQRRRETQV | Yes | Yes | 230 |
| HPV 31 | WRRPRTETQV | Yes | Yes | 231 |
| HPV 35 | WKPTRRETEV | Yes | Yes | 232 |
| HPV 30 | RRTLRRETQV | Yes | Yes | 233 |
| HPV 39 | RRLTRRETQV | Yes | Yes | 234 |
| HPV 45 | RLRRRRETQV | Yes | Yes | 235 |
| HPV 51 | RLQRRNETQV | Yes | Yes | 236 |
| HPV 52 | RLQRRRVTQV | Yes | Yes | 237 |
| HPV 56 | TSREPRESTV | Yes | Yes | 238 |
| HPV 59 | QRQARSETLV | yes | Yes | 239 |
| HPV 58 | RLQRRRQTQV | Yes | Yes | 240 |
| HPV 33 | RLQRRRETAL | Yes | Yes | 241 |
| HPV 66 | TSRQATESTV | Yes | Yes* | 242 |
| HPV 68 | RRRTRQETQV | Yes | Yes | 243 |
| HPV 69 | RRREATETQV | Yes | Yes | 244 |

Table 3A: E6 C-terminal sequences and oncogenicity. HPV variants are listed at the left. Sequences were identified from Genbank sequence records. PL Yes/No was defined by a match or non-match to the consenses determined at Arbor Vita and by Songyang et al. -X-(S/T)-X-(V/I/L). Oncogenicity data collected from National Cancer Institute. *Only found in oncogenic strains co-transfected with other oncogenic proteins.

TABLE 3B

Correlation of recently identified oncogenic E6 proteins

| HPV strain | E6 C-terminal sequence | PL yes/no | oncogenic | Seq ID No |
|---|---|---|---|---|
| HPV 26 | RPRRQTETQV | Yes | Yes | 245 |
| HPV 53 | RHTTATESAV | Yes | Yes | 246 |
| HPV 66 | TSRQATESTV | Yes | Yes | 247 |

TABLE 3B-continued

Correlation of recently identified oncogenic E6 proteins

| HPV strain | E6 C-terminal sequence | PL yes/no | oncogenic | Seq ID No |
|---|---|---|---|---|
| HPV 73 | RCWRPSATVV | Yes | Yes | 248 |
| HPV 82 | PPRQRSETQV | Yes | Yes | 249 |

Table 3B: E6 C-terminal sequences and oncogenicity. HPV variants are listed at the left. Sequences were identified from Genbank sequence records. PL Yes/No was defined by a match or non-match to the consenses determined at Arbor Vita and by Songyang et al. -X-(S/T)-X-(V/I/L). Oncogenicity data on new strains collected from N Engl J Med 2003; 348: 518-527.

These tables provide a classification of the HPV strains based on the sequence of the C-terminal four amino acids of the E6 protein encoded by the HPV genome. The 21 oncogenic strains of HPV fall into one of 10 classes, and HPV strains not specifically listed above may also fall into these classes. As such, it is desirable to detect HPV strains from all 10 classes: the instant methods provide such detection.

EXAMPLE 2

Identification of PDZ Domains that Interact with the C-Termini of Oncogenic E6 Proteins In order to determine the PDZ domains that can be used to detect oncogenic E6 proteins in a diagnostic assay, the 'G assay' (described supra) was used to identify interactions between E6 PLs and PDZ domains. Peptides were synthesized corresponding to the C-terminal amino acid sequences of E6 proteins from oncogenic strains of human papillomavirus. These peptides were assessed for the ability to bind PDZ domains using the G-assay described above and PDZ proteins synthesized from the expression constructs described in greater detail in U.S. patent applications Ser. Nos. 09/710059, 09/724553 and 09/688017. Results of these assays that show a high binding affinity are listed in Table 4 below.

As we can see below, there a large number of PDZ domains that bind some of the oncogenic E6 proteins. However, only the second PDZ domain from MAGI-1 seems to bind all of the oncogenic E6 PLs tested. The PDZ domain of TIP-1 binds all but one of the oncogenic E6 PLs tested, and may be useful in conjunction with MAGI-1 domain 2 for detecting the presence of oncogenic E6 proteins.

In a similar manner, peptides corresponding to the C-terminal ends of several non-oncogenic E6 proteins were tested with the G-assay. None of the peptides showed any affinity for binding PDZ domains.

TABLE 4 higher affinity interactions between HPV E6 PLs and PDZ domains

| HPV strain | PDZ binding partner (signal 4 and 5 of 0-5) | HPV strain | PDZ binding partner (signal 4 and 5 of 0-5) |
|---|---|---|---|
| HPV 35 (TEV) | Atrophin-1 interact. prot. (PDZ # 1, 3, 5) Magi1 (PDZ # 2, 3, 4, 5) Lim-Ril FLJ 11215 MUPP-1 (PDZ #10) | HPV 33 (TAL) | Magi1 (PDZ #2) TIP1 DLG1 Vartul (PDZ #1) KIAA 0807 KIAA 1095 (Semcap3) (PDZ #1) |

TABLE 4-continued higher affinity interactions between HPV E6 PLs and PDZ domains

| HPV strain | PDZ binding partner (signal 4 and 5 of 0-5) | HPV strain | PDZ binding partner (signal 4 and 5 of 0-5) |
|---|---|---|---|
| | KIAA 1095 (PDZ #1)<br>PTN-4<br>INADL (PDZ #8)<br>Vartul (PDZ # 1, 2,3)<br>Syntrophin-1 alpha<br>Syntrophin gamma-1<br>TAX IP2<br>KIAA 0807<br>KIAA 1634 (PDZ #1)<br>DLG1 (PDZ1,2)<br>NeDLG (1, 2, 3,)<br>Sim. Rat outer membrane (PDZ #1)<br>MUPP-1 (PDZ #13)<br>PSD 95 (1,2,3) | | KIAA 1934 (PDZ #1)<br>NeDLG (PDZ #1,2)<br>Rat outer membrane (PDZ #1)<br>PSD 95 (PDZ #3 and 1-3) |
| HPV 58 (TQV) | Atrophin-1 interact. prot. (PDZ # 1)<br>Magi1 (PDZ #2)<br>DLG1 (PDZ1, 2)<br>DLG2 (PDZ #2)<br>KIAA 0807<br>KIAA 1634 (PDZ #1)<br>NeDLG (1, 2)<br>Sim. Rat outer membrane (PDZ #1)<br>PSD 95 (1,2,3)<br>INADL (PDZ #8)<br>TIP-1 | HPV 66 (STV) | DLG1 (PDZ #1, 2)<br>NeDLG (PDZ #2)<br>PSD 95 (PDZ #1, 2, 3)<br>Magi1 (PDZ #2)<br>KIAA 0807<br>KIAA 1634 (PDZ #1)<br>DLG2 (PDZ #2)<br>Rat outer membrane (PDZ #1)<br>NeDLG (1, 2)<br>TIP-1 |
| HPV 16* (TQL) | TIP-1<br>Magi1 (PDZ #2) | HPV 52 (TQV) | Magi1 (PDZ #2) |
| HPV 18* (TQV) | TIP1<br>Magi 1 (PDZ #2) | | |

Table 4: Interactions between the E6 C-termini of several HPV variants and human PDZ domains. HPV strain denotes the strain from which the E6 C-terminal peptide sequence information was taken. Peptides used in the assay varied from 18 to 20 amino acids in length, and the terminal four residues are listed in parenthesis. Names to the right of each HPV E6 variant denote the human PDZ domain(s) (with domain number in parenthesis for proteins with multiple PDZ domains) that saturated binding with the E6 peptide in the G assay (See Description of the Invention). *denotes that the PDZ domains of hDlg1 were not tested against these proteins yet due to limited material, although both have been shown to bind hDlg1 in the literature.

EXAMPLE 3

Generation of Eukaryotic Expression Constructs Bearing DNA Fragments that Encode HPV E6 Genes or Portions of HPV E6 Genes This example describes the cloning of HPV E6 genes or portions of HPV E6 genes into eukaryotic expression vectors in fusion with a number of protein tags, including but not limited to Glutathione S-Transferase (GST), Enhanced Green Fluorescent Protein (EGFP), or Hemagglutinin (HA).

A. Strategy cDNA fragments were generated by RT-PCR from HPV cell line (cervical epidermoid carcinoma, ATCC# CRL-1550 and CRL-1595 for HPV E6 16 and 18, respectively) derived RNA, using random (oligo-nucleotide) primers (Invitrogen Cat.#48190011). DNA fragments corresponding to HPV E6 were generated by standard PCR, using above purified cDNA fragments and specific primers (see Table 5). Primers used were designed to create restriction nuclease recognition sites at the PCR fragment's ends, to allow cloning of those fragments into appropriate expression vectors. Subsequent to PCR, DNA samples were submitted to agarose gel electrophoresis. Bands corresponding to the expected size were excised. DNA was extracted by Sephaglas Band Prep Kit (Amersham Pharmacia Cat#27-9285-01) and digested with appropriate restriction endonuclease. Digested DNA samples were purified once more by gel electrophoresis, according to the same protocol used above. Purified DNA fragments were coprecipitated and ligated with the appropriate linearized vector. After transformation into E. coli, bacterial colonies were screened by colony PCR and restriction digest for the presence and correct orientation of insert. Positive clones were innoculated in liquid culture for large scale DNA purification. The insert and flanking vector sites from the purified plasmid DNA were sequenced to ensure correct sequence of fragments and junctions between the vectors and fusion proteins.

B. Vectors:

Cloning vectors were pGEX-3X (Amersham Pharmacia #27-4803-01), MIE (a derivative of MSCV, containing IRES and EGFP, generated by recombinant DNA technology), pmKit, pcDNA3.1 (Invitrogen, modified to include a HA tag upstream of the cloning site) and pMAL (New England Biolabs Cat#N8076S, polylinker modified in house to include BamH1 and EcoR1 sites).

DNA fragments containing the ATG-start codon and the TAG-stop codon of HPV E6 were cloned into pGEX3x. HPV E6 genes, and 3' truncated (ΔPL) versions, were subsequently cloned into MIE (MSCV-IRES-EGFP) vector, pcDNA-HA vector, and pmKit vector, using the purified HPV E6-pGEX3x fusion plasmid as the PCR template, and using the same purification protocols as listed above. Truncated versions of HPV E6 have a stop codon inserted after the −3 position amino acid, so as to delete the last three amino acids from the coding region of the gene.

C. Constructs:

Primers used to generate DNA fragments by PCR are listed in Table 5. PCR primer combinations and restriction sites for insert and vector are listed below.

TABLE 5

Primers used in cloning of HPV E6 into representative expression vectors.

| ID# (Primer Name) | Primer Sequence | Description | Seq ID |
|---|---|---|---|
| 2548 (1054EF) | AAAAGATCTACAAT ACTATGGCGC | Forward (5' to 3') primer corresponding to HPV E6 18, generates a Bgl II site. Used for cloning into pGEX3x. | 250 |
| 2549 (1058ER) | AGGGAATTCCAGAC TTAATATTATAC | Reverse (3' to 5') primer corresponding to HPV E6 18, generates an EcoR1 site. Used for cloning into pGEX3x. | 251 |
| 2542 (1050EF) | AAAGGATCCATTTT ATGCACCAAAAG | Forward (5' to 3') primer corresponding to HPV E6 16, generates a BamH1 site. Used for cloning into pGEX3x. | 252 |
| 2543 (1051ER) | ATGGAATTCTATCTC CATGCATGATTAC | Reverse (3' to 5') primer corresponding to HPV E6 16, generates an EcoR1 site. Used for cloning into pGEX3x. | 253 |
| 2563 (1071EF) | GAGGAATTCACCAC AATACTATGGCG | Forward (5' to 3') primer corresponding to HPV E6 18, generates an EcoR1 site. Used for cloning into MIE. | 254 |
| 2564 (1072ER) | AGGAGATCTCATAC TTAATATTATAC | Reverse (3' to 5') primer corresponding to HPV E6 18, generates a Bgl II site. Used for cloning into MIE. | 255 |
| 2565 (1073ERPL) | TTGAGATCTTCAGC GTCGTTGGAGTCG | Reverse (3' to 5') primer corresponding to HPV E6 18 ΔPL, generates a Bgl II site. Used for cloning into MIE. | 256 |
| 2560 (1074EF) | AAAGAATTCATTTT ATGCACCAAAAG | Forward (5' to 3') primer corresponding to HPV E6 16, generates an EcoR1 site. Used for cloning into MIE. | 257 |
| 2561 (1075ER) | ATGGGATCCTATCTC CATGCATGATTAC | Reverse (3' to 5') primer corresponding to HPV E6 16, generates a BamH1 site. Used for cloning into MIE. | 258 |
| 2562 (1076ERPL) | CTGGGATCCTCATC AACGTGTTCTTGATG ATC | Reverse (3' to 5') primer corresponding to HPV E6 16 ΔPL, generates a BamH1 site. Used for cloning into MIE. | 259 |
| 2603 (1080EF) | AAGAAAGCTTTTTA TGCACCAAAAGAG | Forward (5' to 3') primer corresponding to HPV E6 16, generates A Hind III site. Used for cloning into pcDNA-HA. | 260 |
| 2604 (1081ER) | AATCAAGCTTTATCT CCATGCATGATTAC | Reverse (3' to 5') primer corresponding to HPV E6 16, generates a Hind III site. Used for cloning into pcDNA-HA. | 261 |
| 2605 (1082ERPL) | GCTGAAGCTTTCAA CGTGTTCTTGATGAT C | Reverse (3' to 5') primer corresponding to HPV E6 16 ΔPL, generates a Hind III site. Used for cloning into pcDNA-HA. | 262 |
| 2606 (1083EF) | AAGCGTCGACTTTA TGCACCAAAAGAG | Forward (5' to 3') primer corresponding, to HPV E6 16, generates a Sal I site. Used for cloning into pmKit. | 263 |
| 2607 (1084ER) | AATGCTCGAGTATC TCCATGCATGATTAC | Reverse (3' to 5') primer corresponding to HPV E6 16, generates a Xho I site. Used for cloning into pmKit. | 264 |

TABLE 5-continued

Primers used in cloning of HPV E6 into representative expression vectors.

| ID# (Primer Name) | Primer Sequence | Description | Seq ID |
|---|---|---|---|
| 2608 (1085ERPL) | GCTGCTCGAGTCAA CGTGTTCTTGATGAT C | Reverse (3' to 5') primer corresponding to HPV E6 16 ΔPL, generates a Xho I site. Used for cloning into pmKit. | 265 |
| 2612 (1086EF) | AGAAGTCGACCACA ATACTATGGCGC | Forward (5' to 3') primer corresponding to HPV E6 18, generates a Sal I site. Used for cloning into pmKit. | 266 |
| 2613 (1087ER) | TAGGCTCGAGCATA CTTAATATTATAC | Reverse (3' to 5') primer corresponding to HPV E6 18, generates a Xho I site. Used for cloning into pmKit. | 267 |
| 2614 (1088ERPL) | CTTGCTCGAGTCAG CGTCGTTGGAGTCG | Reverse (3' to 5') primer corresponding to HPV E6 18 ΔPL, generates a Xho I site. Used for cloning into pmKit. | 268 |
| 2615 (1089EF) | AGAAAAGCTTCACA ATACTATGGCGC | Forward (5' to 3') primer corresponding to HPV E6 18, generates A Hind III site. Used for cloning into pcDNA-HA. | 269 |
| 2616 (1090ER) | TAGAAGCTTGCATA CTTAATATTATAC | Reverse (3' to 5') primer corresponding to HPV E6 18, generates a Hind III site. Used for cloning into pcDNA-HA. | 270 |
| 2617 (1091ERPL) | CTTGAAGCTTTCAGC GTCGTTTGAGGTCG | Reverse (3' to 5') primer corresponding to HPV E6 18 ΔPL, generates a Hind III site. Used for cloning into pcDNA-HA. | 271 |

1. Human Papillomavirus (HPV) E6 16
Acc#:_____
GI#:4927719
Construct: HPV E6 16WT-pGEX-3X
   Primers: 2542 & 2543
   Vector Cloning Sites(5'/3'): Bam H1/EcoR1
   Insert Cloning Sites(5'/3'): BamH1/EcoR1
   pGEX-3X contains GST to the 5' end (upstream) of the cloning site
Construct: HPV E6 16WT-MIE
   Primers: 2560 & 2561
   Vector Cloning Sites(5'/3'): EcoR1/BamH1
   Insert Cloning Sites(5'/3'): EcoR1/BamH1
   MIE contains IRES and EGFP to the 3' end (downstream) of the cloning site
Construct: HPV E6 16ΔPL-MIE
   Primers: 2560 & 2562
   Vector Cloning Sites(5'/3'): EcoR1/BamH1
   Insert Cloning Sites(5'/3'): EcoR1/BamH1
   MIE contains IRES and EGFP to the 3' end (downstream) of the cloning site
Construct: HPV E6 16WT-pcDNA3.1-HA
   Primers: 2603 & 2604
   Vector Cloning Sites(5'/3'): Hind III/Hind III
   Insert Cloning Sites(5'/3'): Hind III/Hind III
   pcDNA3.1 (modified) contains HA to the 5' end (upstream) of the cloning site
Construct: HPV E6 16ΔPL-pcDNA3.1-HA
   Primers: 2603 & 2605
   Vector Cloning Sites(5'/3'): Hind III/Hind III
   Insert Cloning Sites(5'/3'): Hind III/Hind III
   pcDNA3.1 (modified) contains HA to the 5' end (upstream) of the cloning site
Construct: HPV E6 16WT-pmKit
   Primers: 2606 & 2607
   Vector Cloning Sites(5'/3'): Sal I/Xho I
   Insert Cloning Sites(5'/3'): Sal I/Xho I
Construct: HPV E6 16ΔPL-pmKit
   Primers: 2606 & 2608
   Vector Cloning Sites(5'/3'): Sal I/Xho I
   Insert Cloning Sites(5'/3'): Sal I/Xho I 2. Human Papillomavirus (HPV) E6 18
Acc#:_____
GI#:_____
Construct: HPV E6 18WT-pGEX-3X
   Primers: 2548 & 2549
   Vector Cloning Sites(5'/3'): Bam H1/EcoR1
   Insert Cloning Sites(5'/3'): Bgl II/EcoR1
   pGEX-3X contains GST to the 5' end (upstream) of the cloning site
Construct: HPV E6 18WT-MIE
   Primers: 2563 & 2564
   Vector Cloning Sites(5'/3'): EcoR1/BamH1
   Insert Cloning Sites(5'/3'): EcoR1/Bgl II
   MIE contains IRES and EGFP to the 3' end (downstream) of the cloning site
Construct: HPV E6 18ΔPL-MIE
   Primers: 2563 & 2565
   Vector Cloning Sites(5'/3'): EcoR1/BamH1
   Insert Cloning Sites(5'/3'): EcoR1/Bgl II
   MIE contains IRES and EGFP to the 3' end (downstream) of the cloning site
Construct: HPV E6 18WT-pcDNA3 1-HA
   Primers: 2615 & 2616
   Vector Cloning Sites(5'/3'): Hind III/Hind III
   Insert Cloning Sites(5'/3'): Hind III/Hind III pcDNA3.1 (modified) contains HA to the 5' end (upstream) of the cloning site
Construct: HPV E6 18ΔPL-pcDNA3.1-HA
   Primers: 2615 & 2617
   Vector Cloning Sites(5'/3'): Hind III/Hind III
   Insert Cloning Sites(5'/3'): Hind III/Hind III
   pcDNA3.1 (modified) contains HA to the 5' end (upstream) of the cloning site
Construct: HPV E6 18WT-pmKit
   Primers: 2612 & 2613
   Vector Cloning Sites(5'/3'): Sal I/Xho I
   Insert Cloning Sites(5'/3'): Sal I/Xho I
Construct: HPV E6 18ΔPL-pmKit
   Primers: 2612 & 2614
   Vector Cloning Sites(5'/3'): Sal I/Xho I
   Insert Cloning Sites(5'/3'): Sal I/Xho I
D. GST Fusion Protein Production and Purification The constructs using pGEX-3X expression vector were used to make fusion proteins according to the protocol outlined in the GST Fusion System, Second Edition, Revision 2, Pharmacia Biotech. Method II and was optimized for a 1L LgPP.

Purified DNA was transformed into *E. coli* and allowed to grow to an $OD_{600}$ of 0.4-0.8 (600λ). Protein expression was induced for 1-2 hours by addition of IPTG to cell culture. Cells were harvested and lysed. Lysate was collected and GS4B beads (Pharmacia Cat#17-0756-01) were added to bind GST fusion proteins. Beads were isolated and GST fusion proteins were eluted with GEB II. Purified proteins were stored in GEB II at −80° C.

Purified proteins were used for ELISA-based assays and antibody production.

EXAMPLE 4

Generation of Eukaryotic Expression Constructs Bearing DNA Fragments that Encode PDZ Domain Containing Genes or Portions of PDZ Domain Genes This example describes the cloning of PDZ domain containing genes or portions of PDZ domain containing genes were into eukaryotic expression vectors in fusion with a number of protein tags, including but not limited to Glutathione S-Transferase (GST), Enhanced Green Fluorescent Protein (EGFP), or Hemagglutinin (HA).

A. Strategy

DNA fragments corresponding to PDZ domain containing genes were generated by RT-PCR from RNA from a library of individual cell lines (CLONTECH Cat#K4000-1) derived RNA, using random (oligo-nucleotide) primers (Invitrogen Cat.#48190011). DNA fragments corresponding to PDZ domain containing genes or portions of PDZ domain containing genes were generated by standard PCR, using above purified cDNA fragments and specific primers (see Table 6). Primers used were designed to create restriction nuclease recognition sites at the PCR fragment's ends, to allow cloning of those fragments into appropriate expression vectors. Subsequent to PCR, DNA samples were submitted to agarose gel electrophoresis. Bands corresponding to the expected size were excised. DNA was extracted by Sephaglas Band Prep Kit (Amersham Pharmacia Cat#27-9285-01) and digested with appropriate restriction endonuclease. Digested DNA samples were purified once more by gel electrophoresis, according to the same protocol used above. Purified DNA fragments were coprecipitated and ligated with the appropriate linearized vector. After transformation into *E. coli*, bacterial colonies were screened by colony PCR and restriction digest for the presence and correct orientation of insert. Positive clones were innoculated in liquid culture for large scale DNA purification. The insert and flanking vector sites from the purified plasmid DNA were sequenced to ensure correct sequence of fragments and junctions between the vectors and fusion proteins.

B. Vectors:

All PDZ domain-containing genes were cloned into the vector pGEX-3X (Amersham Pharmacia #27-4803-01, Genemed Acc#U13852, GI#595717), containing a tac promoter, GST, Factor Xa, β-lactamase, and lac repressor.

The amino acid sequence of the pGEX-3X coding region including GST, Factor Xa, and the multiple cloning site is listed below. Note that linker sequences between the cloned inserts and GST-Factor Xa vary depending on the restriction endonuclease used for cloning. Amino acids in the translated region below that may change depending on the insertion used are indicated in small caps, and are included as changed in the construct sequence listed in (C).

aa 1-aa 232:
(SEQ ID NO: 272)
MSPILGYWKIKGLVQPTRLLLEYLEEKYEEHLYERDEGDKWRNKKFELGL

EFPNLPYYIDGDVKLTQSMAIIRYIADKHWLGGCPKERAEISMLEGAVLD

IRYGVSRIAYSKDFETLKVDFLSKLPEMLKMFEDRLCHKTYLNGDHVTHP

DFMLYDALDVVLYMDPMCLDAFPKLVCFKKRIEAIPQIDKYLKSSKYIAW

PLQGWQATFGGGDHPPKSDLIEGRipgnss

In addition, TAX Interacting Protein 1 (TIP1), in whole or part, was cloned into many other expression vectors, including but not limited to CD5γ, PEAK10 (both provided by the laboratory of Dr. Brian Seed at Harvard University and generated by recombinant DNA technology, containing an IgG region), and MIN (a derivative of MSCV, containing IRES and NGFR, generated by recombinant DNA technology).

C. Constructs:

Primers used to generate DNA fragments by PCR are listed in Table 6. PCR primer combinations and restriction sites for insert and vector are listed below, along with amino acid translation for insert and restriction sites. Non-native amino acid sequences are shown in lower case.

TABLE 6

Primers used in cloning of DLG 1 (domain 2 of 3), MAGI 1 (domain 2 of 6), and TIP 1 into representative expression vectors.

| ID#(Primer Name) | Primer Sequence | Description | Seq ID |
|---|---|---|---|
| 1928 (654DL1 2F) | AATGGGGATCCAGC TCATTAAAGG | Forward (5' to 3') primer corresponding to DLG 1, domain 2 of 3. Generates a Bam H1 site upstream (5') of the PDZ boundary. Used for cloning into pGEX-3X. | 273 |

TABLE 6-continued

Primers used in cloning of DLG 1 (domain 2 of 3), MAGI 1 (domain 2 of 6), and TIP 1 into representative expression vectors.

| ID#(Primer Name) | Primer Sequence | Description | Seq ID |
|---|---|---|---|
| 1929 (655DL1 2R) | ATACATACTTGTGG AATTCGCCAC | Reverse (3' to 5') primer corresponding to DLG 1, domain 2 of 3. Generates an EcoR1 site downstream (3') of the PDZ boundary. Used for cloning into pGEX-3X. | 274 |
| 1453 (43SBAF) | CACGGATCCCTTTCTG AGTTGAAAGGC | Forward (5' to 3') primer corresponding to MAGI 1, domain 2 of 6. Generates a BamH1 site upstream (5') of the PDZ boundary. Used for cloning into pGEX-3X. | 275 |
| 1454 (436BAR) | TATGAATTCCATCTG GATCAAAAGGCAAT G | Reverse (3' to 5') primer corresponding to MAGI 1, domain 2 of 6. Generates an EcoR1 site downstream (3') of the PDZ boundary. Used for cloning into pGEX-3X. | 276 |
| 399 (86TAF) | CAGGGATCCAAAGA GTTGAAATTCACAA GC | Forward (5' to 3') primer corresponding to TIP1. Generates a Bam H1 site upstream (5') of the PDZ boundary. Used for cloning into pGEX-3X. | 277 |
| 400 (87TAR) | ACGGAATTCTGCAG CGACTGCCGCGTC | Reverse (3' to 5') primer corresponding to TIP1. Generates an EcoR1 site downstream (3') of the PDZ boundary. Used for cloning into pGEX-3X. | 278 |
| 1319 (TIPG5-1) | AGGATCCAGATGTC CTACATCCC | Forward (5' to 3') primer corresponding to TIP1. Generates a Bam H1 site upstream (5') of the start codon. Used for cloning into pGEX-3X. | 279 |
| 1320 (TIPG3-1) | GGAATTCATGGACT GCTGCACGG | Reverse (3' to 5') primer corresponding to TIP1. Generates an EcoR1 site downstream (3') of the stop codon. Used for cloning into pGEX-3X. | 280 |
| 2753 (1109TIF) | AGAGAATTCTCGAG ATGTCCTACATCCC | Forward (5' to 3') primer corresponding to TIP1. Generates an EcoR1 site upstream (5') of the start codon. Used for cloning into MN. | 281 |
| 2762 (1117TIR) | TGGGAATTCCTAGG ACAGCATGGACTG | Reverse (3' to 5') primer corresponding to TIP1. Generates an EcoR1 site downstream (3') of the stop codon. Used for cloning into MN. | 282 |
| 2584 (1080TIF) | CTAGGATCCGGGCC AGCCGGTCACC | Forward (5' to 3') primer corresponding to TIP1. Generates a Bam H1 site upstream (5') of the PDZ boundary. Used for cloning into PEAK10 or CD5γ. | 283 |
| 2585 (1081TIR) | GACGGATCCCCCTG CTGCACGGCCTTCTG | Reverse (3' to 5') primer corresponding to TIP1. Generates a Bam H1 site downstream (3') of the PDZ boundary. Used for cloning into PEAK10 or CD5γ. | 284 |
| 2586 (1082TIR) | GACGAATTCCCCTG CTGCACGGCCTTCTG | Reverse (3' to 5') primer corresponding to TIP1. Generates an EcoR1 site downstream (3') of the PDZ boundary. Used for cloning into PEAK10 or CD5γ. | 285 |
| 2587 (1083TIF) | CTAGAATTCGGGCC AGCCGGTCACC | Forward (5' to 3') primer corresponding to TIP1. Generates an Eco R1 site upstream (5') of the PDZ boundary. Used for cloning into PEAK10 or CD5γ. | 286 |

1. DLG 1, PDZ domain 2 of 3:
Acc#:U13897
GI#:558437
Construct: DLG 1, PDZ domain 2 of 3-pGEX-3X
   Primers: 1928 & 1929
   Vector Cloning Sites(5'/3'): Bam H1/EcoR1
   Insert Cloning Sites(5'/3'): BamH1/EcoR1 aa 1-aa 88

(SEQ ID NO: 287)
giqLIKGPKGLGFSIAGGVGNQHIPGDNSIYVTKIIEGGAAHKDGKLQIG

DKLLAVNNVCLEEVTHEEAVTALKNTSDFVYLKVAnss

2. MAGI 1. PDZ domain 2 of 6:
Acc#:AB010894
GI#:3370997
Construct: MAGI 1, PDZ domain 2 of 6-pGEX-3X
   Primers: 1453 & 1454
   Vector Cloning Sites(5'/3'): Bam H1/EcoR1
   Insert Cloning Sites(5'/3'): BamH1/EcoR1 aa 1-aa 108

(SEQ ID NO: 288)
giPSELKGKFIHTKLRKSSRGFGFTVVGGDEPDEFLQIKSLVLDGPAALD

GKMETGDVIVSVNDTCVLGHTHAQVVKIFQSIPIGASVDLELCRGYPLPF

DPDgihrd

3. TAX Interacting Protein 1 (TIP1):
Acc#:AF028823.2
GI#:11908159
Construct: TIP 1, PDZ domain 1 of 1-pGEX-3X
   Primers: 399& 400
   Vector Cloning Sites(5'/3'): Bam H1/EcoR1
   Insert Cloning Sites(5'/3'): BamH1/EcoR1 aa 1-aa 107

(SEQ ID NO: 289)
giQRVEIHKLRQGENLILGFSIGGGIDQDPSQNPFSEDKTDKGIYVTRVS

EGGPAEIAGLQIGDKIMQVNGVVDMTMVTHDQARKRLTKRSEEVVRLLVT

RQSLQnss

Construct: TIP 1-pGEX-3X
   Primers: 1319& 1320
   Vector Cloning Sites(5'/3'): Bam H1/EcoR1
   Insert Cloning Sites(5'/3'): BamH1/EcoR1 aa 1-aa 128

(SEQ ID NO: 290)
giqMSYIPGQPVTAVVQRVEIHKLRQGENLILGFSIGGGIDQDPSQNPFS

EDKTDKGIYVTRVSEGGPAEIAGLQIGDKIMQVNGWDMTMVTHDQARKRL

TKRSEEVVRLLVTRQSLQKAVQQSMnss

Construct: TIP1-MIN
   Primers: 2753& 2762
   Vector Cloning Sites(5'/3'): EcoR1/EcoR1
   Insert Cloning Sites(5'/3'): EcoR1/EcoR1 aa 1-aa 129

(SEQ ID NO: 291)
agilEMSYIPGQPVTAVVQRVEIHKLRQGENLILGFSIGGGIDQDPSQNP

FSEDKTDKGIYVTRVSEGGPAEIAGLQIGDKIMQVNGWDMTMVTHDQARK

IRLTKRSEEVVRLLVTRQSLQKAVQQSMLS

Construct: TIP1-CD5γ
   Primers: 2584& 2585
   Vector Cloning Sites(5'/3'): Bam H1/Bam H1
   Insert Cloning Sites(5'/3'): BamH1/Bam H1 aa 1-aa 122

(SEQ ID NO: 292)
adPGQPVTAVVQRVEIHKLRQGENLILGFSIGGGIDQDPSQNPFSEDKTD

KGIYVTRVSEGGPAEIAGLQIGDKIMQVNGWDMTMVTHDQARKRLTKRSE

EVVRLLVTRQSLQKAVQQSdpe

D. GST Fusion Protein Production and Purification

The constructs using pGEX-3X expression vector were used to make fusion proteins according to the protocol outlined in the GST Fusion System, Second Edition, Revision 2, Pharmacia Biotech. Method II and was optimized for a 1L LgPP.

Purified DNA was transformed into *E. coli* and allowed to grow to an $OD_{600}$ of 0.4-0.8 (600λ). Protein expression was induced for 1-2 hours by addition of IPTG to cell culture. Cells were harvested and lysed. Lysate was collected and GS4B beads (Pharmacia Cat#17-0756-01) were added to bind GST fusion proteins. Beads were isolated and GST fusion proteins were eluted with GEB II. Purified proteins were stored in GEB II at −80° C.

Purified proteins were used for ELISA-based assays and antibody production.

E. IgG Fusion Protein Production and Purification

The constructs using the CD5 gamma or Peak10IgG expression vectors were used to make fusion protein. Purified DNA vectors were transfected into 293 EBNA T cells under standard growth conditions (DMEM +10% FCS) using standard calcium phosphate precipitation methods (Sambrook, Fritsch and Maniatis, Cold Spring Harbor Press) at a ratio of ~1 ug vector DNA for 1 million cells. This vector results in a fusion protein that is secreted into the growth medium. Transiently transfected cells are tested for peak expression, and growth media containing fusion protein is collected at that maxima (usually 1-2 days). Fusion proteins are either purified using Protein A chromatography or frozen directly in the growth media without addition.

EXAMPLE 5

Tip-1 Specifically Binds to Oncogenic E6 Proteins

A. Abstract

An experiment was conducted to demonstrate and confirm that PDZ domains would only recognize the C-termini of full-length oncogenic HPV E6 proteins and not non-oncogenic E6 variants. This validates the method of using peptides representing the PL sequences of E6 proteins by asking if the PDZ binding can be reproduced using full length E6 fusion proteins.

Briefly, GST-E6 fusion proteins were constructed as described in Example 3 corresponding to the full length protein sequence of E6 from HPV18 (oncogeneic) and HPV11 (non-oncogenic). Using a modified ELISA assay, binding of a TIP-TIP-IgG fusion protein (two copies of the TIP-1 PDZ domain fused to the hIgG constant region, purification of fusion protein partially described in Example 4) to these two E6 variants was assessed.

A subsequent experiment is also shown to demonstrate that the assay for binding to E6 using GST-Tip or GST-Magi fusion proteins is not significantly affected by incubation at 4° C. or room temperature (RT).

B. Modified ELISA Method

Reagents and Materials

Nunc Polysorp 96 well Immuno-plate (Nunc cat#62409-005)
(Maxisorp plates have been shown to have higher background signal)

PBS pH 7.4 (Gibco BRL cat#16777-148) or
AVC phosphate buffered saline, 8 gm NaCl, 0.29 gm KCl, 1.44 gm Na$_2$HPO4, 0.24 gm KH$_2$PO4, add H2O to 1 L and pH 7.4; 0.2 micron filter 2% BSA/PBS (10 g of bovine serum albumin, fraction V (ICN Biomedicals cat#IC15142983) into 500 ml PBS Goat anti-GST mAb stock @ 5 mg/ml, store at 4° C., (Amersham Pharmacia cat#27-4577-01), dilute 1:1000 in PBS, final concentration 5 ug/ml Wash Buffer, 0.2% Tween 20 in 50 mM Tris pH 8.0

TMB ready to use (Dako cat#S 1600)

1M H$_2$SO$_4$ 12 w multichannel pipettor, 50 ml reagent reservoirs, 15 ml polypropylene conical tubes anti E6HPV 18 antibody(OEM Sciences)

Anti-hIgG-HRP (Biomeda)

Protocol

1) Coat plate with 5 ug/ml GST-E6 fusion protein, O/N @ 4° C.
2) Dump proteins out and tap dry
3) Blocking—Add 200 ul per well 2% BSA/PBS, 2 hrs at 4° C.
4) Prepare PDZ proteins (50:50 mixture of supernatant from TIP-TIP-IgG transfection and 2% BSA/PBS)
5) 3× wash with cold PBS
6) Add PDZ protein prepared in step 7 or anti-E6 Ab at 1 ug/ml in 2% BSA/PBS (or anti-GST Ab as control).
7) 3× wash with cold PBS
8) Add appropriate concentration of enzyme-conjugated detection Ab (anti-hIgG-HRP, anti-goat-HRP, or anti-mouse-HRP) 100 ul per well on ice, 20 minutes at 4° C.
9) Turn on plate reader and prepare files
10) 5× wash with Tween wash buffer, avoiding bubbles
11) Using gloves, add TMB substrate at 100 ul per well incubate in dark at room temp
check plate periodically (5, 10, & 20 minutes)
take early readings, if necessary, at 650 nm (blue)
at 30 minutes, stop reaction with 100 ul of 1M H$_2$SO$_4$
take final reading at 450 nm (yellow)

C. Results of Binding Experiments

TIP-1, a representative PDZ domain that binds most oncogenic E6 PLs (EXAMPLE 2), is able to specifically recognize PLs from full length oncogenic E6 variants (HPV18-E6) without binding to non-oncogenic variants (HPV 11-E6; FIG. 1). Furthermore, even unpurified TIP-TIP-IgG fusion protein is able to recognize GST-HPV18E6 fusion protein at levels comparable to an antibody generated against HPV18-E6. Antibodies against GST were used to confirm that the GST-HPV18E6 and GST-HPV11E6 were uniformly plated (data not shown).

Figure 2:
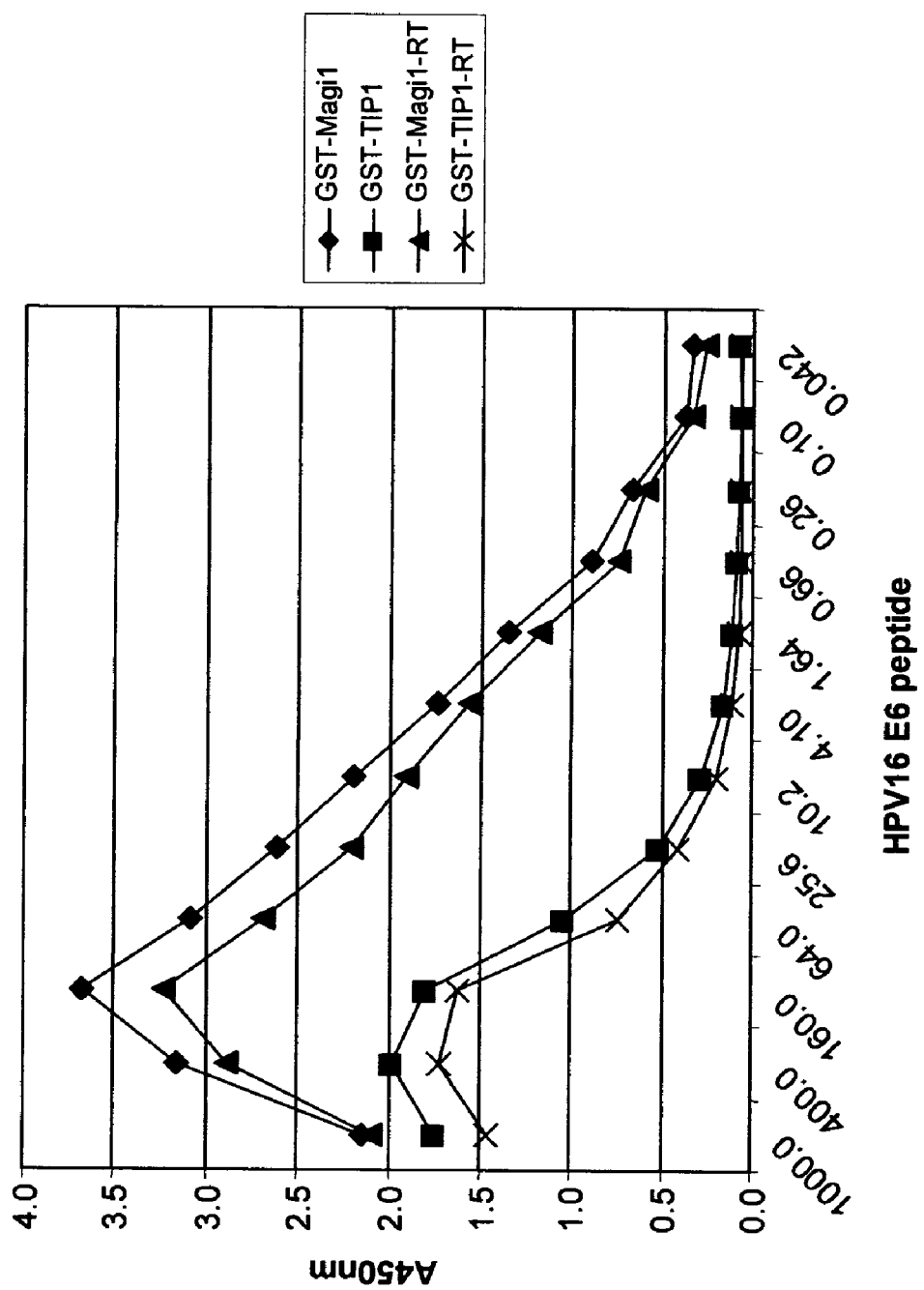
FIG. 2 is a line graph showing that PDZ binding to HPV18 E6 PLs is temperature dependent. This Figure uses a modified ELISA to determine binding of the PDZ domains of TIP-1 or MAGI-1 (domain 2) to a peptide corresponding to the C-terminal 20 AA of the E6 protein from HPV18. Numbers in the legend represent independent experiments. -RT indicates that the association was carried out at room temperature. Data series lacking -RT were allowed to associate at 4° C.

Furthermore, this assay is robust and the off rates are stable enough that the incubation steps of this assay can be performed at 4° C. or RT. Little difference in signal is seen between the two temperatures for either GST-Magi1 of GST-TIP1 binding to E6 (FIG. 2).

E6 activity may be further determined by its ability to bind DNA, or to allow degradation of p53 in the presence of a lysate, Zn2+ binding, etc.

EXAMPLE 6

EC50 Determinations for PDZ Domain Interactions with HPV16 E6

Using the G-assay described above, several GST-PDZ domain fusion proteins were tested to determine their relative binding strength to the PL of the HPV16 E6 protein. Peptide corresponding to the PL of HPV16 E6 was titrated against a constant amount of GST-PDZ domain fusion and the results are shown below. These results demonstrate that although a number of PDZ domains can bind the E6 protein from HPV16, the first functional domain of MAGI1 (domain 2 in this specification) binds the most tightly, making it the most suitable for diagnostic purposes. This is unexpected, especially in conjunction with MAGI1 being the only PDZ domain containing protein demonstrated to bind to all classes of oncogenic E6 proteins identified. Together, these suggest that MAGI1 is a useful capture/detection agent for oncogenic HPV infections.

TABLE 7

EC50 values for HPV16 E6 protein with various PDZ domains

| PDZ gene | EC50[a] [uM] | RNA expression(Cervical cell lines) |
| --- | --- | --- |
| Magi1C (PDZ2) | 0.056 | ++ |
| Magi3 (PDZ1) | 0.31 | neg. |
| SAST1 KIAA | 0.58 | neg. |
| TIP1 | 0.75 | +++ |
| VARTUL | 0.94 | + |
| DLG1 (PDZ2) | ND | ++++ |
| PSD95 (PDZ1-3) | 1.0 | ND |
| SAST2 | 1.2 | ND |
| DLG2 (PDZ3) | 1.6 | ND |
| DLG3 (PDZ1-2) | 3.8 | ND |
| PSD95 (PDZ2) | 6.8 | ND |
| SIP1 (PDZ1) | 7.5 | ND |

Table 7 legend: ND = not done.

EXAMPLE 7

Production of Antibodies Against Purified E6 Fusion Proteins from HPV18

In order to achieve the added benefits of a sandwich ELISA-based diagnostic for oncogenic HPV infection, high-affinity antibodies specific to E6 proteins should be generated. Ideally, monoclonal antibodies could be generated from these animals to have a continually renewable resource for the diagnostic.

Figure 3:
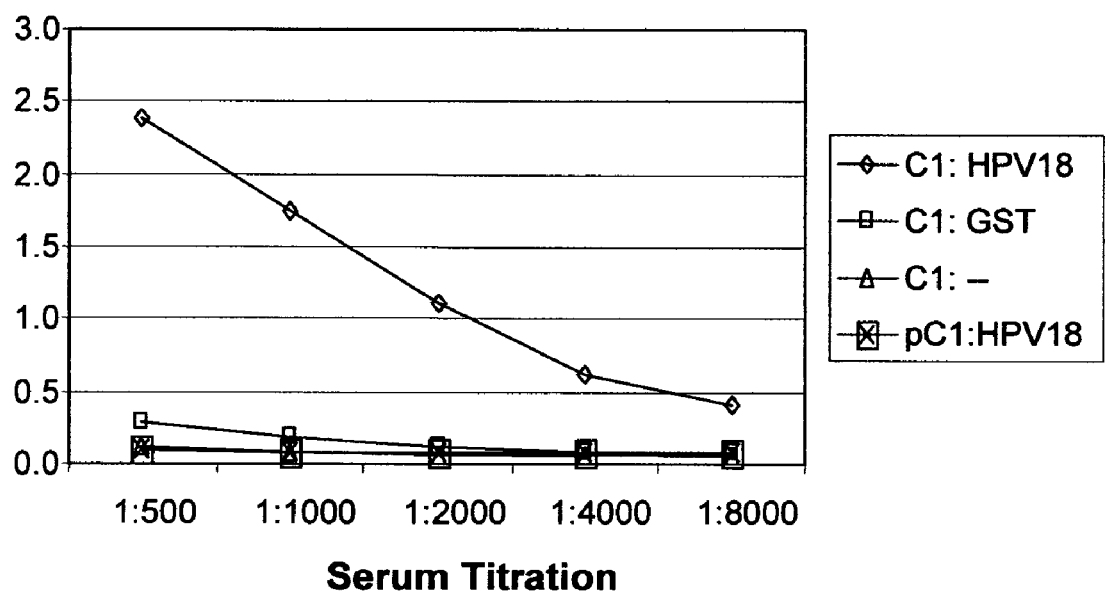
FIG. 3 is a line graph showing anti-HPV18E6 antibody recognition of GST-HPV18E6 fusion protein. Day 28 sera from a Balb/c mouse immunized with HPV18E6 protein was tested for reactivity to either GST-HPV18E6 protein or GST alone.
Figure 4:
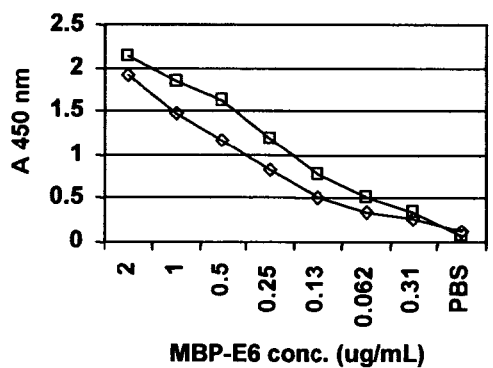
FIGS. 4(A-D) is a panel of four line graphs showing the effect of lysate upon ability of recombinant E6 protein from HPV type 16 to bind different PDZ domains.
Figure 4:
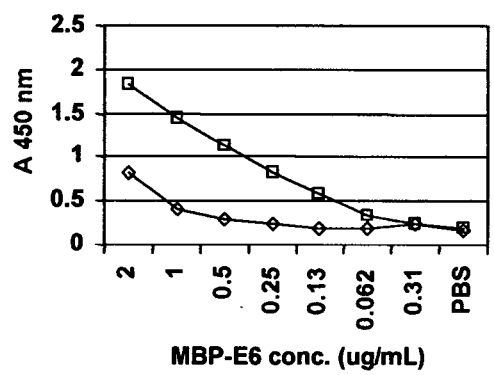
Figure 4:
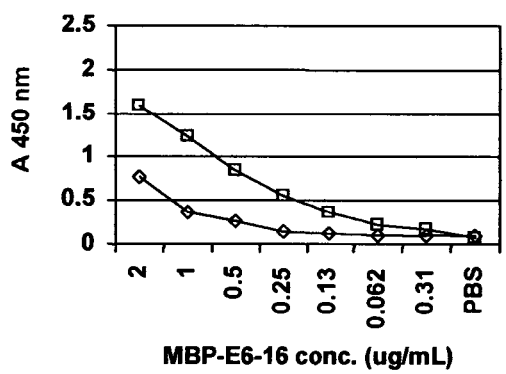
Figure 4:
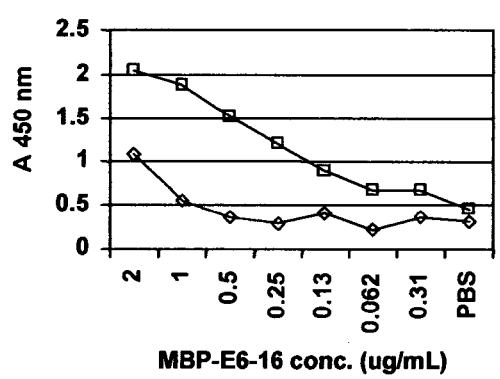

Balb/c mice were injected with 25 ug of bacterially purified GST-HPV18E6 protein at 5 day intervals (Josman Labs). Sera from these mice were collected 3 days after each injection of antigen and tested for reactivity with GST-14PV 18E6 (the immunogen) or GST alone following anti GST-depletion (Pharmacia protocol). The results using sera collected at day 28 are shown in FIG. 3. The sera from this mouse reacts with bacterially purified GST-HPV18-E6 protein but do not react with GST alone. This animal is a good candidate from which to generate a monoclonal antibody by standard methods.

EXAMPLE 8

Pathogen Proteins

Many other proteins from pathogens can be detected using proteins or compounds directed at detection of a PDZ:PL interaction. Table 8 contains some exemplary proteins that could be detected using technology disclosed herein, but is not meant to be limiting in any manner.

TABLE 8

Example Pathogens amenable to PDZ: PL diagnostics

| Pathogen | Protein | Gi or ACC number | PL/PDZ |
| --- | --- | --- | --- |
| Adenovirus | E4 | 19263371 | PL |
| Hepatitis B virus | Protein X | 1175046 | PL |
| Human T Cell Leukemia Virus | TAX | 6983836 | PL |
| Herpesvirus | DNA polymerase | 18307584 | PL |
| Herpesvirus | US2 | 9629443 | PL |

EXAMPLE 9

Quantification of Endogenous E6 Protein in Cells Infected with HPV16

A) Abstract:

Experiments were designed and performed to determine quantities of endogenous E6 protein in HPV16 infected cervical cancer cell lines. Results demonstrate that HPV16 infected cervical cancer cell lines contain in the order of 10,000 to 100,000 molecules E6. From this finding is concluded, that E6 protein can be used as a diagnostic or prognostic marker for cellular HPV infection. Use of protein degradation pathway inhibitors may facilitate such an assay.

B) Methods:

Immunoprecipitation of E6 protein:

HPV16-infected cervical cancer cell lines SiHa and CasKi are washed with cold PBS and resuspended in HEPES lysis buffer (50 mM HEPES pH 7.4, 150 mM NaCl, 10% glycerol, 0.5% triton X-100, 1 mg/ml BSA, one pellet protease inhibitor cocktail (Roche), and 1 mM PMSF) at $2\times10^7$ cells/ml. Lysis proceeds on ice for 30 min. and lysates are cleared by centrifugation at 14,000× g for 5 minutes at 4° C. E6 proteins are immunoprecipitated with a mouse anti-E6 antibody (clone 6F4) and protein G beads (Pharmacia, Piscataway, N.J.). After 2 hours incubation at 4° C. with rotation, beads are washed 3 times with washing Buffer [50 mM HEPES pH 7.4, 150 mM NaCl, 10% glycerol, 0.1% Triton X-100, protease inhibitor cocktail (CALBIOCHEM), 1 mM PMSF]. Pellets are resuspended in SDS-PAGE sample buffer and analyzed by immuno blotting using 6F4 anti-E6 antibody and anti-mouse-IgG-HRP conjugated (Jackson Immuno Research).

Detection of E6 Protein from Cervical Cancer Cell Lysates by Western Technology:

SiHa and CasKi cervical cancer cell lines were lysed at $2\times10^7$ cells/ml in lysis buffer 30 min. on ice. Lysates corresponding to approx. $10^6$ cells are immediately resolved on a 12% SDS-PAGE gel followed by transfer to a PVDF membrane. E6 proteins were detected with 6F4 anti-E6 HPV16 antibody and anti-mouse-IgG-HRP conjugated (Jackson Immuno Research).

Figure 6:
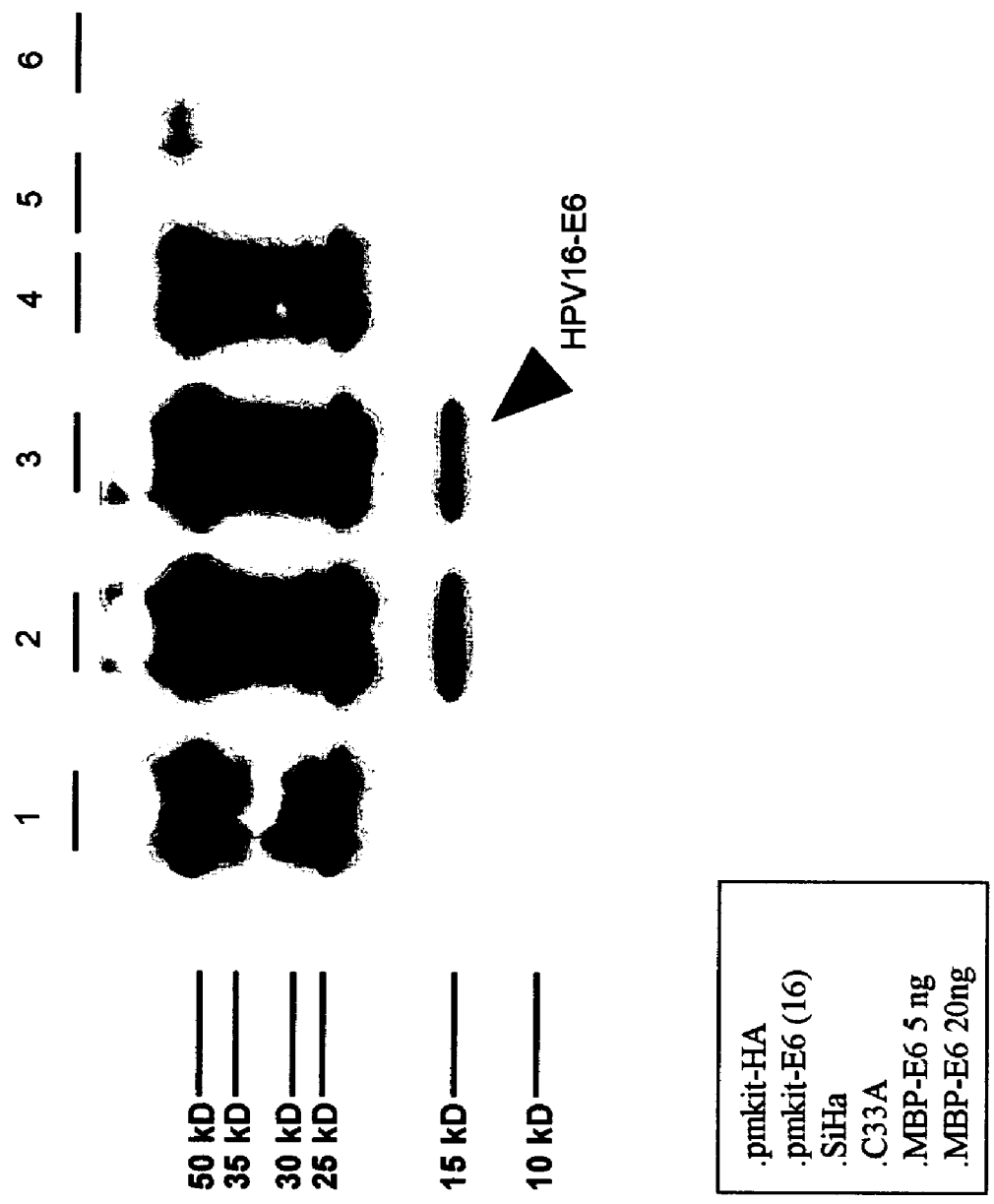
FIG. 6 is an autoradiograph showing the results of a western blot demonstrating detection of endogenous HPV16 E6 protein in the SiHa cervical cancer line.

C) Results:

To determine the apparent molecular weight of endogenous E6 protein as present in cervical cancer cells upon infection with HPV16 and to ensure that a anti E6 monoclonal antibody-specific band seen in PAGE represents viral E6 protein, 293 EBNA-T cells were transfected with a construct expressing untagged E6 protein of HPV type 16. Cell lysates were prepared of those cells, and HPV infected SiHa cervical cancer cells. E6 protein from both lysates (transfected and HPV infected) was immunoprecipitated by use of an anti E6-specific monoclonal antibody. Both lysates were analyzed side by side using PAGE technology (FIG. 6). The E6-specific band obtained for transfected E6 migrates in PAGE at the same level as the anti E6 antibody specific band from SiHa cervical cancer cell lines, thus most strongly suggesting that the product immunoprecipitated with anti E6-specific monoclonal antibody represent viral E6 protein. Using the specific E6 monoclonal antibody, a band of the same size was detected in HPV16 infected cervical cancer cell type CasKi (FIG. 7).

Figure 7:
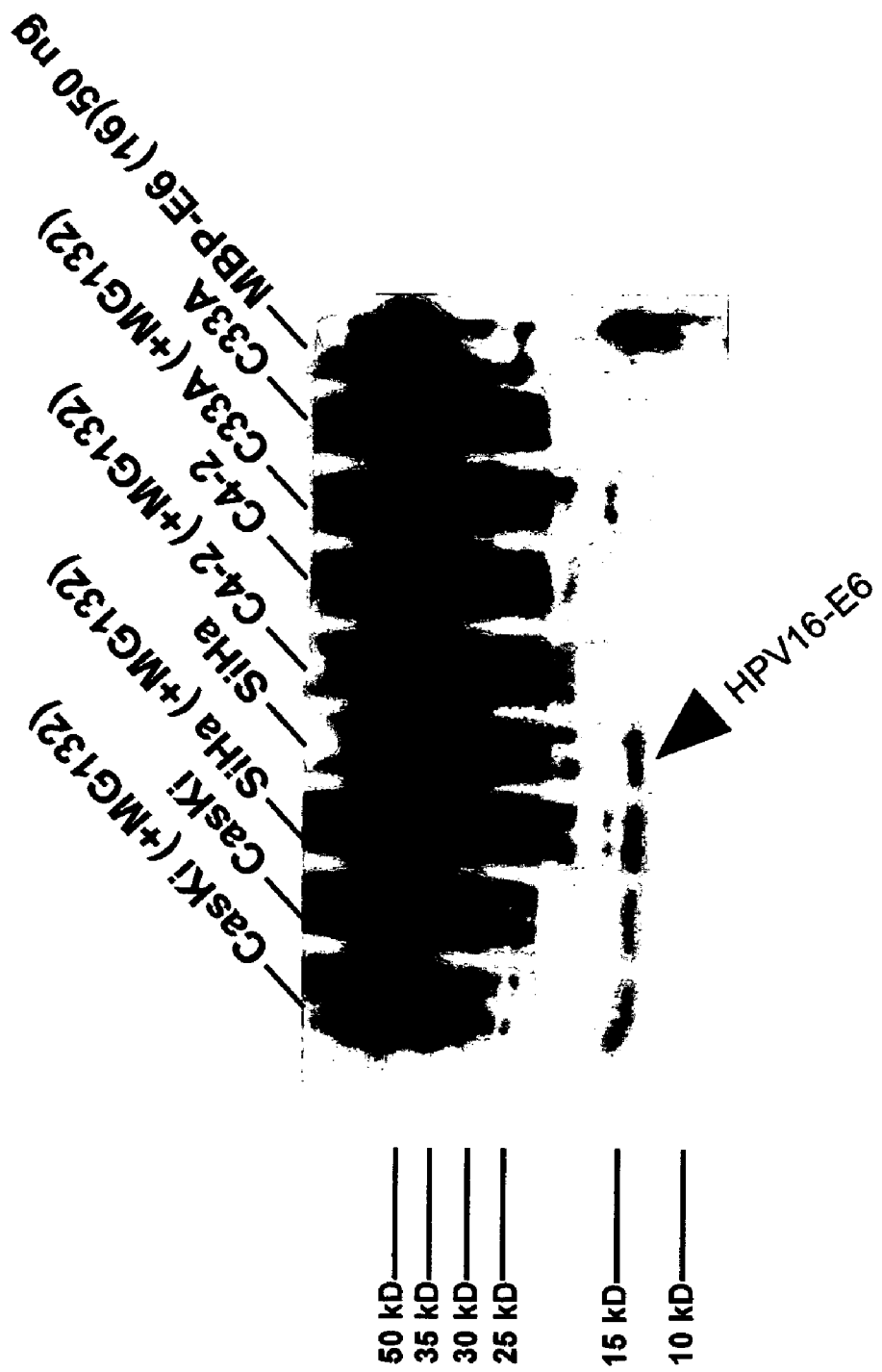
FIG. 7 is an autoradiograph showing that HPV16 E6 protein can be detected in CasKi and SiHa cervical cancer cell lines by western blots, and detection is enhanced when lysates are made in the presence of Proteasome inhibitor.

In a different experimental procedure, endogenous viral E6 protein of HPV 16 infected cervical cancer cell line SiHa and CasKi was directly detected from their cell lysates (FIG. 7). Bands that were dependent on E6-specific monoclonal antibody ran in the same way as the band for cells transfected with E6 encoding vector.

To test, whether E6 in vivo stability can be enhanced by selectively blocking proteasome involved in protein degradation, cell lysates of some samples were treated with proteasome inhibitor MG132. In those samples, the E6 specific band is about 2-3 times more intense. This demonstrates, that addition of an appropriate mixture of protein degradation pathway inhibiting agents can be used to increase the signal specific to E6 protein by augmenting its accumulation temporarily in cells.

Quantities of E6 protein in lysates were measured by comparing E6-Specific signal in PAGE with signals obtained by MBP-E6 (HPV16) fusion protein loaded onto the same gel. In some cases, MBP-E6 fusion protein was digested with factor X to release the E6 portion only. Signal intensity comparison studies demonstrated, that cervical cancer derived cell lines injected with HPV16 (SiHa, CasKi) contain E6 at a concentration of 0.3 to 3 ng per $1\times10^6$ cells. It is concluded, that quantities and stability of E6 are such that detection by an E6-specific (ELISA-) assay will be feasible.

EXAMPLE 10

Oncogenic E6PL-Detector Molecules Bind Selectively Endogenous HPV6E6 Proteins Present in Cell Lysates and can be used to Separate Endogenous E6 Protein from Other Components Present in a Cell Lysate.

A) Abstract

Experiments were undertaken to test, whether oncogenic E6-PL-detector will selectively bind endogenous E6 of cells transfected with E6 encoding vector. Moreover, it was tested whether the oncogenic E6-PL-detector can be used to separate E6 from other molecules in the cell lysate subsequent to binding. Findings demonstrate that oncogenic E6-PL-detector, is selective and can be applied to separate E6 protein from the complex mixture of cell lysate molecules.

B) Methods

Pull Down of E6 Protein with Recombinant PDZ Proteins:

GST-PDZ fusion proteins (i.e. Magi1 PDZ domain #2, Syn2bp, Magi3 PDZ domain #1, Tip 1, PSD-95 PDZ domain #2, and SAST1 were tested in pull down experiments. Briefly, 10 ug recombinant GST-PDZ proteins were incubated with 30 ul of glutathione-sepharose beads in 1 ml of buffer [50 mM HEPES pH 7.4, 150 mM NaCl, 10% glycerol, 0.1% Triton X-100, protease inhibitor cocktail, 1 mM PMSF] for 1 h at 4° C. with rotation. Subsequently, cell lysates of $10^7$ 293 cells transiently transfected with either pMKit-HA-HPV16-E6 or pMKit-HA vector alone were incubated with the beads bound to PDZ proteins for 3 h at 4° C. with rotation. Beads were washed and analyzed in 12% SDS-PAGE gel electrophoresis followed by Western blotting. Membranes were probed with biotin conjugated anti-HA antibodies (clones 3F10, or 12CA5, Boebringer Mannheim) and HRP-Streptavidin (Zymed).

Alternatively, cell lysates from 293 cells transiently transfected with pmKit-HA, pmkit-HPV16-HA-E6 or pmKit-HA-HPV16 E6-ΔPL, were incubated with recombinant GST-Magi1-PDZ domain 2 protein and immobilized on glutathione-sepharose beads and bound fractions were immunoblotted with anti HA antibodies. In parallel, lysates were immunoprecipitated and detected with anti-HA antibodies.

C) Results

Figure 5:
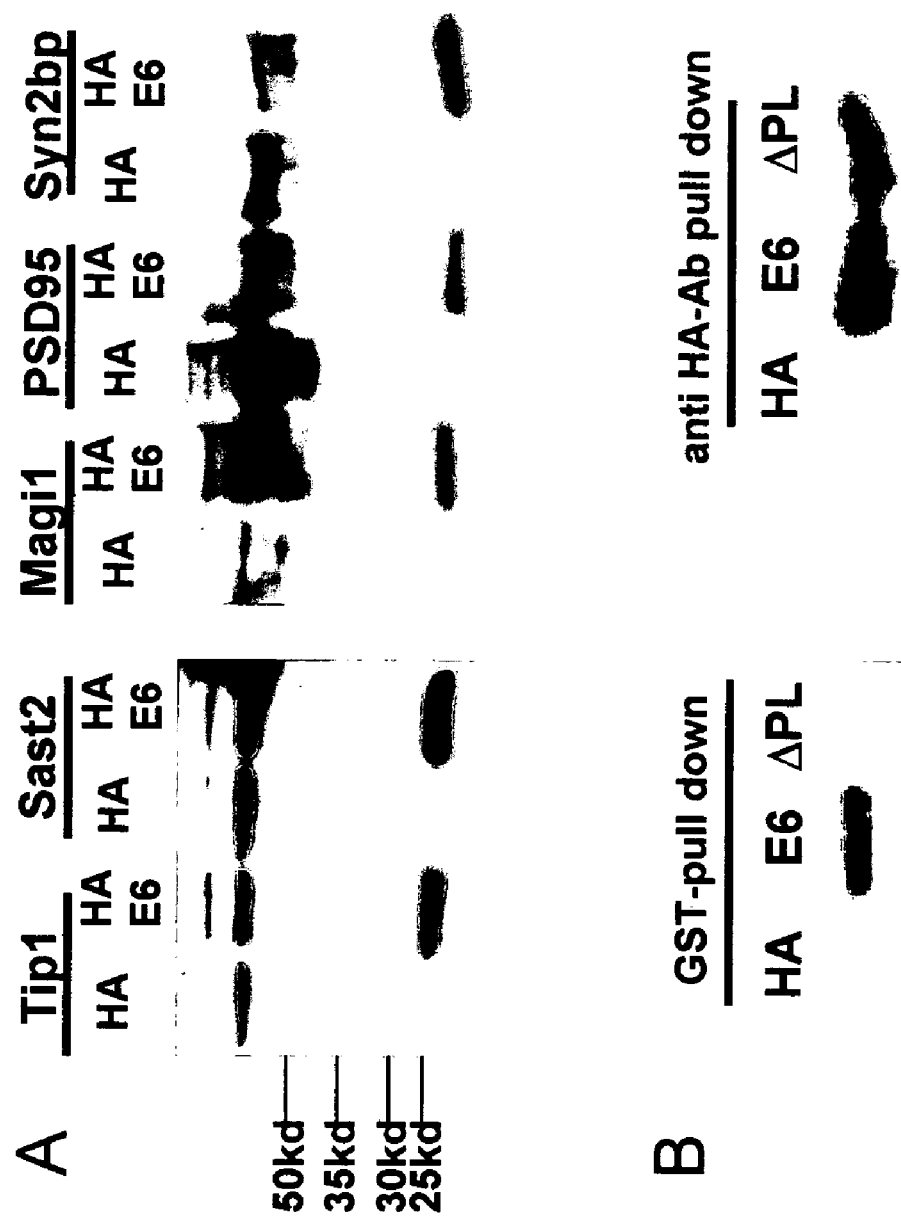
FIGS. 5(A-B) is an autoradiograph showing that several PDZ domains can bind and coprecipitate oncogenic E6 proteins from cells.

G-assay PDZ-E6-PL binding studies and the determination of experimental binding affinities of the E6-PDZ interactions suggested candidate PDZ domains to be tested for the engineering of an oncogenic E6-PL-detector. In a "pull down" experiment, five different PDZ domains (Tip1; Magi1 domain 2; Sast2; Psd95 domain 2; Synaptojanin-2 binding protein) were tested for pull down of endogenous over expressed E6 from cell lysate. Lysates of cells transfected with HA-tagged E6 HPV-16 were incubated with GST-PDZ fusion protein representing the above PDZ domains bound to Sepharose beads (FIG. 5). Control cell samples were transfected with HA expressing constructs. Detection with anti HA monoclonal antibody demonstrates, that E6 is selectively pulled out of cell lysates via the PDZ domain represented by the oncogenic E6-PL-detector of all five GST-PDZ proteins tested (Tip1; Magi1 domain 2; Sast2; Psd95 domain 2; Synaptojanin-2 binding protein). Results shown in FIG. 5B demonstrate that Magi 1-PDZ domain 2 associates with HA-E6 but not with HA-E6ΔPL (lacking the 3 C-terminal amino acids). This method can be used to determine, whether a particular PDZ domain has the capacity of specific E6 binding. The conclusion is made, that competition by potentially PDZ binding proteins represented by the complex mixture of cell lysates and E6 for binding to PDZs can be shifted towards selective binding of E6 by appropriate choice of the specific PDZ domain that constitutes the oncogenic E6-PL detector.

EXAMPLE 11

Endogenous E6 Protein of HPV Infected Cervical Cancer Cell Lines can be Detected in a Sandwich ELISA Via the Oncogenic E6-PL Detector Molecule.

A) Abstract:

Experiments are described, in which the oncogenic E6-PL detector is used to selectively detect presence of E6 protein in HPV infected cells via a sandwich ELISA. The specific capturing of oncogenic E6 but not non-oncogenic E6 demonstrates that the PDZ based oncogenic E6-PL detector can be applied for a E6 detection based diagnostic test for HPV infection and/or cervical cancer test.

B) Methods:

Sandwich type 1 ELISA: Anti-E6 antibody is coated onto a 96-well Polysorp or Maxysorp ELISA plate at 5 ug/ml in PBS (100 ul/well) overnight at 4° C. Plates were washed with PBS and blocked with 200 ul PBS/2% BSA for 2 hours at 4° C. Cell lysates diluted in PBS/2% BSA are added and incubated at room temperature for 1 hour. After 3 washes with PBS, 100 ul of oncogenic E6 detector (for example MAGI1-MAGI1-IgG or GST-MAGI1-PDZ1) at 5 ug/ml was added in PBS/2% BSA, and plates are incubated at room temperature for 45 min. Plates are then washed 3 times with PBS and incubated with anti-hIgG-HRP (Jackson Immuno Research) or anti-GST-HRP (Pharmacia) at the appropriate concentration in PBS/2% BSA at room temperature for 45 minutes. After 5 washes with 50 mM Tris/0.2% Tween-20, plates were incubated with 100 ul /well TMB substrate (Dako Industries). The colorimetric reaction is stopped at appropriate times (usually after 20 minutes) by addition of 100 ul of 0.1 M $H_2SO_4$ and plates read at $A_{450}$ nm in an ELISA plate reader.

In a variant of sandwich 1 ELISA, cell lysates were preincubated with oncogenic E6 detector at 2.5-5 ug/ml final concentration, for 1-2 hours at 4° C., prior to adding to the anti-E6 antibody coated plate.

Sandwich type 2 ELISA: In sandwich 2, reagents and procedures mostly correspond to those used in sandwich 1. In contrast to sandwich 1, 100 ul of oncogenic E6 detector is coated onto the ELISA plate and the anti-E6 antibody is used for detection of oncogenic detector-bound E6, followed by anti-mouse IgG-HRP (Jackson Immuno Research). In a modified version of sandwich 2, biotinylated reagents (anti-E6 antibody or oncogenic detector) will be used followed by streptavidin-HRP to further diminish background and to increase sensitivity.

C) Results:

A sandwich ELISA was conceived in two different variations. In Type 1 sandwich ELISA, E6 protein present in cell lysates in captured by E6-specific monoclonal antibody, and detection of specifically oncogenic variants occurs via the oncogenic E6-PL detector. In the type 2 ELISA set up, oncogenic E6 protein is captured via the oncogenic E6-PL detector to the solid phase and E6 detection occurs via a specific E6 antibody or another E6 binding specific agent like nucleic acid based binding compounds, chemicals binding E6, E6 binding proteins or a combination of those compounds. Cells were lysed directly on a tissue culture plate and lysates were precleared by centrifugation from insoluble components. Lysates were preincubated at 4° C. with oncogenic E6-PL detector, a fusion protein of GST and Magi1 PDZ domain 2. Subsequently, lysates were loaded onto E6-specific antibody coated ELISA plates. Detection occurred via addition of HRP conjugated GST-specific antibody and addition of the HRP substrate TMB after appropriate washes between different incubation steps. Detection signal is constituted by a colorimetric change that is quantified using absorbance measurements at 450 nm.

Figure 8:
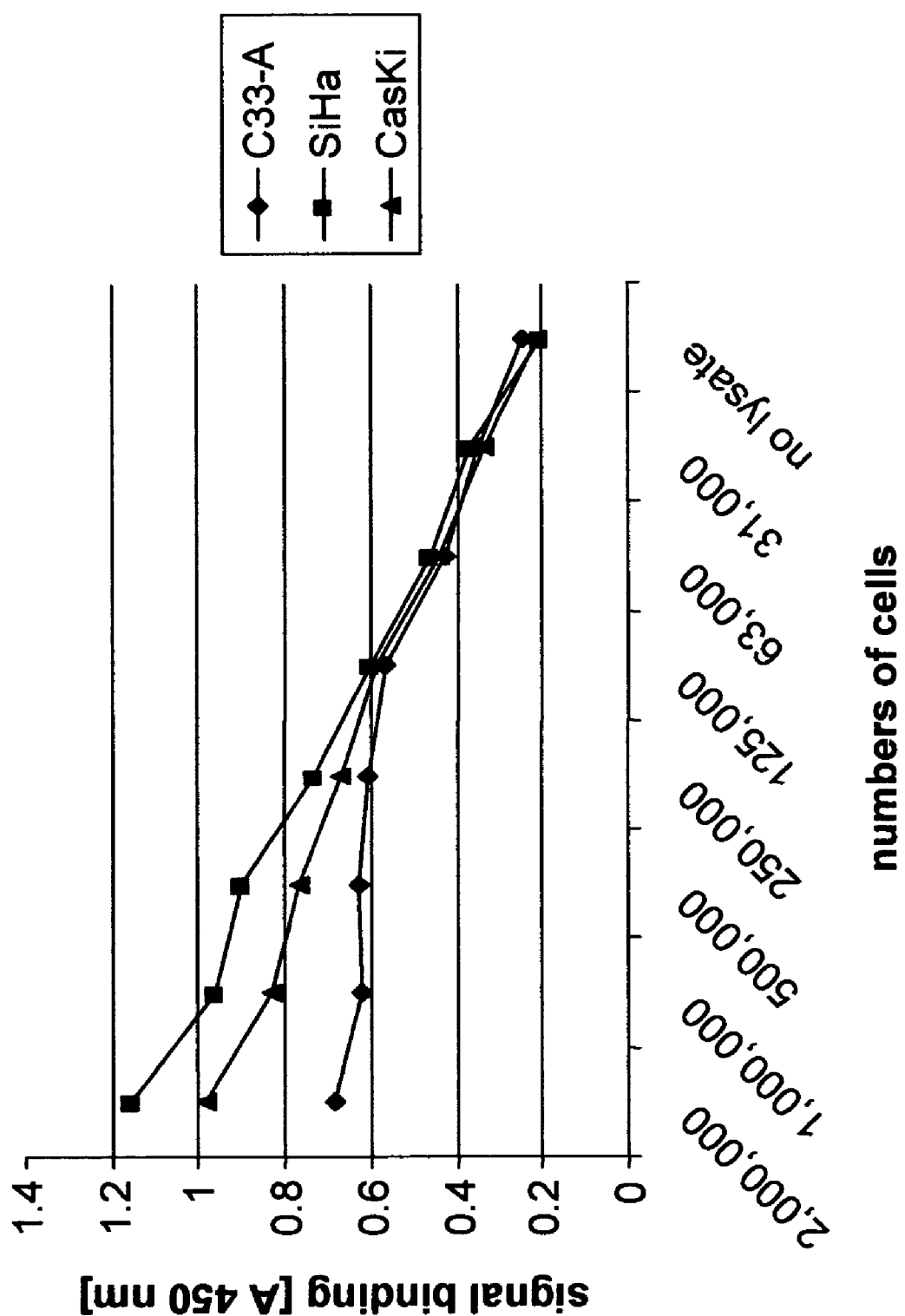
FIG. 8 is a line graph showing ELISA detection of HPV16 E6 protein in SiHa and CasKi cervical cell lines.

Results obtained from a type 1 ELISA assay are shown. HPV 16-E6 of over expressing E6 transfected 293 EBNA-T cells and of HPV16 infected cervical cancer derived cell lines was detected. For HPV infected cells, the detection limit is at approximately 250,000 cells (FIG. 8). It is predicted, that background reduction, detection signal enhancement and E6:PDZ binding enhancement will increase sensitivity to 25,000 cells or less. Background reduction can be achieved by optimizing choice and concentrations of all components in the system, as well as by additional component purification or addition of size exclusion or filtering procedures. Detection signal can be enhanced by use of more sensitive detection systems, for example luminescence based technologies. E6:PDZ binding can be enhanced by modifying the PDZ base of the oncogenic E6-PL detector, and by treating the E6 containing lysates with phosphatases, thus freeing all E6-PL sites from any phosphate that might interfere with, diminish or abrogate E6-PI-specific binding to the oncogenic E6-PL detector.

EXAMPLE 12

Endogenous E6 Protein of HPV Infected Cervical Cancer Cell Lines can be Detected Via a Membrane Bound Oncogenic E6-PL Detector. Membrane Based Detection can be used to Enhance Sensitivity of Oncogenic E6-PL Detector Based Assay.

A) Abstract:

Experiments were conducted to demonstrate that the cervical cancer ELISA test types 1 and 2 can be performed using a membrane based format. In the membrane-based form of the cervical cancer diagnostic kit, the principles of the traditional ELISA based sandwich 1 and 2 are maintained, especially with regard to the capturing or detection of exclusively the oncogenic forms of E6. Sensitivity is found to be largely increased in the membrane based assay versus the traditional ELISA.

B) Methods:

Preblock 12 well coming plates (tissue culture treated with lid, polystyrene, 22 mm well diameter) with 2 ml PBS/2% BSA and then rinse 3× with 2 ml PBS Spot nitrocellulose membrane with 2 ul GST-Magi1 domain 2 solution (88.6, 0.17 mg/ml) using 2 ul pipetman (duplicate spots in 1×1.5 cm membrane, transblot, transfer medium, supported nitrocellulose membrane, catalog no. 162-0097 (0.2 uM), Lot No. 8934). Allow to air dry for ~5-10 minutes.

Hydrate membrane with 1 ml PBS for a couple of minutes in plate.

Block membrane in each well with 1 ml PBS/2% BSA for 30 minutes at room temperature while rocking Wash 3× with PBS ~5-10 minutes/wash, 1 ml/wash, aspirate directly first wash. OK to wash at room temperature.

Incubate membrane with cell lysate, ~300 ul, 3 million cells total, for 30 minutes at room temperature (rock solutions). Also perform 1:10 dilutions (3 million, 300K, 30K, 3K) in PBS/2% BSA (33.33 ul sample, 300 ul PBS/2% BSA)

Wash 3× with PBS, 3-5'/wash, all at 4° C., 1 ml/wash.

Incubate membrane with anti-E6 (6F4) for 30 minutes at 4° C. (1:5000 dilution, or 1:50 of 1:100 6F4 in PBS/2% BSA). (Need 0.4 ml/well, and for 36 wells need 16 ml a) 1) 320 ul of 1:100 6F4, 15.68 ml PBS/2% BSA.

Wash 3× with PBS, 4° C., ~5-10 minutes/wash.

Incubate with HRP-anti-mouse (1:1000) for 30' at 4° C. while rocking(HRP-anti-Mouse Ig Horseradish peroxidase linked whole antibody from Sheep, Amersham, NA931V, lot 213295. Use 400 ul per well. For 36 wells would need a) 16 ul HRP-anti-mouse, 16 ml PBS/2% BSA Wash 5× with PBS at 4° C., ~5-10 minutes rocking/wash, last wash 10 minutes. Then aspirate last wash, and add 1 ml fresh PBS to each well.

Develop with ECL+ system in Petri dish and expose in Kodak film.

Figure 9:
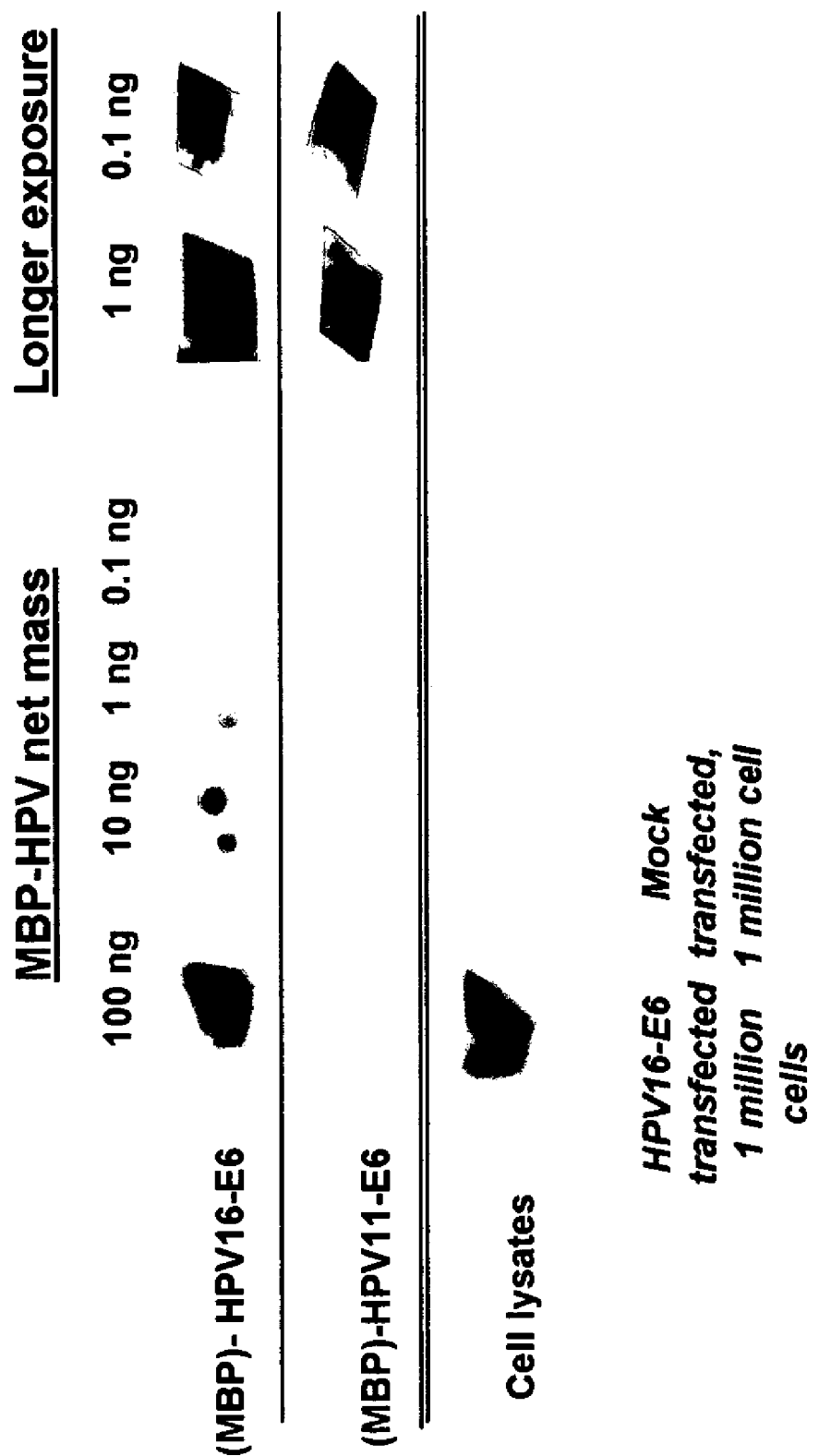
FIG. 9: is an autoradiograph showing dot blot detection of HPV16 E6 protein in cell lysates.

C) Results:

In a sandwich type 2 setup, GST-MAGI1 domain 2 oncogenic E6-PL detector was spotted on a membrane and decreasing quantities of HPV11 and HPV16 MBP-E6 fusion proteins were added for binding. Detection with E6 specific antibodies clearly demonstrated specificity of signal for oncogenic (HPV16), but not non-oncogenic E6 (HPV11). Upon longer exposure (5 minutes), HPV16 MBP-E6 quantities of 0.1 nanogram total were readily detectable (FIG. 9, top).

In the same experiment, lysates of HPV16-E6 transfected cells and mock transfected cells were applied to a membrane based S2 test. E6-specific signal was obtained only for the E6 expressing cells, not for mock transfected cells (FIG. 9, bottom). These results clearly demonstrate that the membrane based cervical cancer test can be executed in a membrane-based format.

Figure 10:
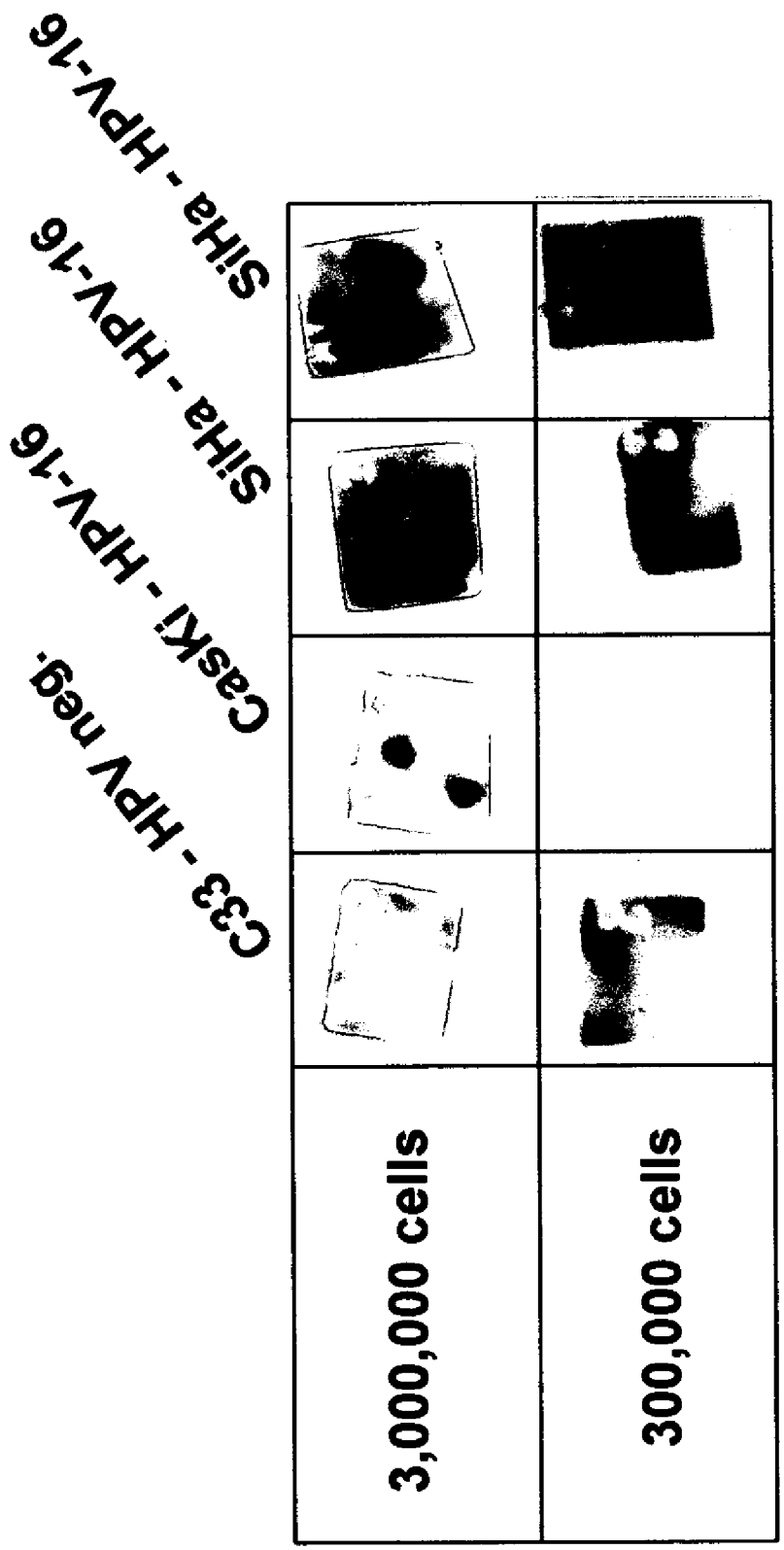
FIG. 10: is an autoradiograph showing dot blot detection of endogenous HPV16 E6 protein in lysates of SiHa and CasKi cervical cell lines.

In a subsequent experiment, lysates of HPV infected cells were tested (FIG. 10). Clearly, only the HPV16-E6 expressing cells are yielding signal (SiHa and CasKi), but not the HPV negative but cervical cancer positive cell line C33. E6-specific signal is obtained at 300.000 cells, indicating that an optimized form of this test may detect HPV-E6 proteins of substantially lower cell numbers.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein and priority documents cited in the Applicant Data Sheet are incorporated by reference in their entirety and for all purposes.

TABLE 9

| Seq Id | name | gi/acc | domain |
|---|---|---|---|
| 1 | 26s subunit p27 | 9184389 | 1 |
| 2 | AF6 | 430993 | 1 |
| 3 | AIPC | 12751451 | 1 |
| 4 | AIPC | 12751451 | 2 |
| 5 | AIPC | 12751451 | 3 |
| 6 | AIPC | 12751451 | 4 |
| 7 | alpha actinin-2 associated LIM protein | 2773059 | 1 |
| 8 | APXL-1 | 13651263 | 1 |
| 9 | Atrophin-1 Interacting Protein | 2947231 | 1 |
| 10 | Atrophin-1 Interacting Protein | 2947231 | 2 |
| 11 | Atrophin-1 Interacting Protein | 2947231 | 3 |
| 12 | Atrophin-1 Interacting Protein | 2947231 | 4 |
| 13 | Atrophin-1 Interacting Protein | 2947231 | 5 |
| 14 | Atrophin-1 Interacting Protein | 2947231 | 6 |
| 15 | CARD11 | 12382772 | 1 |
| 16 | CARD14 | 13129123 | 1 |
| 17 | CASK | 3087815 | 1 |
| 18 | Connector Enhancer | 3930780 | 1 |

TABLE 9-continued

| Seq Id | name | gi/acc | domain |
|---|---|---|---|
| 19 | Cytohesin Binding Protein | 3192908 | 1 |
| 20 | Densin 180 | 16755892 | 1 |
| 21 | DLG1 | 475816 | 1 |
| 22 | DLG1 | 475816 | 2 |
| 23 | DLG1 | 475816 | 3 |
| 24 | DLG2 | 12736552 | 1 |
| 25 | DLG2 | 12736552 | 2 |
| 26 | DLG2 | 12736552 | 3 |
| 27 | DLG5 | 3650451 | 1 |
| 28 | DLG5 | 3650451 | 2 |
| 29 | DLG6, splice variant 1 | 14647140 | 1 |
| 30 | DLG6, splice variant 2 | AB053303 | 1 |
| 31 | DVL1 | 2291005 | 1 |
| 32 | DVL2 | 2291007 | 1 |
| 33 | DVL3 | 6806886 | 1 |
| 34 | ELFIN 1 | 2957144 | 1 |
| 35 | ENIGMA | 561636 | 1 |
| 36 | ERBIN | 8923908 | 1 |
| 37 | EZRIN Binding Protein 50 | 3220018 | 1 |
| 38 | EZRIN Binding Protein 50 | 3220018 | 2 |
| 39 | FLJ00011 | 10440352 | 1 |
| 40 | FLJ11215 | 11436365 | 1 |
| 41 | FLJ12428 | BC012040 | 1 |
| 42 | FLJ12615 | 10434209 | 1 |
| 43 | FLJ20075 | 7019938 | 1 |
| 44 | FLJ21687 | 10437836 | 1 |
| 45 | FLJ31349 | AK055911 | 1 |
| 46 | FLJ32798 | AK057360 | 1 |
| 47 | GRIP 1 | 4539083 | 1 |
| 48 | GRIP 1 | 4539083 | 2 |
| 49 | GRIP 1 | 4539083 | 3 |
| 50 | GRIP 1 | 4539083 | 4 |
| 51 | GRIP 1 | 4539083 | 5 |
| 52 | GRIP 1 | 4539083 | 6 |
| 53 | GRIP 1 | 4539083 | 7 |
| 54 | GTPase Activating Enzyme | 2389008 | 1 |
| 55 | Guanine Exchange Factor | 6650765 | 1 |
| 56 | HEMBA 1000505 | 10436367 | 1 |
| 57 | HEMBA 1000505 | 10436367 | 2 |
| 58 | HEMBA 1003117 | 7022001 | 1 |
| 59 | HTRA3 | AY040094 | 1 |
| 60 | HTRA4 | AL576444 | 1 |
| 61 | INADL | 2370148 | 1 |
| 62 | INADL | 2370148 | 2 |
| 63 | INADL | 2370148 | 3 |
| 64 | INADL | 2370148 | 4 |
| 65 | INADL | 2370148 | 5 |
| 66 | INADL | 2370148 | 6 |
| 67 | INADL | 2370148 | 7 |
| 68 | INADL | 2370148 | 8 |
| 69 | KIAA0147 | 1469875 | 1 |
| 70 | KIAA0147 | 1469875 | 2 |
| 71 | KIAA0147 | 1469875 | 3 |
| 72 | KIAA0147 | 1469875 | 4 |
| 73 | KIAA0303 | 2224546 | 1 |
| 74 | KIAA0313 | 7657260 | 1 |
| 75 | KIAA0316 | 6683123 | 1 |
| 76 | KIAA0340 | 2224620 | 1 |
| 77 | KIAA0380 | 2224700 | 1 |
| 78 | KIAA0382 | 7662087 | 1 |
| 79 | KIAA0440 | 2662160 | 1 |
| 80 | KIAA0545 | 14762850 | 1 |
| 81 | KIAA0559 | 3043641 | 1 |
| 82 | KIAA0561 | 3043645 | 1 |
| 83 | KIAA0613 | 3327039 | 1 |
| 84 | KIAA0751 | 12734165 | 1 |
| 85 | KIAA0807 | 3882334 | 1 |
| 86 | KIAA0858 | 4240204 | 1 |
| 87 | KIAA0902 | 4240292 | 1 |
| 88 | KIAA0967 | 4589577 | 1 |
| 89 | KIAA0973 | 4589589 | 1 |
| 90 | KIAA1095 | 5889526 | 1 |
| 91 | KIAA1095 | 5889526 | 2 |
| 92 | KIAA1202 | 6330421 | 1 |
| 93 | KIAA1222 | 6330610 | 1 |
| 94 | KIAA1284 | 6331369 | 1 |
| 95 | KIAA1389 | 7243158 | 1 |
| 96 | KIAA1415 | 7243210 | 1 |
| 97 | KIAA1526 | 5817166 | 1 |
| 98 | KIAA1526 | 5817166 | 2 |
| 99 | KIAA1526 | 5817166 | 3 |
| 100 | KIAA1620 | 10047316 | 1 |
| 101 | KIAA1634 | 10047344 | 1 |
| 102 | KIAA1634 | 10047344 | 2 |
| 103 | KIAA1634 | 10047344 | 3 |
| 104 | KIAA1634 | 10047344 | 4 |
| 105 | KIAA1634 | 10047344 | 5 |
| 106 | KIAA1719 | 1267982 | 0 |
| 107 | KIAA1719 | 1267982 | 1 |
| 108 | KIAA1719 | 1267982 | 2 |
| 109 | KIAA1719 | 1267982 | 3 |
| 110 | KIAA1719 | 1267982 | 4 |
| 111 | KIAA1719 | 1267982 | 5 |
| 112 | KIAA1719 | 1267982 | 6 |
| 113 | LIM Mystique | 12734250 | 1 |
| 114 | LIM Protein | 3108092 | 1 |
| 115 | LIMK1 | 4587498 | 1 |
| 116 | LIMK2 | 1805593 | 1 |
| 117 | LIM-RIL | 1085021 | 1 |
| 118 | LU-1 | U52111 | 1 |
| 119 | MAGI1 | 3370997 | 1 |
| 120 | MAGI1 | 3370997 | 2 |
| 121 | MAGI1 | 3370997 | 3 |
| 122 | MAGI1 | 3370997 | 4 |
| 123 | MAGI1 | 3370997 | 5 |
| 124 | MAGI1 | 3370997 | 6 |
| 125 | MGC5395 | BC012477 | 1 |
| 126 | MINT1 | 2625024 | 1 |
| 127 | MINT1 | 2625024 | 2 |
| 128 | MINT3 | 3169808 | 1 |
| 129 | MINT3 | 3169808 | 2 |
| 130 | MPP1 | 189785 | 1 |
| 131 | MPP2 | 939884 | 1 |
| 132 | MUPP1 | 2104784 | 1 |
| 133 | MUPP1 | 2104784 | 2 |
| 134 | MUPP1 | 2104784 | 3 |
| 135 | MUPP1 | 2104784 | 4 |
| 136 | MUPP1 | 2104784 | 5 |
| 137 | MUPP1 | 2104784 | 6 |
| 138 | MUPP1 | 2104784 | 7 |
| 139 | MUPP1 | 2104784 | 8 |
| 140 | MUPP1 | 2104784 | 9 |
| 141 | MUPP1 | 2104784 | 10 |
| 142 | MUPP1 | 2104784 | 11 |
| 143 | MUPP1 | 2104784 | 12 |
| 144 | MUPP1 | 2104784 | 13 |
| 145 | NeDLG | 10863920 | 1 |
| 146 | NeDLG | 10863920 | 2 |
| 147 | NeDLG | 10863920 | 3 |
| 148 | Neurabin II | AJ401189 | 1 |
| 149 | NOS1 | 642525 | 1 |
| 150 | novel PDZ gene | 7228177 | 1 |
| 151 | novel PDZ gene | 7228177 | 2 |
| 152 | Novel Serine Protease | 1621243 | 1 |
| 153 | Numb Binding Protein | AK056823 | 1 |
| 154 | Numb Binding Protein | AK056823 | 2 |
| 155 | Numb Binding Protein | AK056823 | 3 |
| 156 | Numb Binding Protein | AK056823 | 4 |
| 157 | Outer Membrane | 7023825 | 1 |
| 158 | p55T | 12733367 | 1 |
| 159 | PAR3 | 8037914 | 1 |
| 160 | PAR3 | 8037914 | 2 |

TABLE 9-continued

| Seq Id | name | gi/acc | domain |
|---|---|---|---|
| 161 | PAR3 | 8037914 | 3 |
| 162 | PAR6 | 2613011 | 1 |
| 163 | PAR6 GAMMA | 13537118 | 1 |
| 164 | PDZ-73 | 5031978 | 1 |
| 165 | PDZ-73 | 5031978 | 2 |
| 166 | PDZ-73 | 5031978 | 3 |
| 167 | PDZK1 | 2944188 | 1 |
| 168 | PDZK1 | 2944188 | 2 |
| 169 | PDZK1 | 2944188 | 3 |
| 170 | PDZK1 | 2944188 | 4 |
| 171 | PICK1 | 4678411 | 1 |
| 172 | PIST | 98374330 | 1 |
| 173 | prIL 16 | 1478492 | 1 |
| 174 | prIL 16 | 1478492 | 2 |
| 175 | PSD95 | 3318652 | 1 |
| 176 | PSD95 | 3318652 | 2 |
| 177 | PSD95 | 3318652 | 3 |
| 178 | PTN-3 | 179912 | 1 |
| 179 | PTN-4 | 190747 | 1 |
| 180 | PTPL1 | 515030 | 1 |
| 181 | PTPL1 | 515030 | 2 |
| 182 | PTPL1 | 515030 | 3 |
| 183 | PTPL1 | 515030 | 4 |
| 184 | PTPL1 | 515030 | 5 |
| 185 | RGS12 | 3290015 | 1 |
| 186 | RGS3 | 18644735 | 1 |
| 187 | Rhophilin-like | 14279408 | 1 |
| 188 | Serine Protease | 2738914 | 1 |
| 189 | Shank 1 | 6049185 | 1 |
| 190 | Shank 3 | * | 1 |
| 191 | Shroom | 18652858 | 1 |
| 192 | SIP1 | 2047327 | 1 |
| 193 | SIP1 | 2047327 | 2 |
| 194 | SITAC-18 | 8886071 | 1 |
| 195 | SITAC-18 | 8886071 | 2 |
| 196 | SSTRIP | 7025450 | 1 |
| 197 | SYNTENIN | 2795862 | 1 |
| 198 | SYNTENIN | 2795862 | 2 |
| 199 | Syntrophin 1 alpha | 1145727 | 1 |
| 200 | Syntrophin beta 2 | 476700 | 1 |
| 201 | Syntrophin gamma 1 | 9507162 | 1 |
| 202 | Syntrophin gamma 2 | 9507164 | 1 |
| 203 | TAX2-like protein | 3253116 | 1 |
| 204 | TIAM 1 | 4507500 | 1 |
| 205 | TIAM 2 | 6912703 | 1 |
| 206 | TIP1 | 2613001 | 1 |
| 207 | TIP2 | 2613003 | 1 |
| 208 | TIP33 | 2613007 | 1 |
| 209 | TIP43 | 2613011 | 1 |
| 210 | X-11 beta | 3005559 | 1 |
| 211 | X-11 beta | 3005559 | 2 |
| 212 | ZO-1 | 292937 | 1 |
| 213 | ZO-1 | 292937 | 2 |
| 214 | ZO-1 | 292937 | 3 |
| 215 | ZO-2 | 12734763 | 1 |
| 216 | ZO-2 | 12734763 | 2 |
| 217 | ZO-2 | 12734763 | 3 |
| 218 | ZO-3 | 10092690 | 1 |
| 219 | ZO-3 | 10092690 | 2 |
| 220 | ZO-3 | 10092690 | 3 |
| 221 | HPV 4 - E6 | | |
| 222 | HPV 11-E6 | | |
| 223 | HPV 20-E6 | | |
| 224 | HPV 24-E6 | | |
| 225 | HPV 28-E6 | | |
| 226 | HPV 36-E6 | | |
| 227 | HPV 48-E6 | | |
| 228 | HPV 50-E6 | | |
| 229 | HPV 16-E6 | | |
| 230 | HPV 18-E6 | | |
| 231 | HPV 31-E6 | | |
| 232 | HPV 35-E6 | | |
| 233 | HPV 30-E6 | | |
| 234 | HPV 39-E6 | | |
| 235 | HPV 45-E6 | | |

TABLE 9-continued

| Seq Id | name | gi/acc | domain |
|---|---|---|---|
| 236 | HPV 51-E6 | | |
| 237 | HPV 52-E6 | | |
| 238 | HPV 56-E6 | | |
| 239 | HPV 59-E6 | | |
| 240 | HPV 58-E6 | | |
| 241 | HPV 33-E6 | | |
| 242 | HPV 66-E6 | | |
| 243 | HPV 68-E6 | | |
| 244 | HPV 69-E6 | | |
| 245 | HPV 26 | | |
| 246 | HPV 53 | | |
| 247 | HPV 66 | | |
| 248 | HPV 73 | | |
| 249 | HPV 82 | | |
| 250 | 2548 (1054EF) | | |
| 251 | 2549 (1058ER) | | |
| 252 | 2542 (1050EF) | | |
| 253 | 2543 (1051ER) | | |
| 254 | 2563 (1071EF) | | |
| 255 | 2564 (1072ER) | | |
| 256 | 2565 (1073ERPL) | | |
| 257 | 2560 (1074EF) | | |
| 258 | 2561 (1075ER) | | |
| 259 | 2562 (1076ERPL) | | |
| 260 | 2603 (1080EF) | | |
| 261 | 2604 (1081ER) | | |
| 262 | 2605 (1082ERPL) | | |
| 263 | 2606 (1083EF) | | |
| 264 | 2607 (1084ER) | | |
| 265 | 2608 (1085ERPL) | | |
| 266 | 2612 (1086ER) | | |
| 267 | 2613 (1087ER) | | |
| 268 | 2614 (1088ERPL) | | |
| 269 | 2615 (1089EF) | | |
| 270 | 2616 (1090ER) | | |
| 271 | 2617 (1091ERPL) | | |
| 272 | GST | | |
| 273 | 1928 (654DL1 2F) | | |
| 274 | 1929 (655DL1 2R) | | |
| 275 | 1453 (435BAF) | | |
| 276 | 1454 (436BAR) | | |
| 277 | 399 (86TAF) | | |
| 278 | 400 (87TAR) | | |
| 279 | 1319 (TIP G5-1) | | |
| 280 | 1320 (TIP G3-1) | | |
| 281 | 2753 (1109TIF) | | |
| 282 | 2762 (1117TIR) | | |
| 283 | 2584 (1080TIF) | | |
| 284 | 2585 (1081TIR) | | |
| 285 | 2586 (1082TIR) | | |
| 286 | 2587 (1083TIF) | | |
| 287 | DLG 1, PDZ d 2 of 3 | | |
| 288 | MAGI 1, PDZ d2 of 6 | | |
| 289 | TIP1 | | |
| 290 | TIP1-FL-pGEX | | |
| 291 | TIP1-Min | | |
| 292 | TIP1-CD5g | | |
| 293 | Magi1D2v2 | | |
| 294 | Magi1D2v3 | | |
| 295 | Magi1D2v4 | | |
| 296 | Magi1D2v5 | | |
| 297 | Magi1D2v6 | | |
| 298 | Magi1D2v7 | | |
| 299 | Magi1D2v8 | | |
| 300 | Magi1D2v9 | | |
| 301 | Magi1D2v10 | | |
| 302 | Magi1D2v11 | | |
| 303 | Magi1D2v12 | | |
| 304 | Magi1D2v13 | | |
| 305 | Magi1D2v14 | | |
| 306 | Magi1D2v15 | | |
| 307 | Magi1D2v16 | | |
| 308 | Magi1D2v17 | | |
| 309 | Magi1D2v18 | | |
| 310 | Magi1D2v19 | | |
| 311 | Magi1D2v20 | | |

TABLE 9-continued

| Seq Id | name | gi/acc | domain |
|---|---|---|---|
| 312 | Magi1D2v21 | | |
| 313 | Magi1D2v22 | | |
| 314 | Magi1D2v23 | | |
| 315 | Magi1D2v24 | | |
| 316 | Magi1D2v25 | | |
| 317 | Magi1D2v26 | | |
| 318 | Magi1D2v27 | | |
| 319 | Magi1D2v28 | | |
| 320 | Magi1D2v29 | | |
| 321 | Magi1D2v30 | | |
| 322 | Magi1D2v31 | | |
| 323 | Magi1D2v32 | | |
| 324 | Magi1D2v33 | | |
| 325 | Magi1D2v34 | | |
| 326 | Magi1D2v35 | | |
| 327 | Magi1D2v36 | | |
| 328 | Magi1D2v37 | | |
| 329 | Magi1D2v38 | | |
| 330 | Magi1D2v39 | | |

What is claimed is:

1. A method of detecting the presence of an oncogenic human papilloma virus (HPV) protein in a sample, said method comprising:

contacting a sample suspected of containing an oncogenic HPV E6 protein with a PDZ domain polypeptide; and detecting any binding of said oncogenic HPV E6 protein in said sample to said PDZ domain polypeptide;

wherein binding of said oncogenic HPV E6 protein to said PDZ domain polypeptide indicates the presence of an oncogenic HPV E6 protein in said sample and wherein said PDZ domain polypeptide is less than 1000 amino acids in length and comprises the amino acid sequence of MAGI-1 PDZ domain 2.

2. The method of claim 1, wherein said PDZ domain peptide binds to HPV E6 protein encoded by HPV strains 16, 18, and 45.

3. The method of claim 1, wherein sample is contacted with multiple PDZ domain polypeptides.

4. The method of claim 1, wherein said PDZ domain polypeptide is a fusion protein.

5. A method for determining if a subject is infected with an oncogenic strain of human papilloma virus (HPV), said method comprising:
   detecting the presence of oncogenic HPV E6 protein in a sample from said subject using an oncogenic HPV E6 protein-binding PDZ domain polypeptide,
   wherein the presence of oncogenic HPV E6 protein indicates that the subject is infected with an oncogenic strain of HPV and
   wherein said PDZ domain polypeptide is less than 1000 amino acids in length and comprises the amino acid sequence of MAGI-1 PDZ domain 2.

6. The method of claim 5, wherein said detecting step further comprises detecting the presence of said oncogenic HPV E6 protein using an antibody that specifically binds to said oncogenic HPV E6 protein.

7. The method of claim 5, wherein said sample is a cervical scrape, biopsy, or lavage.

8. The method of claim 7, wherein said method is an ELISA or a sandwich assay.

9. The method of claim 5, wherein said sample is prepared in the presence of a proteasome inhibitor.

10. The method of claim 5, wherein said method is performed as a part of a test for cervical cancer.

11. The method of claim 1 or 5, wherein said PDZ domain polypeptide is less than 500 amino acids in length.

12. The method of claim 1 or 5, wherein said PDZ domain polypeptide is less than 200 amino acids in length.

13. A method of detecting the presence of an oncogenic human papilloma virus (HPV) protein in a sample, said method comprising:
   contacting a sample suspected of containing an oncogenic HPV E6 protein with a fusion protein that is a fusion of a PDZ polypeptide of less than 1000 amino acids in length and comprising the amino acid sequence of MAGI-1 PDZ domain 2 with a heterologous domain; and
   detecting binding of said oncogenic HPV E6 protein in said sample to MAGI-1 PDZ domain 2 in said fusion protein, wherein binding of said oncogenic HPV E6 protein to MAGI-1 PDZ domain 2 in said fusion protein indicates the presence of an oncogenic HPV E6 protein in said sample.

14. The method of claim 13, wherein PDZ polypeptide is less than 200 amino acids in length.

15. The method of claim 1, 5 or 13, wherein the oncogenic HPV is selected from the group consisting of HPV strain 16, 18, 31, 35, 30, 39, 45, 51, 52, 56, 59, 58, 33, 66, 68, 69, 26, 53, 66, 73, and 82.

* * * * *

UNITED STATES PATENT AND TRADEMARK OFFICE
CERTIFICATE OF CORRECTION

| | | Page 1 of 2 |
|---|---|---|
| PATENT NO. | : 7,312,041 B2 | |
| APPLICATION NO. | : 10/630590 | |
| DATED | : July 29, 2003 | |
| INVENTOR(S) | : Peter S. Lu et al. | |

It is certified that error appears in the above-identified patent and that said Letters Patent is hereby corrected as shown below:

In the Specification:

Please amend the specification as shown:

Col. 1, line 28, please insert directly before the line, "FIELD OF THE INVENTION":

-- SEQUENCE LISTING

The instant application contains a Sequence Listing which has been submitted in ASCII format via EFS-Web and is hereby incorporated by reference in its entirety. Said ASCII copy, created on December 2, 2011, is named 34177151.txt and is 249,790 bytes in size. --

Col. 18, lines 13-47, please delete the paragraph on pages 25-26 that starts with "As noted *supra*," and ends with "Gly—Ile—Pro—*PDZ domain insert*" and replace it with the following paragraph:

As noted *supra*, PCR primers were designed to include endonuclease restriction sites to facilitate ligation of PCR fragments into a GST gene fusion vector (pGEX-3X; Pharmacia, GenBank accession no. XXU13852) in-frame with the glutathione-S transferase coding sequence. This vector contains an IPTG inducible lacZ promoter. The pGEX-3X vector was linearized using *Bam* HI and *Eco* RI or, in some cases, *Eco* RI or *Sma* I, and dephosphorylated. For most cloning approaches, double digestion with Bam HI and Eco RI was performed, so that the ends of the PCR fragments to clone were Bam HI and Eco RI. In some cases, restriction endonuclease combinations used were Bgl II and Eco RI, Bam HI and Mfe I, or Eco RI only, Sma I only, or BamHI only. When more than one PDZ domain was cloned, the DNA portion cloned represents the PDZ domains and the cDNA portion located between individual domains. Precise locations of cloned fragments used in the assays are indicated in US Patent Application (60/360061). DNA linker sequences between the GST portion and Signed and Sealed this
Third Day of January, 2012

David J. Kappos
*Director of the United States Patent and Trademark Office* the PDZ domain containing DNA portion vary slightly, dependent on which of the above described cloning sites and approaches were used. As a consequence, the amino acid sequence of the GST-PDZ fusion protein varies in the linker region between GST and PDZ domain. Protein linker sequences corresponding to different cloning sites/approaches are shown below. Linker sequences (vector DNA encoded) are bold, PDZ domain containing gene derived sequences are in italics.

1) GST—BamHI/*BamHI*— *PDZ domain insert*
   Gly—Ile—*PDZ domain insert*

2) GST—BamHI/*BglII*—*PDZ domain insert*
   Gly—Ile—*PDZ domain insert*

3) GST—EcoRI/*EcoRI*—*PDZ domain insert*
   Gly—Ile—Pro—Gly—Asn—*PDZ domain insert* ('Gly—Ile—Pro—Gly-Asn' disclosed as SEQ ID NO: 331)

4) GST-SmaI/*SmaI*—*PDZ domain insert*
   Gly—Ile—Pro—*PDZ domain insert*

SEQUENCE LISTING

<160> NUMBER OF SEQ ID NOS: 330

<210> SEQ ID NO 1
<211> LENGTH: 87
<212> TYPE: PRT
<213> ORGANISM: Homo sapiens

<400> SEQUENCE: 1

```
Arg Asp Met Ala Glu Ala His Lys Glu Ala Met Ser Arg Lys Leu Gly
 1               5                  10                  15

Gln Ser Glu Ser Gln Gly Pro Pro Arg Ala Phe Ala Lys Val Asn Ser
            20                  25                  30

Ile Ser Pro Gly Ser Pro Ser Ile Ala Gly Leu Gln Val Asp Asp Glu
        35                  40                  45

Ile Val Glu Phe Gly Ser Val Asn Thr Gln Asn Phe Gln Ser Leu His
    50                  55                  60

Asn Ile Gly Ser Val Val Gln His Ser Glu Gly Ala Leu Ala Pro Thr
65                  70                  75                  80

Ile Leu Leu Ser Val Ser Met
                85
```

<210> SEQ ID NO 2
<211> LENGTH: 93
<212> TYPE: PRT
<213> ORGANISM: Homo sapiens

<400> SEQUENCE: 2

```
Leu Arg Lys Glu Pro Glu Ile Ile Thr Val Thr Leu Lys Lys Gln Asn
 1               5                  10                  15

Gly Met Gly Leu Ser Ile Val Ala Ala Lys Gly Ala Gly Gln Asp Lys
            20                  25                  30

Leu Gly Ile Tyr Val Lys Ser Val Val Lys Gly Gly Ala Ala Asp Val
        35                  40                  45

Asp Gly Arg Leu Ala Ala Gly Asp Gln Leu Leu Ser Val Asp Gly Arg
    50                  55                  60

Ser Leu Val Gly Leu Ser Gln Glu Arg Ala Ala Glu Leu Met Thr Arg
65                  70                  75                  80

Thr Ser Ser Val Val Thr Leu Glu Val Ala Lys Gln Gly
                85                  90
```

<210> SEQ ID NO 3
<211> LENGTH: 105

<212> TYPE: PRT
<213> ORGANISM: Homo sapiens

<400> SEQUENCE: 3

```
Leu Ile Arg Pro Ser Val Ile Ser Ile Gly Leu Tyr Lys Glu Lys
  1               5                  10                  15

Gly Lys Gly Leu Gly Phe Ser Ile Ala Gly Gly Arg Asp Cys Ile Arg
                 20                  25                  30

Gly Gln Met Gly Ile Phe Val Lys Thr Ile Phe Pro Asn Gly Ser Ala
             35                  40                  45

Ala Glu Asp Gly Arg Leu Lys Glu Gly Asp Glu Ile Leu Asp Val Asn
 50                  55                  60

Gly Ile Pro Ile Lys Gly Leu Thr Phe Gln Glu Ala Ile His Thr Phe
 65                  70                  75                  80

Lys Gln Ile Arg Ser Gly Leu Phe Val Leu Thr Val Arg Thr Lys Leu
                 85                  90                  95

Val Ser Pro Ser Leu Thr Asn Ser Ser
                100                 105
```

<210> SEQ ID NO 4
<211> LENGTH: 132
<212> TYPE: PRT
<213> ORGANISM: Homo sapiens

<400> SEQUENCE: 4

```
Gly Ile Ser Ser Leu Gly Arg Lys Thr Pro Gly Pro Lys Asp Arg Ile
  1               5                  10                  15

Val Met Glu Val Thr Leu Asn Lys Glu Pro Arg Val Gly Leu Gly Ile
                 20                  25                  30

Gly Ala Cys Cys Leu Ala Leu Glu Asn Ser Pro Pro Gly Ile Tyr Ile
             35                  40                  45

His Ser Leu Ala Pro Gly Ser Val Ala Lys Met Glu Ser Asn Leu Ser
 50                  55                  60

Arg Gly Asp Gln Ile Leu Glu Val Asn Ser Val Asn Val Arg His Ala
 65                  70                  75                  80

Ala Leu Ser Lys Val His Ala Ile Leu Ser Lys Cys Pro Pro Gly Pro
                 85                  90                  95

Val Arg Leu Val Ile Gly Arg His Pro Asn Pro Lys Val Ser Glu Gln
                100                 105                 110

Glu Met Asp Glu Val Ile Ala Arg Ser Thr Tyr Gln Glu Ser Lys Glu
             115                 120                 125

Ala Asn Ser Ser
        130
```

<210> SEQ ID NO 5
<211> LENGTH: 105
<212> TYPE: PRT
<213> ORGANISM: Homo sapiens

<400> SEQUENCE: 5

```
Gln Ser Glu Asn Glu Glu Asp Val Cys Phe Ile Val Leu Asn Arg Lys
  1               5                  10                  15

Glu Gly Ser Gly Leu Gly Phe Ser Val Ala Gly Gly Thr Asp Val Glu
                 20                  25                  30

Pro Lys Ser Ile Thr Val His Arg Val Phe Ser Gln Gly Ala Ala Ser
             35                  40                  45

Gln Glu Gly Thr Met Asn Arg Gly Asp Phe Leu Leu Ser Val Asn Gly
```

```
                  50                  55                  60

Ala Ser Leu Ala Gly Leu Ala His Gly Asn Val Leu Lys Val Leu His
 65                  70                  75                  80

Gln Ala Gln Leu His Lys Asp Ala Leu Val Val Ile Lys Lys Gly Met
                 85                  90                  95

Asp Gln Pro Arg Pro Ser Asn Ser Ser
                100                 105

<210> SEQ ID NO 6
<211> LENGTH: 101
<212> TYPE: PRT
<213> ORGANISM: Homo sapiens

<400> SEQUENCE: 6

Leu Gly Arg Ser Val Ala Val His Asp Ala Leu Cys Val Glu Val Leu
  1               5                  10                  15

Lys Thr Ser Ala Gly Leu Gly Leu Ser Leu Asp Gly Gly Lys Ser Ser
                 20                  25                  30

Val Thr Gly Asp Gly Pro Leu Val Ile Lys Arg Val Tyr Lys Gly Gly
             35                  40                  45

Ala Ala Glu Gln Ala Gly Ile Ile Glu Ala Gly Asp Glu Ile Leu Ala
 50                  55                  60

Ile Asn Gly Lys Pro Leu Val Gly Leu Met His Phe Asp Ala Trp Asn
 65                  70                  75                  80

Ile Met Lys Ser Val Pro Glu Gly Pro Val Gln Leu Leu Ile Arg Lys
                 85                  90                  95

His Arg Asn Ser Ser
                100

<210> SEQ ID NO 7
<211> LENGTH: 74
<212> TYPE: PRT
<213> ORGANISM: Homo sapiens

<400> SEQUENCE: 7

Gln Thr Val Ile Leu Pro Gly Pro Ala Ala Trp Gly Phe Arg Leu Ser
  1               5                  10                  15

Gly Gly Ile Asp Phe Asn Gln Pro Leu Val Ile Thr Arg Ile Thr Pro
                 20                  25                  30

Gly Ser Lys Ala Ala Ala Ala Asn Leu Cys Pro Gly Asp Val Ile Leu
             35                  40                  45

Ala Ile Asp Gly Phe Gly Thr Glu Ser Met Thr His Ala Asp Gly Gln
 50                  55                  60

Asp Arg Ile Lys Ala Ala Glu Phe Ile Val
 65                  70

<210> SEQ ID NO 8
<211> LENGTH: 85
<212> TYPE: PRT
<213> ORGANISM: Homo sapiens

<400> SEQUENCE: 8

Ile Leu Val Glu Val Gln Leu Ser Gly Gly Ala Pro Trp Gly Phe Thr
  1               5                  10                  15

Leu Lys Gly Gly Arg Glu His Gly Glu Pro Leu Val Ile Thr Lys Ile
                 20                  25                  30

Glu Glu Gly Ser Lys Ala Ala Ala Val Asp Lys Leu Leu Ala Gly Asp
             35                  40                  45
```

```
Glu Ile Val Gly Ile Asn Asp Ile Gly Leu Ser Gly Phe Arg Gln Glu
 50                  55                  60

Ala Ile Cys Leu Val Lys Gly Ser His Lys Thr Leu Lys Leu Val Val
 65                  70                  75                  80

Lys Arg Asn Ser Ser
                 85

<210> SEQ ID NO 9
<211> LENGTH: 104
<212> TYPE: PRT
<213> ORGANISM: Homo sapiens

<400> SEQUENCE: 9

Arg Glu Lys Pro Leu Phe Thr Arg Asp Ala Ser Gln Leu Lys Gly Thr
 1               5                  10                  15

Phe Leu Ser Thr Thr Leu Lys Lys Ser Asn Met Gly Phe Gly Phe Thr
                20                  25                  30

Ile Ile Gly Gly Asp Glu Pro Asp Glu Phe Leu Gln Val Lys Ser Val
                35                  40                  45

Ile Pro Asp Gly Pro Ala Ala Gln Asp Gly Lys Met Glu Thr Gly Asp
 50                  55                  60

Val Ile Val Tyr Ile Asn Glu Val Cys Val Leu Gly His Thr His Ala
 65                  70                  75                  80

Asp Val Val Lys Leu Phe Gln Ser Val Pro Ile Gly Gln Ser Val Asn
                85                  90                  95

Leu Val Leu Cys Arg Gly Tyr Pro
                100

<210> SEQ ID NO 10
<211> LENGTH: 91
<212> TYPE: PRT
<213> ORGANISM: Homo sapiens

<400> SEQUENCE: 10

Leu Ser Gly Ala Thr Gln Ala Glu Leu Met Thr Leu Thr Ile Val Lys
 1               5                  10                  15

Gly Ala Gln Gly Phe Gly Phe Thr Ile Ala Asp Ser Pro Thr Gly Gln
                20                  25                  30

Arg Val Lys Gln Ile Leu Asp Ile Gln Gly Cys Pro Gly Leu Cys Glu
                35                  40                  45

Gly Asp Leu Ile Val Glu Ile Asn Gln Gln Asn Val Gln Asn Leu Ser
 50                  55                  60

His Thr Glu Val Val Asp Ile Leu Lys Asp Cys Pro Ile Gly Ser Glu
 65                  70                  75                  80

Thr Ser Leu Ile Ile His Arg Gly Gly Phe Phe
                85                  90

<210> SEQ ID NO 11
<211> LENGTH: 93
<212> TYPE: PRT
<213> ORGANISM: Homo sapiens

<400> SEQUENCE: 11

His Tyr Lys Glu Leu Asp Val His Leu Arg Arg Met Glu Ser Gly Phe
 1               5                  10                  15

Gly Phe Arg Ile Leu Gly Gly Asp Glu Pro Gly Gln Pro Ile Leu Ile
                20                  25                  30
```

```
Gly Ala Val Ile Ala Met Gly Ser Ala Asp Arg Asp Gly Arg Leu His
            35                  40                  45

Pro Gly Asp Glu Leu Val Tyr Val Asp Gly Ile Pro Val Ala Gly Lys
        50                  55                  60

Thr His Arg Tyr Val Ile Asp Leu Met His His Ala Ala Arg Asn Gly
65                  70                  75                  80

Gln Val Asn Leu Thr Val Arg Arg Lys Val Leu Cys Gly
                85                  90
```

<210> SEQ ID NO 12
<211> LENGTH: 106
<212> TYPE: PRT
<213> ORGANISM: Homo sapiens

<400> SEQUENCE: 12

```
Glu Gly Arg Gly Ile Ser Ser His Ser Leu Gln Thr Ser Asp Ala Val
1               5                   10                  15

Ile His Arg Lys Glu Asn Glu Gly Phe Gly Phe Val Ile Ile Ser Ser
                20                  25                  30

Leu Asn Arg Pro Glu Ser Gly Ser Thr Ile Thr Val Pro His Lys Ile
            35                  40                  45

Gly Arg Ile Ile Asp Gly Ser Pro Ala Asp Arg Cys Ala Lys Leu Lys
        50                  55                  60

Val Gly Asp Arg Ile Leu Ala Val Asn Gly Gln Ser Ile Ile Asn Met
65                  70                  75                  80

Pro His Ala Asp Ile Val Lys Leu Ile Lys Asp Ala Gly Leu Ser Val
                85                  90                  95

Thr Leu Arg Ile Ile Pro Gln Glu Leu
            100                 105
```

<210> SEQ ID NO 13
<211> LENGTH: 98
<212> TYPE: PRT
<213> ORGANISM: Homo sapiens

<400> SEQUENCE: 13

```
Leu Ser Asp Tyr Arg Gln Pro Gln Asp Phe Asp Tyr Phe Thr Val Asp
1               5                   10                  15

Met Glu Lys Gly Ala Lys Gly Phe Gly Phe Ser Ile Arg Gly Gly Arg
                20                  25                  30

Glu Tyr Lys Met Asp Leu Tyr Val Leu Arg Leu Ala Glu Asp Gly Pro
            35                  40                  45

Ala Ile Arg Asn Gly Arg Met Arg Val Gly Asp Gln Ile Ile Glu Ile
        50                  55                  60

Asn Gly Glu Ser Thr Arg Asp Met Thr His Ala Arg Ala Ile Glu Leu
65                  70                  75                  80

Ile Lys Ser Gly Gly Arg Arg Val Arg Leu Leu Leu Lys Arg Gly Thr
                85                  90                  95

Gly Gln
```

<210> SEQ ID NO 14
<211> LENGTH: 90
<212> TYPE: PRT
<213> ORGANISM: Homo sapiens

<400> SEQUENCE: 14

```
His Glu Ser Val Ile Gly Arg Asn Pro Glu Gly Gln Leu Gly Phe Glu
1               5                   10                  15
```

```
Leu Lys Gly Gly Ala Glu Asn Gly Gln Phe Pro Tyr Leu Gly Glu Val
            20                  25                  30

Lys Pro Gly Lys Val Ala Tyr Glu Ser Gly Ser Lys Leu Val Ser Glu
            35                  40                  45

Glu Leu Leu Glu Val Asn Glu Thr Pro Val Ala Gly Leu Thr Ile
 50                  55                  60

Arg Asp Val Leu Ala Val Ile Lys His Cys Lys Asp Pro Leu Arg Leu
 65                  70                  75                  80

Lys Cys Val Lys Gln Gly Gly Ile His Arg
                    85                  90

<210> SEQ ID NO 15
<211> LENGTH: 126
<212> TYPE: PRT
<213> ORGANISM: Homo sapiens

<400> SEQUENCE: 15

Asn Leu Met Phe Arg Lys Phe Ser Leu Glu Arg Pro Phe Arg Pro Ser
 1               5                   10                  15

Val Thr Ser Val Gly His Val Arg Gly Pro Gly Pro Ser Val Gln His
            20                  25                  30

Thr Thr Leu Asn Gly Asp Ser Leu Thr Ser Gln Leu Thr Leu Leu Gly
            35                  40                  45

Gly Asn Ala Arg Gly Ser Phe Val His Ser Val Lys Pro Gly Ser Leu
 50                  55                  60

Ala Glu Lys Ala Gly Leu Arg Glu Gly His Gln Leu Leu Leu Leu Glu
 65                  70                  75                  80

Gly Cys Ile Arg Gly Glu Arg Gln Ser Val Pro Leu Asp Thr Cys Thr
                    85                  90                  95

Lys Glu Glu Ala His Trp Thr Ile Gln Arg Cys Ser Gly Pro Val Thr
                100                 105                 110

Leu His Tyr Lys Val Asn His Glu Gly Tyr Arg Lys Leu Val
            115                 120                 125

<210> SEQ ID NO 16
<211> LENGTH: 100
<212> TYPE: PRT
<213> ORGANISM: Homo sapiens

<400> SEQUENCE: 16

Ile Leu Ser Gln Val Thr Met Leu Ala Phe Gln Gly Asp Ala Leu Leu
 1               5                   10                  15

Glu Gln Ile Ser Val Ile Gly Gly Asn Leu Thr Gly Ile Phe Ile His
            20                  25                  30

Arg Val Thr Pro Gly Ser Ala Ala Asp Gln Met Ala Leu Arg Pro Gly
            35                  40                  45

Thr Gln Ile Val Met Val Asp Tyr Glu Ala Ser Glu Pro Leu Phe Lys
 50                  55                  60

Ala Val Leu Glu Asp Thr Thr Leu Glu Glu Ala Val Gly Leu Leu Arg
 65                  70                  75                  80

Arg Val Asp Gly Phe Cys Cys Leu Ser Val Lys Val Asn Thr Asp Gly
                    85                  90                  95

Tyr Lys Arg Leu
            100

<210> SEQ ID NO 17
```

<211> LENGTH: 90
<212> TYPE: PRT
<213> ORGANISM: Homo sapiens

<400> SEQUENCE: 17

Thr Arg Val Arg Leu Val Gln Phe Gln Lys Asn Thr Asp Glu Pro Met
1               5                   10                  15

Gly Ile Thr Leu Lys Met Asn Glu Leu Asn His Cys Ile Val Ala Arg
            20                  25                  30

Ile Met His Gly Gly Met Ile His Arg Gln Gly Thr Leu His Val Gly
        35                  40                  45

Asp Glu Ile Arg Glu Ile Asn Gly Ile Ser Val Ala Asn Gln Thr Val
    50                  55                  60

Glu Gln Leu Gln Lys Met Leu Arg Glu Met Arg Gly Ser Ile Thr Phe
65                  70                  75                  80

Lys Ile Val Pro Ser Tyr Arg Thr Gln Ser
                85                  90

<210> SEQ ID NO 18
<211> LENGTH: 88
<212> TYPE: PRT
<213> ORGANISM: Homo sapiens

<400> SEQUENCE: 18

Leu Glu Gln Lys Ala Val Leu Gln Val Gln Leu Asp Ser Pro Leu
1               5                   10                  15

Gly Leu Glu Ile His Thr Thr Ser Asn Cys Gln His Phe Val Ser Gln
            20                  25                  30

Val Asp Thr Gln Val Pro Thr Asp Ser Arg Leu Gln Ile Gln Pro Gly
        35                  40                  45

Asp Glu Val Val Gln Ile Asn Glu Gln Val Val Gly Trp Pro Arg
    50                  55                  60

Lys Asn Met Val Arg Glu Leu Leu Arg Glu Pro Ala Gly Leu Ser Leu
65                  70                  75                  80

Val Leu Lys Lys Ile Pro Ile Pro
                85

<210> SEQ ID NO 19
<211> LENGTH: 92
<212> TYPE: PRT
<213> ORGANISM: Homo sapiens

<400> SEQUENCE: 19

Gln Arg Lys Leu Val Thr Val Glu Lys Gln Asp Asn Glu Thr Phe Gly
1               5                   10                  15

Phe Glu Ile Gln Ser Tyr Arg Pro Gln Asn Gln Asn Ala Cys Ser Ser
            20                  25                  30

Glu Met Phe Thr Leu Ile Cys Lys Ile Gln Glu Asp Ser Pro Ala His
        35                  40                  45

Cys Ala Gly Leu Gln Ala Gly Asp Val Leu Ala Asn Ile Asn Gly Val
    50                  55                  60

Ser Thr Glu Gly Phe Thr Tyr Lys Gln Val Val Asp Leu Ile Arg Ser
65                  70                  75                  80

Ser Gly Asn Leu Leu Thr Ile Glu Thr Leu Asn Gly
                85                  90

<210> SEQ ID NO 20
<211> LENGTH: 109

```
<212> TYPE: PRT
<213> ORGANISM: Homo sapiens

<400> SEQUENCE: 20

Arg Cys Leu Ile Gln Thr Lys Gly Gln Arg Ser Met Asp Gly Tyr Pro
1               5                   10                  15

Glu Gln Phe Cys Val Arg Ile Glu Lys Asn Pro Gly Leu Gly Phe Ser
            20                  25                  30

Ile Ser Gly Gly Ile Ser Gly Gln Gly Asn Pro Phe Lys Pro Ser Asp
        35                  40                  45

Lys Gly Ile Phe Val Thr Arg Val Gln Pro Asp Gly Pro Ala Ser Asn
50                  55                  60

Leu Leu Gln Pro Gly Asp Lys Ile Leu Gln Ala Asn Gly His Ser Phe
65                  70                  75                  80

Val His Met Glu His Glu Lys Ala Val Leu Leu Lys Ser Phe Gln
                85                  90                  95

Asn Thr Val Asp Leu Val Ile Gln Arg Glu Leu Thr Val
            100                 105

<210> SEQ ID NO 21
<211> LENGTH: 101
<212> TYPE: PRT
<213> ORGANISM: Homo sapiens

<400> SEQUENCE: 21

Ile Gln Val Asn Gly Thr Asp Ala Asp Tyr Glu Tyr Glu Glu Ile Thr
1               5                   10                  15

Leu Glu Arg Gly Asn Ser Gly Leu Gly Phe Ser Ile Ala Gly Gly Thr
            20                  25                  30

Asp Asn Pro His Ile Gly Asp Asp Ser Ser Ile Phe Ile Thr Lys Ile
        35                  40                  45

Ile Thr Gly Gly Ala Ala Ala Gln Asp Gly Arg Leu Arg Val Asn Asp
50                  55                  60

Cys Ile Leu Gln Val Asn Glu Val Asp Val Arg Asp Val Thr His Ser
65                  70                  75                  80

Lys Ala Val Glu Ala Leu Lys Glu Ala Gly Ser Ile Val Arg Leu Tyr
                85                  90                  95

Val Lys Arg Arg Asn
            100

<210> SEQ ID NO 22
<211> LENGTH: 95
<212> TYPE: PRT
<213> ORGANISM: Homo sapiens

<400> SEQUENCE: 22

Ile Gln Leu Ile Lys Gly Pro Lys Gly Leu Gly Phe Ser Ile Ala Gly
1               5                   10                  15

Gly Val Gly Asn Gln His Ile Pro Gly Asp Asn Ser Ile Tyr Val Thr
            20                  25                  30

Lys Ile Ile Glu Gly Gly Ala Ala His Lys Asp Gly Lys Leu Gln Ile
        35                  40                  45

Gly Asp Lys Leu Leu Ala Val Asn Asn Val Cys Leu Glu Glu Val Thr
50                  55                  60

His Glu Glu Ala Val Thr Ala Leu Lys Asn Thr Ser Asp Phe Val Tyr
65                  70                  75                  80

Leu Lys Val Ala Lys Pro Thr Ser Met Tyr Met Asn Asp Gly Asn
```

<210> SEQ ID NO 23
<211> LENGTH: 85
<212> TYPE: PRT
<213> ORGANISM: Homo sapiens

<400> SEQUENCE: 23

```
Ile Leu His Arg Gly Ser Thr Gly Leu Gly Phe Asn Ile Val Gly Gly
 1               5                  10                  15
Glu Asp Gly Glu Gly Ile Phe Ile Ser Phe Ile Leu Ala Gly Gly Pro
            20                  25                  30
Ala Asp Leu Ser Gly Glu Leu Arg Lys Gly Asp Arg Ile Ile Ser Val
        35                  40                  45
Asn Ser Val Asp Leu Arg Ala Ala Ser His Glu Gln Ala Ala Ala Ala
    50                  55                  60
Leu Lys Asn Ala Gly Gln Ala Val Thr Ile Val Ala Gln Tyr Arg Pro
65                  70                  75                  80
Glu Glu Tyr Ser Arg
                85
```

<210> SEQ ID NO 24
<211> LENGTH: 101
<212> TYPE: PRT
<213> ORGANISM: Homo sapiens

<400> SEQUENCE: 24

```
Ile Ser Tyr Val Asn Gly Thr Glu Ile Glu Tyr Glu Phe Glu Glu Ile
 1               5                  10                  15
Thr Leu Glu Arg Gly Asn Ser Gly Leu Gly Phe Ser Ile Ala Gly Gly
            20                  25                  30
Thr Asp Asn Pro His Ile Gly Asp Asp Pro Gly Ile Phe Ile Thr Lys
        35                  40                  45
Ile Ile Pro Gly Gly Ala Ala Ala Glu Asp Gly Arg Leu Arg Val Asn
    50                  55                  60
Asp Cys Ile Leu Arg Val Asn Glu Val Asp Val Ser Glu Val Ser His
65                  70                  75                  80
Ser Lys Ala Val Glu Ala Leu Lys Glu Ala Gly Ser Ile Val Arg Leu
                85                  90                  95
Tyr Val Arg Arg Arg
                100
```

<210> SEQ ID NO 25
<211> LENGTH: 94
<212> TYPE: PRT
<213> ORGANISM: Homo sapiens

<400> SEQUENCE: 25

```
Ile Ser Val Val Glu Ile Lys Leu Phe Lys Gly Pro Lys Gly Leu Gly
 1               5                  10                  15
Phe Ser Ile Ala Gly Gly Val Gly Asn Gln His Ile Pro Gly Asp Asn
            20                  25                  30
Ser Ile Tyr Val Thr Lys Ile Ile Asp Gly Gly Ala Ala Gln Lys Asp
        35                  40                  45
Gly Arg Leu Gln Val Gly Asp Arg Leu Leu Met Val Asn Asn Tyr Ser
    50                  55                  60
Leu Glu Glu Val Thr His Glu Glu Ala Val Ala Ile Leu Lys Asn Thr
65                  70                  75                  80
```

Ser Glu Val Val Tyr Leu Lys Val Gly Asn Pro Thr Thr Ile
                 85                  90

<210> SEQ ID NO 26
<211> LENGTH: 95
<212> TYPE: PRT
<213> ORGANISM: Homo sapiens

<400> SEQUENCE: 26

Ile Trp Ala Val Ser Leu Glu Gly Glu Pro Arg Lys Val Val Leu His
1               5                   10                  15

Lys Gly Ser Thr Gly Leu Gly Phe Asn Ile Val Gly Gly Glu Asp Gly
            20                  25                  30

Glu Gly Ile Phe Val Ser Phe Ile Leu Ala Gly Gly Pro Ala Asp Leu
        35                  40                  45

Ser Gly Glu Leu Gln Arg Gly Asp Gln Ile Leu Ser Val Asn Gly Ile
    50                  55                  60

Asp Leu Arg Gly Ala Ser His Glu Gln Ala Ala Ala Leu Lys Gly
65                  70                  75                  80

Ala Gly Gln Thr Val Thr Ile Ile Ala Gln Tyr Gln Pro Glu Asp
                85                  90                  95

<210> SEQ ID NO 27
<211> LENGTH: 102
<212> TYPE: PRT
<213> ORGANISM: Homo sapiens

<400> SEQUENCE: 27

Gly Ile Pro Tyr Val Glu Glu Pro Arg His Val Lys Val Gln Lys Gly
1               5                   10                  15

Ser Glu Pro Leu Gly Ile Ser Ile Val Ser Gly Glu Lys Gly Gly Ile
            20                  25                  30

Tyr Val Ser Lys Val Thr Val Gly Ser Ile Ala His Gln Ala Gly Leu
        35                  40                  45

Glu Tyr Gly Asp Gln Leu Leu Glu Phe Asn Gly Ile Asn Leu Arg Ser
    50                  55                  60

Ala Thr Glu Gln Gln Ala Arg Leu Ile Ile Gly Gln Gln Cys Asp Thr
65                  70                  75                  80

Ile Thr Ile Leu Ala Gln Tyr Asn Pro His Val His Gln Leu Arg Asn
                85                  90                  95

Ser Ser Glx Leu Thr Asp
            100

<210> SEQ ID NO 28
<211> LENGTH: 103
<212> TYPE: PRT
<213> ORGANISM: Homo sapiens

<400> SEQUENCE: 28

Gly Ile Leu Ala Gly Asp Ala Asn Lys Lys Thr Leu Glu Pro Arg Val
1               5                   10                  15

Val Phe Ile Lys Lys Ser Gln Leu Glu Leu Gly Val His Leu Cys Gly
            20                  25                  30

Gly Asn Leu His Gly Val Phe Val Ala Glu Val Glu Asp Asp Ser Pro
        35                  40                  45

Ala Lys Gly Pro Asp Gly Leu Val Pro Gly Asp Leu Ile Leu Glu Tyr
    50                  55                  60

Gly Ser Leu Asp Val Arg Asn Lys Thr Val Glu Val Tyr Val Glu
65                  70                  75                  80

Met Leu Lys Pro Arg Asp Gly Val Arg Leu Lys Val Gln Tyr Arg Pro
                85                  90                  95

Glu Glu Phe Ile Val Thr Asp
            100

<210> SEQ ID NO 29
<211> LENGTH: 141
<212> TYPE: PRT
<213> ORGANISM: Homo sapiens

<400> SEQUENCE: 29

Pro Thr Ser Pro Glu Ile Gln Glu Leu Arg Gln Met Leu Gln Ala Pro
1               5                   10                  15

His Phe Lys Ala Leu Leu Ser Ala His Asp Thr Ile Ala Gln Lys Asp
                20                  25                  30

Phe Glu Pro Leu Leu Pro Pro Leu Pro Asp Asn Ile Pro Glu Ser Glu
            35                  40                  45

Glu Ala Met Arg Ile Val Cys Leu Val Lys Asn Gln Gln Pro Leu Gly
        50                  55                  60

Ala Thr Ile Lys Arg His Glu Met Thr Gly Asp Ile Leu Val Ala Arg
65                  70                  75                  80

Ile Ile His Gly Gly Leu Ala Glu Arg Ser Gly Leu Leu Tyr Ala Gly
                85                  90                  95

Asp Lys Leu Val Glu Val Asn Gly Val Ser Val Glu Gly Leu Asp Pro
            100                 105                 110

Glu Gln Val Ile His Ile Leu Ala Met Ser Arg Gly Thr Ile Met Phe
        115                 120                 125

Lys Val Val Pro Val Ser Asp Pro Pro Val Asn Ser Ser
    130                 135                 140

<210> SEQ ID NO 30
<211> LENGTH: 97
<212> TYPE: PRT
<213> ORGANISM: Homo sapiens

<400> SEQUENCE: 30

Pro Thr Ser Pro Glu Ile Gln Glu Leu Arg Gln Met Leu Gln Ala Pro
1               5                   10                  15

His Phe Lys Gly Ala Thr Ile Lys Arg His Glu Met Thr Gly Asp Ile
                20                  25                  30

Leu Val Ala Arg Ile Ile His Gly Gly Leu Ala Glu Arg Ser Gly Leu
            35                  40                  45

Leu Tyr Ala Gly Asp Lys Leu Val Glu Val Asn Gly Val Ser Val Glu
        50                  55                  60

Gly Leu Asp Pro Glu Gln Val Ile His Ile Leu Ala Met Ser Arg Gly
65                  70                  75                  80

Thr Ile Met Phe Lys Val Val Pro Val Ser Asp Pro Pro Val Asn Ser
                85                  90                  95

Ser

<210> SEQ ID NO 31
<211> LENGTH: 93
<212> TYPE: PRT
<213> ORGANISM: Homo sapiens

<400> SEQUENCE: 31

```
Leu Asn Ile Val Thr Val Thr Leu Asn Met Glu Arg His His Phe Leu
  1               5                  10                  15

Gly Ile Ser Ile Val Gly Gln Ser Asn Asp Arg Gly Asp Gly Gly Ile
             20                  25                  30

Tyr Ile Gly Ser Ile Met Lys Gly Gly Ala Val Ala Ala Asp Gly Arg
             35                  40                  45

Ile Glu Pro Gly Asp Met Leu Leu Gln Val Asn Asp Val Asn Phe Glu
 50                  55                  60

Asn Met Ser Asn Asp Asp Ala Val Arg Val Leu Arg Glu Ile Val Ser
 65                  70                  75                  80

Gln Thr Gly Pro Ile Ser Leu Thr Val Ala Lys Cys Trp
                 85                  90
```

<210> SEQ ID NO 32
<211> LENGTH: 100
<212> TYPE: PRT
<213> ORGANISM: Homo sapiens

<400> SEQUENCE: 32

```
Leu Asn Ile Ile Thr Val Thr Leu Asn Met Glu Lys Tyr Asn Phe Leu
  1               5                  10                  15

Gly Ile Ser Ile Val Gly Gln Ser Asn Glu Arg Gly Asp Gly Gly Ile
             20                  25                  30

Tyr Ile Gly Ser Ile Met Lys Gly Gly Ala Val Ala Ala Asp Gly Arg
             35                  40                  45

Ile Glu Pro Gly Asp Met Leu Leu Gln Val Asn Asp Met Asn Phe Glu
 50                  55                  60

Asn Met Ser Asn Asp Asp Ala Val Arg Val Leu Arg Asp Ile Val His
 65                  70                  75                  80

Lys Pro Gly Pro Ile Val Leu Thr Val Ala Lys Cys Trp Asp Pro Ser
                 85                  90                  95

Pro Gln Asn Ser
            100
```

<210> SEQ ID NO 33
<211> LENGTH: 95
<212> TYPE: PRT
<213> ORGANISM: Homo sapiens

<400> SEQUENCE: 33

```
Ile Ile Thr Val Thr Leu Asn Met Glu Lys Tyr Asn Phe Leu Gly Ile
  1               5                  10                  15

Ser Ile Val Gly Gln Ser Asn Glu Arg Gly Asp Gly Gly Ile Tyr Ile
             20                  25                  30

Gly Ser Ile Met Lys Gly Gly Ala Val Ala Ala Asp Gly Arg Ile Glu
             35                  40                  45

Pro Gly Asp Met Leu Leu Gln Val Asn Glu Ile Asn Phe Glu Asn Met
 50                  55                  60

Ser Asn Asp Asp Ala Val Arg Val Leu Arg Glu Ile Val His Lys Pro
 65                  70                  75                  80

Gly Pro Ile Thr Leu Thr Val Ala Lys Cys Trp Asp Pro Ser Pro
                 85                  90                  95
```

<210> SEQ ID NO 34
<211> LENGTH: 92
<212> TYPE: PRT
<213> ORGANISM: Homo sapiens

```
<400> SEQUENCE: 34

Thr Thr Gln Gln Ile Asp Leu Gln Gly Pro Gly Pro Trp Gly Phe Arg
1               5                   10                  15

Leu Val Gly Arg Lys Asp Phe Glu Gln Pro Leu Ala Ile Ser Arg Val
            20                  25                  30

Thr Pro Gly Ser Lys Ala Ala Leu Ala Asn Leu Cys Ile Gly Asp Val
        35                  40                  45

Ile Thr Ala Ile Asp Gly Glu Asn Thr Ser Asn Met Thr His Leu Glu
    50                  55                  60

Ala Gln Asn Arg Ile Lys Gly Cys Thr Asp Asn Leu Thr Leu Thr Val
65                  70                  75                  80

Ala Arg Ser Glu His Lys Val Trp Ser Pro Leu Val
                85                  90

<210> SEQ ID NO 35
<211> LENGTH: 89
<212> TYPE: PRT
<213> ORGANISM: Homo sapiens

<400> SEQUENCE: 35

Ile Phe Met Asp Ser Phe Lys Val Val Leu Glu Gly Pro Ala Pro Trp
1               5                   10                  15

Gly Phe Arg Leu Gln Gly Gly Lys Asp Phe Asn Val Pro Leu Ser Ile
            20                  25                  30

Ser Arg Leu Thr Pro Gly Gly Lys Ala Ala Gln Ala Gly Val Ala Val
        35                  40                  45

Gly Asp Trp Val Leu Ser Ile Asp Gly Glu Asn Ala Gly Ser Leu Thr
    50                  55                  60

His Ile Glu Ala Gln Asn Lys Ile Arg Ala Cys Gly Glu Arg Leu Ser
65                  70                  75                  80

Leu Gly Leu Ser Arg Ala Gln Pro Val
                85

<210> SEQ ID NO 36
<211> LENGTH: 100
<212> TYPE: PRT
<213> ORGANISM: Homo sapiens

<400> SEQUENCE: 36

Gln Gly His Glu Leu Ala Lys Gln Glu Ile Arg Val Arg Val Glu Lys
1               5                   10                  15

Asp Pro Glu Leu Gly Phe Ser Ile Ser Gly Gly Val Gly Gly Arg Gly
            20                  25                  30

Asn Pro Phe Arg Pro Asp Asp Gly Ile Phe Val Thr Arg Val Gln
            35                  40                  45

Pro Glu Gly Pro Ala Ser Lys Leu Leu Gln Pro Gly Asp Lys Ile Ile
    50                  55                  60

Gln Ala Asn Gly Tyr Ser Phe Ile Asn Ile Glu His Gly Gln Ala Val
65                  70                  75                  80

Ser Leu Leu Lys Thr Phe Gln Asn Thr Val Glu Leu Ile Ile Val Arg
                85                  90                  95

Glu Val Ser Ser
                100

<210> SEQ ID NO 37
<211> LENGTH: 87
```

```
<212> TYPE: PRT
<213> ORGANISM: Homo sapiens

<400> SEQUENCE: 37

Ile Leu Cys Cys Leu Glu Lys Gly Pro Asn Gly Tyr Gly Phe His Leu
1               5                   10                  15

His Gly Glu Lys Gly Lys Leu Gly Gln Tyr Ile Arg Leu Val Glu Pro
            20                  25                  30

Gly Ser Pro Ala Glu Lys Ala Gly Leu Leu Ala Gly Asp Arg Leu Val
        35                  40                  45

Glu Val Asn Gly Glu Asn Val Glu Lys Glu Thr His Gln Gln Val Val
    50                  55                  60

Ser Arg Ile Arg Ala Ala Leu Asn Ala Val Arg Leu Leu Val Val Asp
65                  70                  75                  80

Pro Glu Phe Ile Val Thr Asp
                85

<210> SEQ ID NO 38
<211> LENGTH: 92
<212> TYPE: PRT
<213> ORGANISM: Homo sapiens

<400> SEQUENCE: 38

Ile Arg Leu Cys Thr Met Lys Lys Gly Pro Ser Gly Tyr Gly Phe Asn
1               5                   10                  15

Leu His Ser Asp Lys Ser Lys Pro Gly Gln Phe Ile Arg Ser Val Asp
            20                  25                  30

Pro Asp Ser Pro Ala Glu Ala Ser Gly Leu Arg Ala Gln Asp Arg Ile
        35                  40                  45

Val Glu Val Asn Gly Val Cys Met Glu Gly Lys Gln His Gly Asp Val
    50                  55                  60

Val Ser Ala Ile Arg Ala Gly Gly Asp Glu Thr Lys Leu Leu Val Val
65                  70                  75                  80

Asp Arg Glu Thr Asp Glu Phe Phe Met Asn Ser Ser
                85                  90

<210> SEQ ID NO 39
<211> LENGTH: 107
<212> TYPE: PRT
<213> ORGANISM: Homo sapiens

<400> SEQUENCE: 39

Lys Asn Pro Ser Gly Glu Leu Lys Thr Val Thr Leu Ser Lys Met Lys
1               5                   10                  15

Gln Ser Leu Gly Ile Ser Ile Ser Gly Gly Ile Glu Ser Lys Val Gln
            20                  25                  30

Pro Met Val Lys Ile Glu Lys Ile Phe Pro Gly Gly Ala Ala Phe Leu
        35                  40                  45

Ser Gly Ala Leu Gln Ala Gly Phe Glu Leu Val Ala Val Asp Gly Glu
    50                  55                  60

Asn Leu Glu Gln Val Thr His Gln Arg Ala Val Asp Thr Ile Arg Arg
65                  70                  75                  80

Ala Tyr Arg Asn Lys Ala Arg Glu Pro Met Glu Leu Val Val Arg Val
                85                  90                  95

Pro Gly Pro Ser Pro Arg Pro Ser Pro Ser Asp
            100                 105
```

-continued

```
<210> SEQ ID NO 40
<211> LENGTH: 97
<212> TYPE: PRT
<213> ORGANISM: Homo sapiens

<400> SEQUENCE: 40

Glu Gly His Ser His Pro Arg Val Val Glu Leu Pro Lys Thr Glu Glu
1               5                   10                  15

Gly Leu Gly Phe Asn Ile Met Gly Gly Lys Glu Gln Asn Ser Pro Ile
                20                  25                  30

Tyr Ile Ser Arg Ile Ile Pro Gly Gly Ile Ala Asp Arg His Gly Gly
            35                  40                  45

Leu Lys Arg Gly Asp Gln Leu Leu Ser Val Asn Gly Val Ser Val Glu
    50                  55                  60

Gly Glu His His Glu Lys Ala Val Glu Leu Leu Lys Ala Ala Gln Gly
65                  70                  75                  80

Lys Val Lys Leu Val Val Arg Tyr Thr Pro Lys Val Leu Glu Glu Met
                85                  90                  95

Glu

<210> SEQ ID NO 41
<211> LENGTH: 88
<212> TYPE: PRT
<213> ORGANISM: Homo sapiens

<400> SEQUENCE: 41

Pro Gly Ala Pro Tyr Ala Arg Lys Thr Phe Thr Ile Val Gly Asp Ala
1               5                   10                  15

Val Gly Trp Gly Phe Val Val Arg Gly Ser Lys Pro Cys His Ile Gln
                20                  25                  30

Ala Val Asp Pro Ser Gly Pro Ala Ala Ala Gly Met Lys Val Cys
            35                  40                  45

Gln Phe Val Val Ser Val Asn Gly Leu Asn Val Leu His Val Asp Tyr
    50                  55                  60

Arg Thr Val Ser Asn Leu Ile Leu Thr Gly Pro Arg Thr Ile Val Met
65                  70                  75                  80

Glu Val Met Glu Glu Leu Glu Cys
                85

<210> SEQ ID NO 42
<211> LENGTH: 97
<212> TYPE: PRT
<213> ORGANISM: Homo sapiens

<400> SEQUENCE: 42

Gly Gln Tyr Gly Gly Glu Thr Val Lys Ile Val Arg Ile Glu Lys Ala
1               5                   10                  15

Arg Asp Ile Pro Leu Gly Ala Thr Val Arg Asn Glu Met Asp Ser Val
                20                  25                  30

Ile Ile Ser Arg Ile Val Lys Gly Gly Ala Ala Glu Lys Ser Gly Leu
            35                  40                  45

Leu His Glu Gly Asp Glu Val Leu Glu Ile Asn Gly Ile Glu Ile Arg
    50                  55                  60

Gly Lys Asp Val Asn Glu Val Phe Asp Leu Leu Ser Asp Met His Gly
65                  70                  75                  80

Thr Leu Thr Phe Val Leu Ile Pro Ser Gln Gln Ile Lys Pro Pro Pro
                85                  90                  95
```

Ala

<210> SEQ ID NO 43
<211> LENGTH: 98
<212> TYPE: PRT
<213> ORGANISM: Homo sapiens

<400> SEQUENCE: 43

```
Ile Leu Ala His Val Lys Gly Ile Glu Lys Glu Val Asn Val Tyr Lys
  1               5                  10                  15

Ser Glu Asp Ser Leu Gly Leu Thr Ile Thr Asp Asn Gly Val Gly Tyr
             20                  25                  30

Ala Phe Ile Lys Arg Ile Lys Asp Gly Gly Val Ile Asp Ser Val Lys
         35                  40                  45

Thr Ile Cys Val Gly Asp His Ile Glu Ser Ile Asn Gly Glu Asn Ile
     50                  55                  60

Val Gly Trp Arg His Tyr Asp Val Ala Lys Lys Leu Lys Glu Leu Lys
 65                  70                  75                  80

Lys Glu Glu Leu Phe Thr Met Lys Leu Ile Glu Pro Lys Lys Ala Phe
                 85                  90                  95

Glu Ile
```

<210> SEQ ID NO 44
<211> LENGTH: 104
<212> TYPE: PRT
<213> ORGANISM: Homo sapiens

<400> SEQUENCE: 44

```
Lys Pro Ser Gln Ala Ser Gly His Phe Ser Val Glu Leu Val Arg Gly
  1               5                  10                  15

Tyr Ala Gly Phe Gly Leu Thr Leu Gly Gly Gly Arg Asp Val Ala Gly
             20                  25                  30

Asp Thr Pro Leu Ala Val Arg Gly Leu Leu Lys Asp Gly Pro Ala Gln
         35                  40                  45

Arg Cys Gly Arg Leu Glu Val Gly Asp Leu Val Leu His Ile Asn Gly
     50                  55                  60

Glu Ser Thr Gln Gly Leu Thr His Ala Gln Ala Val Glu Arg Ile Arg
 65                  70                  75                  80

Ala Gly Gly Pro Gln Leu His Leu Val Ile Arg Arg Pro Leu Glu Thr
                 85                  90                  95

His Pro Gly Lys Pro Arg Gly Val
                100
```

<210> SEQ ID NO 45
<211> LENGTH: 107
<212> TYPE: PRT
<213> ORGANISM: Homo sapiens

<400> SEQUENCE: 45

```
Pro Val Met Ser Gln Cys Ala Cys Leu Glu Glu Val His Leu Pro Asn
  1               5                  10                  15

Ile Lys Pro Gly Glu Gly Leu Gly Met Tyr Ile Lys Ser Thr Tyr Asp
             20                  25                  30

Gly Leu His Val Ile Thr Gly Thr Thr Glu Asn Ser Pro Ala Asp Arg
         35                  40                  45

Ser Gln Lys Ile His Ala Gly Asp Glu Val Ile Gln Val Asn Gln Gln
     50                  55                  60
```

```
Thr Val Val Gly Trp Gln Leu Lys Asn Leu Val Lys Lys Leu Arg Glu
 65                  70                  75                  80

Asn Pro Thr Gly Val Val Leu Leu Lys Lys Arg Pro Thr Gly Ser
                 85                  90                  95

Phe Asn Phe Thr Pro Glu Phe Ile Val Thr Asp
                100                 105
```

<210> SEQ ID NO 46
<211> LENGTH: 100
<212> TYPE: PRT
<213> ORGANISM: Homo sapiens

<400> SEQUENCE: 46

```
Leu Asp Asp Glu Glu Asp Ser Val Lys Ile Ile Arg Leu Val Lys Asn
 1               5                  10                  15

Arg Glu Pro Leu Gly Ala Thr Ile Lys Lys Asp Glu Gln Thr Gly Ala
                20                  25                  30

Ile Ile Val Ala Arg Ile Met Arg Gly Gly Ala Ala Asp Arg Ser Gly
                35                  40                  45

Leu Ile His Val Gly Asp Glu Leu Arg Glu Val Asn Gly Ile Pro Val
 50                  55                  60

Glu Asp Lys Arg Pro Glu Glu Ile Ile Gln Ile Leu Ala Gln Ser Gln
 65                  70                  75                  80

Gly Ala Ile Thr Phe Lys Ile Ile Pro Gly Ser Lys Glu Glu Thr Pro
                85                  90                  95

Ser Asn Ser Ser
                100
```

<210> SEQ ID NO 47
<211> LENGTH: 83
<212> TYPE: PRT
<213> ORGANISM: Homo sapiens

<400> SEQUENCE: 47

```
Val Val Glu Leu Met Lys Lys Glu Gly Thr Thr Leu Gly Leu Thr Val
 1               5                  10                  15

Ser Gly Gly Ile Asp Lys Asp Gly Lys Pro Arg Val Ser Asn Leu Arg
                20                  25                  30

Gln Gly Gly Ile Ala Ala Arg Ser Asp Gln Leu Asp Val Gly Asp Tyr
                35                  40                  45

Ile Lys Ala Val Asn Gly Ile Asn Leu Ala Lys Phe Arg His Asp Glu
                50                  55                  60

Ile Ile Ser Leu Leu Lys Asn Val Gly Glu Arg Val Val Leu Glu Val
 65                  70                  75                  80

Glu Tyr Glu
```

<210> SEQ ID NO 48
<211> LENGTH: 110
<212> TYPE: PRT
<213> ORGANISM: Homo sapiens

<400> SEQUENCE: 48

```
Arg Ser Ser Val Ile Phe Arg Thr Val Glu Val Thr Leu His Lys Glu
 1               5                  10                  15

Gly Asn Thr Phe Gly Phe Val Ile Arg Gly Gly Ala His Asp Asp Arg
                20                  25                  30

Asn Lys Ser Arg Pro Val Val Ile Thr Cys Val Arg Pro Gly Gly Pro
                35                  40                  45
```

```
Ala Asp Arg Glu Gly Thr Ile Lys Pro Gly Asp Arg Leu Leu Ser Val
         50                  55                  60

Asp Gly Ile Arg Leu Leu Gly Thr Thr His Ala Glu Ala Met Ser Ile
 65                  70                  75                  80

Leu Lys Gln Cys Gly Gln Glu Ala Ala Leu Leu Ile Glu Tyr Asp Val
                 85                  90                  95

Ser Val Met Asp Ser Val Ala Thr Ala Ser Gly Asn Ser Ser
            100                 105                 110

<210> SEQ ID NO 49
<211> LENGTH: 106
<212> TYPE: PRT
<213> ORGANISM: Homo sapiens

<400> SEQUENCE: 49

His Val Ala Thr Ala Ser Gly Pro Leu Leu Val Glu Val Ala Lys Thr
 1               5                  10                  15

Pro Gly Ala Ser Leu Gly Val Ala Leu Thr Thr Ser Met Cys Cys Asn
                 20                  25                  30

Lys Gln Val Ile Val Ile Asp Lys Ile Lys Ser Ala Ser Ile Ala Asp
             35                  40                  45

Arg Cys Gly Ala Leu His Val Gly Asp His Ile Leu Ser Ile Asp Gly
     50                  55                  60

Thr Ser Met Glu Tyr Cys Thr Leu Ala Glu Ala Thr Gln Phe Leu Ala
 65                  70                  75                  80

Asn Thr Thr Asp Gln Val Lys Leu Glu Ile Leu Pro His His Gln Thr
                 85                  90                  95

Arg Leu Ala Leu Lys Gly Pro Asn Ser Ser
            100                 105

<210> SEQ ID NO 50
<211> LENGTH: 97
<212> TYPE: PRT
<213> ORGANISM: Homo sapiens

<400> SEQUENCE: 50

Thr Glu Thr Thr Glu Val Val Leu Thr Ala Asp Pro Val Thr Gly Phe
 1               5                  10                  15

Gly Ile Gln Leu Gln Gly Ser Val Phe Ala Thr Glu Thr Leu Ser Ser
                 20                  25                  30

Pro Pro Leu Ile Ser Tyr Ile Glu Ala Asp Ser Pro Ala Glu Arg Cys
             35                  40                  45

Gly Val Leu Gln Ile Gly Asp Arg Val Met Ala Ile Asn Gly Ile Pro
     50                  55                  60

Thr Glu Asp Ser Thr Phe Glu Glu Ala Ser Gln Leu Leu Arg Asp Ser
 65                  70                  75                  80

Ser Ile Thr Ser Lys Val Thr Leu Glu Ile Glu Phe Asp Val Ala Glu
                 85                  90                  95

Ser

<210> SEQ ID NO 51
<211> LENGTH: 101
<212> TYPE: PRT
<213> ORGANISM: Homo sapiens

<400> SEQUENCE: 51

Ala Glu Ser Val Ile Pro Ser Ser Gly Thr Phe His Val Lys Leu Pro
```

```
  1               5                  10                 15
Lys Lys His Asn Val Glu Leu Gly Ile Thr Ile Ser Ser Pro Ser Ser
                 20                 25                 30

Arg Lys Pro Gly Asp Pro Leu Val Ile Ser Asp Ile Lys Lys Gly Ser
             35                 40                 45

Val Ala His Arg Thr Gly Thr Leu Glu Leu Gly Asp Lys Leu Leu Ala
         50                 55                 60

Ile Asp Asn Ile Arg Leu Asp Asn Cys Ser Met Glu Asp Ala Val Gln
 65                 70                 75                 80

Ile Leu Gln Gln Cys Glu Asp Leu Val Lys Leu Lys Ile Arg Lys Asp
                 85                 90                 95

Glu Asp Asn Ser Asp
            100
```

<210> SEQ ID NO 52
<211> LENGTH: 90
<212> TYPE: PRT
<213> ORGANISM: Homo sapiens

<400> SEQUENCE: 52

```
Ile Tyr Thr Val Glu Leu Lys Arg Tyr Gly Gly Pro Leu Gly Ile Thr
 1               5                  10                 15

Ile Ser Gly Thr Glu Glu Pro Phe Asp Pro Ile Ile Ile Ser Ser Leu
                 20                 25                 30

Thr Lys Gly Gly Leu Ala Glu Arg Thr Gly Ala Ile His Ile Gly Asp
             35                 40                 45

Arg Ile Leu Ala Ile Asn Ser Ser Ser Leu Lys Gly Lys Pro Leu Ser
         50                 55                 60

Glu Ala Ile His Leu Leu Gln Met Ala Gly Glu Thr Val Thr Leu Lys
 65                 70                 75                 80

Ile Lys Lys Gln Thr Asp Ala Gln Ser Ala
                 85                 90
```

<210> SEQ ID NO 53
<211> LENGTH: 95
<212> TYPE: PRT
<213> ORGANISM: Homo sapiens

<400> SEQUENCE: 53

```
Ile Met Ser Pro Thr Pro Val Glu Leu His Lys Val Thr Leu Tyr Lys
 1               5                  10                 15

Asp Ser Asp Met Glu Asp Phe Gly Phe Ser Val Ala Asp Gly Leu Leu
                 20                 25                 30

Glu Lys Gly Val Tyr Val Lys Asn Ile Arg Pro Ala Gly Pro Gly Asp
             35                 40                 45

Leu Gly Gly Leu Lys Pro Tyr Asp Arg Leu Leu Gln Val Asn His Val
         50                 55                 60

Arg Thr Arg Asp Phe Asp Cys Cys Leu Val Val Pro Leu Ile Ala Glu
 65                 70                 75                 80

Ser Gly Asn Lys Leu Asp Leu Val Ile Ser Arg Asn Pro Leu Ala
                 85                 90                 95
```

<210> SEQ ID NO 54
<211> LENGTH: 88
<212> TYPE: PRT
<213> ORGANISM: Homo sapiens

<400> SEQUENCE: 54

```
Ser Arg Gly Cys Glu Thr Arg Glu Leu Ala Leu Pro Arg Asp Gly Gln
1               5                   10                  15

Gly Arg Leu Gly Phe Glu Val Asp Ala Glu Gly Phe Val Thr His Val
            20                  25                  30

Glu Arg Phe Thr Phe Ala Glu Thr Ala Gly Leu Arg Pro Gly Ala Arg
        35                  40                  45

Leu Leu Arg Val Cys Gly Gln Thr Leu Pro Ser Leu Arg Pro Glu Ala
    50                  55                  60

Ala Ala Gln Leu Leu Arg Ser Ala Pro Lys Val Cys Val Thr Val Leu
65                  70                  75                  80

Pro Pro Asp Glu Ser Gly Arg Pro
                85

<210> SEQ ID NO 55
<211> LENGTH: 95
<212> TYPE: PRT
<213> ORGANISM: Homo sapiens

<400> SEQUENCE: 55

Ala Lys Ala Lys Trp Arg Gln Val Val Leu Gln Lys Ala Ser Arg Glu
1               5                   10                  15

Ser Pro Leu Gln Phe Ser Leu Asn Gly Gly Ser Glu Lys Gly Phe Gly
            20                  25                  30

Ile Phe Val Glu Gly Val Glu Pro Gly Ser Lys Ala Ala Asp Ser Gly
        35                  40                  45

Leu Lys Arg Gly Asp Gln Ile Met Glu Val Asn Gly Gln Asn Phe Glu
    50                  55                  60

Asn Ile Thr Phe Met Lys Ala Val Glu Ile Leu Arg Asn Asn Thr His
65                  70                  75                  80

Leu Ala Leu Thr Val Lys Thr Asn Ile Phe Val Phe Lys Glu Leu
                85                  90                  95

<210> SEQ ID NO 56
<211> LENGTH: 89
<212> TYPE: PRT
<213> ORGANISM: Homo sapiens

<400> SEQUENCE: 56

Leu Glu Asn Val Ile Ala Lys Ser Leu Leu Ile Lys Ser Asn Glu Gly
1               5                   10                  15

Ser Tyr Gly Phe Gly Leu Glu Asp Lys Asn Lys Val Pro Ile Ile Lys
            20                  25                  30

Leu Val Glu Lys Gly Ser Asn Ala Glu Met Ala Gly Met Glu Val Gly
        35                  40                  45

Lys Lys Ile Phe Ala Ile Asn Gly Asp Leu Val Phe Met Arg Pro Phe
    50                  55                  60

Asn Glu Val Asp Cys Phe Leu Lys Ser Cys Leu Asn Ser Arg Lys Pro
65                  70                  75                  80

Leu Arg Val Leu Val Ser Thr Lys Pro
                85

<210> SEQ ID NO 57
<211> LENGTH: 82
<212> TYPE: PRT
<213> ORGANISM: Homo sapiens

<400> SEQUENCE: 57
```

```
Pro Arg Glu Thr Val Lys Ile Pro Asp Ser Ala Asp Gly Leu Gly Phe
 1               5                  10                  15

Gln Ile Arg Gly Phe Gly Pro Ser Val Val His Ala Val Gly Arg Gly
            20                  25                  30

Thr Val Ala Ala Ala Gly Leu His Pro Gly Gln Cys Ile Ile Lys
        35                  40                  45

Val Asn Gly Ile Asn Val Ser Lys Glu Thr His Ala Ser Val Ile Ala
    50                  55                  60

His Val Thr Ala Cys Arg Lys Tyr Arg Pro Thr Lys Gln Asp Ser
65                  70                  75                  80

Ile Gln
```

<210> SEQ ID NO 58
<211> LENGTH: 100
<212> TYPE: PRT
<213> ORGANISM: Homo sapiens

<400> SEQUENCE: 58

```
Glu Asp Phe Cys Tyr Val Phe Thr Val Glu Leu Glu Arg Gly Pro Ser
 1               5                  10                  15

Gly Leu Gly Met Gly Leu Ile Asp Gly Met His Thr His Leu Gly Ala
            20                  25                  30

Pro Gly Leu Tyr Ile Gln Thr Leu Leu Pro Gly Ser Pro Ala Ala Ala
        35                  40                  45

Asp Gly Arg Leu Ser Leu Gly Asp Arg Ile Leu Glu Val Asn Gly Ser
    50                  55                  60

Ser Leu Leu Gly Leu Gly Tyr Leu Arg Ala Val Asp Leu Ile Arg His
65                  70                  75                  80

Gly Gly Lys Lys Met Arg Phe Leu Val Ala Lys Ser Asp Val Glu Thr
                85                  90                  95

Ala Lys Lys Ile
           100
```

<210> SEQ ID NO 59
<211> LENGTH: 109
<212> TYPE: PRT
<213> ORGANISM: Homo sapiens

<400> SEQUENCE: 59

```
Leu Thr Glu Phe Gln Asp Lys Gln Ile Lys Asp Trp Lys Lys Arg Phe
 1               5                  10                  15

Ile Gly Ile Arg Met Arg Thr Ile Thr Pro Ser Leu Val Asp Glu Leu
            20                  25                  30

Lys Ala Ser Asn Pro Asp Phe Pro Glu Val Ser Ser Gly Ile Tyr Val
        35                  40                  45

Gln Glu Val Ala Pro Asn Ser Pro Ser Gln Arg Gly Gly Ile Gln Asp
    50                  55                  60

Gly Asp Ile Ile Val Lys Val Asn Gly Arg Pro Leu Val Asp Ser Ser
65                  70                  75                  80

Glu Leu Gln Glu Ala Val Leu Thr Glu Ser Pro Leu Leu Leu Glu Val
                85                  90                  95

Arg Arg Gly Asn Asp Asp Leu Leu Phe Ser Asn Ser Ser
           100                 105
```

<210> SEQ ID NO 60
<211> LENGTH: 97
<212> TYPE: PRT

-continued

<213> ORGANISM: Homo sapiens

<400> SEQUENCE: 60

His Lys Lys Tyr Leu Gly Leu Gln Met Leu Ser Leu Thr Val Pro Leu
1               5                   10                  15

Ser Glu Glu Leu Lys Met His Tyr Pro Asp Phe Pro Asp Val Ser Ser
            20                  25                  30

Gly Val Tyr Val Cys Lys Val Val Glu Gly Thr Ala Ala Gln Ser Ser
        35                  40                  45

Gly Leu Arg Asp His Asp Val Ile Val Asn Ile Asn Gly Lys Pro Ile
    50                  55                  60

Thr Thr Thr Thr Asp Val Val Lys Ala Leu Asp Ser Asp Ser Leu Ser
65                  70                  75                  80

Met Ala Val Leu Arg Gly Lys Asp Asn Leu Leu Leu Thr Val Asn Ser
                85                  90                  95

Ser

<210> SEQ ID NO 61
<211> LENGTH: 104
<212> TYPE: PRT
<213> ORGANISM: Homo sapiens

<400> SEQUENCE: 61

Ile Trp Gln Ile Glu Tyr Ile Asp Ile Glu Arg Pro Ser Thr Gly Gly
1               5                   10                  15

Leu Gly Phe Ser Val Val Ala Leu Arg Ser Gln Asn Leu Gly Lys Val
            20                  25                  30

Asp Ile Phe Val Lys Asp Val Gln Pro Gly Ser Val Ala Asp Arg Asp
        35                  40                  45

Gln Arg Leu Lys Glu Asn Asp Gln Ile Leu Ala Ile Asn His Thr Pro
    50                  55                  60

Leu Asp Gln Asn Ile Ser His Gln Gln Ala Ile Ala Leu Leu Gln Gln
65                  70                  75                  80

Thr Thr Gly Ser Leu Arg Leu Ile Val Ala Arg Glu Pro Val His Thr
                85                  90                  95

Lys Ser Ser Thr Ser Ser Ser Glu
            100

<210> SEQ ID NO 62
<211> LENGTH: 78
<212> TYPE: PRT
<213> ORGANISM: Homo sapiens

<400> SEQUENCE: 62

Pro Gly His Val Glu Val Glu Leu Ile Asn Asp Gly Ser Gly Leu
1               5                   10                  15

Gly Phe Gly Ile Val Gly Gly Lys Thr Ser Gly Val Val Arg Thr
            20                  25                  30

Ile Val Pro Gly Gly Leu Ala Asp Arg Asp Gly Arg Leu Gln Thr Gly
        35                  40                  45

Asp His Ile Leu Lys Ile Gly Gly Thr Asn Val Gln Gly Met Thr Ser
    50                  55                  60

Glu Gln Val Ala Gln Val Leu Arg Asn Cys Gly Asn Ser Ser
65                  70                  75

<210> SEQ ID NO 63
<211> LENGTH: 111

```
<212> TYPE: PRT
<213> ORGANISM: Homo sapiens

<400> SEQUENCE: 63

Pro Gly Ser Asp Ser Ser Leu Phe Glu Thr Tyr Asn Val Glu Leu Val
1               5                   10                  15

Arg Lys Asp Gly Gln Ser Leu Gly Ile Arg Ile Val Gly Tyr Val Gly
            20                  25                  30

Thr Ser His Thr Gly Glu Ala Ser Gly Ile Tyr Val Lys Ser Ile Ile
        35                  40                  45

Pro Gly Ser Ala Ala Tyr His Asn Gly His Ile Gln Val Asn Asp Lys
    50                  55                  60

Ile Val Ala Val Asp Gly Val Asn Ile Gln Gly Phe Ala Asn His Asp
65                  70                  75                  80

Val Val Glu Val Leu Arg Asn Ala Gly Gln Val Val His Leu Thr Leu
                85                  90                  95

Val Arg Arg Lys Thr Ser Ser Thr Ser Arg Ile His Arg Asp
            100                 105                 110

<210> SEQ ID NO 64
<211> LENGTH: 96
<212> TYPE: PRT
<213> ORGANISM: Homo sapiens

<400> SEQUENCE: 64

Asn Ser Asp Asp Ala Glu Leu Gln Lys Tyr Ser Lys Leu Leu Pro Ile
1               5                   10                  15

His Thr Leu Arg Leu Gly Val Glu Val Asp Ser Phe Asp Gly His His
            20                  25                  30

Tyr Ile Ser Ser Ile Val Ser Gly Gly Pro Val Asp Thr Leu Gly Leu
        35                  40                  45

Leu Gln Pro Glu Asp Glu Leu Leu Glu Val Asn Gly Met Gln Leu Tyr
    50                  55                  60

Gly Lys Ser Arg Arg Glu Ala Val Ser Phe Leu Lys Glu Val Pro Pro
65                  70                  75                  80

Pro Phe Thr Leu Val Cys Cys Arg Arg Leu Phe Asp Asp Glu Ala Ser
                85                  90                  95

<210> SEQ ID NO 65
<211> LENGTH: 102
<212> TYPE: PRT
<213> ORGANISM: Homo sapiens

<400> SEQUENCE: 65

Leu Ser Ser Pro Glu Val Lys Ile Val Glu Leu Val Lys Asp Cys Lys
1               5                   10                  15

Gly Leu Gly Phe Ser Ile Leu Asp Tyr Gln Asp Pro Leu Asp Pro Thr
            20                  25                  30

Arg Ser Val Ile Val Ile Arg Ser Leu Val Ala Asp Gly Val Ala Glu
        35                  40                  45

Arg Ser Gly Gly Leu Leu Pro Gly Asp Arg Leu Val Ser Val Asn Glu
    50                  55                  60

Tyr Cys Leu Asp Asn Thr Ser Leu Ala Glu Ala Val Glu Ile Leu Lys
65                  70                  75                  80

Ala Val Pro Pro Gly Leu Val His Leu Gly Ile Cys Lys Pro Leu Val
                85                  90                  95

Glu Phe Ile Val Thr Asp
```

-continued

100

<210> SEQ ID NO 66
<211> LENGTH: 119
<212> TYPE: PRT
<213> ORGANISM: Homo sapiens

<400> SEQUENCE: 66

```
Pro Asn Phe Ser His Trp Gly Pro Pro Arg Ile Val Glu Ile Phe Arg
 1               5                  10                  15

Glu Pro Asn Val Ser Leu Gly Ile Ser Ile Val Val Gly Gln Thr Val
            20                  25                  30

Ile Lys Arg Leu Lys Asn Gly Glu Glu Leu Lys Gly Ile Phe Ile Lys
        35                  40                  45

Gln Val Leu Glu Asp Ser Pro Ala Gly Lys Thr Asn Ala Leu Lys Thr
    50                  55                  60

Gly Asp Lys Ile Leu Glu Val Ser Gly Val Asp Leu Gln Asn Ala Ser
65                  70                  75                  80

His Ser Glu Ala Val Glu Ala Ile Lys Asn Ala Gly Asn Pro Val Val
                85                  90                  95

Phe Ile Val Gln Ser Leu Ser Ser Thr Pro Arg Val Ile Pro Asn Val
                100                 105                 110

His Asn Lys Ala Asn Ser Ser
        115
```

<210> SEQ ID NO 67
<211> LENGTH: 99
<212> TYPE: PRT
<213> ORGANISM: Homo sapiens

<400> SEQUENCE: 67

```
Pro Gly Glu Leu His Ile Ile Glu Leu Glu Lys Asp Lys Asn Gly Leu
 1               5                  10                  15

Gly Leu Ser Leu Ala Gly Asn Lys Asp Arg Ser Arg Met Ser Ile Phe
            20                  25                  30

Val Val Gly Ile Asn Pro Glu Gly Pro Ala Ala Ala Asp Gly Arg Met
        35                  40                  45

Arg Ile Gly Asp Glu Leu Leu Glu Ile Asn Asn Gln Ile Leu Tyr Gly
    50                  55                  60

Arg Ser His Gln Asn Ala Ser Ala Ile Ile Lys Thr Ala Pro Ser Lys
65                  70                  75                  80

Val Lys Leu Val Phe Ile Arg Asn Glu Asp Ala Val Asn Gln Met Ala
                85                  90                  95

Asn Ser Ser
```

<210> SEQ ID NO 68
<211> LENGTH: 93
<212> TYPE: PRT
<213> ORGANISM: Homo sapiens

<400> SEQUENCE: 68

```
Pro Ala Thr Cys Pro Ile Val Pro Gly Gln Glu Met Ile Ile Glu Ile
 1               5                  10                  15

Ser Lys Gly Arg Ser Gly Leu Gly Leu Ser Ile Val Gly Gly Lys Asp
            20                  25                  30

Thr Pro Leu Asn Ala Ile Val Ile His Glu Val Tyr Glu Glu Gly Ala
        35                  40                  45
```

```
Ala Ala Arg Asp Gly Arg Leu Trp Ala Gly Asp Gln Ile Leu Glu Val
    50                  55                  60
Asn Gly Val Asp Leu Arg Asn Ser Ser His Glu Glu Ala Ile Thr Ala
 65                  70                  75                  80
Leu Arg Gln Thr Pro Gln Lys Val Arg Leu Val Val Tyr
                 85                  90
```

<210> SEQ ID NO 69
<211> LENGTH: 103
<212> TYPE: PRT
<213> ORGANISM: Homo sapiens

<400> SEQUENCE: 69

```
Ile Leu Thr Leu Thr Ile Leu Arg Gln Thr Gly Gly Leu Gly Ile Ser
  1               5                  10                  15
Ile Ala Gly Gly Lys Gly Ser Thr Pro Tyr Lys Gly Asp Asp Glu Gly
                 20                  25                  30
Ile Phe Ile Ser Arg Val Ser Glu Gly Pro Ala Ala Arg Ala Gly
                 35                  40                  45
Val Arg Val Gly Asp Lys Leu Leu Glu Val Asn Gly Val Ala Leu Gln
 50                  55                  60
Gly Ala Glu His His Glu Ala Val Glu Ala Leu Arg Gly Ala Gly Thr
 65                  70                  75                  80
Ala Val Gln Met Arg Val Trp Arg Glu Arg Met Val Glu Pro Glu Asn
                 85                  90                  95
Ala Glu Phe Ile Val Thr Asp
                100
```

<210> SEQ ID NO 70
<211> LENGTH: 97
<212> TYPE: PRT
<213> ORGANISM: Homo sapiens

<400> SEQUENCE: 70

```
Pro Leu Arg Gln Arg His Val Ala Cys Leu Ala Arg Ser Glu Arg Gly
  1               5                  10                  15
Leu Gly Phe Ser Ile Ala Gly Gly Lys Gly Ser Thr Pro Tyr Arg Ala
                 20                  25                  30
Gly Asp Ala Gly Ile Phe Val Ser Arg Ile Ala Glu Gly Gly Ala Ala
                 35                  40                  45
His Arg Ala Gly Thr Leu Gln Val Gly Asp Arg Val Leu Ser Ile Asn
 50                  55                  60
Gly Val Asp Val Thr Glu Ala Arg His Asp His Ala Val Ser Leu Leu
 65                  70                  75                  80
Thr Ala Ala Ser Pro Thr Ile Ala Leu Leu Leu Glu Arg Glu Ala Gly
                 85                  90                  95
Gly
```

<210> SEQ ID NO 71
<211> LENGTH: 106
<212> TYPE: PRT
<213> ORGANISM: Homo sapiens

<400> SEQUENCE: 71

```
Ile Leu Glu Gly Pro Tyr Pro Val Glu Glu Ile Arg Leu Pro Arg Ala
  1               5                  10                  15
Gly Gly Pro Leu Gly Leu Ser Ile Val Gly Gly Ser Asp His Ser Ser
                 20                  25                  30
```

```
His Pro Phe Gly Val Gln Glu Pro Gly Val Phe Ile Ser Lys Val Leu
        35                  40                  45

Pro Arg Gly Leu Ala Ala Arg Ser Gly Leu Arg Val Gly Asp Arg Ile
    50                  55                  60

Leu Ala Val Asn Gly Gln Asp Val Arg Asp Ala Thr His Gln Glu Ala
65                  70                  75                  80

Val Ser Ala Leu Leu Arg Pro Cys Leu Glu Leu Ser Leu Leu Val Arg
                85                  90                  95

Arg Asp Pro Ala Glu Phe Ile Val Thr Asp
            100                 105
```

<210> SEQ ID NO 72
<211> LENGTH: 105
<212> TYPE: PRT
<213> ORGANISM: Homo sapiens

<400> SEQUENCE: 72

```
Arg Glu Leu Cys Ile Gln Lys Ala Pro Gly Glu Arg Leu Gly Ile Ser
1               5                   10                  15

Ile Arg Gly Gly Ala Arg Gly His Ala Gly Asn Pro Arg Asp Pro Thr
            20                  25                  30

Asp Glu Gly Ile Phe Ile Ser Lys Val Ser Pro Thr Gly Ala Ala Gly
        35                  40                  45

Arg Asp Gly Arg Leu Arg Val Gly Leu Arg Leu Leu Glu Val Asn Gln
    50                  55                  60

Gln Ser Leu Leu Gly Leu Thr His Gly Glu Ala Val Gln Leu Leu Arg
65                  70                  75                  80

Ser Val Gly Asp Thr Leu Thr Val Leu Val Cys Asp Gly Phe Glu Ala
                85                  90                  95

Ser Thr Asp Ala Ala Leu Glu Val Ser
            100                 105
```

<210> SEQ ID NO 73
<211> LENGTH: 91
<212> TYPE: PRT
<213> ORGANISM: Homo sapiens

<400> SEQUENCE: 73

```
Pro His Gln Pro Ile Val Ile His Ser Ser Gly Lys Asn Tyr Gly Phe
1               5                   10                  15

Thr Ile Arg Ala Ile Arg Val Tyr Val Gly Asp Ser Asp Ile Tyr Thr
            20                  25                  30

Val His His Ile Val Trp Asn Val Glu Glu Gly Ser Pro Ala Cys Gln
        35                  40                  45

Ala Gly Leu Lys Ala Gly Asp Leu Ile Thr His Ile Asn Gly Glu Pro
    50                  55                  60

Val His Gly Leu Val His Thr Glu Val Ile Glu Leu Leu Leu Lys Ser
65                  70                  75                  80

Gly Asn Lys Val Ser Ile Thr Thr Thr Pro Phe
                85                  90
```

<210> SEQ ID NO 74
<211> LENGTH: 105
<212> TYPE: PRT
<213> ORGANISM: Homo sapiens

<400> SEQUENCE: 74

```
Ile Leu Ala Cys Ala Ala Lys Ala Lys Arg Arg Leu Met Thr Leu Thr
1               5                   10                  15

Lys Pro Ser Arg Glu Ala Pro Leu Pro Phe Ile Leu Leu Gly Gly Ser
            20                  25                  30

Glu Lys Gly Phe Gly Ile Phe Val Asp Ser Val Asp Ser Gly Ser Lys
        35                  40                  45

Ala Thr Glu Ala Gly Leu Lys Arg Gly Asp Gln Ile Leu Glu Val Asn
50                  55                  60

Gly Gln Asn Phe Glu Asn Ile Gln Leu Ser Lys Ala Met Glu Ile Leu
65                  70                  75                  80

Arg Asn Asn Thr His Leu Ser Ile Thr Val Lys Thr Asn Leu Phe Val
                85                  90                  95

Phe Lys Glu Leu Leu Thr Asn Ser Ser
            100                 105

<210> SEQ ID NO 75
<211> LENGTH: 88
<212> TYPE: PRT
<213> ORGANISM: Homo sapiens

<400> SEQUENCE: 75

Ile Pro Pro Ala Pro Arg Lys Val Glu Met Arg Arg Asp Pro Val Leu
1               5                   10                  15

Gly Phe Gly Phe Val Ala Gly Ser Glu Lys Pro Val Val Arg Ser
            20                  25                  30

Val Thr Pro Gly Gly Pro Ser Glu Gly Lys Leu Ile Pro Gly Asp Gln
        35                  40                  45

Ile Val Met Ile Asn Asp Glu Pro Val Ser Ala Ala Pro Arg Glu Arg
50                  55                  60

Val Ile Asp Leu Val Arg Ser Cys Lys Glu Ser Ile Leu Leu Thr Val
65                  70                  75                  80

Ile Gln Pro Tyr Pro Ser Pro Lys
                85

<210> SEQ ID NO 76
<211> LENGTH: 101
<212> TYPE: PRT
<213> ORGANISM: Homo sapiens

<400> SEQUENCE: 76

Leu Asn Lys Arg Thr Thr Met Pro Lys Asp Ser Gly Ala Leu Leu Gly
1               5                   10                  15

Leu Lys Val Val Gly Gly Lys Met Thr Asp Leu Gly Arg Leu Gly Ala
            20                  25                  30

Phe Ile Thr Lys Val Lys Lys Gly Ser Leu Ala Asp Val Val Gly His
        35                  40                  45

Leu Arg Ala Gly Asp Glu Val Leu Glu Trp Asn Gly Lys Pro Leu Pro
50                  55                  60

Gly Ala Thr Asn Glu Glu Val Tyr Asn Ile Ile Leu Glu Ser Lys Ser
65                  70                  75                  80

Glu Pro Gln Val Glu Ile Ile Val Ser Arg Pro Ile Gly Asp Ile Pro
                85                  90                  95

Arg Ile His Arg Asp
                100

<210> SEQ ID NO 77
<211> LENGTH: 79
```

```
<212> TYPE: PRT
<213> ORGANISM: Homo sapiens

<400> SEQUENCE: 77

Gln Arg Cys Val Ile Ile Gln Lys Asp Gln His Gly Phe Gly Phe Thr
1               5                   10                  15

Val Ser Gly Asp Arg Ile Val Leu Val Gln Ser Val Arg Pro Gly Gly
            20                  25                  30

Ala Ala Met Lys Ala Gly Val Lys Glu Gly Asp Arg Ile Ile Lys Val
        35                  40                  45

Asn Gly Thr Met Val Thr Asn Ser Ser His Leu Glu Val Val Lys Leu
50                  55                  60

Ile Lys Ser Gly Ala Tyr Val Ala Leu Thr Leu Leu Gly Ser Ser
65                  70                  75

<210> SEQ ID NO 78
<211> LENGTH: 87
<212> TYPE: PRT
<213> ORGANISM: Homo sapiens

<400> SEQUENCE: 78

Ile Leu Val Gln Arg Cys Val Ile Ile Gln Lys Asp Asp Asn Gly Phe
1               5                   10                  15

Gly Leu Thr Val Ser Gly Asp Asn Pro Val Phe Val Gln Ser Val Lys
            20                  25                  30

Glu Asp Gly Ala Ala Met Arg Ala Gly Val Gln Thr Gly Asp Arg Ile
        35                  40                  45

Ile Lys Val Asn Gly Thr Leu Val Thr His Ser Asn His Leu Glu Val
50                  55                  60

Val Lys Leu Ile Lys Ser Gly Ser Tyr Val Ala Leu Thr Val Gln Gly
65                  70                  75                  80

Arg Pro Pro Gly Asn Ser Ser
                85

<210> SEQ ID NO 79
<211> LENGTH: 79
<212> TYPE: PRT
<213> ORGANISM: Homo sapiens

<400> SEQUENCE: 79

Ser Val Glu Met Thr Leu Arg Arg Asn Gly Leu Gly Gln Leu Gly Phe
1               5                   10                  15

His Val Asn Tyr Glu Gly Ile Val Ala Asp Val Glu Pro Tyr Gly Tyr
            20                  25                  30

Ala Trp Gln Ala Gly Leu Arg Gln Gly Ser Arg Leu Val Glu Ile Cys
        35                  40                  45

Lys Val Ala Val Ala Thr Leu Ser His Glu Gln Met Ile Asp Leu Leu
    50                  55                  60

Arg Thr Ser Val Thr Val Lys Val Val Ile Pro Pro His Asp
65                  70                  75

<210> SEQ ID NO 80
<211> LENGTH: 96
<212> TYPE: PRT
<213> ORGANISM: Homo sapiens

<400> SEQUENCE: 80

Leu Lys Val Met Thr Ser Gly Trp Glu Thr Val Asp Met Thr Leu Arg
1               5                   10                  15
```

Arg Asn Gly Leu Gly Gln Leu Gly Phe His Val Lys Tyr Asp Gly Thr
            20                  25                  30

Val Ala Glu Val Glu Asp Tyr Gly Phe Ala Trp Gln Ala Gly Leu Arg
        35                  40                  45

Gln Gly Ser Arg Leu Val Glu Ile Cys Lys Val Ala Val Val Thr Leu
    50                  55                  60

Thr His Asp Gln Met Ile Asp Leu Leu Arg Thr Ser Val Thr Val Lys
65                  70                  75                  80

Val Val Ile Ile Pro Pro Phe Glu Asp Gly Thr Pro Arg Arg Gly Trp
                85                  90                  95

<210> SEQ ID NO 81
<211> LENGTH: 105
<212> TYPE: PRT
<213> ORGANISM: Homo sapiens

<400> SEQUENCE: 81

His Tyr Ile Phe Pro His Ala Arg Ile Lys Ile Thr Arg Asp Ser Lys
1               5                   10                  15

Asp His Thr Val Ser Gly Asn Gly Leu Gly Ile Arg Ile Val Gly Gly
            20                  25                  30

Lys Glu Ile Pro Gly His Ser Gly Glu Ile Gly Ala Tyr Ile Ala Lys
        35                  40                  45

Ile Leu Pro Gly Gly Ser Ala Glu Gln Thr Gly Lys Leu Met Glu Gly
    50                  55                  60

Met Gln Val Leu Glu Trp Asn Gly Ile Pro Leu Thr Ser Lys Thr Tyr
65                  70                  75                  80

Glu Glu Val Gln Ser Ile Ile Ser Gln Gln Ser Gly Glu Ala Glu Ile
                85                  90                  95

Cys Val Arg Leu Asp Leu Asn Met Leu
            100                 105

<210> SEQ ID NO 82
<211> LENGTH: 103
<212> TYPE: PRT
<213> ORGANISM: Homo sapiens

<400> SEQUENCE: 82

Leu Cys Gly Ser Leu Arg Pro Pro Ile Val Ile His Ser Ser Gly Lys
1               5                   10                  15

Lys Tyr Gly Phe Ser Leu Arg Ala Ile Arg Val Tyr Met Gly Asp Ser
            20                  25                  30

Asp Val Tyr Thr Val His His Val Val Trp Ser Val Glu Asp Gly Ser
        35                  40                  45

Pro Ala Gln Glu Ala Gly Leu Arg Ala Gly Asp Leu Ile Thr His Ile
    50                  55                  60

Asn Gly Glu Ser Val Leu Gly Leu Val His Met Asp Val Val Glu Leu
65                  70                  75                  80

Leu Leu Lys Ser Gly Asn Lys Ile Ser Leu Arg Thr Thr Ala Leu Glu
                85                  90                  95

Asn Thr Ser Ile Lys Val Gly
            100

<210> SEQ ID NO 83
<211> LENGTH: 86
<212> TYPE: PRT
<213> ORGANISM: Homo sapiens

```
<400> SEQUENCE: 83

Ser Tyr Ser Val Thr Leu Thr Gly Pro Gly Pro Trp Gly Phe Arg Leu
 1               5                  10                  15

Gln Gly Gly Lys Asp Phe Asn Met Pro Leu Thr Ile Ser Arg Ile Thr
             20                  25                  30

Pro Gly Ser Lys Ala Ala Gln Ser Gln Leu Ser Gln Gly Asp Leu Val
         35                  40                  45

Val Ala Ile Asp Gly Val Asn Thr Asp Thr Met Thr His Leu Glu Ala
     50                  55                  60

Gln Asn Lys Ile Lys Ser Ala Ser Tyr Asn Leu Ser Leu Thr Leu Gln
 65                  70                  75                  80

Lys Ser Lys Asn Ser Ser
                 85

<210> SEQ ID NO 84
<211> LENGTH: 91
<212> TYPE: PRT
<213> ORGANISM: Homo sapiens

<400> SEQUENCE: 84

Ile Ser Arg Asp Ser Gly Ala Met Leu Gly Leu Lys Val Val Gly Gly
 1               5                  10                  15

Lys Met Thr Glu Ser Gly Arg Leu Cys Ala Phe Ile Thr Lys Val Lys
             20                  25                  30

Lys Gly Ser Leu Ala Asp Thr Val Gly His Leu Arg Pro Gly Asp Glu
         35                  40                  45

Val Leu Glu Trp Asn Gly Arg Leu Leu Gln Gly Ala Thr Phe Glu Glu
     50                  55                  60

Val Tyr Asn Ile Ile Leu Glu Ser Lys Pro Glu Pro Gln Val Glu Leu
 65                  70                  75                  80

Val Val Ser Arg Pro Ile Ala Ile His Arg Asp
                 85                  90

<210> SEQ ID NO 85
<211> LENGTH: 101
<212> TYPE: PRT
<213> ORGANISM: Homo sapiens

<400> SEQUENCE: 85

Ile Ser Ala Leu Gly Ser Met Arg Pro Pro Ile Ile Ile His Arg Ala
 1               5                  10                  15

Gly Lys Lys Tyr Gly Phe Thr Leu Arg Ala Ile Arg Val Tyr Met Gly
             20                  25                  30

Asp Ser Asp Val Tyr Thr Val His His Met Val Trp His Val Glu Asp
         35                  40                  45

Gly Gly Pro Ala Ser Glu Ala Gly Leu Arg Gln Gly Asp Leu Ile Thr
     50                  55                  60

His Val Asn Gly Glu Pro Val His Gly Leu Val His Thr Glu Val Val
 65                  70                  75                  80

Glu Leu Ile Leu Lys Ser Gly Asn Lys Val Ala Ile Ser Thr Thr Pro
                 85                  90                  95

Leu Glu Asn Ser Ser
                100

<210> SEQ ID NO 86
<211> LENGTH: 94
```

```
<212> TYPE: PRT
<213> ORGANISM: Homo sapiens

<400> SEQUENCE: 86

Phe Ser Asp Met Arg Ile Ser Ile Asn Gln Thr Pro Gly Lys Ser Leu
 1               5                  10                  15

Asp Phe Gly Phe Thr Ile Lys Trp Asp Ile Pro Gly Ile Phe Val Ala
            20                  25                  30

Ser Val Glu Ala Gly Ser Pro Ala Glu Phe Ser Gln Leu Gln Val Asp
        35                  40                  45

Asp Glu Ile Ile Ala Ile Asn Asn Thr Lys Phe Ser Tyr Asn Asp Ser
    50                  55                  60

Lys Glu Trp Glu Ala Met Ala Lys Ala Gln Glu Thr Gly His Leu
 65                 70                  75                  80

Val Met Asp Val Arg Arg Tyr Gly Lys Ala Gly Ser Pro Glu
                85                  90

<210> SEQ ID NO 87
<211> LENGTH: 98
<212> TYPE: PRT
<213> ORGANISM: Homo sapiens

<400> SEQUENCE: 87

Gln Ser Ala His Leu Glu Val Ile Gln Leu Ala Asn Ile Lys Pro Ser
 1               5                  10                  15

Glu Gly Leu Gly Met Tyr Ile Lys Ser Thr Tyr Asp Gly Leu His Val
            20                  25                  30

Ile Thr Gly Thr Thr Glu Asn Ser Pro Ala Asp Arg Cys Lys Lys Ile
        35                  40                  45

His Ala Gly Asp Glu Val Ile Gln Val Asn His Gln Thr Val Val Gly
    50                  55                  60

Trp Gln Leu Lys Asn Leu Val Asn Ala Leu Arg Glu Asp Pro Ser Gly
 65                 70                  75                  80

Val Ile Leu Thr Leu Lys Lys Arg Pro Gln Ser Met Leu Thr Ser Ala
                85                  90                  95

Pro Ala

<210> SEQ ID NO 88
<211> LENGTH: 100
<212> TYPE: PRT
<213> ORGANISM: Homo sapiens

<400> SEQUENCE: 88

Ile Leu Thr Gln Thr Leu Ile Pro Val Arg His Thr Val Lys Ile Asp
 1               5                  10                  15

Lys Asp Thr Leu Leu Gln Asp Tyr Gly Phe His Ile Ser Glu Ser Leu
            20                  25                  30

Pro Leu Thr Val Val Ala Val Thr Ala Gly Gly Ser Ala His Gly Lys
        35                  40                  45

Leu Phe Pro Gly Asp Gln Ile Leu Gln Met Asn Asn Glu Pro Ala Glu
    50                  55                  60

Asp Leu Ser Trp Glu Arg Ala Val Asp Ile Leu Arg Glu Ala Glu Asp
 65                 70                  75                  80

Ser Leu Ser Ile Thr Val Val Arg Cys Thr Ser Gly Val Pro Lys Ser
                85                  90                  95

Ser Asn Ser Ser
            100
```

<210> SEQ ID NO 89
<211> LENGTH: 93
<212> TYPE: PRT
<213> ORGANISM: Homo sapiens

<400> SEQUENCE: 89

```
Gly Leu Arg Ser Pro Ile Thr Ile Gln Arg Ser Gly Lys Lys Tyr Gly
1               5                   10                  15

Phe Thr Leu Arg Ala Ile Arg Val Tyr Met Gly Asp Thr Asp Val Tyr
                20                  25                  30

Ser Val His His Ile Val Trp His Val Glu Glu Gly Gly Pro Ala Gln
            35                  40                  45

Glu Ala Gly Leu Cys Ala Gly Asp Leu Ile Thr His Val Asn Gly Glu
        50                  55                  60

Pro Val His Gly Met Val His Pro Glu Val Val Glu Leu Ile Leu Lys
65                  70                  75                  80

Ser Gly Asn Lys Val Ala Val Thr Thr Thr Pro Phe Glu
                85                  90
```

<210> SEQ ID NO 90
<211> LENGTH: 107
<212> TYPE: PRT
<213> ORGANISM: Homo sapiens

<400> SEQUENCE: 90

```
Gln Gly Glu Glu Thr Lys Ser Leu Thr Leu Val Leu His Arg Asp Ser
1               5                   10                  15

Gly Ser Leu Gly Phe Asn Ile Ile Gly Gly Arg Pro Ser Val Asp Asn
                20                  25                  30

His Asp Gly Ser Ser Glu Gly Ile Phe Val Ser Lys Ile Val Asp
            35                  40                  45

Ser Gly Pro Ala Ala Lys Glu Gly Leu Gln Ile His Asp Arg Ile
        50                  55                  60

Ile Glu Val Asn Gly Arg Asp Leu Ser Arg Ala Thr His Asp Gln Ala
65                  70                  75                  80

Val Glu Ala Phe Lys Thr Ala Lys Glu Pro Ile Val Val Gln Val Leu
                85                  90                  95

Arg Arg Thr Pro Arg Thr Lys Met Phe Thr Pro
                100                 105
```

<210> SEQ ID NO 91
<211> LENGTH: 101
<212> TYPE: PRT
<213> ORGANISM: Homo sapiens

<400> SEQUENCE: 91

```
Gln Glu Met Asp Arg Glu Glu Leu Glu Leu Glu Glu Val Asp Leu Tyr
1               5                   10                  15

Arg Met Asn Ser Gln Asp Lys Leu Gly Leu Thr Val Cys Tyr Arg Thr
                20                  25                  30

Asp Asp Glu Asp Asp Ile Gly Ile Tyr Ile Ser Glu Ile Asp Pro Asn
            35                  40                  45

Ser Ile Ala Ala Lys Asp Gly Arg Ile Arg Glu Gly Asp Arg Ile Ile
        50                  55                  60

Gln Ile Asn Gly Ile Glu Val Gln Asn Arg Glu Glu Ala Val Ala Leu
65                  70                  75                  80
```

```
Leu Thr Ser Glu Glu Asn Lys Asn Phe Ser Leu Leu Ile Ala Arg Pro
                85                  90                  95
Glu Leu Gln Leu Asp
            100

<210> SEQ ID NO 92
<211> LENGTH: 91
<212> TYPE: PRT
<213> ORGANISM: Homo sapiens

<400> SEQUENCE: 92

Arg Ser Phe Gln Tyr Val Pro Val Gln Leu Gln Gly Gly Ala Pro Trp
1               5                   10                  15
Gly Phe Thr Leu Lys Gly Gly Leu Glu His Cys Glu Pro Leu Thr Val
                20                  25                  30
Ser Lys Ile Glu Asp Gly Gly Lys Ala Ala Leu Ser Gln Lys Met Arg
            35                  40                  45
Thr Gly Asp Glu Leu Val Asn Ile Asn Gly Thr Pro Leu Tyr Gly Ser
        50                  55                  60
Arg Gln Glu Ala Leu Ile Leu Ile Lys Gly Ser Phe Arg Ile Leu Lys
65                  70                  75                  80
Leu Ile Val Arg Arg Asn Ala Pro Val Ser
                85                  90

<210> SEQ ID NO 93
<211> LENGTH: 102
<212> TYPE: PRT
<213> ORGANISM: Homo sapiens

<400> SEQUENCE: 93

Ile Leu Glu Lys Leu Glu Leu Phe Pro Val Glu Leu Glu Lys Asp Glu
1               5                   10                  15
Asp Gly Leu Gly Ile Ser Ile Ile Gly Met Gly Val Gly Ala Asp Ala
                20                  25                  30
Gly Leu Glu Lys Leu Gly Ile Phe Val Lys Thr Val Thr Glu Gly Gly
            35                  40                  45
Ala Ala Gln Arg Asp Gly Arg Ile Gln Val Asn Asp Gln Ile Val Glu
    50                  55                  60
Val Asp Gly Ile Ser Leu Val Gly Val Thr Gln Asn Phe Ala Ala Thr
65                  70                  75                  80
Val Leu Arg Asn Thr Lys Gly Asn Val Arg Phe Val Ile Gly Arg Glu
                85                  90                  95
Lys Pro Gly Gln Val Ser
            100

<210> SEQ ID NO 94
<211> LENGTH: 113
<212> TYPE: PRT
<213> ORGANISM: Homo sapiens

<400> SEQUENCE: 94

Lys Asp Val Asn Val Tyr Val Asn Pro Lys Lys Leu Thr Val Ile Lys
1               5                   10                  15
Ala Lys Glu Gln Leu Lys Leu Leu Glu Val Leu Val Gly Ile Ile His
                20                  25                  30
Gln Thr Lys Trp Ser Trp Arg Arg Thr Gly Lys Gln Gly Asp Gly Glu
            35                  40                  45
Arg Leu Val Val His Gly Leu Leu Pro Gly Gly Ser Ala Met Lys Ser
```

```
                    50                  55                  60
Gly Gln Val Leu Ile Gly Asp Val Leu Val Ala Val Asn Asp Val Asp
 65                  70                  75                  80

Val Thr Thr Glu Asn Ile Glu Arg Val Leu Ser Cys Ile Pro Gly Pro
                 85                  90                  95

Met Gln Val Lys Leu Thr Phe Glu Asn Ala Tyr Asp Val Lys Arg Glu
                100                 105                 110

Thr

<210> SEQ ID NO 95
<211> LENGTH: 90
<212> TYPE: PRT
<213> ORGANISM: Homo sapiens

<400> SEQUENCE: 95

Thr Arg Gly Cys Glu Thr Val Glu Met Thr Leu Arg Arg Asn Gly Leu
  1               5                  10                  15

Gly Gln Leu Gly Phe His Val Asn Phe Glu Gly Ile Val Ala Asp Val
                 20                  25                  30

Glu Pro Phe Gly Phe Ala Trp Lys Ala Gly Leu Arg Gln Gly Ser Arg
             35                  40                  45

Leu Val Glu Ile Cys Lys Val Ala Val Ala Thr Leu Thr His Glu Gln
 50                  55                  60

Met Ile Asp Leu Leu Arg Thr Ser Val Thr Val Lys Val Val Ile Ile
 65                  70                  75                  80

Gln Pro His Asp Asp Gly Ser Pro Arg Arg
                 85                  90

<210> SEQ ID NO 96
<211> LENGTH: 96
<212> TYPE: PRT
<213> ORGANISM: Homo sapiens

<400> SEQUENCE: 96

Val Glu Asn Ile Leu Ala Lys Arg Leu Leu Ile Leu Pro Gln Glu Glu
  1               5                  10                  15

Asp Tyr Gly Phe Asp Ile Glu Glu Lys Asn Lys Ala Val Val Val Lys
                 20                  25                  30

Ser Val Gln Arg Gly Ser Leu Ala Glu Val Ala Gly Leu Gln Val Gly
             35                  40                  45

Arg Lys Ile Tyr Ser Ile Asn Glu Asp Leu Val Phe Leu Arg Pro Phe
 50                  55                  60

Ser Glu Val Glu Ser Ile Leu Asn Gln Ser Phe Cys Ser Arg Arg Pro
 65                  70                  75                  80

Leu Arg Leu Leu Val Ala Thr Lys Ala Lys Glu Ile Ile Lys Ile Pro
                 85                  90                  95

<210> SEQ ID NO 97
<211> LENGTH: 103
<212> TYPE: PRT
<213> ORGANISM: Homo sapiens

<400> SEQUENCE: 97

Pro Asp Ser Ala Gly Pro Gly Glu Val Arg Leu Val Ser Leu Arg Arg
  1               5                  10                  15

Ala Lys Ala His Glu Gly Leu Gly Phe Ser Ile Arg Gly Gly Ser Glu
                 20                  25                  30
```

```
His Gly Val Gly Ile Tyr Val Ser Leu Val Glu Pro Gly Ser Leu Ala
            35                  40                  45

Glu Lys Glu Gly Leu Arg Val Gly Asp Gln Ile Leu Arg Val Asn Asp
 50                  55                  60

Lys Ser Leu Ala Arg Val Thr His Ala Glu Ala Val Lys Ala Leu Lys
 65                  70                  75                  80

Gly Ser Lys Lys Leu Val Leu Ser Val Tyr Ser Ala Gly Arg Ile Pro
                 85                  90                  95

Gly Gly Tyr Val Thr Asn His
            100

<210> SEQ ID NO 98
<211> LENGTH: 100
<212> TYPE: PRT
<213> ORGANISM: Homo sapiens

<400> SEQUENCE: 98

Leu Gln Gly Gly Asp Glu Lys Lys Val Asn Leu Val Leu Gly Asp Gly
 1               5                  10                  15

Arg Ser Leu Gly Leu Thr Ile Arg Gly Gly Ala Glu Tyr Gly Leu Gly
             20                  25                  30

Ile Tyr Ile Thr Gly Val Asp Pro Gly Ser Glu Ala Glu Gly Ser Gly
            35                  40                  45

Leu Lys Val Gly Asp Gln Ile Leu Glu Val Asn Trp Arg Ser Phe Leu
 50                  55                  60

Asn Ile Leu His Asp Glu Ala Val Arg Leu Leu Lys Ser Ser Arg His
 65                  70                  75                  80

Leu Ile Leu Thr Val Lys Asp Val Gly Arg Leu Pro His Ala Arg Thr
                 85                  90                  95

Thr Val Asp Glu
            100

<210> SEQ ID NO 99
<211> LENGTH: 87
<212> TYPE: PRT
<213> ORGANISM: Homo sapiens

<400> SEQUENCE: 99

Trp Thr Ser Gly Ala His Val His Ser Gly Pro Cys Glu Glu Lys Cys
 1               5                  10                  15

Gly His Pro Gly His Arg Gln Pro Leu Pro Arg Ile Val Thr Ile Gln
             20                  25                  30

Arg Gly Gly Ser Ala His Asn Cys Gly Gln Leu Lys Val Gly His Val
            35                  40                  45

Ile Leu Glu Val Asn Gly Leu Thr Leu Arg Gly Lys Glu His Arg Glu
 50                  55                  60

Ala Ala Arg Ile Ile Ala Glu Ala Phe Lys Thr Lys Asp Arg Asp Tyr
 65                  70                  75                  80

Ile Asp Phe Leu Asp Ser Leu
                 85

<210> SEQ ID NO 100
<211> LENGTH: 100
<212> TYPE: PRT
<213> ORGANISM: Homo sapiens

<400> SEQUENCE: 100

Glu Leu Arg Arg Ala Glu Leu Val Glu Ile Ile Val Glu Thr Glu Ala
 1               5                  10                  15
```

```
                 1               5                  10                 15
Gln Thr Gly Val Ser Gly Ile Asn Val Ala Gly Gly Lys Glu Gly
                20                 25                 30

Ile Phe Val Arg Glu Leu Arg Glu Asp Ser Pro Ala Ala Arg Ser Leu
                35                 40                 45

Ser Leu Gln Glu Gly Asp Gln Leu Leu Ser Ala Arg Val Phe Phe Glu
                50                 55                 60

Asn Phe Lys Tyr Glu Asp Ala Leu Arg Leu Leu Gln Cys Ala Glu Pro
 65                 70                 75                 80

Tyr Lys Val Ser Phe Cys Leu Lys Arg Thr Val Pro Thr Gly Asp Leu
                85                 90                 95

Ala Leu Arg Pro
            100

<210> SEQ ID NO 101
<211> LENGTH: 102
<212> TYPE: PRT
<213> ORGANISM: Homo sapiens

<400> SEQUENCE: 101

Pro Ser Gln Leu Lys Gly Val Leu Val Arg Ala Ser Leu Lys Lys Ser
 1               5                  10                 15

Thr Met Gly Phe Gly Phe Thr Ile Ile Gly Gly Asp Arg Pro Asp Glu
                20                 25                 30

Phe Leu Gln Val Lys Asn Val Leu Lys Asp Gly Pro Ala Ala Gln Asp
                35                 40                 45

Gly Lys Ile Ala Pro Gly Asp Val Ile Val Asp Ile Asn Gly Asn Cys
                50                 55                 60

Val Leu Gly His Thr His Ala Asp Val Val Gln Met Phe Gln Leu Val
 65                 70                 75                 80

Pro Val Asn Gln Tyr Val Asn Leu Thr Leu Cys Arg Gly Tyr Pro Leu
                85                 90                 95

Pro Asp Asp Ser Glu Asp
            100

<210> SEQ ID NO 102
<211> LENGTH: 100
<212> TYPE: PRT
<213> ORGANISM: Homo sapiens

<400> SEQUENCE: 102

Ala Ser Ser Gly Ser Ser Gln Pro Glu Leu Val Thr Ile Pro Leu Ile
 1               5                  10                 15

Lys Gly Pro Lys Gly Phe Gly Phe Ala Ile Ala Asp Ser Pro Thr Gly
                20                 25                 30

Gln Lys Val Lys Met Ile Leu Asp Ser Gln Trp Cys Gln Gly Leu Gln
                35                 40                 45

Lys Gly Asp Ile Ile Lys Glu Ile Tyr His Gln Asn Val Gln Asn Leu
                50                 55                 60

Thr His Leu Gln Val Val Glu Val Leu Lys Gln Phe Pro Val Gly Ala
 65                 70                 75                 80

Asp Val Pro Leu Leu Ile Leu Arg Gly Gly Pro Pro Ser Pro Thr Lys
                85                 90                 95

Thr Ala Lys Met
            100
```

```
<210> SEQ ID NO 103
<211> LENGTH: 143
<212> TYPE: PRT
<213> ORGANISM: Homo sapiens

<400> SEQUENCE: 103

Leu Tyr Glu Asp Lys Pro Pro Leu Thr Asn Thr Phe Leu Ile Ser Asn
1               5                   10                  15

Pro Arg Thr Thr Ala Asp Pro Arg Ile Leu Tyr Glu Asp Lys Pro Pro
            20                  25                  30

Asn Thr Lys Asp Leu Asp Val Phe Leu Arg Lys Gln Glu Ser Gly Phe
        35                  40                  45

Gly Phe Arg Val Leu Gly Gly Asp Pro Asp Gln Ser Ile Tyr Ile
    50                  55                  60

Gly Ala Ile Ile Pro Leu Gly Ala Ala Glu Lys Asp Gly Arg Leu Arg
65                  70                  75                  80

Ala Ala Asp Glu Leu Met Cys Ile Asp Gly Ile Pro Val Lys Gly Lys
                85                  90                  95

Ser His Lys Gln Val Leu Asp Leu Met Thr Thr Ala Ala Arg Asn Gly
            100                 105                 110

His Val Leu Leu Thr Val Arg Arg Lys Ile Phe Tyr Gly Glu Lys Gln
        115                 120                 125

Pro Glu Asp Asp Ser Gly Ser Pro Gly Ile His Arg Glu Leu Thr
    130                 135                 140

<210> SEQ ID NO 104
<211> LENGTH: 102
<212> TYPE: PRT
<213> ORGANISM: Homo sapiens

<400> SEQUENCE: 104

Pro Ala Pro Gln Glu Pro Tyr Asp Val Val Leu Gln Arg Lys Glu Asn
1               5                   10                  15

Glu Gly Phe Gly Phe Val Ile Leu Thr Ser Lys Asn Lys Pro Pro Pro
            20                  25                  30

Gly Val Ile Pro His Lys Ile Gly Arg Val Ile Glu Gly Ser Pro Ala
        35                  40                  45

Asp Arg Cys Gly Lys Leu Lys Val Gly Asp His Ile Ser Ala Val Asn
    50                  55                  60

Gly Gln Ser Ile Val Glu Leu Ser His Asp Asn Ile Val Gln Leu Ile
65                  70                  75                  80

Lys Asp Ala Gly Val Thr Val Thr Leu Thr Val Ile Ala Glu Glu Glu
                85                  90                  95

His His Gly Pro Pro Ser
            100

<210> SEQ ID NO 105
<211> LENGTH: 98
<212> TYPE: PRT
<213> ORGANISM: Homo sapiens

<400> SEQUENCE: 105

Gln Asn Leu Gly Cys Tyr Pro Val Glu Leu Glu Arg Gly Pro Arg Gly
1               5                   10                  15

Phe Gly Phe Ser Leu Arg Gly Gly Lys Glu Tyr Asn Met Gly Leu Phe
            20                  25                  30

Ile Leu Arg Leu Ala Glu Asp Gly Pro Ala Ile Lys Asp Gly Arg Ile
        35                  40                  45
```

His Val Gly Asp Gln Ile Val Glu Ile Asn Gly Glu Pro Thr Gln Gly
    50                  55                  60

Ile Thr His Thr Arg Ala Ile Glu Leu Ile Gln Ala Gly Gly Asn Lys
65                  70                  75                  80

Val Leu Leu Leu Arg Pro Gly Thr Gly Leu Ile Pro Asp His Gly
                85                  90                  95

Leu Ala

<210> SEQ ID NO 106
<211> LENGTH: 84
<212> TYPE: PRT
<213> ORGANISM: Homo sapiens

<400> SEQUENCE: 106

Ile Thr Val Val Glu Leu Ile Lys Lys Glu Gly Ser Thr Leu Gly Leu
1               5                   10                  15

Thr Ile Ser Gly Gly Thr Asp Lys Asp Gly Lys Pro Arg Val Ser Asn
                20                  25                  30

Leu Arg Pro Gly Gly Leu Ala Ala Arg Ser Asp Leu Leu Asn Ile Gly
            35                  40                  45

Asp Tyr Ile Arg Ser Val Asn Gly Ile His Leu Thr Arg Leu Arg His
        50                  55                  60

Asp Glu Ile Ile Thr Leu Leu Lys Asn Val Gly Glu Arg Val Val Leu
65                  70                  75                  80

Glu Val Glu Tyr

<210> SEQ ID NO 107
<211> LENGTH: 92
<212> TYPE: PRT
<213> ORGANISM: Homo sapiens

<400> SEQUENCE: 107

Ile Leu Asp Val Ser Leu Tyr Lys Glu Gly Asn Ser Phe Gly Phe Val
1               5                   10                  15

Leu Arg Gly Gly Ala His Glu Asp Gly His Lys Ser Arg Pro Leu Val
                20                  25                  30

Leu Thr Tyr Val Arg Pro Gly Gly Pro Ala Asp Arg Glu Gly Ser Leu
            35                  40                  45

Lys Val Gly Asp Arg Leu Leu Ser Val Asp Gly Ile Pro Leu His Gly
        50                  55                  60

Ala Ser His Ala Thr Ala Leu Ala Thr Leu Arg Gln Cys Ser His Glu
65                  70                  75                  80

Ala Leu Phe Gln Val Glu Tyr Asp Val Ala Thr Pro
                85                  90

<210> SEQ ID NO 108
<211> LENGTH: 102
<212> TYPE: PRT
<213> ORGANISM: Homo sapiens

<400> SEQUENCE: 108

Ile His Thr Val Ala Asn Ala Ser Gly Pro Leu Met Val Glu Ile Val
1               5                   10                  15

Lys Thr Pro Gly Ser Ala Leu Gly Ile Ser Leu Thr Thr Ser Leu
                20                  25                  30

Arg Asn Lys Ser Val Ile Thr Ile Asp Arg Ile Lys Pro Ala Ser Val
            35                  40                  45

```
Val Asp Arg Ser Gly Ala Leu His Pro Gly Asp His Ile Leu Ser Ile
 50                  55                  60

Asp Gly Thr Ser Met Glu His Cys Ser Leu Leu Glu Ala Thr Lys Leu
 65                  70                  75                  80

Leu Ala Ser Ile Ser Glu Lys Val Arg Leu Glu Ile Leu Pro Val Pro
                 85                  90                  95

Gln Ser Gln Arg Pro Leu
            100

<210> SEQ ID NO 109
<211> LENGTH: 103
<212> TYPE: PRT
<213> ORGANISM: Homo sapiens

<400> SEQUENCE: 109

Ile Gln Ile Val His Thr Glu Thr Thr Glu Val Val Leu Cys Gly Asp
 1               5                  10                  15

Pro Leu Ser Gly Phe Gly Leu Gln Leu Gln Gly Gly Ile Phe Ala Thr
                20                  25                  30

Glu Thr Leu Ser Ser Pro Pro Leu Val Cys Phe Ile Glu Pro Asp Ser
            35                  40                  45

Pro Ala Glu Arg Cys Gly Leu Leu Gln Val Gly Asp Arg Val Leu Ser
        50                  55                  60

Ile Asn Gly Ile Ala Thr Glu Asp Gly Thr Met Glu Glu Ala Asn Gln
 65                  70                  75                  80

Leu Leu Arg Asp Ala Ala Leu Ala His Lys Val Val Leu Glu Val Glu
                 85                  90                  95

Phe Asp Val Ala Glu Ser Val
            100

<210> SEQ ID NO 110
<211> LENGTH: 103
<212> TYPE: PRT
<213> ORGANISM: Homo sapiens

<400> SEQUENCE: 110

Ile Gln Phe Asp Val Ala Glu Ser Val Ile Pro Ser Ser Gly Thr Phe
 1               5                  10                  15

His Val Lys Leu Pro Lys Lys Arg Ser Val Glu Leu Gly Ile Thr Ile
                20                  25                  30

Ser Ser Ala Ser Arg Lys Arg Gly Glu Pro Leu Ile Ile Ser Asp Ile
            35                  40                  45

Lys Lys Gly Ser Val Ala His Arg Thr Gly Thr Leu Glu Pro Gly Asp
        50                  55                  60

Lys Leu Leu Ala Ile Asp Asn Ile Arg Leu Asp Asn Cys Pro Met Glu
 65                  70                  75                  80

Asp Ala Val Gln Ile Leu Arg Gln Cys Glu Asp Leu Val Lys Leu Lys
                 85                  90                  95

Ile Arg Lys Asp Glu Asp Asn
            100

<210> SEQ ID NO 111
<211> LENGTH: 94
<212> TYPE: PRT
<213> ORGANISM: Homo sapiens

<400> SEQUENCE: 111
```

```
Ile Gln Thr Thr Gly Ala Val Ser Tyr Thr Val Glu Leu Lys Arg Tyr
 1               5                  10                  15

Gly Gly Pro Leu Gly Ile Thr Ile Ser Gly Thr Glu Pro Phe Asp
            20                  25                  30

Pro Ile Val Ile Ser Gly Leu Thr Lys Arg Gly Leu Ala Glu Arg Thr
            35                  40                  45

Gly Ala Ile His Val Gly Asp Arg Ile Leu Ala Ile Asn Asn Val Ser
 50                  55                  60

Leu Lys Gly Arg Pro Leu Ser Glu Ala Ile His Leu Leu Gln Val Ala
 65                  70                  75                  80

Gly Glu Thr Val Thr Leu Lys Ile Lys Lys Gln Leu Asp Arg
                 85                  90
```

<210> SEQ ID NO 112
<211> LENGTH: 105
<212> TYPE: PRT
<213> ORGANISM: Homo sapiens

<400> SEQUENCE: 112

```
Ile Leu Glu Met Glu Glu Leu Leu Pro Thr Pro Leu Glu Met His
 1               5                  10                  15

Lys Val Thr Leu His Lys Asp Pro Met Arg His Asp Phe Gly Phe Ser
                20                  25                  30

Val Ser Asp Gly Leu Leu Glu Lys Gly Val Tyr Val His Thr Val Arg
            35                  40                  45

Pro Asp Gly Pro Ala His Arg Gly Gly Leu Gln Pro Phe Asp Arg Val
 50                  55                  60

Leu Gln Val Asn His Val Arg Thr Arg Asp Phe Asp Cys Cys Leu Ala
 65                  70                  75                  80

Val Pro Leu Leu Ala Glu Ala Gly Asp Val Leu Glu Leu Ile Ile Ser
                 85                  90                  95

Arg Lys Pro His Thr Ala His Ser Ser
                100                 105
```

<210> SEQ ID NO 113
<211> LENGTH: 91
<212> TYPE: PRT
<213> ORGANISM: Homo sapiens

<400> SEQUENCE: 113

```
Met Ala Leu Thr Val Asp Val Ala Gly Pro Ala Pro Trp Gly Phe Arg
 1               5                  10                  15

Ile Thr Gly Gly Arg Asp Phe His Thr Pro Ile Met Val Thr Lys Val
                20                  25                  30

Ala Glu Arg Gly Lys Ala Lys Asp Ala Asp Leu Arg Pro Gly Asp Ile
            35                  40                  45

Ile Val Ala Ile Asn Gly Glu Ser Ala Glu Gly Met Leu His Ala Glu
 50                  55                  60

Ala Gln Ser Lys Ile Arg Gln Ser Pro Ser Pro Leu Arg Leu Gln Leu
 65                  70                  75                  80

Asp Arg Ser Gln Ala Thr Ser Pro Gly Gln Thr
                 85                  90
```

<210> SEQ ID NO 114
<211> LENGTH: 84
<212> TYPE: PRT
<213> ORGANISM: Homo sapiens

```
<400> SEQUENCE: 114

Ser Asn Tyr Ser Val Ser Leu Val Gly Pro Ala Pro Trp Gly Phe Arg
 1               5                  10                  15

Leu Gln Gly Gly Lys Asp Phe Asn Met Pro Leu Thr Ile Ser Ser Leu
            20                  25                  30

Lys Asp Gly Gly Lys Ala Ala Gln Ala Asn Val Arg Ile Gly Asp Val
        35                  40                  45

Val Leu Ser Ile Asp Gly Ile Asn Ala Gln Gly Met Thr His Leu Glu
 50                  55                  60

Ala Gln Asn Lys Ile Lys Gly Cys Thr Gly Ser Leu Asn Met Thr Leu
 65                  70                  75                  80

Gln Arg Ala Ser

<210> SEQ ID NO 115
<211> LENGTH: 133
<212> TYPE: PRT
<213> ORGANISM: Homo sapiens

<400> SEQUENCE: 115

Thr Leu Val Glu His Ser Lys Leu Tyr Cys Gly His Cys Tyr Tyr Gln
 1               5                  10                  15

Thr Val Val Thr Pro Val Ile Glu Gln Ile Leu Pro Asp Ser Pro Gly
            20                  25                  30

Ser His Leu Pro His Thr Val Thr Leu Val Ser Ile Pro Ala Ser Ser
        35                  40                  45

His Gly Lys Arg Gly Leu Ser Val Ser Ile Asp Pro Pro His Gly Pro
 50                  55                  60

Pro Gly Cys Gly Thr Glu His Ser His Thr Val Arg Val Gln Gly Val
 65                  70                  75                  80

Asp Pro Gly Cys Met Ser Pro Asp Val Lys Asn Ser Ile His Val Gly
                85                  90                  95

Asp Arg Ile Leu Glu Ile Asn Gly Thr Pro Ile Arg Asn Val Pro Leu
            100                 105                 110

Asp Glu Ile Asp Leu Leu Ile Gln Glu Thr Ser Arg Leu Leu Gln Leu
        115                 120                 125

Thr Leu Glu His Asp
    130

<210> SEQ ID NO 116
<211> LENGTH: 92
<212> TYPE: PRT
<213> ORGANISM: Homo sapiens

<400> SEQUENCE: 116

Pro Tyr Ser Val Thr Leu Ile Ser Met Pro Ala Thr Thr Glu Gly Arg
 1               5                  10                  15

Arg Gly Phe Ser Val Ser Val Glu Ser Ala Cys Ser Asn Tyr Ala Thr
            20                  25                  30

Thr Val Gln Val Lys Glu Val Asn Arg Met His Ile Ser Pro Asn Asn
        35                  40                  45

Arg Asn Ala Ile His Pro Gly Asp Arg Ile Leu Glu Ile Asn Gly Thr
 50                  55                  60

Pro Val Arg Thr Leu Arg Val Glu Glu Val Glu Asp Ala Ile Ser Gln
 65                  70                  75                  80

Thr Ser Gln Thr Leu Gln Leu Leu Ile Glu His Asp
                85                  90
```

<210> SEQ ID NO 117
<211> LENGTH: 82
<212> TYPE: PRT
<213> ORGANISM: Homo sapiens

<400> SEQUENCE: 117

Ile His Ser Val Thr Leu Arg Gly Pro Ser Pro Trp Gly Phe Arg Leu
1               5                   10                  15

Val Gly Arg Asp Phe Ser Ala Pro Leu Thr Ile Ser Arg Val His Ala
            20                  25                  30

Gly Ser Lys Ala Ser Leu Ala Ala Leu Cys Pro Gly Asp Leu Ile Gln
        35                  40                  45

Ala Ile Asn Gly Glu Ser Thr Glu Leu Met Thr His Leu Glu Ala Gln
50                  55                  60

Asn Arg Ile Lys Gly Cys His Asp His Leu Thr Leu Ser Val Ser Arg
65                  70                  75                  80

Pro Glu

<210> SEQ ID NO 118
<211> LENGTH: 74
<212> TYPE: PRT
<213> ORGANISM: Homo sapiens

<400> SEQUENCE: 118

Val Cys Tyr Arg Thr Asp Asp Glu Glu Asp Leu Gly Ile Tyr Val Gly
1               5                   10                  15

Glu Val Asn Pro Asn Ser Ile Ala Ala Lys Asp Gly Arg Ile Arg Glu
            20                  25                  30

Gly Asp Arg Ile Ile Gln Ile Asn Gly Val Asp Val Gln Asn Arg Glu
        35                  40                  45

Glu Ala Val Ala Ile Leu Ser Gln Glu Glu Asn Thr Asn Ile Ser Leu
50                  55                  60

Leu Val Ala Arg Pro Glu Ser Gln Leu Ala
65                  70

<210> SEQ ID NO 119
<211> LENGTH: 103
<212> TYPE: PRT
<213> ORGANISM: Homo sapiens

<400> SEQUENCE: 119

Ile Gln Lys Lys Asn His Trp Thr Ser Arg Val His Glu Cys Thr Val
1               5                   10                  15

Lys Arg Gly Pro Gln Gly Glu Leu Gly Val Thr Val Leu Gly Gly Ala
            20                  25                  30

Glu His Gly Glu Phe Pro Tyr Val Gly Ala Val Ala Ala Val Glu Ala
        35                  40                  45

Ala Gly Leu Pro Gly Gly Gly Glu Gly Pro Arg Leu Gly Glu Gly Glu
50                  55                  60

Leu Leu Leu Glu Val Gln Gly Val Arg Val Ser Gly Leu Pro Arg Tyr
65                  70                  75                  80

Asp Val Leu Gly Val Ile Asp Ser Cys Lys Glu Ala Val Thr Phe Lys
            85                  90                  95

Ala Val Arg Gln Gly Gly Arg
            100

```
<210> SEQ ID NO 120
<211> LENGTH: 104
<212> TYPE: PRT
<213> ORGANISM: Homo sapiens

<400> SEQUENCE: 120

Pro Ser Glu Leu Lys Gly Lys Phe Ile His Thr Lys Leu Arg Lys Ser
1               5                   10                  15

Ser Arg Gly Phe Gly Phe Thr Val Val Gly Asp Glu Pro Asp Glu
            20                  25                  30

Phe Leu Gln Ile Lys Ser Leu Val Leu Asp Gly Pro Ala Ala Leu Asp
                35                  40                  45

Gly Lys Met Glu Thr Gly Asp Val Ile Val Ser Val Asn Asp Thr Cys
50                  55                  60

Val Leu Gly His Thr His Ala Gln Val Val Lys Ile Phe Gln Ser Ile
65                  70                  75                  80

Pro Ile Gly Ala Ser Val Asp Leu Glu Leu Cys Arg Gly Tyr Pro Leu
                85                  90                  95

Pro Phe Asp Pro Asp Pro Asn
            100

<210> SEQ ID NO 121
<211> LENGTH: 92
<212> TYPE: PRT
<213> ORGANISM: Homo sapiens

<400> SEQUENCE: 121

Pro Ala Thr Gln Pro Glu Leu Ile Thr Val His Ile Val Lys Gly Pro
1               5                   10                  15

Met Gly Phe Gly Phe Thr Ile Ala Asp Ser Pro Gly Gly Gly Gln
            20                  25                  30

Arg Val Lys Gln Ile Val Asp Ser Pro Arg Cys Arg Gly Leu Lys Glu
                35                  40                  45

Gly Asp Leu Ile Val Glu Val Asn Lys Lys Asn Val Gln Ala Leu Thr
50                  55                  60

His Asn Gln Val Val Asp Met Leu Val Glu Cys Pro Lys Gly Ser Glu
65                  70                  75                  80

Val Thr Leu Leu Val Gln Arg Gly Gly Asn Leu Ser
                85                  90

<210> SEQ ID NO 122
<211> LENGTH: 102
<212> TYPE: PRT
<213> ORGANISM: Homo sapiens

<400> SEQUENCE: 122

Pro Asp Tyr Gln Glu Gln Asp Ile Phe Leu Trp Arg Lys Glu Thr Gly
1               5                   10                  15

Phe Gly Phe Arg Ile Leu Gly Gly Asn Glu Pro Gly Glu Pro Ile Tyr
            20                  25                  30

Ile Gly His Ile Val Pro Leu Gly Ala Ala Asp Thr Asp Gly Arg Leu
                35                  40                  45

Arg Ser Gly Asp Glu Leu Ile Cys Val Asp Gly Thr Pro Val Ile Gly
50                  55                  60

Lys Ser His Gln Leu Val Val Gln Leu Met Gln Gln Ala Ala Lys Gln
65                  70                  75                  80

Gly His Val Asn Leu Thr Val Arg Arg Lys Val Val Phe Ala Val Pro
                85                  90                  95
```

```
Lys Thr Glu Asn Ser Ser
            100

<210> SEQ ID NO 123
<211> LENGTH: 112
<212> TYPE: PRT
<213> ORGANISM: Homo sapiens

<400> SEQUENCE: 123

Gly Val Val Ser Thr Val Val Gln Pro Tyr Asp Val Glu Ile Arg Arg
 1               5                  10                  15

Gly Glu Asn Glu Gly Phe Gly Phe Val Ile Val Ser Ser Val Ser Arg
                20                  25                  30

Pro Glu Ala Gly Thr Thr Phe Ala Gly Asn Ala Cys Val Ala Met Pro
             35                  40                  45

His Lys Ile Gly Arg Ile Ile Glu Gly Ser Pro Ala Asp Arg Cys Gly
         50                  55                  60

Lys Leu Lys Val Gly Asp Arg Ile Leu Ala Val Asn Gly Cys Ser Ile
 65                  70                  75                  80

Thr Asn Lys Ser His Ser Asp Ile Val Asn Leu Ile Lys Glu Ala Gly
                 85                  90                  95

Asn Thr Val Thr Leu Arg Ile Ile Pro Gly Asp Glu Ser Ser Asn Ala
                100                 105                 110

<210> SEQ ID NO 124
<211> LENGTH: 91
<212> TYPE: PRT
<213> ORGANISM: Homo sapiens

<400> SEQUENCE: 124

Gln Ala Thr Gln Glu Gln Asp Phe Tyr Thr Val Glu Leu Glu Arg Gly
 1               5                  10                  15

Ala Lys Gly Phe Gly Phe Ser Leu Arg Gly Gly Arg Glu Tyr Asn Met
                20                  25                  30

Asp Leu Tyr Val Leu Arg Leu Ala Glu Asp Gly Pro Ala Glu Arg Cys
             35                  40                  45

Gly Lys Met Arg Ile Gly Asp Glu Ile Leu Glu Ile Asn Gly Glu Thr
         50                  55                  60

Thr Lys Asn Met Lys His Ser Arg Ala Ile Glu Leu Ile Lys Asn Gly
 65                  70                  75                  80

Gly Arg Arg Val Arg Leu Phe Leu Lys Arg Gly
                 85                  90

<210> SEQ ID NO 125
<211> LENGTH: 100
<212> TYPE: PRT
<213> ORGANISM: Homo sapiens

<400> SEQUENCE: 125

Pro Ala Lys Met Glu Lys Glu Glu Thr Thr Arg Glu Leu Leu Leu Pro
 1               5                  10                  15

Asn Trp Gln Gly Ser Gly Ser His Gly Leu Thr Ile Ala Gln Arg Asp
                20                  25                  30

Asp Gly Val Phe Val Gln Glu Val Thr Gln Asn Ser Pro Ala Ala Arg
             35                  40                  45

Thr Gly Val Val Lys Glu Gly Asp Gln Ile Val Gly Ala Thr Ile Tyr
         50                  55                  60
```

```
Phe Asp Asn Leu Gln Ser Gly Glu Val Thr Gln Leu Leu Asn Thr Met
 65                  70                  75                  80

Gly His His Thr Val Gly Leu Lys Leu His Arg Lys Gly Asp Arg Ser
                 85                  90                  95

Pro Asn Ser Ser
            100

<210> SEQ ID NO 126
<211> LENGTH: 97
<212> TYPE: PRT
<213> ORGANISM: Homo sapiens

<400> SEQUENCE: 126

Ser Glu Asn Cys Lys Val Phe Ile Glu Lys Gln Lys Gly Glu Ile Leu
  1               5                  10                  15

Gly Val Val Ile Val Glu Ser Gly Trp Gly Ser Ile Leu Pro Thr Val
                 20                  25                  30

Ile Ile Ala Asn Met Met His Gly Gly Pro Ala Glu Lys Ser Gly Lys
             35                  40                  45

Leu Asn Ile Gly Asp Gln Ile Met Ser Ile Asn Gly Thr Ser Leu Val
 50                  55                  60

Gly Leu Pro Leu Ser Thr Cys Gln Ser Ile Ile Lys Gly Leu Lys Asn
 65                  70                  75                  80

Gln Ser Arg Val Lys Leu Asn Ile Val Arg Cys Pro Pro Val Asn Ser
                 85                  90                  95

Ser

<210> SEQ ID NO 127
<211> LENGTH: 92
<212> TYPE: PRT
<213> ORGANISM: Homo sapiens

<400> SEQUENCE: 127

Leu Arg Cys Pro Pro Val Thr Thr Val Leu Ile Arg Arg Pro Asp Leu
  1               5                  10                  15

Arg Tyr Gln Leu Gly Phe Ser Val Gln Asn Gly Ile Ile Cys Ser Leu
                 20                  25                  30

Met Arg Gly Gly Ile Ala Glu Arg Gly Gly Val Arg Val Gly His Arg
             35                  40                  45

Ile Ile Glu Ile Asn Gly Gln Ser Val Val Ala Thr Pro His Glu Lys
 50                  55                  60

Ile Val His Ile Leu Ser Asn Ala Val Gly Glu Ile His Met Lys Thr
 65                  70                  75                  80

Met Pro Ala Ala Met Tyr Arg Leu Leu Asn Ser Ser
                 85                  90

<210> SEQ ID NO 128
<211> LENGTH: 103
<212> TYPE: PRT
<213> ORGANISM: Homo sapiens

<400> SEQUENCE: 128

Leu Ser Asn Ser Asp Asn Cys Arg Glu Val His Leu Glu Lys Arg Arg
  1               5                  10                  15

Gly Glu Gly Leu Gly Val Ala Leu Val Glu Ser Gly Trp Gly Ser Leu
                 20                  25                  30

Leu Pro Thr Ala Val Ile Ala Asn Leu Leu His Gly Gly Pro Ala Glu
             35                  40                  45
```

-continued

Arg Ser Gly Ala Leu Ser Ile Gly Asp Arg Leu Thr Ala Ile Asn Gly
        50                  55                  60

Thr Ser Leu Val Gly Leu Pro Leu Ala Ala Cys Gln Ala Ala Val Arg
65                  70                  75                  80

Glu Thr Lys Ser Gln Thr Ser Val Thr Leu Ser Ile Val His Cys Pro
                85                  90                  95

Pro Val Thr Thr Ala Ile Met
            100

<210> SEQ ID NO 129
<211> LENGTH: 92
<212> TYPE: PRT
<213> ORGANISM: Homo sapiens

<400> SEQUENCE: 129

Leu Val His Cys Pro Val Thr Thr Ala Ile Ile His Arg Pro His
1               5                   10                  15

Ala Arg Glu Gln Leu Gly Phe Cys Val Glu Asp Gly Ile Ile Cys Ser
                20                  25                  30

Leu Leu Arg Gly Gly Ile Ala Glu Arg Gly Gly Ile Arg Val Gly His
            35                  40                  45

Arg Ile Ile Glu Ile Asn Gly Gln Ser Val Val Ala Thr Pro His Ala
        50                  55                  60

Arg Ile Ile Glu Leu Leu Thr Glu Ala Tyr Gly Glu Val His Ile Lys
65                  70                  75                  80

Thr Met Pro Ala Ala Thr Tyr Arg Leu Leu Thr Gly
                85                  90

<210> SEQ ID NO 130
<211> LENGTH: 86
<212> TYPE: PRT
<213> ORGANISM: Homo sapiens

<400> SEQUENCE: 130

Arg Lys Val Arg Leu Ile Gln Phe Glu Lys Val Thr Glu Glu Pro Met
1               5                   10                  15

Gly Ile Thr Leu Lys Leu Asn Glu Lys Gln Ser Cys Thr Val Ala Arg
                20                  25                  30

Ile Leu His Gly Gly Met Ile His Arg Gln Gly Ser Leu His Val Gly
            35                  40                  45

Asp Glu Ile Leu Glu Ile Asn Gly Thr Asn Val Thr Asn His Ser Val
        50                  55                  60

Asp Gln Leu Gln Lys Ala Met Lys Glu Thr Lys Gly Met Ile Ser Leu
65                  70                  75                  80

Lys Val Ile Pro Asn Gln
                85

<210> SEQ ID NO 131
<211> LENGTH: 89
<212> TYPE: PRT
<213> ORGANISM: Homo sapiens

<400> SEQUENCE: 131

Pro Val Pro Pro Asp Ala Val Arg Met Val Gly Ile Arg Lys Thr Ala
1               5                   10                  15

Gly Glu His Leu Gly Val Thr Phe Arg Val Glu Gly Gly Glu Leu Val
                20                  25                  30

```
Ile Ala Arg Ile Leu His Gly Gly Met Val Ala Gln Gln Gly Leu Leu
            35                  40                  45

His Val Gly Asp Ile Ile Lys Glu Val Asn Gly Gln Pro Val Gly Ser
     50                  55                  60

Asp Pro Arg Ala Leu Gln Glu Leu Leu Arg Asn Ala Ser Gly Ser Val
 65                  70                  75                  80

Ile Leu Lys Ile Leu Pro Asn Tyr Gln
                 85
```

<210> SEQ ID NO 132
<211> LENGTH: 99
<212> TYPE: PRT
<213> ORGANISM: Homo sapiens

<400> SEQUENCE: 132

```
Gln Gly Arg His Val Glu Val Phe Glu Leu Leu Lys Pro Pro Ser Gly
 1               5                  10                  15

Gly Leu Gly Phe Ser Val Val Gly Leu Arg Ser Glu Asn Arg Gly Glu
            20                  25                  30

Leu Gly Ile Phe Val Gln Glu Ile Gln Glu Gly Ser Val Ala His Arg
        35                  40                  45

Asp Gly Arg Leu Lys Glu Thr Asp Gln Ile Leu Ala Ile Asn Gly Gln
 50                  55                  60

Ala Leu Asp Gln Thr Ile Thr His Gln Gln Ala Ile Ser Ile Leu Gln
 65                  70                  75                  80

Lys Ala Lys Asp Thr Val Gln Leu Val Ile Ala Arg Gly Ser Leu Pro
                 85                  90                  95

Gln Leu Val
```

<210> SEQ ID NO 133
<211> LENGTH: 97
<212> TYPE: PRT
<213> ORGANISM: Homo sapiens

<400> SEQUENCE: 133

```
Pro Val His Trp Gln His Met Glu Thr Ile Glu Leu Val Asn Asp Gly
 1               5                  10                  15

Ser Gly Leu Gly Phe Gly Ile Ile Gly Gly Lys Ala Thr Gly Val Ile
            20                  25                  30

Val Lys Thr Ile Leu Pro Gly Gly Val Ala Asp Gln His Gly Arg Leu
        35                  40                  45

Cys Ser Gly Asp His Ile Leu Lys Ile Gly Asp Thr Asp Leu Ala Gly
 50                  55                  60

Met Ser Ser Glu Gln Val Ala Gln Val Leu Arg Gln Cys Gly Asn Arg
 65                  70                  75                  80

Val Lys Leu Met Ile Ala Arg Gly Ala Ile Glu Glu Arg Thr Ala Pro
                 85                  90                  95

Thr
```

<210> SEQ ID NO 134
<211> LENGTH: 98
<212> TYPE: PRT
<213> ORGANISM: Homo sapiens

<400> SEQUENCE: 134

```
Gln Glu Ser Glu Thr Phe Asp Val Glu Leu Thr Lys Asn Val Gln Gly
 1               5                  10                  15
```

-continued

```
Leu Gly Ile Thr Ile Ala Gly Tyr Ile Gly Asp Lys Lys Leu Glu Pro
            20                  25                  30

Ser Gly Ile Phe Val Lys Ser Ile Thr Lys Ser Ser Ala Val Glu His
        35                  40                  45

Asp Gly Arg Ile Gln Ile Gly Asp Gln Ile Ile Ala Val Asp Gly Thr
 50                  55                  60

Asn Leu Gln Gly Phe Thr Asn Gln Gln Ala Val Glu Val Leu Arg His
 65                  70                  75                  80

Thr Gly Gln Thr Val Leu Leu Thr Leu Met Arg Arg Gly Met Lys Gln
                85                  90                  95

Glu Ala
```

<210> SEQ ID NO 135
<211> LENGTH: 92
<212> TYPE: PRT
<213> ORGANISM: Homo sapiens

<400> SEQUENCE: 135

```
Leu Asn Tyr Glu Ile Val Val Ala His Val Ser Lys Phe Ser Glu Asn
 1               5                  10                  15

Ser Gly Leu Gly Ile Ser Leu Glu Ala Thr Val Gly His His Phe Ile
            20                  25                  30

Arg Ser Val Leu Pro Glu Gly Pro Val Gly His Ser Gly Lys Leu Phe
        35                  40                  45

Ser Gly Asp Glu Leu Leu Glu Val Asn Gly Ile Thr Leu Leu Gly Glu
 50                  55                  60

Asn His Gln Asp Val Val Asn Ile Leu Lys Glu Leu Pro Ile Glu Val
 65                  70                  75                  80

Thr Met Val Cys Cys Arg Arg Thr Val Pro Pro Thr
                85                  90
```

<210> SEQ ID NO 136
<211> LENGTH: 100
<212> TYPE: PRT
<213> ORGANISM: Homo sapiens

<400> SEQUENCE: 136

```
Trp Glu Ala Gly Ile Gln His Ile Glu Leu Glu Lys Gly Ser Lys Gly
 1               5                  10                  15

Leu Gly Phe Ser Ile Leu Asp Tyr Gln Asp Pro Ile Asp Pro Ala Ser
            20                  25                  30

Thr Val Ile Ile Ile Arg Ser Leu Val Pro Gly Gly Ile Ala Glu Lys
        35                  40                  45

Asp Gly Arg Leu Leu Pro Gly Asp Arg Leu Met Phe Val Asn Asp Val
 50                  55                  60

Asn Leu Glu Asn Ser Ser Leu Glu Glu Ala Val Glu Ala Leu Lys Gly
 65                  70                  75                  80

Ala Pro Ser Gly Thr Val Arg Ile Gly Val Ala Lys Pro Leu Pro Leu
                85                  90                  95

Ser Pro Glu Glu
            100
```

<210> SEQ ID NO 137
<211> LENGTH: 99
<212> TYPE: PRT
<213> ORGANISM: Homo sapiens

<400> SEQUENCE: 137

```
Arg Asn Val Ser Lys Glu Ser Phe Glu Arg Thr Ile Asn Ile Ala Lys
 1               5                  10                  15
Gly Asn Ser Ser Leu Gly Met Thr Val Ser Ala Asn Lys Asp Gly Leu
                20                  25                  30
Gly Met Ile Val Arg Ser Ile Ile His Gly Gly Ala Ile Ser Arg Asp
            35                  40                  45
Gly Arg Ile Ala Ile Gly Asp Cys Ile Leu Ser Ile Asn Glu Glu Ser
        50                  55                  60
Thr Ile Ser Val Thr Asn Ala Gln Ala Arg Ala Met Leu Arg Arg His
65                  70                  75                  80
Ser Leu Ile Gly Pro Asp Ile Lys Ile Thr Tyr Val Pro Ala Glu His
                85                  90                  95
Leu Glu Glu
```

<210> SEQ ID NO 138
<211> LENGTH: 112
<212> TYPE: PRT
<213> ORGANISM: Homo sapiens

<400> SEQUENCE: 138

```
Leu Asn Trp Asn Gln Pro Arg Arg Val Glu Leu Trp Arg Glu Pro Ser
 1               5                  10                  15
Lys Ser Leu Gly Ile Ser Ile Val Gly Gly Arg Gly Met Gly Ser Arg
                20                  25                  30
Leu Ser Asn Gly Glu Val Met Arg Gly Ile Phe Ile Lys His Val Leu
            35                  40                  45
Glu Asp Ser Pro Ala Gly Lys Asn Gly Thr Leu Lys Pro Gly Asp Arg
        50                  55                  60
Ile Val Glu Val Asp Gly Met Asp Leu Arg Asp Ala Ser His Glu Gln
65                  70                  75                  80
Ala Val Glu Ala Ile Arg Lys Ala Gly Asn Pro Val Val Phe Met Val
                85                  90                  95
Gln Ser Ile Ile Asn Arg Pro Arg Lys Ser Pro Leu Pro Ser Leu Leu
            100                 105                 110
```

<210> SEQ ID NO 139
<211> LENGTH: 95
<212> TYPE: PRT
<213> ORGANISM: Homo sapiens

<400> SEQUENCE: 139

```
Leu Thr Gly Glu Leu His Met Ile Glu Leu Glu Lys Gly His Ser Gly
 1               5                  10                  15
Leu Gly Leu Ser Leu Ala Gly Asn Lys Asp Arg Ser Arg Met Ser Val
                20                  25                  30
Phe Ile Val Gly Ile Asp Pro Asn Gly Ala Ala Gly Lys Asp Gly Arg
            35                  40                  45
Leu Gln Ile Ala Asp Glu Leu Leu Glu Ile Asn Gly Gln Ile Leu Tyr
        50                  55                  60
Gly Arg Ser His Gln Asn Ala Ser Ser Ile Ile Lys Cys Ala Pro Ser
65                  70                  75                  80
Lys Val Lys Ile Ile Phe Ile Arg Asn Lys Asp Ala Val Asn Gln
                85                  90                  95
```

<210> SEQ ID NO 140
<211> LENGTH: 94

<212> TYPE: PRT
<213> ORGANISM: Homo sapiens

<400> SEQUENCE: 140

```
Leu Ser Ser Phe Lys Asn Val Gln His Leu Glu Leu Pro Lys Asp Gln
1               5                   10                  15

Gly Gly Leu Gly Ile Ala Ile Ser Glu Glu Asp Thr Leu Ser Gly Val
            20                  25                  30

Ile Ile Lys Ser Leu Thr Glu His Gly Val Ala Ala Thr Asp Gly Arg
        35                  40                  45

Leu Lys Val Gly Asp Gln Ile Leu Ala Val Asp Asp Glu Ile Val Val
    50                  55                  60

Gly Tyr Pro Ile Glu Lys Phe Ile Ser Leu Leu Lys Thr Ala Lys Met
65                  70                  75                  80

Thr Val Lys Leu Thr Ile His Ala Glu Asn Pro Asp Ser Gln
                85                  90
```

<210> SEQ ID NO 141
<211> LENGTH: 95
<212> TYPE: PRT
<213> ORGANISM: Homo sapiens

<400> SEQUENCE: 141

```
Leu Pro Gly Cys Glu Thr Thr Ile Glu Ile Ser Lys Gly Arg Thr Gly
1               5                   10                  15

Leu Gly Leu Ser Ile Val Gly Gly Ser Asp Thr Leu Leu Gly Ala Ile
            20                  25                  30

Ile Ile His Glu Val Tyr Glu Glu Gly Ala Ala Cys Lys Asp Gly Arg
        35                  40                  45

Leu Trp Ala Gly Asp Gln Ile Leu Glu Val Asn Gly Ile Asp Leu Arg
    50                  55                  60

Lys Ala Thr His Asp Glu Ala Ile Asn Val Leu Arg Gln Thr Pro Gln
65                  70                  75                  80

Arg Val Arg Leu Thr Leu Tyr Arg Asp Glu Ala Pro Tyr Lys Glu
                85                  90                  95
```

<210> SEQ ID NO 142
<211> LENGTH: 98
<212> TYPE: PRT
<213> ORGANISM: Homo sapiens

<400> SEQUENCE: 142

```
Lys Glu Glu Glu Val Cys Asp Thr Leu Thr Ile Glu Leu Gln Lys Lys
1               5                   10                  15

Pro Gly Lys Gly Leu Gly Leu Ser Ile Val Gly Lys Arg Asn Asp Thr
            20                  25                  30

Gly Val Phe Val Ser Asp Ile Val Lys Gly Gly Ile Ala Asp Ala Asp
        35                  40                  45

Gly Arg Leu Met Gln Gly Asp Gln Ile Leu Met Val Asn Gly Glu Asp
    50                  55                  60

Val Arg Asn Ala Thr Gln Glu Ala Val Ala Ala Leu Leu Lys Cys Ser
65                  70                  75                  80

Leu Gly Thr Val Thr Leu Glu Val Gly Arg Ile Lys Ala Gly Pro Phe
                85                  90                  95

His Ser
```

<210> SEQ ID NO 143

<211> LENGTH: 96
<212> TYPE: PRT
<213> ORGANISM: Homo sapiens

<400> SEQUENCE: 143

Leu Gln Gly Leu Arg Thr Val Glu Met Lys Lys Gly Pro Thr Asp Ser
1               5                   10                  15

Leu Gly Ile Ser Ile Ala Gly Gly Val Gly Ser Pro Leu Gly Asp Val
            20                  25                  30

Pro Ile Phe Ile Ala Met Met His Pro Thr Gly Val Ala Ala Gln Thr
        35                  40                  45

Gln Lys Leu Arg Val Gly Asp Arg Ile Val Thr Ile Cys Gly Thr Ser
50                  55                  60

Thr Glu Gly Met Thr His Thr Gln Ala Val Asn Leu Leu Lys Asn Ala
65                  70                  75                  80

Ser Gly Ser Ile Glu Met Gln Val Val Ala Gly Gly Asp Val Ser Val
                85                  90                  95

<210> SEQ ID NO 144
<211> LENGTH: 91
<212> TYPE: PRT
<213> ORGANISM: Homo sapiens

<400> SEQUENCE: 144

Leu Gly Pro Pro Gln Cys Lys Ser Ile Thr Leu Glu Arg Gly Pro Asp
1               5                   10                  15

Gly Leu Gly Phe Ser Ile Val Gly Gly Tyr Gly Ser Pro His Gly Asp
            20                  25                  30

Leu Pro Ile Tyr Val Lys Thr Val Phe Ala Lys Gly Ala Ala Ser Glu
        35                  40                  45

Asp Gly Arg Leu Lys Arg Gly Asp Gln Ile Ile Ala Val Asn Gly Gln
50                  55                  60

Ser Leu Glu Gly Val Thr His Glu Glu Ala Val Ala Ile Leu Lys Arg
65                  70                  75                  80

Thr Lys Gly Thr Val Thr Leu Met Val Leu Ser
                85                  90

<210> SEQ ID NO 145
<211> LENGTH: 93
<212> TYPE: PRT
<213> ORGANISM: Homo sapiens

<400> SEQUENCE: 145

Ile Gln Tyr Glu Glu Ile Val Leu Glu Arg Gly Asn Ser Gly Leu Gly
1               5                   10                  15

Phe Ser Ile Ala Gly Gly Ile Asp Asn Pro His Val Pro Asp Asp Pro
            20                  25                  30

Gly Ile Phe Ile Thr Lys Ile Ile Pro Gly Gly Ala Ala Ala Met Asp
        35                  40                  45

Gly Arg Leu Gly Val Asn Asp Cys Val Leu Arg Val Asn Glu Val Glu
50                  55                  60

Val Ser Glu Val Val His Ser Arg Ala Val Glu Ala Leu Lys Glu Ala
65                  70                  75                  80

Gly Pro Val Val Arg Leu Val Val Arg Arg Arg Gln Asn
                85                  90

<210> SEQ ID NO 146
<211> LENGTH: 90

<212> TYPE: PRT
<213> ORGANISM: Homo sapiens

<400> SEQUENCE: 146

Ile Thr Leu Leu Lys Gly Pro Lys Gly Leu Gly Phe Ser Ile Ala Gly
1               5                   10                  15

Gly Ile Gly Asn Gln His Ile Pro Gly Asp Asn Ser Ile Tyr Ile Thr
            20                  25                  30

Lys Ile Ile Glu Gly Gly Ala Ala Gln Lys Asp Gly Arg Leu Gln Ile
        35                  40                  45

Gly Asp Arg Leu Leu Ala Val Asn Asn Thr Asn Leu Gln Asp Val Arg
    50                  55                  60

His Glu Glu Ala Val Ala Ser Leu Lys Asn Thr Ser Asp Met Val Tyr
65                  70                  75                  80

Leu Lys Val Ala Lys Pro Gly Ser Leu Glu
                85                  90

<210> SEQ ID NO 147
<211> LENGTH: 119
<212> TYPE: PRT
<213> ORGANISM: Homo sapiens

<400> SEQUENCE: 147

Ile Leu Leu His Lys Gly Ser Thr Gly Leu Gly Phe Asn Ile Val Gly
1               5                   10                  15

Gly Glu Asp Gly Glu Gly Ile Phe Val Ser Phe Ile Leu Ala Gly Gly
            20                  25                  30

Pro Ala Asp Leu Ser Gly Glu Leu Arg Arg Gly Asp Arg Ile Leu Ser
        35                  40                  45

Val Asn Gly Val Asn Leu Arg Asn Ala Thr His Glu Gln Ala Ala Ala
    50                  55                  60

Ala Leu Lys Arg Ala Gly Gln Ser Val Thr Ile Val Ala Gln Tyr Arg
65                  70                  75                  80

Pro Glu Glu Tyr Ser Arg Phe Glu Ser Lys Ile His Asp Leu Arg Glu
                85                  90                  95

Gln Met Met Asn Ser Ser Met Ser Ser Gly Ser Gly Ser Leu Arg Thr
            100                 105                 110

Ser Glu Lys Arg Ser Leu Glu
        115

<210> SEQ ID NO 148
<211> LENGTH: 111
<212> TYPE: PRT
<213> ORGANISM: Homo sapiens

<400> SEQUENCE: 148

Cys Val Glu Arg Leu Glu Leu Phe Pro Val Glu Leu Glu Lys Asp Ser
1               5                   10                  15

Glu Gly Leu Gly Ile Ser Ile Ile Gly Met Gly Ala Gly Ala Asp Met
            20                  25                  30

Gly Leu Glu Lys Leu Gly Ile Phe Val Lys Thr Val Thr Glu Gly Gly
        35                  40                  45

Ala Ala His Arg Asp Gly Arg Ile Gln Val Asn Asp Leu Leu Val Glu
    50                  55                  60

Val Asp Gly Thr Ser Leu Val Gly Val Thr Gln Ser Phe Ala Ala Ser
65                  70                  75                  80

Val Leu Arg Asn Thr Lys Gly Arg Val Arg Phe Met Ile Gly Arg Glu

-continued

```
                85                  90                  95
Arg Pro Gly Glu Gln Ser Glu Val Ala Gln Arg Ile His Arg Asp
            100                 105                 110
```

<210> SEQ ID NO 149
<211> LENGTH: 90
<212> TYPE: PRT
<213> ORGANISM: Homo sapiens

<400> SEQUENCE: 149

```
Ile Gln Pro Asn Val Ile Ser Val Arg Leu Phe Lys Arg Lys Val Gly
 1               5                  10                  15

Gly Leu Gly Phe Leu Val Lys Glu Arg Val Ser Lys Pro Pro Val Ile
                20                  25                  30

Ile Ser Asp Leu Ile Arg Gly Gly Ala Ala Glu Gln Ser Gly Leu Ile
            35                  40                  45

Gln Ala Gly Asp Ile Ile Leu Ala Val Asn Gly Arg Pro Leu Val Asp
         50                  55                  60

Leu Ser Tyr Asp Ser Ala Leu Glu Val Leu Arg Gly Ile Ala Ser Glu
 65                  70                  75                  80

Thr His Val Val Leu Ile Leu Arg Gly Pro
                 85                  90
```

<210> SEQ ID NO 150
<211> LENGTH: 107
<212> TYPE: PRT
<213> ORGANISM: Homo sapiens

<400> SEQUENCE: 150

```
Gln Ala Asn Ser Asp Glu Ser Asp Ile Ile His Ser Val Arg Val Glu
 1               5                  10                  15

Lys Ser Pro Ala Gly Arg Leu Gly Phe Ser Val Arg Gly Gly Ser Glu
                20                  25                  30

His Gly Leu Gly Ile Phe Val Ser Lys Val Glu Glu Gly Ser Ser Ala
            35                  40                  45

Glu Arg Ala Gly Leu Cys Val Gly Asp Lys Ile Thr Glu Val Asn Gly
         50                  55                  60

Leu Ser Leu Glu Ser Thr Thr Met Gly Ser Ala Val Lys Val Leu Thr
 65                  70                  75                  80

Ser Ser Ser Arg Leu His Met Met Val Arg Arg Met Gly Arg Val Pro
                 85                  90                  95

Gly Ile Lys Phe Ser Lys Glu Lys Asn Ser Ser
            100                 105
```

<210> SEQ ID NO 151
<211> LENGTH: 106
<212> TYPE: PRT
<213> ORGANISM: Homo sapiens

<400> SEQUENCE: 151

```
Pro Ser Asp Thr Ser Ser Glu Asp Gly Val Arg Arg Ile Val His Leu
 1               5                  10                  15

Tyr Thr Thr Ser Asp Asp Phe Cys Leu Gly Phe Asn Ile Arg Gly Gly
                20                  25                  30

Lys Glu Phe Gly Leu Gly Ile Tyr Val Ser Lys Val Asp His Gly Gly
            35                  40                  45

Leu Ala Glu Glu Asn Gly Ile Lys Val Gly Asp Gln Val Leu Ala Ala
         50                  55                  60
```

-continued

Asn Gly Val Arg Phe Asp Asp Ile Ser His Ser Gln Ala Val Glu Val
65                  70                  75                  80

Leu Lys Gly Gln Thr His Ile Met Leu Thr Ile Lys Glu Thr Gly Arg
                85                  90                  95

Tyr Pro Ala Tyr Lys Glu Met Asn Ser Ser
            100                 105

<210> SEQ ID NO 152
<211> LENGTH: 115
<212> TYPE: PRT
<213> ORGANISM: Homo sapiens

<400> SEQUENCE: 152

Lys Ile Lys Lys Phe Leu Thr Glu Ser His Asp Arg Gln Ala Lys Gly
1               5                   10                  15

Lys Ala Ile Thr Lys Lys Tyr Ile Gly Ile Arg Met Met Ser Leu
            20                  25                  30

Thr Ser Ser Lys Ala Lys Glu Leu Lys Asp Arg His Arg Asp Phe Pro
            35                  40                  45

Asp Val Ile Ser Gly Ala Tyr Ile Ile Glu Val Ile Pro Asp Thr Pro
    50                  55                  60

Ala Glu Ala Gly Gly Leu Lys Glu Asn Asp Val Ile Ile Ser Ile Asn
65                  70                  75                  80

Gly Gln Ser Val Val Ser Ala Asn Asp Val Ser Asp Val Ile Lys Arg
                85                  90                  95

Glu Ser Thr Leu Asn Met Val Val Arg Arg Gly Asn Glu Asp Ile Met
                100                 105                 110

Ile Thr Val
        115

<210> SEQ ID NO 153
<211> LENGTH: 100
<212> TYPE: PRT
<213> ORGANISM: Homo sapiens

<400> SEQUENCE: 153

Pro Asp Gly Glu Ile Thr Ser Ile Lys Ile Asn Arg Val Asp Pro Ser
1               5                   10                  15

Glu Ser Leu Ser Ile Arg Leu Val Gly Gly Ser Glu Thr Pro Leu Val
                20                  25                  30

His Ile Ile Ile Gln His Ile Tyr Arg Asp Gly Val Ile Ala Arg Asp
            35                  40                  45

Gly Arg Leu Leu Pro Gly Asp Ile Ile Leu Lys Val Asn Gly Met Asp
    50                  55                  60

Ile Ser Asn Val Pro His Asn Tyr Ala Val Arg Leu Leu Arg Gln Pro
65                  70                  75                  80

Cys Gln Val Leu Trp Leu Thr Val Met Arg Glu Gln Lys Phe Arg Ser
                85                  90                  95

Arg Asn Ser Ser
            100

<210> SEQ ID NO 154
<211> LENGTH: 101
<212> TYPE: PRT
<213> ORGANISM: Homo sapiens

<400> SEQUENCE: 154

His Arg Pro Arg Asp Asp Ser Phe His Val Ile Leu Asn Lys Ser Ser
1               5                   10                  15

Pro Glu Glu Gln Leu Gly Ile Lys Leu Val Arg Lys Val Asp Glu Pro
                20                  25                  30

Gly Val Phe Ile Phe Asn Val Leu Asp Gly Gly Val Ala Tyr Arg His
            35                  40                  45

Gly Gln Leu Glu Glu Asn Asp Arg Val Leu Ala Ile Asn Gly His Asp
50                      55                  60

Leu Arg Tyr Gly Ser Pro Glu Ser Ala Ala His Leu Ile Gln Ala Ser
65                  70                  75                  80

Glu Arg Arg Val His Leu Val Val Ser Arg Gln Val Arg Gln Arg Ser
                85                  90                  95

Pro Glu Asn Ser Ser
            100

<210> SEQ ID NO 155
<211> LENGTH: 104
<212> TYPE: PRT
<213> ORGANISM: Homo sapiens

<400> SEQUENCE: 155

Pro Thr Ile Thr Cys His Glu Lys Val Val Asn Ile Gln Lys Asp Pro
1               5                   10                  15

Gly Glu Ser Leu Gly Met Thr Val Ala Gly Gly Ala Ser His Arg Glu
                20                  25                  30

Trp Asp Leu Pro Ile Tyr Val Ile Ser Val Glu Pro Gly Gly Val Ile
            35                  40                  45

Ser Arg Asp Gly Arg Ile Lys Thr Gly Asp Ile Leu Leu Asn Val Asp
50                      55                  60

Gly Val Glu Leu Thr Glu Val Ser Arg Ser Glu Ala Val Ala Leu Leu
65                  70                  75                  80

Lys Arg Thr Ser Ser Ser Ile Val Leu Lys Ala Leu Glu Val Lys Glu
                85                  90                  95

Tyr Glu Pro Gln Glu Phe Ile Val
            100

<210> SEQ ID NO 156
<211> LENGTH: 99
<212> TYPE: PRT
<213> ORGANISM: Homo sapiens

<400> SEQUENCE: 156

Pro Arg Cys Leu Tyr Asn Cys Lys Asp Ile Val Leu Arg Arg Asn Thr
1               5                   10                  15

Ala Gly Ser Leu Gly Phe Cys Ile Val Gly Gly Tyr Glu Glu Tyr Asn
                20                  25                  30

Gly Asn Lys Pro Phe Phe Ile Lys Ser Ile Val Glu Gly Thr Pro Ala
            35                  40                  45

Tyr Asn Asp Gly Arg Ile Arg Cys Gly Asp Ile Leu Leu Ala Val Asn
50                      55                  60

Gly Arg Ser Thr Ser Gly Met Ile His Ala Cys Leu Ala Arg Leu Leu
65                  70                  75                  80

Lys Glu Leu Lys Gly Arg Ile Thr Leu Thr Ile Val Ser Trp Pro Gly
                85                  90                  95

Thr Phe Leu

<210> SEQ ID NO 157
<211> LENGTH: 101
<212> TYPE: PRT
<213> ORGANISM: Homo sapiens

<400> SEQUENCE: 157

Leu Leu Thr Glu Glu Ile Asn Leu Thr Arg Gly Pro Ser Gly Leu
1               5                   10                  15

Gly Phe Asn Ile Val Gly Gly Thr Asp Gln Gln Tyr Val Ser Asn Asp
            20                  25                  30

Ser Gly Ile Tyr Val Ser Arg Ile Lys Glu Asn Gly Ala Ala Ala Leu
        35                  40                  45

Asp Gly Arg Leu Gln Glu Gly Asp Lys Ile Leu Ser Val Asn Gly Gln
    50                  55                  60

Asp Leu Lys Asn Leu Leu His Gln Asp Ala Val Asp Leu Phe Arg Asn
65                  70                  75                  80

Ala Gly Tyr Ala Val Ser Leu Arg Val Gln His Arg Leu Gln Val Gln
                85                  90                  95

Asn Gly Ile His Ser
            100

<210> SEQ ID NO 158
<211> LENGTH: 94
<212> TYPE: PRT
<213> ORGANISM: Homo sapiens

<400> SEQUENCE: 158

Pro Val Asp Ala Ile Arg Ile Leu Gly Ile His Lys Arg Ala Gly Glu
1               5                   10                  15

Pro Leu Gly Val Thr Phe Arg Val Glu Asn Asn Asp Leu Val Ile Ala
            20                  25                  30

Arg Ile Leu His Gly Gly Met Ile Asp Arg Gln Gly Leu Leu His Val
        35                  40                  45

Gly Asp Ile Ile Lys Glu Val Asn Gly His Glu Val Gly Asn Asn Pro
    50                  55                  60

Lys Glu Leu Gln Glu Leu Leu Lys Asn Ile Ser Gly Ser Val Thr Leu
65                  70                  75                  80

Lys Ile Leu Pro Ser Tyr Arg Asp Thr Ile Thr Pro Gln Gln
                85                  90

<210> SEQ ID NO 159
<211> LENGTH: 93
<212> TYPE: PRT
<213> ORGANISM: Homo sapiens

<400> SEQUENCE: 159

Asp Asp Met Val Lys Leu Val Glu Val Pro Asn Asp Gly Gly Pro Leu
1               5                   10                  15

Gly Ile His Val Val Pro Phe Ser Ala Arg Gly Gly Arg Thr Leu Gly
            20                  25                  30

Leu Leu Val Lys Arg Leu Glu Lys Gly Gly Lys Ala Glu His Glu Asn
        35                  40                  45

Leu Phe Arg Glu Asn Asp Cys Ile Val Arg Ile Asn Asp Gly Asp Leu
    50                  55                  60

Arg Asn Arg Arg Phe Glu Gln Ala Gln His Met Phe Arg Gln Ala Met
65                  70                  75                  80

Arg Thr Pro Ile Ile Trp Phe His Val Val Pro Ala Ala
                85                  90

<210> SEQ ID NO 160
<211> LENGTH: 94
<212> TYPE: PRT
<213> ORGANISM: Homo sapiens

<400> SEQUENCE: 160

Gly Lys Arg Leu Asn Ile Gln Leu Lys Lys Gly Thr Glu Gly Leu Gly
1               5                   10                  15

Phe Ser Ile Thr Ser Arg Asp Val Thr Ile Gly Gly Ser Ala Pro Ile
                20                  25                  30

Tyr Val Lys Asn Ile Leu Pro Arg Gly Ala Ala Ile Gln Asp Gly Arg
            35                  40                  45

Leu Lys Ala Gly Asp Arg Leu Ile Glu Val Asn Gly Val Asp Leu Val
        50                  55                  60

Gly Lys Ser Gln Glu Glu Val Val Ser Leu Leu Arg Ser Thr Lys Met
65                  70                  75                  80

Glu Gly Thr Val Ser Leu Leu Val Phe Arg Gln Glu Asp Ala
                85                  90

<210> SEQ ID NO 161
<211> LENGTH: 103
<212> TYPE: PRT
<213> ORGANISM: Homo sapiens

<400> SEQUENCE: 161

Thr Pro Asp Gly Thr Arg Glu Phe Leu Thr Phe Glu Val Pro Leu Asn
1               5                   10                  15

Asp Ser Gly Ser Ala Gly Leu Gly Val Ser Val Lys Gly Asn Arg Ser
                20                  25                  30

Lys Glu Asn His Ala Asp Leu Gly Ile Phe Val Lys Ser Ile Ile Asn
            35                  40                  45

Gly Gly Ala Ala Ser Lys Asp Gly Arg Leu Arg Val Asn Asp Gln Leu
        50                  55                  60

Ile Ala Val Asn Gly Glu Ser Leu Leu Gly Lys Thr Asn Gln Asp Ala
65                  70                  75                  80

Met Glu Thr Leu Arg Arg Ser Met Ser Thr Glu Gly Asn Lys Arg Gly
                85                  90                  95

Met Ile Gln Leu Ile Val Ala
            100

<210> SEQ ID NO 162
<211> LENGTH: 102
<212> TYPE: PRT
<213> ORGANISM: Homo sapiens

<400> SEQUENCE: 162

Leu Pro Glu Thr His Arg Arg Val Arg Leu His Lys His Gly Ser Asp
1               5                   10                  15

Arg Pro Leu Gly Phe Tyr Ile Arg Asp Gly Met Ser Val Arg Val Ala
                20                  25                  30

Pro Gln Gly Leu Glu Arg Val Pro Gly Ile Phe Ile Ser Arg Leu Val
            35                  40                  45

Arg Gly Gly Leu Ala Glu Ser Thr Gly Leu Leu Ala Val Ser Asp Glu
        50                  55                  60

Ile Leu Glu Val Asn Gly Ile Glu Val Ala Gly Lys Thr Leu Asp Gln
65                  70                  75                  80

-continued

```
Val Thr Asp Met Met Val Ala Asn Ser His Asn Leu Ile Val Thr Val
                85                  90                  95

Lys Pro Ala Asn Gln Arg
            100

<210> SEQ ID NO 163
<211> LENGTH: 111
<212> TYPE: PRT
<213> ORGANISM: Homo sapiens

<400> SEQUENCE: 163

Ile Asp Val Asp Leu Val Pro Glu Thr His Arg Arg Val Arg Leu His
1               5                   10                  15

Arg His Gly Cys Glu Lys Pro Leu Gly Phe Tyr Ile Arg Asp Gly Ala
            20                  25                  30

Ser Val Arg Val Thr Pro His Gly Leu Glu Lys Val Pro Gly Ile Phe
        35                  40                  45

Ile Ser Arg Met Val Pro Gly Gly Leu Ala Glu Ser Thr Gly Leu Leu
    50                  55                  60

Ala Val Asn Asp Glu Val Leu Glu Val Asn Gly Ile Glu Val Ala Gly
65                  70                  75                  80

Lys Thr Leu Asp Gln Val Thr Asp Met Met Ile Ala Asn Ser His Asn
                85                  90                  95

Leu Ile Val Thr Val Lys Pro Ala Asn Gln Arg Asn Asn Val Val
            100                 105                 110

<210> SEQ ID NO 164
<211> LENGTH: 100
<212> TYPE: PRT
<213> ORGANISM: Homo sapiens

<400> SEQUENCE: 164

Arg Ser Arg Lys Leu Lys Glu Val Arg Leu Asp Arg Leu His Pro Glu
1               5                   10                  15

Gly Leu Gly Leu Ser Val Arg Gly Gly Leu Glu Phe Gly Cys Gly Leu
            20                  25                  30

Phe Ile Ser His Leu Ile Lys Gly Gly Gln Ala Asp Ser Val Gly Leu
        35                  40                  45

Gln Val Gly Asp Glu Ile Val Arg Ile Asn Gly Tyr Ser Ile Ser Ser
    50                  55                  60

Cys Thr His Glu Glu Val Ile Asn Leu Ile Arg Thr Lys Lys Thr Val
65                  70                  75                  80

Ser Ile Lys Val Arg His Ile Gly Leu Ile Pro Val Lys Ser Ser Pro
                85                  90                  95

Asp Glu Phe His
            100

<210> SEQ ID NO 165
<211> LENGTH: 102
<212> TYPE: PRT
<213> ORGANISM: Homo sapiens

<400> SEQUENCE: 165

Ile Pro Gly Asn Arg Glu Asn Lys Glu Lys Lys Val Phe Ile Ser Leu
1               5                   10                  15

Val Gly Ser Arg Gly Leu Gly Cys Ser Ile Ser Ser Gly Pro Ile Gln
            20                  25                  30

Lys Pro Gly Ile Phe Ile Ser His Val Lys Pro Gly Ser Leu Ser Ala
```

```
                35                  40                  45
Glu Val Gly Leu Glu Ile Gly Asp Gln Ile Val Glu Val Asn Gly Val
 50                  55                  60
Asp Phe Ser Asn Leu Asp His Lys Glu Ala Val Asn Val Leu Lys Ser
 65                  70                  75                  80
Ser Arg Ser Leu Thr Ile Ser Ile Val Ala Ala Gly Arg Glu Leu
                 85                  90                  95
Phe Met Thr Asp Glu Phe
             100

<210> SEQ ID NO 166
<211> LENGTH: 103
<212> TYPE: PRT
<213> ORGANISM: Homo sapiens

<400> SEQUENCE: 166

Pro Glu Gln Ile Met Gly Lys Asp Val Arg Leu Leu Arg Ile Lys Lys
 1               5                  10                  15
Glu Gly Ser Leu Asp Leu Ala Leu Glu Gly Gly Val Asp Ser Pro Ile
                20                  25                  30
Gly Lys Val Val Val Ser Ala Val Tyr Glu Arg Gly Ala Ala Glu Arg
                35                  40                  45
His Gly Gly Ile Val Lys Gly Asp Glu Ile Met Ala Ile Asn Gly Lys
 50                  55                  60
Ile Val Thr Asp Tyr Thr Leu Ala Glu Ala Asp Ala Ala Leu Gln Lys
 65                  70                  75                  80
Ala Trp Asn Gln Gly Gly Asp Trp Ile Asp Leu Val Val Ala Val Cys
                 85                  90                  95
Pro Pro Lys Glu Tyr Asp Asp
             100

<210> SEQ ID NO 167
<211> LENGTH: 103
<212> TYPE: PRT
<213> ORGANISM: Homo sapiens

<400> SEQUENCE: 167

Leu Thr Ser Thr Phe Asn Pro Arg Glu Cys Lys Leu Ser Lys Gln Glu
 1               5                  10                  15
Gly Gln Asn Tyr Gly Phe Phe Leu Arg Ile Glu Lys Asp Thr Glu Gly
                20                  25                  30
His Leu Val Arg Val Val Glu Lys Cys Ser Pro Ala Glu Lys Ala Gly
                35                  40                  45
Leu Gln Asp Gly Asp Arg Val Leu Arg Ile Asn Gly Val Phe Val Asp
 50                  55                  60
Lys Glu Glu His Met Gln Val Val Asp Leu Val Arg Lys Ser Gly Asn
 65                  70                  75                  80
Ser Val Thr Leu Leu Val Leu Asp Gly Asp Ser Tyr Glu Lys Ala Gly
                 85                  90                  95
Ser Pro Gly Ile His Arg Asp
             100

<210> SEQ ID NO 168
<211> LENGTH: 92
<212> TYPE: PRT
<213> ORGANISM: Homo sapiens

<400> SEQUENCE: 168
```

```
Arg Leu Cys Tyr Leu Val Lys Glu Gly Ser Tyr Gly Phe Ser Leu
  1               5                  10                  15

Lys Thr Val Gln Gly Lys Lys Gly Val Tyr Met Thr Asp Ile Thr Pro
             20                  25                  30

Gln Gly Val Ala Met Arg Ala Gly Val Leu Ala Asp Asp His Leu Ile
         35                  40                  45

Glu Val Asn Gly Glu Asn Val Glu Asp Ala Ser His Glu Val Val
 50                  55                  60

Glu Lys Val Lys Ser Gly Ser Arg Val Met Phe Leu Leu Val Asp
 65              70                  75                  80

Lys Glu Thr Asp Lys Arg Glu Phe Ile Val Thr Asp
             85                  90
```

<210> SEQ ID NO 169
<211> LENGTH: 112
<212> TYPE: PRT
<213> ORGANISM: Homo sapiens

<400> SEQUENCE: 169

```
Gln Phe Lys Arg Glu Thr Ala Ser Leu Lys Leu Leu Pro His Gln Pro
  1               5                  10                  15

Arg Ile Val Glu Met Lys Lys Gly Ser Asn Gly Tyr Gly Phe Tyr Leu
             20                  25                  30

Arg Ala Gly Ser Glu Gln Lys Gly Gln Ile Ile Lys Asp Ile Asp Ser
         35                  40                  45

Gly Ser Pro Ala Glu Glu Ala Gly Leu Lys Asn Asn Asp Leu Val Val
 50                  55                  60

Ala Val Asn Gly Glu Ser Val Glu Thr Leu Asp His Asp Ser Val Val
 65              70                  75                  80

Glu Met Ile Arg Lys Gly Gly Asp Gln Thr Ser Leu Leu Val Val Asp
             85                  90                  95

Lys Glu Thr Asp Asn Met Tyr Arg Leu Ala Glu Phe Ile Val Thr Asp
            100                 105                 110
```

<210> SEQ ID NO 170
<211> LENGTH: 95
<212> TYPE: PRT
<213> ORGANISM: Homo sapiens

<400> SEQUENCE: 170

```
Pro Asp Thr Thr Glu Val Asp His Lys Pro Lys Leu Cys Arg Leu
  1               5                  10                  15

Ala Lys Gly Glu Asn Gly Tyr Gly Phe His Leu Asn Ala Ile Arg Gly
             20                  25                  30

Leu Pro Gly Ser Phe Ile Lys Glu Val Gln Lys Gly Gly Pro Ala Asp
         35                  40                  45

Leu Ala Gly Leu Glu Asp Glu Asp Val Ile Ile Glu Val Asn Gly Val
 50                  55                  60

Asn Val Leu Asp Glu Pro Tyr Glu Lys Val Val Asp Arg Ile Gln Ser
 65              70                  75                  80

Ser Gly Lys Asn Val Thr Leu Leu Val Glx Gly Lys Asn Ser Ser
             85                  90                  95
```

<210> SEQ ID NO 171
<211> LENGTH: 89
<212> TYPE: PRT
<213> ORGANISM: Homo sapiens -continued

```
<400> SEQUENCE: 171

Pro Thr Val Pro Gly Lys Val Thr Leu Gln Lys Asp Ala Gln Asn Leu
1               5                   10                  15

Ile Gly Ile Ser Ile Gly Gly Ala Gln Tyr Cys Pro Cys Leu Tyr
            20                  25                  30

Ile Val Gln Val Phe Asp Asn Thr Pro Ala Ala Leu Asp Gly Thr Val
            35                  40                  45

Ala Ala Gly Asp Glu Ile Thr Gly Val Asn Gly Arg Ser Ile Lys Gly
        50                  55                  60

Lys Thr Lys Val Glu Val Ala Lys Met Ile Gln Glu Val Lys Gly Glu
65                  70                  75                  80

Val Thr Ile His Tyr Asn Lys Leu Gln
                85

<210> SEQ ID NO 172
<211> LENGTH: 98
<212> TYPE: PRT
<213> ORGANISM: Homo sapiens

<400> SEQUENCE: 172

Ser Gln Gly Val Gly Pro Ile Arg Lys Val Leu Leu Leu Lys Glu Asp
1               5                   10                  15

His Glu Gly Leu Gly Ile Ser Ile Thr Gly Gly Lys Glu His Gly Val
            20                  25                  30

Pro Ile Leu Ile Ser Glu Ile His Pro Gly Gln Pro Ala Asp Arg Cys
            35                  40                  45

Gly Gly Leu His Val Gly Asp Ala Ile Leu Ala Val Asn Gly Val Asn
        50                  55                  60

Leu Arg Asp Thr Lys His Lys Glu Ala Val Thr Ile Leu Ser Gln Gln
65                  70                  75                  80

Arg Gly Glu Ile Glu Phe Glu Val Val Tyr Val Ala Pro Glu Val Asp
                85                  90                  95

Ser Asp

<210> SEQ ID NO 173
<211> LENGTH: 97
<212> TYPE: PRT
<213> ORGANISM: Homo sapiens

<400> SEQUENCE: 173

Ile His Val Thr Ile Leu His Lys Glu Glu Gly Ala Gly Leu Gly Phe
1               5                   10                  15

Ser Leu Ala Gly Gly Ala Asp Leu Glu Asn Lys Val Ile Thr Val His
            20                  25                  30

Arg Val Phe Pro Asn Gly Leu Ala Ser Gln Glu Gly Thr Ile Gln Lys
            35                  40                  45

Gly Asn Glu Val Leu Ser Ile Asn Gly Lys Ser Leu Lys Gly Thr Thr
        50                  55                  60

His His Asp Ala Leu Ala Ile Leu Arg Gln Ala Arg Glu Pro Arg Gln
65                  70                  75                  80

Ala Val Ile Val Thr Arg Lys Leu Thr Pro Glu Glu Phe Ile Val Thr
                85                  90                  95

Asp

<210> SEQ ID NO 174
```

```
<211> LENGTH: 98
<212> TYPE: PRT
<213> ORGANISM: Homo sapiens

<400> SEQUENCE: 174

Thr Ala Glu Ala Thr Val Cys Thr Val Thr Leu Glu Lys Met Ser Ala
 1               5                  10                  15

Gly Leu Gly Phe Ser Leu Glu Gly Gly Lys Gly Ser Leu His Gly Asp
                20                  25                  30

Lys Pro Leu Thr Ile Asn Arg Ile Phe Lys Gly Ala Ala Ser Glu Gln
                35                  40                  45

Ser Glu Thr Val Gln Pro Gly Asp Glu Ile Leu Gln Leu Gly Gly Thr
 50                      55                  60

Ala Met Gln Gly Leu Thr Arg Phe Glu Ala Trp Asn Ile Ile Lys Ala
 65                  70                  75                  80

Leu Pro Asp Gly Pro Val Thr Ile Val Ile Arg Arg Lys Ser Leu Gln
                 85                  90                  95

Ser Lys

<210> SEQ ID NO 175
<211> LENGTH: 98
<212> TYPE: PRT
<213> ORGANISM: Homo sapiens

<400> SEQUENCE: 175

Leu Glu Tyr Glu Ile Thr Leu Glu Arg Gly Asn Ser Gly Leu Gly Phe
 1               5                  10                  15

Ser Ile Ala Gly Gly Thr Asp Asn Pro His Ile Gly Asp Asp Pro Ser
                20                  25                  30

Ile Phe Ile Thr Lys Ile Ile Pro Gly Gly Ala Ala Ala Gln Asp Gly
                35                  40                  45

Arg Leu Arg Val Asn Asp Ser Ile Leu Phe Val Asn Glu Val Asp Val
 50                      55                  60

Arg Glu Val Thr His Ser Ala Ala Val Glu Ala Leu Lys Glu Ala Gly
 65                  70                  75                  80

Ser Ile Val Arg Leu Tyr Val Met Arg Arg Lys Pro Pro Ala Glu Asn
                 85                  90                  95

Ser Ser

<210> SEQ ID NO 176
<211> LENGTH: 105
<212> TYPE: PRT
<213> ORGANISM: Homo sapiens

<400> SEQUENCE: 176

His Val Met Arg Arg Lys Pro Pro Ala Glu Lys Val Met Glu Ile Lys
 1               5                  10                  15

Leu Ile Lys Gly Pro Lys Gly Leu Gly Phe Ser Ile Ala Gly Gly Val
                20                  25                  30

Gly Asn Gln His Ile Pro Gly Asp Asn Ser Ile Tyr Val Thr Lys Ile
                35                  40                  45

Ile Glu Gly Gly Ala Ala His Lys Asp Gly Arg Leu Gln Ile Gly Asp
 50                      55                  60

Lys Ile Leu Ala Val Asn Ser Val Gly Leu Glu Asp Val Met His Glu
 65                  70                  75                  80

Asp Ala Val Ala Ala Leu Lys Asn Thr Tyr Asp Val Val Tyr Leu Lys
                 85                  90                  95
```

```
Val Ala Lys Pro Ser Asn Ala Tyr Leu
            100                 105
```

<210> SEQ ID NO 177
<211> LENGTH: 97
<212> TYPE: PRT
<213> ORGANISM: Homo sapiens

<400> SEQUENCE: 177

```
Arg Glu Asp Ile Pro Arg Glu Pro Arg Arg Ile Val Ile His Arg Gly
 1               5                  10                  15

Ser Thr Gly Leu Gly Phe Asn Ile Val Gly Gly Glu Asp Gly Glu Gly
                20                  25                  30

Ile Phe Ile Ser Phe Ile Leu Ala Gly Gly Pro Ala Asp Leu Ser Gly
                35                  40                  45

Glu Leu Arg Lys Gly Asp Gln Ile Leu Ser Val Asn Gly Val Asp Leu
    50                  55                  60

Arg Asn Ala Ser His Glu Gln Ala Ala Ile Ala Leu Lys Asn Ala Gly
65                  70                  75                  80

Gln Thr Val Thr Ile Ile Ala Gln Tyr Lys Pro Glu Phe Ile Val Thr
                85                  90                  95

Asp
```

<210> SEQ ID NO 178
<211> LENGTH: 88
<212> TYPE: PRT
<213> ORGANISM: Homo sapiens

<400> SEQUENCE: 178

```
Leu Ile Arg Ile Thr Pro Asp Glu Asp Gly Lys Phe Gly Phe Asn Leu
 1               5                  10                  15

Lys Gly Gly Val Asp Gln Lys Met Pro Leu Val Val Ser Arg Ile Asn
                20                  25                  30

Pro Glu Ser Pro Ala Asp Thr Cys Ile Pro Lys Leu Asn Glu Gly Asp
                35                  40                  45

Gln Ile Val Leu Ile Asn Gly Arg Asp Ile Ser Glu His Thr His Asp
    50                  55                  60

Gln Val Val Met Phe Ile Lys Ala Ser Arg Glu Ser His Ser Arg Glu
65                  70                  75                  80

Leu Ala Leu Val Ile Arg Arg Arg
                85
```

<210> SEQ ID NO 179
<211> LENGTH: 88
<212> TYPE: PRT
<213> ORGANISM: Homo sapiens

<400> SEQUENCE: 179

```
Ile Arg Met Lys Pro Asp Glu Asn Gly Arg Phe Gly Phe Asn Val Lys
 1               5                  10                  15

Gly Gly Tyr Asp Gln Lys Met Pro Val Ile Val Ser Arg Val Ala Pro
                20                  25                  30

Gly Thr Pro Ala Asp Leu Cys Val Pro Arg Leu Asn Glu Gly Asp Gln
                35                  40                  45

Val Val Leu Ile Asn Gly Arg Asp Ile Ala Glu His Thr His Asp Gln
    50                  55                  60

Val Val Leu Phe Ile Lys Ala Ser Cys Glu Arg His Ser Gly Glu Leu
```

```
            65                  70                  75                  80
Met Leu Leu Val Arg Pro Asn Ala
                85

<210> SEQ ID NO 180
<211> LENGTH: 106
<212> TYPE: PRT
<213> ORGANISM: Homo sapiens

<400> SEQUENCE: 180

Pro Glu Arg Glu Ile Thr Leu Val Asn Leu Lys Lys Asp Ala Lys Tyr
  1               5                  10                  15

Gly Leu Gly Phe Gln Ile Ile Gly Glu Lys Met Gly Arg Leu Asp
                 20                  25                  30

Leu Gly Ile Phe Ile Ser Ser Val Ala Pro Gly Pro Ala Asp Phe
             35                  40                  45

His Gly Cys Leu Lys Pro Gly Asp Arg Leu Ile Ser Val Asn Ser Val
         50                  55                  60

Ser Leu Glu Gly Val Ser His His Ala Ala Ile Glu Ile Leu Gln Asn
 65                  70                  75                  80

Ala Pro Glu Asp Val Thr Leu Val Ile Ser Gln Pro Lys Glu Lys Ile
                 85                  90                  95

Ser Lys Val Pro Ser Thr Pro Val His Leu
                100                 105

<210> SEQ ID NO 181
<211> LENGTH: 95
<212> TYPE: PRT
<213> ORGANISM: Homo sapiens

<400> SEQUENCE: 181

Gly Asp Ile Phe Glu Val Glu Leu Ala Lys Asn Asp Asn Ser Leu Gly
  1               5                  10                  15

Ile Ser Val Thr Gly Gly Val Asn Thr Ser Val Arg His Gly Gly Ile
                 20                  25                  30

Tyr Val Lys Ala Val Ile Pro Gln Gly Ala Ala Glu Ser Asp Gly Arg
             35                  40                  45

Ile His Lys Gly Asp Arg Val Leu Ala Val Asn Gly Val Ser Leu Glu
         50                  55                  60

Gly Ala Thr His Lys Gln Ala Val Glu Thr Leu Arg Asn Thr Gly Gln
 65                  70                  75                  80

Val Val His Leu Leu Leu Glu Lys Gly Gln Ser Pro Thr Ser Lys
                 85                  90                  95

<210> SEQ ID NO 182
<211> LENGTH: 104
<212> TYPE: PRT
<213> ORGANISM: Homo sapiens

<400> SEQUENCE: 182

Thr Glu Glu Asn Thr Phe Glu Val Lys Leu Phe Lys Asn Ser Ser Gly
  1               5                  10                  15

Leu Gly Phe Ser Phe Ser Arg Glu Asp Asn Leu Ile Pro Glu Gln Ile
                 20                  25                  30

Asn Ala Ser Ile Val Arg Val Lys Lys Leu Phe Ala Gly Gln Pro Ala
             35                  40                  45

Ala Glu Ser Gly Lys Ile Asp Val Gly Asp Val Ile Leu Lys Val Asn
         50                  55                  60
```

```
Gly Ala Ser Leu Lys Gly Leu Ser Gln Gln Glu Val Ile Ser Ala Leu
65                  70                  75                  80

Arg Gly Thr Ala Pro Glu Val Phe Leu Leu Cys Arg Pro Pro
                85                  90                  95

Gly Val Leu Pro Glu Ile Asp Thr
            100
```

<210> SEQ ID NO 183
<211> LENGTH: 98
<212> TYPE: PRT
<213> ORGANISM: Homo sapiens

<400> SEQUENCE: 183

```
Glu Leu Glu Val Glu Leu Leu Ile Thr Leu Ile Lys Ser Glu Lys Ala
1               5                   10                  15

Ser Leu Gly Phe Thr Val Thr Lys Gly Asn Gln Arg Ile Gly Cys Tyr
            20                  25                  30

Val His Asp Val Ile Gln Asp Pro Ala Lys Ser Asp Gly Arg Leu Lys
        35                  40                  45

Pro Gly Asp Arg Leu Ile Lys Val Asn Asp Thr Asp Val Thr Asn Met
50                  55                  60

Thr His Thr Asp Ala Val Asn Leu Leu Arg Ala Ala Ser Lys Thr Val
65                  70                  75                  80

Arg Leu Val Ile Gly Arg Val Leu Glu Leu Pro Arg Ile Pro Met Leu
                85                  90                  95

Pro His
```

<210> SEQ ID NO 184
<211> LENGTH: 94
<212> TYPE: PRT
<213> ORGANISM: Homo sapiens

<400> SEQUENCE: 184

```
Met Leu Pro His Leu Leu Pro Asp Ile Thr Leu Thr Cys Asn Lys Glu
1               5                   10                  15

Glu Leu Gly Phe Ser Leu Cys Gly Gly His Asp Ser Leu Tyr Gln Val
            20                  25                  30

Val Tyr Ile Ser Asp Ile Asn Pro Arg Ser Val Ala Ala Ile Glu Gly
        35                  40                  45

Asn Leu Gln Leu Leu Asp Val Ile His Tyr Val Asn Gly Val Ser Thr
50                  55                  60

Gln Gly Met Thr Leu Glu Glu Val Asn Arg Ala Leu Asp Met Ser Leu
65                  70                  75                  80

Pro Ser Leu Val Leu Lys Ala Thr Arg Asn Asp Leu Pro Val
                85                  90
```

<210> SEQ ID NO 185
<211> LENGTH: 93
<212> TYPE: PRT
<213> ORGANISM: Homo sapiens

<400> SEQUENCE: 185

```
Arg Pro Ser Pro Arg Val Arg Ser Val Glu Val Ala Arg Gly Arg
1               5                   10                  15

Ala Gly Tyr Gly Phe Thr Leu Ser Gly Gln Ala Pro Cys Val Leu Ser
            20                  25                  30

Cys Val Met Arg Gly Ser Pro Ala Asp Phe Val Gly Leu Arg Ala Gly
```

```
                35                  40                  45
Asp Gln Ile Leu Ala Val Asn Glu Ile Asn Val Lys Lys Ala Ser His
                50                  55                  60

Glu Asp Val Val Lys Leu Ile Gly Lys Cys Ser Gly Val Leu His Met
 65                  70                  75                  80

Val Ile Ala Glu Gly Val Gly Arg Phe Glu Ser Cys Ser
                85                  90

<210> SEQ ID NO 186
<211> LENGTH: 96
<212> TYPE: PRT
<213> ORGANISM: Homo sapiens

<400> SEQUENCE: 186

Leu Cys Ser Glu Arg Arg Tyr Arg Gln Ile Thr Ile Pro Arg Gly Lys
  1               5                  10                  15

Asp Gly Phe Gly Phe Thr Ile Cys Cys Asp Ser Pro Val Arg Val Gln
                 20                  25                  30

Ala Val Asp Ser Gly Gly Pro Ala Glu Arg Ala Gly Leu Gln Gln Leu
             35                  40                  45

Asp Thr Val Leu Gln Leu Asn Glu Arg Pro Val Glu His Trp Lys Cys
         50                  55                  60

Val Glu Leu Ala His Glu Ile Arg Ser Cys Pro Ser Glu Ile Ile Leu
 65                  70                  75                  80

Leu Val Trp Arg Met Val Pro Gln Val Lys Pro Gly Ile His Arg Asp
                 85                  90                  95

<210> SEQ ID NO 187
<211> LENGTH: 104
<212> TYPE: PRT
<213> ORGANISM: Homo sapiens

<400> SEQUENCE: 187

Ile Ser Phe Ser Ala Asn Lys Arg Trp Thr Pro Pro Arg Ser Ile Arg
  1               5                  10                  15

Phe Thr Ala Glu Glu Gly Asp Leu Gly Phe Thr Leu Arg Gly Asn Ala
                 20                  25                  30

Pro Val Gln Val His Phe Leu Asp Pro Tyr Cys Ser Ala Ser Val Ala
             35                  40                  45

Gly Ala Arg Glu Gly Asp Tyr Ile Val Ser Ile Gln Leu Val Asp Cys
         50                  55                  60

Lys Trp Leu Thr Leu Ser Glu Val Met Lys Leu Leu Lys Ser Phe Gly
 65                  70                  75                  80

Glu Asp Glu Ile Glu Met Lys Val Val Ser Leu Leu Asp Ser Thr Ser
                 85                  90                  95

Ser Met His Asn Lys Ser Ala Thr
            100

<210> SEQ ID NO 188
<211> LENGTH: 109
<212> TYPE: PRT
<213> ORGANISM: Homo sapiens

<400> SEQUENCE: 188

Arg Gly Glu Lys Lys Asn Ser Ser Gly Ile Ser Gly Ser Gln Arg
  1               5                  10                  15

Arg Tyr Ile Gly Val Met Met Leu Thr Leu Ser Pro Ser Ile Leu Ala
                 20                  25                  30
```

```
Glu Leu Gln Leu Arg Glu Pro Ser Phe Pro Asp Val Gln His Gly Val
         35                  40                  45

Leu Ile His Lys Val Ile Leu Gly Ser Pro Ala His Arg Ala Gly Leu
     50                  55                  60

Arg Pro Gly Asp Val Ile Leu Ala Ile Gly Glu Gln Met Val Gln Asn
 65                  70                  75                  80

Ala Glu Asp Val Tyr Glu Ala Val Arg Thr Gln Ser Gln Leu Ala Val
                 85                  90                  95

Gln Ile Arg Arg Gly Arg Glu Thr Leu Thr Leu Tyr Val
            100                 105

<210> SEQ ID NO 189
<211> LENGTH: 111
<212> TYPE: PRT
<213> ORGANISM: Homo sapiens

<400> SEQUENCE: 189

Glu Glu Lys Thr Val Val Leu Gln Lys Lys Asp Asn Glu Gly Phe Gly
 1               5                  10                  15

Phe Val Leu Arg Gly Ala Lys Ala Asp Thr Pro Ile Glu Glu Phe Thr
             20                  25                  30

Pro Thr Pro Ala Phe Pro Ala Leu Gln Tyr Leu Glu Ser Val Asp Glu
         35                  40                  45

Gly Gly Val Ala Trp Gln Ala Gly Leu Arg Thr Gly Asp Phe Leu Ile
     50                  55                  60

Glu Val Asn Asn Glu Asn Val Val Lys Val Gly His Arg Gln Val Val
 65                  70                  75                  80

Asn Met Ile Arg Gln Gly Gly Asn His Leu Val Leu Lys Val Val Thr
                 85                  90                  95

Val Thr Arg Asn Leu Asp Pro Asp Asp Thr Ala Arg Lys Lys Ala
            100                 105                 110

<210> SEQ ID NO 190
<211> LENGTH: 110
<212> TYPE: PRT
<213> ORGANISM: Homo sapiens

<400> SEQUENCE: 190

Ser Asp Tyr Val Ile Asp Asp Lys Val Ala Val Leu Gln Lys Arg Asp
 1               5                  10                  15

His Glu Gly Phe Gly Phe Val Leu Arg Gly Ala Lys Ala Glu Thr Pro
             20                  25                  30

Ile Glu Glu Phe Thr Pro Thr Pro Ala Phe Pro Ala Leu Gln Tyr Leu
         35                  40                  45

Glu Ser Val Asp Val Glu Gly Val Ala Trp Arg Ala Gly Leu Arg Thr
     50                  55                  60

Gly Asp Phe Leu Ile Glu Val Asn Gly Val Asn Val Val Lys Val Gly
 65                  70                  75                  80

His Lys Gln Val Val Ala Leu Ile Arg Gln Gly Gly Asn Arg Leu Val
                 85                  90                  95

Met Lys Val Val Ser Val Thr Arg Lys Pro Glu Glu Asp Gly
            100                 105                 110

<210> SEQ ID NO 191
<211> LENGTH: 91
<212> TYPE: PRT
<213> ORGANISM: Homo sapiens
```

```
<400> SEQUENCE: 191

Ile Tyr Leu Glu Ala Phe Leu Glu Gly Gly Ala Pro Trp Gly Phe Thr
 1               5                  10                  15

Leu Lys Gly Gly Leu Glu His Gly Glu Pro Leu Ile Ile Ser Lys Val
            20                  25                  30

Glu Glu Gly Gly Lys Ala Asp Thr Leu Ser Ser Lys Leu Gln Ala Gly
        35                  40                  45

Asp Glu Val Val His Ile Asn Glu Val Thr Leu Ser Ser Arg Lys
 50                  55                  60

Glu Ala Val Ser Leu Val Lys Gly Ser Tyr Lys Thr Leu Arg Leu Val
65                  70                  75                  80

Val Arg Arg Asp Val Cys Thr Asp Pro Gly His
                85                  90

<210> SEQ ID NO 192
<211> LENGTH: 83
<212> TYPE: PRT
<213> ORGANISM: Homo sapiens

<400> SEQUENCE: 192

Ile Arg Leu Cys Arg Leu Val Arg Gly Glu Gln Gly Tyr Gly Phe His
 1               5                  10                  15

Leu His Gly Glu Lys Gly Arg Arg Gly Gln Phe Ile Arg Arg Val Glu
            20                  25                  30

Pro Gly Ser Pro Ala Glu Ala Ala Leu Arg Ala Gly Asp Arg Leu
        35                  40                  45

Val Glu Val Asn Gly Val Asn Val Glu Gly Glu Thr His His Gln Val
 50                  55                  60

Val Gln Arg Ile Lys Ala Val Glu Gly Gln Thr Arg Leu Leu Val Val
65                  70                  75                  80

Asp Gln Asn

<210> SEQ ID NO 193
<211> LENGTH: 84
<212> TYPE: PRT
<213> ORGANISM: Homo sapiens

<400> SEQUENCE: 193

Ile Arg His Leu Arg Lys Gly Pro Gln Gly Tyr Gly Phe Asn Leu His
 1               5                  10                  15

Ser Asp Lys Ser Arg Pro Gly Gln Tyr Ile Arg Ser Val Asp Pro Gly
            20                  25                  30

Ser Pro Ala Ala Arg Ser Gly Leu Arg Ala Gln Asp Arg Leu Ile Glu
        35                  40                  45

Val Asn Gly Gln Asn Val Glu Gly Leu Arg His Ala Glu Val Val Ala
 50                  55                  60

Ser Ile Lys Ala Arg Glu Asp Glu Ala Arg Leu Leu Val Val Asp Pro
65                  70                  75                  80

Glu Thr Asp Glu

<210> SEQ ID NO 194
<211> LENGTH: 92
<212> TYPE: PRT
<213> ORGANISM: Homo sapiens

<400> SEQUENCE: 194
```

```
Pro Gly Val Arg Glu Ile His Leu Cys Lys Asp Glu Arg Lys Thr
 1               5                  10                  15

Gly Leu Arg Leu Arg Lys Val Asp Gln Gly Leu Phe Val Gln Leu Val
                20                  25                  30

Gln Ala Asn Thr Pro Ala Ser Leu Val Gly Leu Arg Phe Gly Asp Gln
            35                  40                  45

Leu Leu Gln Ile Asp Gly Arg Asp Cys Ala Gly Trp Ser Ser His Lys
 50                  55                  60

Ala His Gln Val Val Lys Lys Ala Ser Gly Asp Lys Ile Val Val Val
 65                  70                  75                  80

Val Arg Asp Arg Pro Phe Gln Arg Thr Val Thr Met
                85                  90

<210> SEQ ID NO 195
<211> LENGTH: 90
<212> TYPE: PRT
<213> ORGANISM: Homo sapiens

<400> SEQUENCE: 195

Pro Phe Gln Arg Thr Val Thr Met His Lys Asp Ser Met Gly His Val
 1               5                  10                  15

Gly Phe Val Ile Lys Lys Gly Lys Ile Val Ser Leu Val Lys Gly Ser
                20                  25                  30

Ser Ala Ala Arg Asn Gly Leu Leu Thr Asn His Tyr Val Cys Glu Val
            35                  40                  45

Asp Gly Gln Asn Val Ile Gly Leu Lys Asp Lys Lys Ile Met Glu Ile
 50                  55                  60

Leu Ala Thr Ala Gly Asn Val Val Thr Leu Thr Ile Ile Pro Ser Val
 65                  70                  75                  80

Ile Tyr Glu His Ile Val Glu Phe Ile Val
                85                  90

<210> SEQ ID NO 196
<211> LENGTH: 109
<212> TYPE: PRT
<213> ORGANISM: Homo sapiens

<400> SEQUENCE: 196

Leu Lys Glu Lys Thr Val Leu Leu Gln Lys Lys Asp Ser Glu Gly Phe
 1               5                  10                  15

Gly Phe Val Leu Arg Gly Ala Lys Ala Gln Thr Pro Ile Glu Glu Phe
                20                  25                  30

Thr Pro Thr Pro Ala Phe Pro Ala Leu Gln Tyr Leu Glu Ser Val Asp
            35                  40                  45

Glu Gly Gly Val Ala Trp Arg Ala Gly Leu Arg Met Gly Asp Phe Leu
 50                  55                  60

Ile Glu Val Asn Gly Gln Asn Val Val Lys Val Gly His Arg Gln Val
 65                  70                  75                  80

Val Asn Met Ile Arg Gln Gly Gly Asn Thr Leu Met Val Lys Val Val
                85                  90                  95

Met Val Thr Arg His Pro Asp Met Asp Glu Ala Val Gln
            100                 105

<210> SEQ ID NO 197
<211> LENGTH: 88
<212> TYPE: PRT
<213> ORGANISM: Homo sapiens
```

-continued

```
<400> SEQUENCE: 197

Leu Glu Ile Lys Gln Gly Ile Arg Glu Val Ile Leu Cys Lys Asp Gln
1               5                   10                  15

Asp Gly Lys Ile Gly Leu Arg Leu Lys Ser Ile Asp Asn Gly Ile Phe
            20                  25                  30

Val Gln Leu Val Gln Ala Asn Ser Pro Ala Ser Leu Val Gly Leu Arg
        35                  40                  45

Phe Gly Asp Gln Val Leu Gln Ile Asn Gly Glu Asn Cys Ala Gly Trp
    50                  55                  60

Ser Ser Asp Lys Ala His Lys Val Leu Lys Gln Ala Phe Gly Glu Lys
65                  70                  75                  80

Ile Thr Met Arg Ile His Arg Asp
                85

<210> SEQ ID NO 198
<211> LENGTH: 75
<212> TYPE: PRT
<213> ORGANISM: Homo sapiens

<400> SEQUENCE: 198

Arg Asp Arg Pro Phe Glu Arg Thr Ile Thr Met His Lys Asp Ser Thr
1               5                   10                  15

Gly His Val Gly Phe Ile Phe Lys Asn Gly Lys Ile Thr Ser Ile Val
            20                  25                  30

Lys Asp Ser Ser Ala Ala Arg Asn Gly Leu Leu Thr Glu His Asn Ile
        35                  40                  45

Cys Glu Ile Asn Gly Gln Asn Val Ile Gly Leu Lys Asp Ser Gln Ile
    50                  55                  60

Ala Asp Ile Leu Ser Thr Ser Gly Asn Ser Ser
65                  70                  75

<210> SEQ ID NO 199
<211> LENGTH: 94
<212> TYPE: PRT
<213> ORGANISM: Homo sapiens

<400> SEQUENCE: 199

Gln Arg Arg Arg Val Thr Val Arg Lys Ala Asp Ala Gly Gly Leu Gly
1               5                   10                  15

Ile Ser Ile Lys Gly Gly Arg Glu Asn Lys Met Pro Ile Leu Ile Ser
            20                  25                  30

Lys Ile Phe Lys Gly Leu Ala Ala Asp Gln Thr Glu Ala Leu Phe Val
        35                  40                  45

Gly Asp Ala Ile Leu Ser Val Asn Gly Glu Asp Leu Ser Ser Ala Thr
    50                  55                  60

His Asp Glu Ala Val Gln Val Leu Lys Lys Thr Gly Lys Glu Val Val
65                  70                  75                  80

Leu Glu Val Lys Tyr Met Lys Asp Val Ser Pro Tyr Phe Lys
                85                  90

<210> SEQ ID NO 200
<211> LENGTH: 89
<212> TYPE: PRT
<213> ORGANISM: Homo sapiens

<400> SEQUENCE: 200

Ile Arg Val Val Lys Gln Glu Ala Gly Gly Leu Gly Ile Ser Ile Lys
1               5                   10                  15
```

```
Gly Gly Arg Glu Asn Arg Met Pro Ile Leu Ile Ser Lys Ile Phe Pro
            20                  25                  30

Gly Leu Ala Ala Asp Gln Ser Arg Ala Leu Arg Leu Gly Asp Ala Ile
        35                  40                  45

Leu Ser Val Asn Gly Thr Asp Leu Arg Gln Ala Thr His Asp Gln Ala
    50                  55                  60

Val Gln Ala Leu Lys Arg Ala Gly Lys Glu Val Leu Glu Val Lys
65                  70                  75                  80

Phe Ile Arg Glu Phe Ile Val Thr Asp
                85
```

<210> SEQ ID NO 201
<211> LENGTH: 101
<212> TYPE: PRT
<213> ORGANISM: Homo sapiens

<400> SEQUENCE: 201

```
Glu Pro Phe Tyr Ser Gly Glu Arg Thr Val Thr Ile Arg Arg Gln Thr
1               5                   10                  15

Val Gly Gly Phe Gly Leu Ser Ile Lys Gly Gly Ala Glu His Asn Ile
            20                  25                  30

Pro Val Val Ser Lys Ile Ser Lys Glu Gln Arg Ala Glu Leu Ser
        35                  40                  45

Gly Leu Leu Phe Ile Gly Asp Ala Ile Leu Gln Ile Asn Gly Ile Asn
    50                  55                  60

Val Arg Lys Cys Arg His Glu Glu Val Val Gln Val Leu Arg Asn Ala
65                  70                  75                  80

Gly Glu Glu Val Thr Leu Thr Val Ser Phe Leu Lys Arg Ala Pro Ala
                85                  90                  95

Phe Leu Lys Leu Pro
            100
```

<210> SEQ ID NO 202
<211> LENGTH: 99
<212> TYPE: PRT
<213> ORGANISM: Homo sapiens

<400> SEQUENCE: 202

```
Ser His Gln Gly Arg Asn Arg Arg Thr Val Thr Leu Arg Arg Gln Pro
1               5                   10                  15

Val Gly Gly Leu Gly Leu Ser Ile Lys Gly Gly Ser Glu His Asn Val
            20                  25                  30

Pro Val Val Ile Ser Lys Ile Phe Glu Asp Gln Ala Ala Asp Gln Thr
        35                  40                  45

Gly Met Leu Phe Val Gly Asp Ala Val Leu Gln Val Asn Gly Ile His
    50                  55                  60

Val Glu Asn Ala Thr His Glu Glu Val Val His Leu Leu Arg Asn Ala
65                  70                  75                  80

Gly Asp Glu Val Thr Ile Thr Val Glu Tyr Leu Arg Glu Ala Pro Ala
                85                  90                  95

Phe Leu Lys
```

<210> SEQ ID NO 203
<211> LENGTH: 91
<212> TYPE: PRT
<213> ORGANISM: Homo sapiens -continued

```
<400> SEQUENCE: 203

Arg Gly Glu Thr Lys Glu Val Glu Val Thr Lys Thr Glu Asp Ala Leu
  1               5                  10                  15

Gly Leu Thr Ile Thr Asp Asn Gly Ala Gly Tyr Ala Phe Ile Lys Arg
             20                  25                  30

Ile Lys Glu Gly Ser Ile Ile Asn Arg Ile Glu Ala Val Cys Val Gly
         35                  40                  45

Asp Ser Ile Glu Ala Ile Asn Asp His Ser Ile Val Gly Cys Arg His
     50                  55                  60

Tyr Glu Val Ala Lys Met Leu Arg Glu Leu Pro Lys Ser Gln Pro Phe
 65                  70                  75                  80

Thr Leu Arg Leu Val Gln Pro Lys Arg Ala Phe
                 85                  90

<210> SEQ ID NO 204
<211> LENGTH: 88
<212> TYPE: PRT
<213> ORGANISM: Homo sapiens

<400> SEQUENCE: 204

His Ser Ile His Ile Glu Lys Ser Asp Thr Ala Ala Asp Thr Tyr Gly
  1               5                  10                  15

Phe Ser Leu Ser Ser Val Glu Asp Gly Ile Arg Arg Leu Tyr Val
             20                  25                  30

Asn Ser Val Lys Glu Thr Gly Leu Ala Ser Lys Lys Gly Leu Lys Ala
         35                  40                  45

Gly Asp Glu Ile Leu Glu Ile Asn Asn Arg Ala Ala Asp Ala Leu Asn
     50                  55                  60

Ser Ser Met Leu Lys Asp Phe Leu Ser Gln Pro Ser Leu Gly Leu Leu
 65                  70                  75                  80

Val Arg Thr Tyr Pro Glu Leu Glu
                 85

<210> SEQ ID NO 205
<211> LENGTH: 97
<212> TYPE: PRT
<213> ORGANISM: Homo sapiens

<400> SEQUENCE: 205

Pro Leu Asn Val Tyr Asp Val Gln Leu Thr Lys Thr Gly Ser Val Cys
  1               5                  10                  15

Asp Phe Gly Phe Ala Val Thr Ala Gln Val Asp Glu Arg Gln His Leu
             20                  25                  30

Ser Arg Ile Phe Ile Ser Asp Val Leu Pro Asp Gly Leu Ala Tyr Gly
         35                  40                  45

Glu Gly Leu Arg Lys Gly Asn Glu Ile Met Thr Leu Asn Gly Glu Ala
     50                  55                  60

Val Ser Asp Leu Asp Leu Lys Gln Met Glu Ala Leu Phe Ser Glu Lys
 65                  70                  75                  80

Ser Val Gly Leu Thr Leu Ile Ala Arg Pro Pro Asp Thr Lys Ala Thr
                 85                  90                  95

Leu

<210> SEQ ID NO 206
<211> LENGTH: 103
<212> TYPE: PRT
<213> ORGANISM: Homo sapiens
```

<400> SEQUENCE: 206

Gln Arg Val Glu Ile His Lys Leu Arg Gln Gly Glu Asn Leu Ile Leu
1               5                   10                  15

Gly Phe Ser Ile Gly Gly Ile Asp Gln Asp Pro Ser Gln Asn Pro
            20                  25                  30

Phe Ser Glu Asp Lys Thr Asp Lys Gly Ile Tyr Val Thr Arg Val Ser
            35                  40                  45

Glu Gly Gly Pro Ala Glu Ile Ala Gly Leu Gln Ile Gly Asp Lys Ile
50                  55                  60

Met Gln Val Asn Gly Trp Asp Met Thr Met Val Thr His Asp Gln Ala
65                  70                  75                  80

Arg Lys Arg Leu Thr Lys Arg Ser Glu Glu Val Val Arg Leu Leu Val
                85                  90                  95

Thr Arg Gln Ser Leu Gln Lys
            100

<210> SEQ ID NO 207
<211> LENGTH: 86
<212> TYPE: PRT
<213> ORGANISM: Homo sapiens

<400> SEQUENCE: 207

Arg Lys Glu Val Glu Val Phe Lys Ser Glu Asp Ala Leu Gly Leu Thr
1               5                   10                  15

Ile Thr Asp Asn Gly Ala Gly Tyr Ala Phe Ile Lys Arg Ile Lys Glu
            20                  25                  30

Gly Ser Val Ile Asp His Ile His Leu Ile Ser Val Gly Asp Met Ile
            35                  40                  45

Glu Ala Ile Asn Gly Gln Ser Leu Leu Gly Cys Arg His Tyr Glu Val
50                  55                  60

Ala Arg Leu Leu Lys Glu Leu Pro Arg Gly Arg Thr Phe Thr Leu Lys
65                  70                  75                  80

Leu Thr Glu Pro Arg Lys
            85

<210> SEQ ID NO 208
<211> LENGTH: 91
<212> TYPE: PRT
<213> ORGANISM: Homo sapiens

<400> SEQUENCE: 208

His Ser His Pro Arg Val Val Glu Leu Pro Lys Thr Asp Glu Gly Leu
1               5                   10                  15

Gly Phe Asn Val Met Gly Gly Lys Glu Gln Asn Ser Pro Ile Tyr Ile
            20                  25                  30

Ser Arg Ile Ile Pro Gly Gly Val Ala Glu Arg His Gly Gly Leu Lys
            35                  40                  45

Arg Gly Asp Gln Leu Leu Ser Val Asn Gly Val Ser Val Glu Gly Glu
50                  55                  60

His His Glu Lys Ala Val Glu Leu Leu Lys Ala Ala Lys Asp Ser Val
65                  70                  75                  80

Lys Leu Val Val Arg Tyr Thr Pro Lys Val Leu
            85                  90

<210> SEQ ID NO 209
<211> LENGTH: 96

```
<212> TYPE: PRT
<213> ORGANISM: Homo sapiens

<400> SEQUENCE: 209

Ile Ser Asn Gln Lys Arg Gly Val Lys Val Leu Lys Gln Glu Leu Gly
1               5                   10                  15

Gly Leu Gly Ile Ser Ile Lys Gly Gly Lys Glu Asn Lys Met Pro Ile
            20                  25                  30

Leu Ile Ser Lys Ile Phe Lys Gly Leu Ala Ala Asp Gln Thr Gln Ala
        35                  40                  45

Leu Tyr Val Gly Asp Ala Ile Leu Ser Val Asn Gly Ala Asp Leu Arg
    50                  55                  60

Asp Ala Thr His Asp Glu Ala Val Gln Ala Leu Lys Arg Ala Gly Lys
65                  70                  75                  80

Glu Val Leu Leu Glu Val Lys Tyr Met Arg Glu Ala Thr Pro Tyr Val
                85                  90                  95

<210> SEQ ID NO 210
<211> LENGTH: 110
<212> TYPE: PRT
<213> ORGANISM: Homo sapiens

<400> SEQUENCE: 210

Ile His Phe Ser Asn Ser Glu Asn Cys Lys Glu Leu Gln Leu Glu Lys
1               5                   10                  15

His Lys Gly Glu Ile Leu Gly Val Val Val Glu Ser Gly Trp Gly Gly
            20                  25                  30

Ser Ile Leu Pro Thr Val Ile Leu Ala Asn Met Met Asn Gly Gly Pro
        35                  40                  45

Ala Ala Arg Ser Gly Lys Leu Ser Ile Gly Asp Gln Ile Met Ser Ile
    50                  55                  60

Asn Gly Thr Ser Leu Val Gly Leu Pro Leu Ala Thr Cys Gln Gly Ile
65                  70                  75                  80

Ile Lys Gly Leu Lys Asn Gln Thr Gln Val Lys Leu Asn Ile Val Ser
                85                  90                  95

Cys Pro Pro Val Thr Thr Val Leu Ile Lys Arg Asn Ser Ser
            100                 105                 110

<210> SEQ ID NO 211
<211> LENGTH: 94
<212> TYPE: PRT
<213> ORGANISM: Homo sapiens

<400> SEQUENCE: 211

Ile Pro Pro Val Thr Thr Val Leu Ile Lys Arg Pro Asp Leu Lys Tyr
1               5                   10                  15

Gln Leu Gly Phe Ser Val Gln Asn Gly Ile Ile Cys Ser Leu Met Arg
            20                  25                  30

Gly Gly Ile Ala Glu Arg Gly Gly Val Arg Val Gly His Arg Ile Ile
        35                  40                  45

Glu Ile Asn Gly Gln Ser Val Val Ala Thr Ala His Glu Lys Ile Val
    50                  55                  60

Gln Ala Leu Ser Asn Ser Val Gly Glu Ile His Met Lys Thr Met Pro
65                  70                  75                  80

Ala Ala Met Phe Arg Leu Leu Thr Gly Gln Glu Asn Ser Ser
                85                  90
```

```
<210> SEQ ID NO 212
<211> LENGTH: 101
<212> TYPE: PRT
<213> ORGANISM: Homo sapiens

<400> SEQUENCE: 212

Ile Trp Glu Gln His Thr Val Thr Leu His Arg Ala Pro Gly Phe Gly
 1               5                  10                  15

Phe Gly Ile Ala Ile Ser Gly Gly Arg Asp Asn Pro His Phe Gln Ser
             20                  25                  30

Gly Glu Thr Ser Ile Val Ile Ser Asp Val Leu Lys Gly Pro Ala
         35                  40                  45

Glu Gly Gln Leu Gln Glu Asn Asp Arg Val Ala Met Val Asn Gly Val
     50                  55                  60

Ser Met Asp Asn Val Glu His Ala Phe Ala Val Gln Gln Leu Arg Lys
 65                  70                  75                  80

Ser Gly Lys Asn Ala Lys Ile Thr Ile Arg Arg Lys Lys Val Gln
                 85                  90                  95

Ile Pro Asn Ser Ser
            100

<210> SEQ ID NO 213
<211> LENGTH: 95
<212> TYPE: PRT
<213> ORGANISM: Homo sapiens

<400> SEQUENCE: 213

Ile Ser Ser Gln Pro Ala Lys Pro Thr Lys Val Thr Leu Val Lys Ser
 1               5                  10                  15

Arg Lys Asn Glu Glu Tyr Gly Leu Arg Leu Ala Ser His Ile Phe Val
             20                  25                  30

Lys Glu Ile Ser Gln Asp Ser Leu Ala Ala Arg Asp Gly Asn Ile Gln
         35                  40                  45

Glu Gly Asp Val Val Leu Lys Ile Asn Gly Thr Val Thr Glu Asn Met
     50                  55                  60

Ser Leu Thr Asp Ala Lys Thr Leu Ile Glu Arg Ser Lys Gly Lys Leu
 65                  70                  75                  80

Lys Met Val Val Gln Arg Asp Arg Ala Thr Leu Leu Asn Ser Ser
                 85                  90                  95

<210> SEQ ID NO 214
<211> LENGTH: 90
<212> TYPE: PRT
<213> ORGANISM: Homo sapiens

<400> SEQUENCE: 214

Ile Arg Met Lys Leu Val Lys Phe Arg Lys Gly Asp Ser Val Gly Leu
 1               5                  10                  15

Arg Leu Ala Gly Gly Asn Asp Val Gly Ile Phe Val Ala Gly Val Leu
             20                  25                  30

Glu Asp Ser Pro Ala Ala Lys Glu Gly Leu Glu Glu Gly Asp Gln Ile
         35                  40                  45

Leu Arg Val Asn Asn Val Asp Phe Thr Asn Ile Ile Arg Glu Glu Ala
     50                  55                  60

Val Leu Phe Leu Leu Asp Leu Pro Lys Gly Glu Glu Val Thr Ile Leu
 65                  70                  75                  80

Ala Gln Lys Lys Lys Asp Val Phe Ser Asn
                 85                  90
```

<210> SEQ ID NO 215
<211> LENGTH: 96
<212> TYPE: PRT
<213> ORGANISM: Homo sapiens

<400> SEQUENCE: 215

Leu Ile Trp Glu Gln Tyr Thr Val Thr Leu Gln Lys Asp Ser Lys Arg
1               5                   10                  15

Gly Phe Gly Ile Ala Val Ser Gly Arg Asp Asn Pro His Phe Glu
            20                  25                  30

Asn Gly Glu Thr Ser Ile Val Ile Ser Asp Val Leu Pro Gly Gly Pro
            35                  40                  45

Ala Asp Gly Leu Leu Gln Glu Asn Asp Arg Val Val Met Val Asn Gly
50                  55                  60

Thr Pro Met Glu Asp Val Leu His Ser Phe Ala Val Gln Gln Leu Arg
65                  70                  75                  80

Lys Ser Gly Lys Val Ala Ala Ile Val Val Lys Arg Pro Arg Lys Val
                85                  90                  95

<210> SEQ ID NO 216
<211> LENGTH: 79
<212> TYPE: PRT
<213> ORGANISM: Homo sapiens

<400> SEQUENCE: 216

Arg Val Leu Leu Met Lys Ser Arg Ala Asn Glu Glu Tyr Gly Leu Arg
1               5                   10                  15

Leu Gly Ser Gln Ile Phe Val Lys Glu Met Thr Arg Thr Gly Leu Ala
            20                  25                  30

Thr Lys Asp Gly Asn Leu His Glu Gly Asp Ile Ile Leu Lys Ile Asn
            35                  40                  45

Gly Thr Val Thr Glu Asn Met Ser Leu Thr Asp Ala Arg Lys Leu Ile
50                  55                  60

Glu Lys Ser Arg Gly Lys Leu Gln Leu Val Val Leu Arg Asp Ser
65                  70                  75

<210> SEQ ID NO 217
<211> LENGTH: 90
<212> TYPE: PRT
<213> ORGANISM: Homo sapiens

<400> SEQUENCE: 217

His Ala Pro Asn Thr Lys Met Val Arg Phe Lys Lys Gly Asp Ser Val
1               5                   10                  15

Gly Leu Arg Leu Ala Gly Gly Asn Asp Val Gly Ile Phe Val Ala Gly
            20                  25                  30

Ile Gln Glu Gly Thr Ser Ala Glu Gln Glu Gly Leu Gln Glu Gly Asp
            35                  40                  45

Gln Ile Leu Lys Val Asn Thr Gln Asp Phe Arg Gly Leu Val Arg Glu
50                  55                  60

Asp Ala Val Leu Tyr Leu Leu Glu Ile Pro Lys Gly Glu Met Val Thr
65                  70                  75                  80

Ile Leu Ala Gln Ser Arg Ala Asp Val Tyr
                85                  90

<210> SEQ ID NO 218
<211> LENGTH: 106

```
<212> TYPE: PRT
<213> ORGANISM: Homo sapiens

<400> SEQUENCE: 218

Ile Pro Gly Asn Ser Thr Ile Trp Glu Gln His Thr Ala Thr Leu Ser
  1               5                  10                  15

Lys Asp Pro Arg Arg Gly Phe Gly Ile Ala Ile Ser Gly Gly Arg Asp
             20                  25                  30

Arg Pro Gly Gly Ser Met Val Val Ser Asp Val Val Pro Gly Gly Pro
         35                  40                  45

Ala Glu Gly Arg Leu Gln Thr Gly Asp His Ile Val Met Val Asn Gly
 50                  55                  60

Val Ser Met Glu Asn Ala Thr Ser Ala Phe Ala Ile Gln Ile Leu Lys
 65                  70                  75                  80

Thr Cys Thr Lys Met Ala Asn Ile Thr Val Lys Arg Pro Arg Arg Ile
                 85                  90                  95

His Leu Pro Ala Glu Phe Ile Val Thr Asp
            100                 105

<210> SEQ ID NO 219
<211> LENGTH: 98
<212> TYPE: PRT
<213> ORGANISM: Homo sapiens

<400> SEQUENCE: 219

Gln Asp Val Gln Met Lys Pro Val Lys Ser Val Leu Val Lys Arg Arg
  1               5                  10                  15

Asp Ser Glu Glu Phe Gly Val Lys Leu Gly Ser Gln Ile Phe Ile Lys
             20                  25                  30

His Ile Thr Asp Ser Gly Leu Ala Ala Arg His Arg Gly Leu Gln Glu
         35                  40                  45

Gly Asp Leu Ile Leu Gln Ile Asn Gly Val Ser Ser Gln Asn Leu Ser
 50                  55                  60

Leu Asn Asp Thr Arg Arg Leu Ile Glu Lys Ser Glu Gly Lys Leu Ser
 65                  70                  75                  80

Leu Leu Val Leu Arg Asp Arg Gly Gln Phe Leu Val Asn Ile Pro Asn
                 85                  90                  95

Ser Ser

<210> SEQ ID NO 220
<211> LENGTH: 104
<212> TYPE: PRT
<213> ORGANISM: Homo sapiens

<400> SEQUENCE: 220

Arg Gly Tyr Ser Pro Asp Thr Arg Val Val Arg Phe Leu Lys Gly Lys
  1               5                  10                  15

Ser Ile Gly Leu Arg Leu Ala Gly Gly Asn Asp Val Gly Ile Phe Val
             20                  25                  30

Ser Gly Val Gln Ala Gly Ser Pro Ala Asp Gly Gln Gly Ile Gln Glu
         35                  40                  45

Gly Asp Gln Ile Leu Gln Val Asn Asp Val Pro Phe Gln Asn Leu Thr
 50                  55                  60

Arg Glu Glu Ala Val Gln Phe Leu Leu Gly Leu Pro Pro Gly Glu Glu
 65                  70                  75                  80

Met Glu Leu Val Thr Gln Arg Lys Gln Asp Ile Phe Trp Lys Met Val
                 85                  90                  95
```

Gln Ser Glu Phe Ile Val Thr Asp
            100

<210> SEQ ID NO 221
<211> LENGTH: 10
<212> TYPE: PRT
<213> ORGANISM: Homo sapiens

<400> SEQUENCE: 221

Gly Tyr Cys Arg Asn Cys Ile Arg Lys Gln
1               5                   10

<210> SEQ ID NO 222
<211> LENGTH: 10
<212> TYPE: PRT
<213> ORGANISM: Homo sapiens

<400> SEQUENCE: 222

Trp Thr Thr Cys Met Glu Asp Leu Leu Pro
1               5                   10

<210> SEQ ID NO 223
<211> LENGTH: 10
<212> TYPE: PRT
<213> ORGANISM: Homo sapiens

<400> SEQUENCE: 223

Gly Ile Cys Arg Leu Cys Lys His Phe Gln
1               5                   10

<210> SEQ ID NO 224
<211> LENGTH: 10
<212> TYPE: PRT
<213> ORGANISM: Homo sapiens

<400> SEQUENCE: 224

Lys Gly Leu Cys Arg Gln Cys Lys Gln Ile
1               5                   10

<210> SEQ ID NO 225
<211> LENGTH: 10
<212> TYPE: PRT
<213> ORGANISM: Homo sapiens

<400> SEQUENCE: 225

Trp Leu Arg Cys Thr Val Arg Ile Pro Gln
1               5                   10

<210> SEQ ID NO 226
<211> LENGTH: 10
<212> TYPE: PRT
<213> ORGANISM: Homo sapiens

<400> SEQUENCE: 226

Arg Gln Cys Lys His Phe Tyr Asn Asp Trp
1               5                   10

<210> SEQ ID NO 227
<211> LENGTH: 10
<212> TYPE: PRT
<213> ORGANISM: Homo sapiens

<400> SEQUENCE: 227

Cys Arg Asn Cys Ile Ser His Glu Gly Arg

<210> SEQ ID NO 228
<211> LENGTH: 10
<212> TYPE: PRT
<213> ORGANISM: Homo sapiens

<400> SEQUENCE: 228

Cys Cys Arg Asn Cys Tyr Glu His Glu Gly
1               5                   10

<210> SEQ ID NO 229
<211> LENGTH: 10
<212> TYPE: PRT
<213> ORGANISM: Homo sapiens

<400> SEQUENCE: 229

Ser Ser Arg Thr Arg Arg Glu Thr Gln Leu
1               5                   10

<210> SEQ ID NO 230
<211> LENGTH: 10
<212> TYPE: PRT
<213> ORGANISM: Homo sapiens

<400> SEQUENCE: 230

Arg Leu Gln Arg Arg Arg Glu Thr Gln Val
1               5                   10

<210> SEQ ID NO 231
<211> LENGTH: 10
<212> TYPE: PRT
<213> ORGANISM: Homo sapiens

<400> SEQUENCE: 231

Trp Arg Arg Pro Arg Thr Glu Thr Gln Val
1               5                   10

<210> SEQ ID NO 232
<211> LENGTH: 10
<212> TYPE: PRT
<213> ORGANISM: Homo sapiens

<400> SEQUENCE: 232

Trp Lys Pro Thr Arg Arg Glu Thr Glu Val
1               5                   10

<210> SEQ ID NO 233
<211> LENGTH: 10
<212> TYPE: PRT
<213> ORGANISM: Homo sapiens

<400> SEQUENCE: 233

Arg Arg Thr Leu Arg Arg Glu Thr Gln Val
1               5                   10

<210> SEQ ID NO 234
<211> LENGTH: 10
<212> TYPE: PRT
<213> ORGANISM: Homo sapiens

<400> SEQUENCE: 234

Arg Arg Leu Thr Arg Arg Glu Thr Gln Val
1               5                   10

```
<210> SEQ ID NO 235
<211> LENGTH: 10
<212> TYPE: PRT
<213> ORGANISM: Homo sapiens

<400> SEQUENCE: 235

Arg Leu Arg Arg Arg Glu Thr Gln Val
1               5                   10

<210> SEQ ID NO 236
<211> LENGTH: 10
<212> TYPE: PRT
<213> ORGANISM: Homo sapiens

<400> SEQUENCE: 236

Arg Leu Gln Arg Arg Asn Glu Thr Gln Val
1               5                   10

<210> SEQ ID NO 237
<211> LENGTH: 10
<212> TYPE: PRT
<213> ORGANISM: Homo sapiens

<400> SEQUENCE: 237

Arg Leu Gln Arg Arg Val Thr Gln Val
1               5                   10

<210> SEQ ID NO 238
<211> LENGTH: 10
<212> TYPE: PRT
<213> ORGANISM: Homo sapiens

<400> SEQUENCE: 238

Thr Ser Arg Glu Pro Arg Glu Ser Thr Val
1               5                   10

<210> SEQ ID NO 239
<211> LENGTH: 10
<212> TYPE: PRT
<213> ORGANISM: Homo sapiens

<400> SEQUENCE: 239

Gln Arg Gln Ala Arg Ser Glu Thr Leu Val
1               5                   10

<210> SEQ ID NO 240
<211> LENGTH: 10
<212> TYPE: PRT
<213> ORGANISM: Homo sapiens

<400> SEQUENCE: 240

Arg Leu Gln Arg Arg Arg Gln Thr Gln Val
1               5                   10

<210> SEQ ID NO 241
<211> LENGTH: 10
<212> TYPE: PRT
<213> ORGANISM: Homo sapiens

<400> SEQUENCE: 241

Arg Leu Gln Arg Arg Arg Glu Thr Ala Leu
1               5                   10

<210> SEQ ID NO 242
```

```
<211> LENGTH: 10
<212> TYPE: PRT
<213> ORGANISM: Homo sapiens

<400> SEQUENCE: 242

Thr Ser Arg Gln Ala Thr Glu Ser Thr Val
1               5                   10

<210> SEQ ID NO 243
<211> LENGTH: 10
<212> TYPE: PRT
<213> ORGANISM: Homo sapiens

<400> SEQUENCE: 243

Arg Arg Arg Thr Arg Gln Glu Thr Gln Val
1               5                   10

<210> SEQ ID NO 244
<211> LENGTH: 10
<212> TYPE: PRT
<213> ORGANISM: Homo sapiens

<400> SEQUENCE: 244

Arg Arg Arg Glu Ala Thr Glu Thr Gln Val
1               5                   10

<210> SEQ ID NO 245
<211> LENGTH: 10
<212> TYPE: PRT
<213> ORGANISM: Homo sapiens

<400> SEQUENCE: 245

Arg Pro Arg Arg Gln Thr Glu Thr Gln Val
1               5                   10

<210> SEQ ID NO 246
<211> LENGTH: 10
<212> TYPE: PRT
<213> ORGANISM: Homo sapiens

<400> SEQUENCE: 246

Arg His Thr Thr Ala Thr Glu Ser Ala Val
1               5                   10

<210> SEQ ID NO 247
<211> LENGTH: 10
<212> TYPE: PRT
<213> ORGANISM: Homo sapiens

<400> SEQUENCE: 247

Thr Ser Arg Gln Ala Thr Glu Ser Thr Val
1               5                   10

<210> SEQ ID NO 248
<211> LENGTH: 10
<212> TYPE: PRT
<213> ORGANISM: Homo sapiens

<400> SEQUENCE: 248

Arg Cys Trp Arg Pro Ser Ala Thr Val Val
1               5                   10

<210> SEQ ID NO 249
<211> LENGTH: 10
<212> TYPE: PRT
```

<213> ORGANISM: Homo sapiens

<400> SEQUENCE: 249

Pro Pro Arg Gln Arg Ser Glu Thr Gln Val
 1               5                  10

<210> SEQ ID NO 250
<211> LENGTH: 24
<212> TYPE: DNA
<213> ORGANISM: Homo sapiens

<400> SEQUENCE: 250
aaaagatcta caatactatg gcgc                                          24

<210> SEQ ID NO 251
<211> LENGTH: 26
<212> TYPE: DNA
<213> ORGANISM: Homo sapiens

<400> SEQUENCE: 251
agggaattcc agacttaata ttatac                                        26

<210> SEQ ID NO 252
<211> LENGTH: 26
<212> TYPE: DNA
<213> ORGANISM: Homo sapiens

<400> SEQUENCE: 252
aaaggatcca ttttatgcac caaaag                                        26

<210> SEQ ID NO 253
<211> LENGTH: 28
<212> TYPE: DNA
<213> ORGANISM: Homo sapiens

<400> SEQUENCE: 253
atggaattct atctccatgc atgattac                                      28

<210> SEQ ID NO 254
<211> LENGTH: 26
<212> TYPE: DNA
<213> ORGANISM: Homo sapiens

<400> SEQUENCE: 254
gaggaattca ccacaatact atggcg                                        26

<210> SEQ ID NO 255
<211> LENGTH: 26
<212> TYPE: DNA
<213> ORGANISM: Homo sapiens

<400> SEQUENCE: 255
aggagatctc atacttaata ttatac                                        26

<210> SEQ ID NO 256
<211> LENGTH: 27
<212> TYPE: DNA
<213> ORGANISM: Homo sapiens

<400> SEQUENCE: 256
ttgagatctt cagcgtcgtt ggagtcg                                       27

<210> SEQ ID NO 257

```
<211> LENGTH: 26
<212> TYPE: DNA
<213> ORGANISM: Homo sapiens

<400> SEQUENCE: 257
aaagaattca ttttatgcac caaaag                                    26

<210> SEQ ID NO 258
<211> LENGTH: 28
<212> TYPE: DNA
<213> ORGANISM: Homo sapiens

<400> SEQUENCE: 258
atgggatcct atctccatgc atgattac                                  28

<210> SEQ ID NO 259
<211> LENGTH: 32
<212> TYPE: DNA
<213> ORGANISM: Homo sapiens

<400> SEQUENCE: 259
ctgggatcct catcaacgtg ttcttgatga tc                             32

<210> SEQ ID NO 260
<211> LENGTH: 27
<212> TYPE: DNA
<213> ORGANISM: Homo sapiens

<400> SEQUENCE: 260
aagaaagctt tttatgcacc aaaagag                                   27

<210> SEQ ID NO 261
<211> LENGTH: 29
<212> TYPE: DNA
<213> ORGANISM: Homo sapiens

<400> SEQUENCE: 261
aatcaagctt tatctccatg catgattac                                 29

<210> SEQ ID NO 262
<211> LENGTH: 30
<212> TYPE: DNA
<213> ORGANISM: Homo sapiens

<400> SEQUENCE: 262
gctgaagctt tcaacgtgtt cttgatgatc                                30

<210> SEQ ID NO 263
<211> LENGTH: 27
<212> TYPE: DNA
<213> ORGANISM: Homo sapiens

<400> SEQUENCE: 263
aagcgtcgac tttatgcacc aaaagag                                   27

<210> SEQ ID NO 264
<211> LENGTH: 29
<212> TYPE: DNA
<213> ORGANISM: Homo sapiens

<400> SEQUENCE: 264
aatgctcgag tatctccatg catgattac                                 29
```

<210> SEQ ID NO 265
<211> LENGTH: 30
<212> TYPE: DNA
<213> ORGANISM: Homo sapiens

<400> SEQUENCE: 265
gctgctcgag tcaacgtgtt cttgatgatc                              30

<210> SEQ ID NO 266
<211> LENGTH: 26
<212> TYPE: DNA
<213> ORGANISM: Homo sapiens

<400> SEQUENCE: 266
agaagtcgac cacaatacta tggcgc                                  26

<210> SEQ ID NO 267
<211> LENGTH: 27
<212> TYPE: DNA
<213> ORGANISM: Homo sapiens

<400> SEQUENCE: 267
taggctcgag catacttaat attatac                                 27

<210> SEQ ID NO 268
<211> LENGTH: 28
<212> TYPE: DNA
<213> ORGANISM: Homo sapiens

<400> SEQUENCE: 268
cttgctcgag tcagcgtcgt tggagtcg                                28

<210> SEQ ID NO 269
<211> LENGTH: 26
<212> TYPE: DNA
<213> ORGANISM: Homo sapiens

<400> SEQUENCE: 269
agaaaagctt cacaatacta tggcgc                                  26

<210> SEQ ID NO 270
<211> LENGTH: 27
<212> TYPE: DNA
<213> ORGANISM: Homo sapiens

<400> SEQUENCE: 270
tagaagcttg catacttaat attatac                                 27

<210> SEQ ID NO 271
<211> LENGTH: 28
<212> TYPE: DNA
<213> ORGANISM: Homo sapiens

<400> SEQUENCE: 271
cttgaagctt tcagcgtcgt tgaggtcg                                28

<210> SEQ ID NO 272
<211> LENGTH: 225
<212> TYPE: PRT
<213> ORGANISM: Homo sapiens

<400> SEQUENCE: 272

Met Ser Pro Ile Leu Gly Tyr Trp Lys Ile Lys Gly Leu Val Gln Pro
 1               5                  10                  15

```
Thr Arg Leu Leu Leu Glu Tyr Leu Glu Glu Lys Tyr Glu Glu His Leu
             20                  25                  30
Tyr Glu Arg Asp Glu Gly Asp Lys Trp Arg Asn Lys Lys Phe Glu Leu
         35                  40                  45
Gly Leu Glu Phe Pro Asn Leu Pro Tyr Tyr Ile Asp Gly Asp Val Lys
     50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
             100                 105                 110
Lys Asp Phe Glu Thr Leu Lys Val Asp Phe Leu Ser Lys Leu Pro Glu
         115                 120                 125
Met Leu Lys Met Phe Glu Asp Arg Leu Cys His Lys Thr Tyr Leu Asn
     130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                 165                 170                 175
Val Cys Phe Lys Lys Arg Ile Glu Ala Ile Pro Gln Ile Asp Lys Tyr
             180                 185                 190
Leu Lys Ser Ser Lys Tyr Ile Ala Trp Pro Leu Gln Gly Trp Gln Ala
         195                 200                 205
Thr Phe Gly Gly Gly Asp His Pro Pro Lys Ser Asp Leu Ile Glu Gly
     210                 215                 220
Arg
225

<210> SEQ ID NO 273
<211> LENGTH: 24
<212> TYPE: DNA
<213> ORGANISM: Homo sapiens

<400> SEQUENCE: 273
aatggggatc cagctcatta aagg                                            24

<210> SEQ ID NO 274
<211> LENGTH: 24
<212> TYPE: DNA
<213> ORGANISM: Homo sapiens

<400> SEQUENCE: 274
atacatactt gtggaattcg ccac                                            24

<210> SEQ ID NO 275
<211> LENGTH: 26
<212> TYPE: DNA
<213> ORGANISM: Homo sapiens

<400> SEQUENCE: 275
cacggatccc ttctgagttg aaaggc                                          26

<210> SEQ ID NO 276
<211> LENGTH: 30
<212> TYPE: DNA
<213> ORGANISM: Homo sapiens
```

-continued

```
<400> SEQUENCE: 276
tatgaattcc atctggatca aaaggcaatg                                    30

<210> SEQ ID NO 277
<211> LENGTH: 30
<212> TYPE: DNA
<213> ORGANISM: Homo sapiens

<400> SEQUENCE: 277
cagggatcca aagagttgaa attcacaagc                                    30

<210> SEQ ID NO 278
<211> LENGTH: 27
<212> TYPE: DNA
<213> ORGANISM: Homo sapiens

<400> SEQUENCE: 278
acggaattct gcagcgactg ccgcgtc                                       27

<210> SEQ ID NO 279
<211> LENGTH: 23
<212> TYPE: DNA
<213> ORGANISM: Homo sapiens

<400> SEQUENCE: 279
aggatccaga tgtcctacat ccc                                           23

<210> SEQ ID NO 280
<211> LENGTH: 23
<212> TYPE: DNA
<213> ORGANISM: Homo sapiens

<400> SEQUENCE: 280
ggaattcatg gactgctgca cgg                                           23

<210> SEQ ID NO 281
<211> LENGTH: 28
<212> TYPE: DNA
<213> ORGANISM: Homo sapiens

<400> SEQUENCE: 281
agagaattct cgagatgtcc tacatccc                                      28

<210> SEQ ID NO 282
<211> LENGTH: 27
<212> TYPE: DNA
<213> ORGANISM: Homo sapiens

<400> SEQUENCE: 282
tgggaattcc taggacagca tggactg                                       27

<210> SEQ ID NO 283
<211> LENGTH: 25
<212> TYPE: DNA
<213> ORGANISM: Homo sapiens

<400> SEQUENCE: 283
ctaggatccg ggccagccgg tcacc                                         25

<210> SEQ ID NO 284
<211> LENGTH: 29
<212> TYPE: DNA
<213> ORGANISM: Homo sapiens
```

```
<400> SEQUENCE: 284
gacggatccc cctgctgcac ggccttctg                                              29

<210> SEQ ID NO 285
<211> LENGTH: 29
<212> TYPE: DNA
<213> ORGANISM: Homo sapiens

<400> SEQUENCE: 285
gacgaattcc cctgctgcac ggccttctg                                              29

<210> SEQ ID NO 286
<211> LENGTH: 25
<212> TYPE: DNA
<213> ORGANISM: Homo sapiens

<400> SEQUENCE: 286
ctagaattcg ggccagccgg tcacc                                                  25

<210> SEQ ID NO 287
<211> LENGTH: 82
<212> TYPE: PRT
<213> ORGANISM: Homo sapiens

<400> SEQUENCE: 287
```

Leu Ile Lys Gly Pro Lys Gly Leu Gly Phe Ser Ile Ala Gly Gly Val
1               5                   10                  15

Gly Asn Gln His Ile Pro Gly Asp Asn Ser Ile Tyr Val Thr Lys Ile
                20                  25                  30

Ile Glu Gly Gly Ala Ala His Lys Asp Gly Lys Leu Gln Ile Gly Asp
            35                  40                  45

Lys Leu Leu Ala Val Asn Asn Val Cys Leu Glu Glu Val Thr His Glu
        50                  55                  60

Glu Ala Val Thr Ala Leu Lys Asn Thr Ser Asp Phe Val Tyr Leu Lys
65                  70                  75                  80

Val Ala

```
<210> SEQ ID NO 288
<211> LENGTH: 101
<212> TYPE: PRT
<213> ORGANISM: Homo sapiens

<400> SEQUENCE: 288
```

Pro Ser Glu Leu Lys Gly Lys Phe Ile His Thr Lys Leu Arg Lys Ser
1               5                   10                  15

Ser Arg Gly Phe Gly Phe Thr Val Val Gly Gly Asp Glu Pro Asp Glu
                20                  25                  30

Phe Leu Gln Ile Lys Ser Leu Val Leu Asp Gly Pro Ala Ala Leu Asp
            35                  40                  45

Gly Lys Met Glu Thr Gly Asp Val Ile Val Ser Val Asn Asp Thr Cys
        50                  55                  60

Val Leu Gly His Thr His Ala Gln Val Val Lys Ile Phe Gln Ser Ile
65                  70                  75                  80

Pro Ile Gly Ala Ser Val Asp Leu Glu Leu Cys Arg Gly Tyr Pro Leu
                85                  90                  95

Pro Phe Asp Pro Asp
                100

```
<210> SEQ ID NO 289
<211> LENGTH: 102
<212> TYPE: PRT
<213> ORGANISM: Homo sapiens

<400> SEQUENCE: 289

Gln Arg Val Glu Ile His Lys Leu Arg Gln Gly Glu Asn Leu Ile Leu
 1               5                  10                  15

Gly Phe Ser Ile Gly Gly Ile Asp Gln Asp Pro Ser Gln Asn Pro
            20                  25                  30

Phe Ser Glu Asp Lys Thr Asp Lys Gly Ile Tyr Val Thr Arg Val Ser
        35                  40                  45

Glu Gly Gly Pro Ala Glu Ile Ala Gly Leu Gln Ile Gly Asp Lys Ile
 50                  55                  60

Met Gln Val Asn Gly Trp Asp Met Thr Met Val Thr His Asp Gln Ala
 65                  70                  75                  80

Arg Lys Arg Leu Thr Lys Arg Ser Glu Glu Val Val Arg Leu Leu Val
                85                  90                  95

Thr Arg Gln Ser Leu Gln
            100

<210> SEQ ID NO 290
<211> LENGTH: 122
<212> TYPE: PRT
<213> ORGANISM: Homo sapiens

<400> SEQUENCE: 290

Met Ser Tyr Ile Pro Gly Gln Pro Val Thr Ala Val Val Gln Arg Val
 1               5                  10                  15

Glu Ile His Lys Leu Arg Gln Gly Glu Asn Leu Ile Leu Gly Phe Ser
            20                  25                  30

Ile Gly Gly Gly Ile Asp Gln Asp Pro Ser Gln Asn Pro Phe Ser Glu
        35                  40                  45

Asp Lys Thr Asp Lys Gly Ile Tyr Val Thr Arg Val Ser Glu Gly Gly
 50                  55                  60

Pro Ala Glu Ile Ala Gly Leu Gln Ile Gly Asp Lys Ile Met Gln Val
 65                  70                  75                  80

Asn Gly Trp Asp Met Thr Met Val Thr His Asp Gln Ala Arg Lys Arg
                85                  90                  95

Leu Thr Lys Arg Ser Glu Glu Val Val Arg Leu Leu Val Thr Arg Gln
            100                 105                 110

Ser Leu Gln Lys Ala Val Gln Gln Ser Met
        115                 120

<210> SEQ ID NO 291
<211> LENGTH: 125
<212> TYPE: PRT
<213> ORGANISM: Homo sapiens

<400> SEQUENCE: 291

Glu Met Ser Tyr Ile Pro Gly Gln Pro Val Thr Ala Val Val Gln Arg
 1               5                  10                  15

Val Glu Ile His Lys Leu Arg Gln Gly Glu Asn Leu Ile Leu Gly Phe
            20                  25                  30

Ser Ile Gly Gly Gly Ile Asp Gln Asp Pro Ser Gln Asn Pro Phe Ser
        35                  40                  45

Glu Asp Lys Thr Asp Lys Gly Ile Tyr Val Thr Arg Val Ser Glu Gly
```

```
                50              55              60
Gly Pro Ala Glu Ile Ala Gly Leu Gln Ile Gly Asp Lys Ile Met Gln
 65              70              75              80

Val Asn Gly Trp Asp Met Thr Met Val Thr His Asp Gln Ala Arg Lys
                 85              90              95

Arg Leu Thr Lys Arg Ser Glu Glu Val Arg Leu Leu Val Thr Arg
                100             105             110

Gln Ser Leu Gln Lys Ala Val Gln Gln Ser Met Leu Ser
            115             120             125

<210> SEQ ID NO 292
<211> LENGTH: 117
<212> TYPE: PRT
<213> ORGANISM: Homo sapiens

<400> SEQUENCE: 292

Pro Gly Gln Pro Val Thr Ala Val Val Gln Arg Val Glu Ile His Lys
 1               5              10              15

Leu Arg Gln Gly Glu Asn Leu Ile Leu Gly Phe Ser Ile Gly Gly Gly
                20              25              30

Ile Asp Gln Asp Pro Ser Gln Asn Pro Phe Ser Glu Asp Lys Thr Asp
             35              40              45

Lys Gly Ile Tyr Val Thr Arg Val Ser Glu Gly Gly Pro Ala Glu Ile
 50              55              60

Ala Gly Leu Gln Ile Gly Asp Lys Ile Met Gln Val Asn Gly Trp Asp
 65              70              75              80

Met Thr Met Val Thr His Asp Gln Ala Arg Lys Arg Leu Thr Lys Arg
                 85              90              95

Ser Glu Glu Val Val Arg Leu Leu Val Thr Arg Gln Ser Leu Gln Lys
                100             105             110

Ala Val Gln Gln Ser
            115

<210> SEQ ID NO 293
<211> LENGTH: 72
<212> TYPE: PRT
<213> ORGANISM: Homo sapiens

<400> SEQUENCE: 293

Arg Lys Ser Ser Arg Gly Phe Gly Phe Thr Val Val Gly Gly Asp Glu
 1               5              10              15

Pro Asp Glu Phe Leu Gln Ile Lys Ser Leu Val Leu Asp Gly Pro Ala
                20              25              30

Ala Leu Asp Gly Lys Met Glu Thr Gly Asp Val Ile Val Ser Val Asn
             35              40              45

Asp Thr Cys Val Leu Gly His Thr His Ala Gln Val Val Lys Ile Phe
 50              55              60

Gln Ser Ile Pro Ile Gly Ala Ser
 65              70

<210> SEQ ID NO 294
<211> LENGTH: 76
<212> TYPE: PRT
<213> ORGANISM: Homo sapiens

<400> SEQUENCE: 294

Phe Ile His Thr Lys Leu Arg Lys Ser Ser Arg Gly Phe Gly Phe Thr
 1               5              10              15
```

-continued

Val Val Gly Gly Asp Glu Pro Asp Glu Phe Leu Gln Ile Lys Ser Leu
            20                  25                  30

Val Leu Asp Gly Pro Ala Ala Leu Asp Gly Lys Met Glu Thr Gly Asp
        35                  40                  45

Val Ile Val Ser Val Asn Asp Thr Cys Val Leu Gly His Thr His Ala
    50                  55                  60

Gln Val Val Lys Ile Phe Gln Ser Ile Pro Ile Gly
65                  70                  75

<210> SEQ ID NO 295
<211> LENGTH: 85
<212> TYPE: PRT
<213> ORGANISM: Homo sapiens

<400> SEQUENCE: 295

Phe Ile His Thr Lys Leu Arg Lys Ser Ser Arg Gly Phe Gly Phe Thr
1               5                   10                  15

Val Val Gly Gly Asp Glu Pro Asp Glu Phe Leu Gln Ile Lys Ser Leu
            20                  25                  30

Val Leu Asp Gly Pro Ala Ala Leu Asp Gly Lys Met Glu Thr Gly Asp
        35                  40                  45

Val Ile Val Ser Val Asn Asp Thr Cys Val Leu Gly His Thr His Ala
    50                  55                  60

Gln Val Val Lys Ile Phe Gln Ser Ile Pro Ile Gly Ala Ser Val Asp
65                  70                  75                  80

Leu Glu Leu Cys Arg
                85

<210> SEQ ID NO 296
<211> LENGTH: 78
<212> TYPE: PRT
<213> ORGANISM: Homo sapiens

<400> SEQUENCE: 296

Lys Ser Ser Arg Gly Phe Gly Phe Thr Val Val Gly Gly Asp Glu Pro
1               5                   10                  15

Asp Glu Phe Leu Gln Ile Lys Ser Leu Val Leu Asp Gly Pro Ala Ala
            20                  25                  30

Leu Asp Gly Lys Met Glu Thr Gly Asp Val Ile Val Ser Val Asn Asp
        35                  40                  45

Thr Cys Val Leu Gly His Thr His Ala Gln Val Val Lys Ile Phe Gln
    50                  55                  60

Ser Ile Pro Ile Gly Ala Ser Val Asp Leu Glu Leu Cys Arg
65                  70                  75

<210> SEQ ID NO 297
<211> LENGTH: 88
<212> TYPE: PRT
<213> ORGANISM: Homo sapiens

<400> SEQUENCE: 297

Phe Ile His Thr Lys Leu Arg Lys Ser Ser Arg Gly Phe Gly Phe Thr
1               5                   10                  15

Val Val Gly Gly Asp Glu Pro Asp Glu Phe Leu Gln Ile Lys Ser Leu
            20                  25                  30

Val Leu Asp Gly Pro Ala Ala Leu Asp Gly Lys Met Glu Thr Gly Asp
        35                  40                  45

-continued

Val Ile Val Ser Val Asn Asp Thr Cys Val Leu Gly His Thr His Ala
        50                  55                  60

Gln Val Val Lys Ile Phe Gln Ser Ile Pro Ile Gly Ala Ser Val Asp
 65                  70                  75                  80

Leu Glu Leu Cys Arg Gly Tyr Pro
                85

<210> SEQ ID NO 298
<211> LENGTH: 88
<212> TYPE: PRT
<213> ORGANISM: Homo sapiens

<400> SEQUENCE: 298

Lys Gly Lys Phe Ile His Thr Lys Leu Arg Lys Ser Ser Arg Gly Phe
 1               5                  10                  15

Gly Phe Thr Val Val Gly Gly Asp Glu Pro Asp Glu Phe Leu Gln Ile
                20                  25                  30

Lys Ser Leu Val Leu Asp Gly Pro Ala Ala Leu Asp Gly Lys Met Glu
         35                  40                  45

Thr Gly Asp Val Ile Val Ser Val Asn Asp Thr Cys Val Leu Gly His
 50                  55                  60

Thr His Ala Gln Val Val Lys Ile Phe Gln Ser Ile Pro Ile Gly Ala
 65                  70                  75                  80

Ser Val Asp Leu Glu Leu Cys Arg
                85

<210> SEQ ID NO 299
<211> LENGTH: 81
<212> TYPE: PRT
<213> ORGANISM: Homo sapiens

<400> SEQUENCE: 299

Lys Gly Lys Phe Ile His Thr Lys Leu Arg Lys Ser Ser Arg Gly Phe
 1               5                  10                  15

Gly Phe Thr Val Val Gly Gly Asp Glu Pro Asp Glu Phe Leu Gln Ile
                20                  25                  30

Lys Ser Leu Val Leu Asp Gly Pro Ala Ala Leu Asp Gly Lys Met Glu
         35                  40                  45

Thr Gly Asp Val Ile Val Ser Val Asn Asp Thr Cys Val Leu Gly His
 50                  55                  60

Thr His Ala Gln Val Val Lys Ile Phe Gln Ser Ile Pro Ile Gly Ala
 65                  70                  75                  80

Ser

<210> SEQ ID NO 300
<211> LENGTH: 94
<212> TYPE: PRT
<213> ORGANISM: Homo sapiens

<400> SEQUENCE: 300

Glu Leu Lys Gly Lys Phe Ile His Thr Lys Leu Arg Lys Ser Ser Arg
 1               5                  10                  15

Gly Phe Gly Phe Thr Val Val Gly Gly Asp Glu Pro Asp Glu Phe Leu
                20                  25                  30

Gln Ile Lys Ser Leu Val Leu Asp Gly Pro Ala Ala Leu Asp Gly Lys
         35                  40                  45

Met Glu Thr Gly Asp Val Ile Val Ser Val Asn Asp Thr Cys Val Leu
 50                  55                  60

Gly His Thr His Ala Gln Val Val Lys Ile Phe Gln Ser Ile Pro Ile
65                  70                  75                  80

Gly Ala Ser Val Asp Leu Glu Leu Cys Arg Gly Tyr Pro Leu
                85                  90

<210> SEQ ID NO 301
<211> LENGTH: 99
<212> TYPE: PRT
<213> ORGANISM: Homo sapiens

<400> SEQUENCE: 301

Ser Glu Leu Lys Gly Lys Phe Ile His Thr Lys Leu Arg Lys Ser Ser
1               5                   10                  15

Arg Gly Phe Gly Phe Thr Val Val Gly Gly Asp Glu Pro Asp Glu Phe
                20                  25                  30

Leu Gln Ile Lys Ser Leu Val Leu Asp Gly Pro Ala Ala Leu Asp Gly
            35                  40                  45

Lys Met Glu Thr Gly Asp Val Ile Val Ser Val Asn Asp Thr Cys Val
50                  55                  60

Leu Gly His Thr His Ala Gln Val Val Lys Ile Phe Gln Ser Ile Pro
65                  70                  75                  80

Ile Gly Ala Ser Val Asp Leu Glu Leu Cys Arg Gly Tyr Pro Leu Pro
                85                  90                  95

Phe Asp Pro

<210> SEQ ID NO 302
<211> LENGTH: 72
<212> TYPE: PRT
<213> ORGANISM: Homo sapiens

<400> SEQUENCE: 302

Arg Lys Ser Ala Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 303
<211> LENGTH: 72
<212> TYPE: PRT
<213> ORGANISM: Homo sapiens

<400> SEQUENCE: 303

Arg Lys Ser Ser Arg Gly Phe Gly Phe Thr Val Val Gly Gly Glu Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 304
<211> LENGTH: 72
<212> TYPE: PRT
<213> ORGANISM: Homo sapiens

<400> SEQUENCE: 304

Arg Lys Ser Ser Arg Gly Phe Gly Phe Thr Val Val Gly Gly Asp Glu
1               5                   10                  15

Pro Asp Glu Phe Leu Gln Leu Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 305
<211> LENGTH: 72
<212> TYPE: PRT
<213> ORGANISM: Homo sapiens

<400> SEQUENCE: 305

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ser Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 306
<211> LENGTH: 72
<212> TYPE: PRT
<213> ORGANISM: Homo sapiens

<400> SEQUENCE: 306

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Arg Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 307
<211> LENGTH: 72
<212> TYPE: PRT
<213> ORGANISM: Homo sapiens

<400> SEQUENCE: 307

-continued

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ala Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 308
<211> LENGTH: 72
<212> TYPE: PRT
<213> ORGANISM: Homo sapiens

<400> SEQUENCE: 308

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Glu Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 309
<211> LENGTH: 72
<212> TYPE: PRT
<213> ORGANISM: Homo sapiens

<400> SEQUENCE: 309

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Leu Leu Gly His Thr His Ala Gln Val Val Lys Ile Phe
    50                  55                  60

Gln Ser Ile Pro Ile Gly Ala Ser
65                  70

<210> SEQ ID NO 310
<211> LENGTH: 72
<212> TYPE: PRT
<213> ORGANISM: Homo sapiens

<400> SEQUENCE: 310

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ser Gln Val Val Lys Ile Phe

```
                    50                  55                  60
Gln Ser Ile Pro Ile Gly Ala Ser
 65                  70
```

<210> SEQ ID NO 311
<211> LENGTH: 72
<212> TYPE: PRT
<213> ORGANISM: Homo sapiens

<400> SEQUENCE: 311

```
Arg Lys Ser Ser Arg Gly Phe Gly Phe Thr Val Val Gly Gly Asp Glu
 1               5                  10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Leu Phe
        50                  55                  60

Gln Ser Ile Pro Ile Gly Ala Ser
 65                  70
```

<210> SEQ ID NO 312
<211> LENGTH: 72
<212> TYPE: PRT
<213> ORGANISM: Homo sapiens

<400> SEQUENCE: 312

```
Arg Lys Ser Ser Arg Gly Phe Gly Phe Thr Val Val Gly Gly Asp Glu
 1               5                  10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ser Ser
 65                  70
```

<210> SEQ ID NO 313
<211> LENGTH: 72
<212> TYPE: PRT
<213> ORGANISM: Homo sapiens

<400> SEQUENCE: 313

```
Arg Lys Ser Thr Arg Gly Phe Gly Phe Thr Val Val Gly Gly Asp Glu
 1               5                  10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
 65                  70
```

<210> SEQ ID NO 314
<211> LENGTH: 72
<212> TYPE: PRT
<213> ORGANISM: Homo sapiens -continued

```
<400> SEQUENCE: 314

Arg Lys Ser Ser Arg Gly Phe Gly Phe Thr Val Val Gly Gly Asp Glu
1               5                   10                  15

Pro Gly Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 315
<211> LENGTH: 72
<212> TYPE: PRT
<213> ORGANISM: Homo sapiens

<400> SEQUENCE: 315

Arg Lys Ser Ser Arg Gly Phe Gly Phe Thr Val Val Gly Gly Asp Glu
1               5                   10                  15

Pro Asp Glu Phe Leu Gln Ile Lys Ser Leu Ala Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 316
<211> LENGTH: 72
<212> TYPE: PRT
<213> ORGANISM: Homo sapiens

<400> SEQUENCE: 316

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Ala Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 317
<211> LENGTH: 72
<212> TYPE: PRT
<213> ORGANISM: Homo sapiens

<400> SEQUENCE: 317

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Ala Asp Val Ile Val Ser Val Asn
```

```
            35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 318
<211> LENGTH: 72
<212> TYPE: PRT
<213> ORGANISM: Homo sapiens

<400> SEQUENCE: 318

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Ala Val Leu Gly His Thr His Ala Gln Val Val Lys Ile Phe
    50                  55                  60

Gln Ser Ile Pro Ile Gly Ala Ser
65                  70

<210> SEQ ID NO 319
<211> LENGTH: 72
<212> TYPE: PRT
<213> ORGANISM: Homo sapiens

<400> SEQUENCE: 319

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Ala Val Lys Ile Phe
    50                  55                  60

Gln Ser Ile Pro Ile Gly Ala Ser
65                  70

<210> SEQ ID NO 320
<211> LENGTH: 72
<212> TYPE: PRT
<213> ORGANISM: Homo sapiens

<400> SEQUENCE: 320

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
    50                  55                  60

Gln Ser Ile Ala Ile Gly Ala Ser
65                  70

<210> SEQ ID NO 321
```

```
<211> LENGTH: 72
<212> TYPE: PRT
<213> ORGANISM: Homo sapiens

<400> SEQUENCE: 321

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ala
65                  70

<210> SEQ ID NO 322
<211> LENGTH: 72
<212> TYPE: PRT
<213> ORGANISM: Homo sapiens

<400> SEQUENCE: 322

Arg Lys Ser Ser Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 323
<211> LENGTH: 72
<212> TYPE: PRT
<213> ORGANISM: Homo sapiens

<400> SEQUENCE: 323

Arg Lys Ser Ser Arg Gly Phe Gly Phe Thr Val Val Gly Gly Leu Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Gly Ala Ser
65                  70

<210> SEQ ID NO 324
<211> LENGTH: 72
<212> TYPE: PRT
<213> ORGANISM: Homo sapiens

<400> SEQUENCE: 324

Arg Lys Ser Ser Arg Gly Phe Gly Phe Thr Val Val Gly Gly Asp Glu
1               5                   10                  15

Pro Asp Glu Phe Leu Gln Ile Thr Ser Leu Val Leu Asp Gly Pro Ala
```

```
                   20                  25                  30

Ala Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 325
<211> LENGTH: 72
<212> TYPE: PRT
<213> ORGANISM: Homo sapiens

<400> SEQUENCE: 325

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Gly Leu Asp Gly Lys Met Glu Thr Gly Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 326
<211> LENGTH: 72
<212> TYPE: PRT
<213> ORGANISM: Homo sapiens

<400> SEQUENCE: 326

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Ser Asp Val Ile Val Ser Val Asn
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70

<210> SEQ ID NO 327
<211> LENGTH: 72
<212> TYPE: PRT
<213> ORGANISM: Homo sapiens

<400> SEQUENCE: 327

Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
                20                  25                  30

Ala Leu Asp Gly Lys Met Glu Thr Gly Asp Val Ile Val Ser Val Lys
            35                  40                  45

Asp Thr Cys Val Leu Gly His Thr His Ala Gln Val Val Lys Ile Phe
        50                  55                  60

Gln Ser Ile Pro Ile Gly Ala Ser
65                  70
```

<210> SEQ ID NO 328
<211> LENGTH: 72
<212> TYPE: PRT
<213> ORGANISM: Homo sapiens

<400> SEQUENCE: 328

```
Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Phe His Thr His Ala Gln Val Val Lys Ile Phe
    50                  55                  60

Gln Ser Ile Pro Ile Gly Ala Ser
65                  70
```

<210> SEQ ID NO 329
<211> LENGTH: 72
<212> TYPE: PRT
<213> ORGANISM: Homo sapiens

<400> SEQUENCE: 329

```
Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Asn Val Lys Ile Phe
    50                  55                  60

Gln Ser Ile Pro Ile Gly Ala Ser
65                  70
```

<210> SEQ ID NO 330
<211> LENGTH: 72
<212> TYPE: PRT
<213> ORGANISM: Homo sapiens

<400> SEQUENCE: 330

```
Arg Lys Ser Ser Arg Gly Phe Gly Phe Thr Val Val Gly Gly Asp Glu
1               5                   10                  15

Pro Asp Glu Phe Leu Gln Ile Lys Ser Leu Val Leu Asp Gly Pro Ala
            20                  25                  30

Ala Leu Asp Gly Lys Met Glu Thr Gly Asp Val Ile Val Ser Val Asn
        35                  40                  45

Asp Thr Cys Val Leu Gly His Thr His Ala Gln Val Val Lys Ile Phe
    50                  55                  60

Gln Ser Ile Pro Ile Ser Ala Ser
65                  70
```